United States Patent
Gotoh et al.

(10) Patent No.: US 9,631,142 B2
(45) Date of Patent: Apr. 25, 2017

(54) PIPERIDINE DERIVATIVE, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Tokyo (JP); Keiji Kimura, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/859,615

(22) Filed: Sep. 21, 2015

(65) Prior Publication Data

US 2016/0090534 A1 Mar. 31, 2016

(30) Foreign Application Priority Data

Sep. 24, 2014 (JP) ................................. 2014-193237

(51) Int. Cl.
*G02F 1/1333* (2006.01)
*C09K 19/34* (2006.01)
(Continued)

(52) U.S. Cl.
CPC ........ *C09K 19/3458* (2013.01); *C07D 211/46* (2013.01); *C07D 211/58* (2013.01); *C07D 211/94* (2013.01); *C07D 401/14* (2013.01); *C07D 405/14* (2013.01); *C09K 19/3066* (2013.01); *C09K 19/3483* (2013.01); *C09K 19/52* (2013.01); *C09K 2019/0448* (2013.01); *C09K 2019/122* (2013.01); *C09K 2019/123* (2013.01); *C09K 2019/301* (2013.01); *C09K 2019/3004* (2013.01); *C09K 2019/308* (2013.01); *C09K 2019/3016* (2013.01); *C09K 2019/3025* (2013.01); *C09K 2019/3027* (2013.01); *C09K 2019/3071* (2013.01); *C09K 2019/3077* (2013.01); *C09K 2019/3078* (2013.01); *C09K 2019/3083* (2013.01);
(Continued)

(58) Field of Classification Search
CPC ............ C09K 19/3458; C09K 19/3066; C09K 19/3483; C09K 19/52; C09K 2019/3077; C09K 2019/308; C09K 2019/3083; C09K 2019/3422; C09K 2019/3078; C09K 2019/3425; C09K 2019/3071; C09K 2019/0448; C09K 2019/122; C09K 2019/123; C09K 2019/3004; C09K 2019/301; C09K 2019/3016; C09K 2019/3025; C09K 2019/3027; C07D 211/46; C07D 211/94; C07D 211/52; C07D 401/14; C07D 405/14

USPC ............. 252/299.01, 299.6, 299.61; 348/182
See application file for complete search history.

(56) References Cited

U.S. PATENT DOCUMENTS

| | | |
|---|---|---|
| 8,349,210 B2 | 1/2013 | Xu |
| 8,431,039 B2 | 4/2013 | Dai et al. |
| 2015/0159088 A1 | 6/2015 | Goebel et al. |

FOREIGN PATENT DOCUMENTS

| | | |
|---|---|---|
| DE | 10 2011 013 007 A | 10/2011 |
| JP | 2012-224632 A | 11/2012 |

*Primary Examiner* — Geraldina Visconti
(74) *Attorney, Agent, or Firm* — Greenblum & Bernstein, P.L.C.

(57) ABSTRACT

To provide a compound having an effect for preventing photolysis of a liquid crystal composition, and having a high solubility in the liquid crystal composition, a liquid crystal composition containing the compound, and a liquid crystal display device including the composition. The compound is represented by formula (1), a liquid crystal composition contains the compound, and a liquid crystal display device includes the composition:

$$M(Z-Q)_a(R^b)_b \quad (1)$$

wherein, in formula (1), a is 1 to 4, and b is a numerical value: (4−a); M is an organic group; Z is a single bond or the like; and Q is a monovalent group represented by formula (Q-1), (Q-2) or (Q-3), in which $R^a$ and $R^b$ are hydrogen, alkyl or the like.

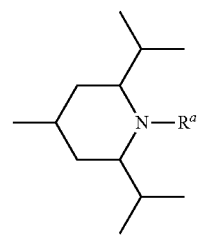

(Q-1)

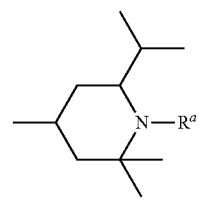

(Q-2)

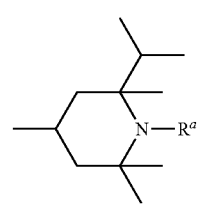

(Q-3)

14 Claims, No Drawings

(51) Int. Cl.
  *C09K 19/30* (2006.01)
  *C07D 211/46* (2006.01)
  *C07D 211/94* (2006.01)
  *C07D 211/58* (2006.01)
  *C07D 401/14* (2006.01)
  *C07D 405/14* (2006.01)
  *C09K 19/52* (2006.01)
  C09K 19/04 (2006.01)
  C09K 19/12 (2006.01)

(52) U.S. Cl.
  CPC ................ *C09K 2019/3422* (2013.01); *C09K 2019/3425* (2013.01)

PIPERIDINE DERIVATIVE, LIQUID CRYSTAL COMPOSITION AND LIQUID CRYSTAL DISPLAY DEVICE

TECHNICAL FIELD

The present invention relates to a piperidine derivative, a liquid crystal composition and a liquid crystal display device. More specifically, the invention relates to an isopropylpiperidine derivative, a liquid crystal composition that contains the compound and has a positive or negative dielectric anisotropy, and a liquid crystal display device including the composition.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode, and a field-induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type according to a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving the characteristics of the composition. Table 1 below summarizes a relationship of the characteristics between two aspects. The characteristics of the composition will be further described based on a commercially available AM device. A temperature range of the nematic phase relates to a temperature range in which the device can be used. A preferred maximum temperature of the nematic phase is approximately 70° C. or higher and a preferred minimum temperature of the nematic phase is approximately −10° C. or lower. A viscosity of the composition relates to a response time in the device. A short response time is preferred for displaying moving images on the device. A shorter response time even by one millisecond is desirable. Accordingly, a small viscosity in the composition is preferred. A small viscosity at a low temperature is further preferred.

TABLE 1

| | Characteristics of Composition and AM Device | |
| --- | --- | --- |
| No. | Characteristics of Composition | Characteristics of AM Device |
| 1 | Wide temperature range of a nematic phase | Wide usable temperature range |
| 2 | Small viscosity [1] | Short response time |
| 3 | Suitable optical anisotropy | Large contrast ratio |

TABLE 1-continued

| | Characteristics of Composition and AM Device | |
| --- | --- | --- |
| No. | Characteristics of Composition | Characteristics of AM Device |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |
| 7 | Large elastic constant | Large contrast ratio and short response time |

[1] A composition can be injected into a liquid crystal display device in a shorter period of time.

An optical anisotropy of the composition relates to a contrast ratio in the device. According to the mode of the device, a suitable optical anisotropy such as a large optical anisotropy or a small optical anisotropy is required. A product ($\Delta n \times d$) of the optical anisotropy ($\Delta n$) of the composition and a cell gap (d) in the device is designed so as to maximize the contrast ratio. A suitable value of the product depends on a type of the operating mode. A composition having a large optical anisotropy is preferred for a device having a small cell gap. A large value of dielectric anisotropy in the composition contributes to a low threshold voltage, a small electric power consumption and a large contrast ratio in the device. Accordingly, the large positive or negative value of dielectric anisotropy is preferred. A large specific resistance in the composition contributes to a large voltage holding ratio and a large contrast ratio in the device. Accordingly, a composition having a large specific resistance at room temperature and also at a high temperature in an initial stage is preferred. A composition having a large specific resistance at room temperature and also at a high temperature even after the device has been used for a long period of time is preferred. Stability of the composition to ultraviolet light and heat relates to a service life of the device. In the case where the stability is high, the device has a long service life. Such characteristics are preferred for an AM device for use in a liquid crystal projector, a liquid crystal television and so forth.

A liquid crystal composition containing a polymer is used for a liquid crystal display device having the polymer sustained alignment (PSA) mode. First, a composition to which a small amount of polymerizable compound is added is injected into the device. Next, the composition is irradiated with ultraviolet light while voltage is applied between substrates of the device. The polymerizable compound is polymerized to form a network structure of the polymer in the composition. In the composition, alignment of liquid crystal molecules can be controlled by the polymer, and therefore a response time of the device is shortened and image persistence is improved. Such an effect of the polymer can be expected for a device having a mode such as the TN mode, the ECB mode, the OCB mode, the IPS mode, the VA mode, the FFS mode and the FPA mode.

The liquid crystal composition is prepared by mixing the liquid crystal compounds. An additive such as a polymerizable compound, a polymerization initiator, a polymerization inhibitor, an optically active compound, an antioxidant, an ultraviolet light absorber, a light stabilizer, a heat stabilizer and an antifoaming agent is added to the composition, when necessary. Among the compounds described above, the light stabilizer is effective in preventing a liquid crystal compound from being decomposed by light from backlight or the sun. The high voltage holding ratio in the device is maintained by the effect described above, and therefore a long service life of the device is achieved. A hindered amine light stabilizer (HALS) is suitable for such a purpose. However, development of a further excellent light stabilizer is expected.

CITATION LIST

Patent Literature

Patent literature No. 1: DE 102011013007 A.
Patent literature No. 2: JP 2012-224632 A.
Patent literature No. 3: U.S. Pat. No. 8,349,210 B.
Patent literature No. 4: U.S. Pat. No. 8,431,039 B.

SUMMARY OF INVENTION

Technical Problem

A first object of the invention is to provide a compound having an effect of preventing photolysis of a liquid crystal composition, and having a high solubility in the liquid crystal composition. A second object is to provide a liquid crystal composition containing the compound and satisfying at least one of characteristics such as a high maximum temperature of a nematic phase, a low minimum temperature of the nematic phase, a small viscosity, a suitable optical anisotropy, a large dielectric anisotropy, a large specific resistance, a high stability to ultraviolet light, a high stability to heat and a large elastic constant. The object is also to provide a liquid crystal composition being stable to light. A third object is to provide a liquid crystal display device including the composition and having a wide temperature range in which the device can be used, a short response time, a high voltage holding ratio, a low threshold voltage, a large contrast ratio and a long service life.

Solution to Problem

The invention relates to a compound represented by formula (1), a liquid crystal composition containing the compound, and a liquid crystal display device including the composition:

$$M(Z-Q)_a(R^b)_b \quad (1)$$

wherein, in formula (1),
a is 1, 2, 3 or 4;
b is a numerical value: (4−a) obtained by subtracting a from 4;
M is an organic group, and
Z is a single bond, —O—, —COO— or —OCO—; and
Q is a monovalent group represented by formula (Q-1), (Q-2) or (Q-3), in which $R^a$ is hydrogen, —O., —OH or —$R^1$;

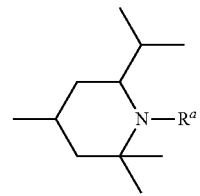

(Q-1)

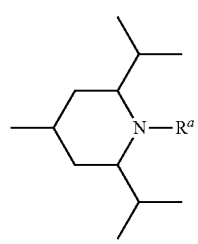

(Q-2)

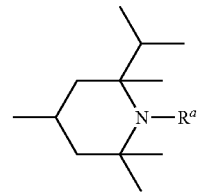

(Q-3)

$R^b$ is hydrogen, fluorine or —$R^2$; and
$R^1$ and $R^2$ are independently alkyl having 1 to 20 carbons, arylalkyl having 1 to 20 carbons or aryl having 1 to 20 carbons, and in the alkyl, at least one of —$CH_2$— may be replaced by —O—, —CO—, —COO—, —OCO— or —$NHR^3$—, and —$CH_3$ located at a terminal may be replaced by —$NHR^3$ or —$NR^4R^5$ in which $R^3$, $R^4$ and $R^5$ are independently alkyl having 1 to 10 carbons.

Advantageous Effects of Invention

A first advantage of the invention is to provide a compound having an effect of preventing photolysis of a liquid crystal composition, and having a high solubility in the liquid crystal composition. A second advantage is to provide a liquid crystal composition containing the compound and satisfying at least one of characteristics such as a high maximum temperature of a nematic phase, a low minimum temperature of the nematic phase, a small viscosity, a suitable optical anisotropy, a large dielectric anisotropy, a large specific resistance, a high stability to ultraviolet light, a high stability to heat and a large elastic constant. The advantage is also to provide a liquid crystal composition being stable to light. A third object is to provide a liquid crystal display device including the composition and having a wide temperature range in which the device can be used, a short response time, a high voltage holding ratio, a low threshold voltage, a large contrast ratio and a long service life.

DESCRIPTION OF EMBODIMENTS

Usage of terms herein is as described below. "Liquid crystal compound" is a generic term for a compound having a liquid crystal phase such as a nematic phase and a smectic phase, and a compound having no liquid crystal phase but to be added for the purpose of adjusting characteristics of a composition, such as a maximum temperature, a minimum temperature, viscosity and a dielectric anisotropy. The compounds have a 6-membered ring such as 1,4-cyclohexylene and 1,4-phenylene, and a rod like molecular structure. A liquid crystal composition is prepared by mixing such liquid crystal compounds. A ratio (content) of the liquid crystal compounds is expressed in terms of weight percent (% by weight) based on the weight of the liquid crystal composition. An additive such as a polymerizable compound, a polymerization initiator, a polymerization inhibitor, an optically active compound, an antioxidant, an ultraviolet light absorber, a light stabilizer, a heat stabilizer and an antifoaming agent is added to the composition, when necessary. A ratio (content) of the additive is expressed in terms of weight percent (% by weight) based on the weight of the liquid crystal composition in a manner similar to the ratio of the liquid crystal compounds. Weight parts per million (ppm) may be occasionally used.

A liquid crystal display device is a generic term for a liquid crystal display panel and a liquid crystal display module. A liquid crystal compound, the liquid crystal composition and the liquid crystal display device may be occasionally abbreviated as "compound," "composition" and "device," respectively. A clearing point is a transition temperature between the liquid crystal phase and an isotropic phase in the liquid crystal compound. A minimum temperature of the liquid crystal phase is a transition temperature between a solid and the liquid crystal phase (the smectic phase, the nematic phase or the like) in the liquid crystal compound. A maximum temperature of the nematic phase is a transition temperature between the nematic phase and the isotropic phase in the liquid crystal composition, and may be occasionally abbreviated as a maximum temperature. A minimum temperature of the nematic phase may be occasionally abbreviated as a minimum temperature.

A compound represented by formula (1) may be occasionally abbreviated as compound (1). Compound (1) means one compound, a mixture of two compounds or a mixture of three or more compounds represented by formula (1). A same rule also applies to a compound represented by formula (2) or the like. In formula (1), when a is 2, two of Q exists. In the compound, two groups represented by two of Q may be identical or different. A same rule also applies to two of arbitrary Q when a is larger than 2. A same rule also applies to a symbol such as Z and $R^b$. Two of Q exists in formula (1-2). In the compound, two groups represented by two of Q may be identical or different. A same rule also applies to formula (1-3) or the like in which Q exists in the number larger than 2. A same rule also applies to a symbol such as Z and $R^b$.

In formulas (2) to (15), a symbol such as $B^1$, $C^1$ or the like surrounded by a hexagonal shape corresponds to ring $B^1$, ring $C^1$ or the like, respectively. A symbol of terminal group $R^{11}$ is used for a plurality of compounds. In the compounds, two groups represented by two of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule also applies to a symbol of any other terminal group, a ring, a bonding group or the like. In formula (8), when i is 2, two of ring $D^1$ exists. In the compound, two groups represented by two of ring $D^1$ may be identical or different. A same rule also applies to two of arbitrary ring $D^1$ when i is larger than 2. A same rule also applies to a symbol of any other ring, a bonding group or the like.

An expression in the context of "at least one of 'A' may be replaced by 'B'" means that, when the number of 'A' is one, a position of 'A' is arbitrary, and also when the number of 'A' is two or more, positions thereof can be freely selected without restriction. An expression in the context of "at least one of A may be replaced by B, C or D" means inclusion of a case where at least one of A is replaced by B, a case where at least one of A is replaced by C, and a case where at least one of A is replaced by D, and also a case where a plurality of A are replaced by at least two of B, C and D. For example, alkyl in which at least one of —$CH_2$— (or —$CH_2CH_2$—) may be replaced by —O— (or —CH=CH—) includes alkyl, alkenyl, alkoxy, alkoxyalkyl, alkoxyalkenyl and alkenyloxyalkyl. In addition, a case where two of successive —$CH_2$— is replaced by —O— to form —O—O— is not preferred. In alkyl or the like, a case where —$CH_2$— of a methyl moiety (—$CH_2$—H) is replaced by —O— to form —O—H is not preferred, either.

Then, 2-fluoro-1,4-phenylene means two divalent groups described below. In a chemical formula thereof, fluorine may be leftward (L) or may be rightward (R). A same rule also applies to an asymmetrical divalent group derived by eliminating two of hydrogen from a ring, such as tetrahydropyran-2,5-diyl.

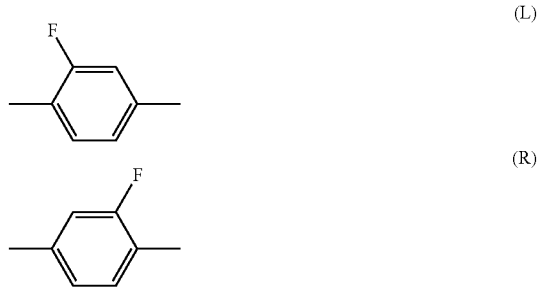

The invention includes items described below.

Item 1. A compound represented by formula (1):

$$M(Z-Q)_a(R^b)_b \qquad (1)$$

wherein, in formula (1), a is 1, 2, 3 or 4, and b is a numerical value: (4−a) obtained by subtracting a from 4;

M is an organic group;

Z is a single bond, —O—, —COO— or —OCO—;

Q is a monovalent group represented by formula (Q-1), (Q-2) or (Q-3), in which $R^a$ is hydrogen, —O., —OH or —$R^1$;

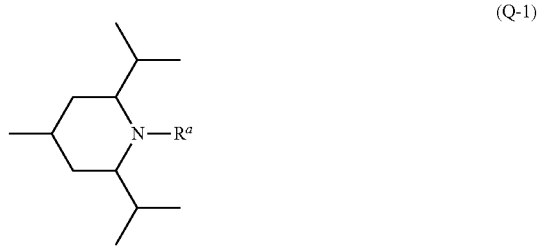

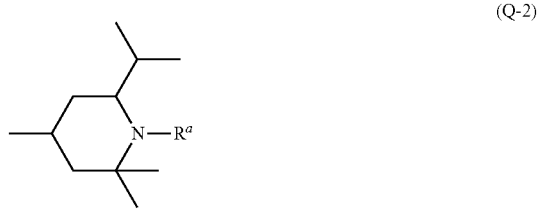

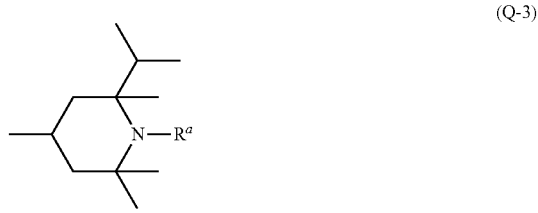

$R^b$ is hydrogen, fluorine or —$R^2$; and $R^1$ and $R^2$ are independently alkyl having 1 to 20 carbons, arylalkyl having 1 to 20 carbons or aryl having 1 to 20 carbons, and in the alkyl, at least one of —CH$_2$— may be replaced by —O—, —CO—, —COO—, —OCO— or —NR$^3$—, and —CH$_3$ located at a terminal may be replaced by —NHR$^3$ or —NR$^4$R$^5$, in which R$^3$, R$^4$ and R$^5$ are independently alkyl having 1 to 10 carbons.

Item 2. The compound according to item 1, represented by any of formulas (1-1) to (1-4):

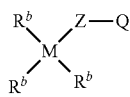
(1-1)

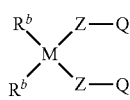
(1-2)

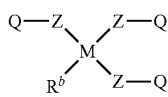
(1-3)

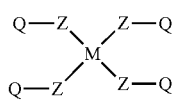
(1-4)

wherein, in formulas (1-1) to (1-4),

M is an aliphatic hydrocarbon group having 1 to 20 carbons or an aromatic hydrocarbon group having 1 to 20 carbons, and in the groups, at least one of —CH$_2$— may be replaced by —O— or —S—, one or two of —CH=CH— may be replaced by —CH=N—, and at least one of hydrogen may be replaced by fluorine or chlorine;

Z is a single bond, —O—, —COO— or —OCO—;

Q is a monovalent group represented by formula (Q-1), (Q-2) or (Q-3), in which $R^a$ is hydrogen, —O., —OH or —R$^1$;

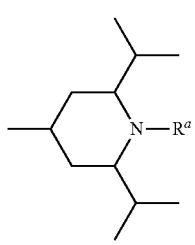
(Q-1)

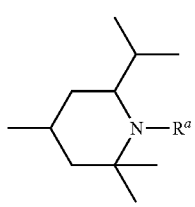
(Q-2)

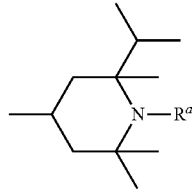
(Q-3)

$R^b$ is hydrogen, fluorine or —$R^2$;

$R^1$ and $R^2$ are independently alkyl having 1 to 20 carbons, arylalkyl having 1 to 20 carbons or aryl having 1 to 20 carbons, and in the alkyl, at least one of —CH$_2$— may be replaced by —O—, —CO—, —COO— or —OCO—, and —CH$_3$ located at a terminal may be replaced by —NHR$^3$ or —NR$^4$R$^5$, in which R$^3$, R$^4$ and R$^5$ are independently alkyl having 1 to 10 carbons.

Item 3. The compound according to item 1 or 2, represented by any of formulas (1-1a) to (1-4a):

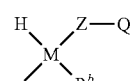
(1-1a)

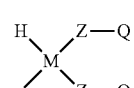
(1-2a)

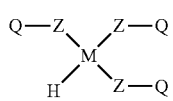
(1-3a)

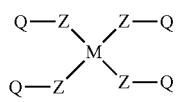
(1-4a)

wherein, in formulas (1-1a) to (1-4a),

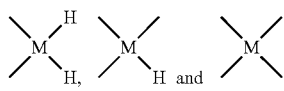

are a divalent group, a trivalent group or a tetravalent group derived by eliminating hydrogen from alkane having 1 to 15 carbons, alkane having 1 to 15 carbons in which at least one of —CH$_2$— is replaced by —O—, cyclohexane, bicyclohexane, decahydronaphthalene, tetrahydropyran, dioxane, benzene, benzene in which at least one of hydrogen is replaced by fluorine, biphenyl, naphthalene, pyridine or pyrimidine;

Z is a single bond, —O—, —COO— or —OCO—;

Q is a monovalent group represented by formula (Q-1), (Q-2) or (Q-3), in which $R^a$ is hydrogen, —O., —OH or —R$^1$;

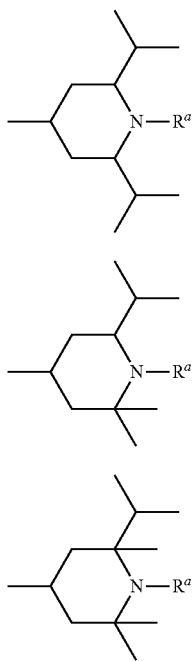
(Q-1)

(Q-2)

(Q-3)

$R^b$ is hydrogen, fluorine or —$R^2$; and $R^1$ and $R^2$ are independently alkyl having 1 to 20 carbons, arylalkyl having 1 to 20 carbons or aryl having 1 to 20 carbons, and in the alkyl, at least one of —$CH_2$— may be replaced by —O—, and —$CH_3$ located at a terminal may be replaced by —$NHR^3$ or —$NR^4R^5$, in which $R^3$, $R^4$ and $R^5$ are independently alkyl having 1 to 10 carbons.

Item 4. The compound according to item 3, wherein, in formulas (1-1a) to (1-4a) according to item 3,

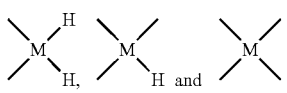

are each any of a divalent group represented by formulas (M-1) to (M-7), a trivalent group represented by formulas (M-8) to (M-23) and a tetravalent group represented by formulas (M-24) to (M-42):

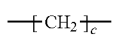
(M-1)

(M-2)

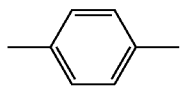
(M-3)

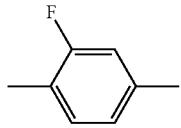
(M-4)

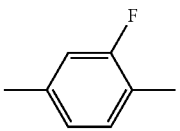
(M-5)

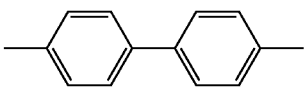
(M-6)

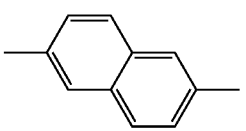
(M-7)

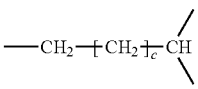
(M-8)

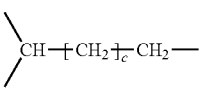
(M-9)

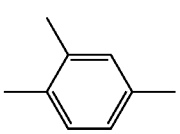
(M-10)

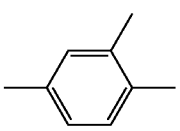
(M-11)

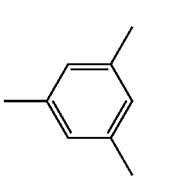
(M-12)

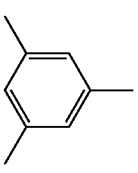
(M-13)

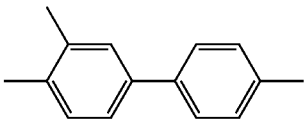
(M-14)

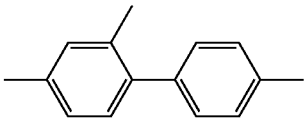
(M-15)

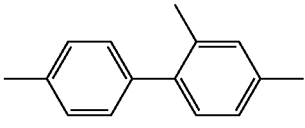
(M-16)

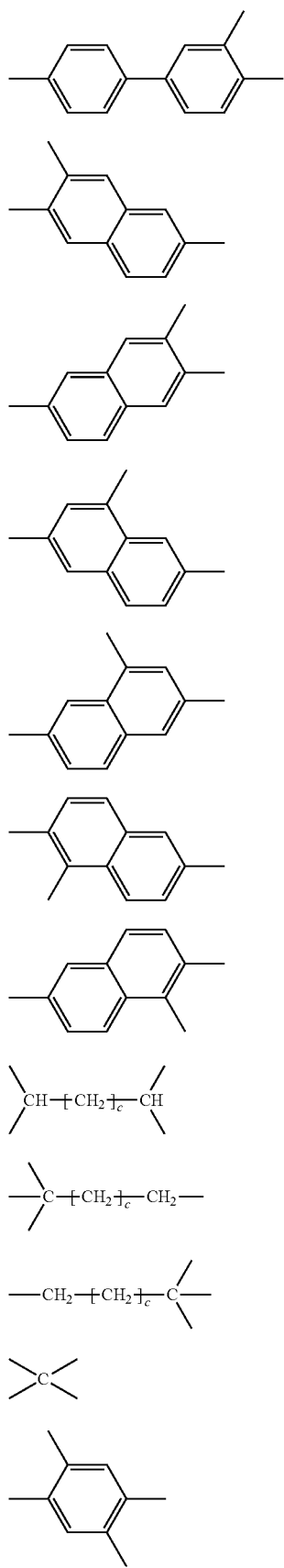
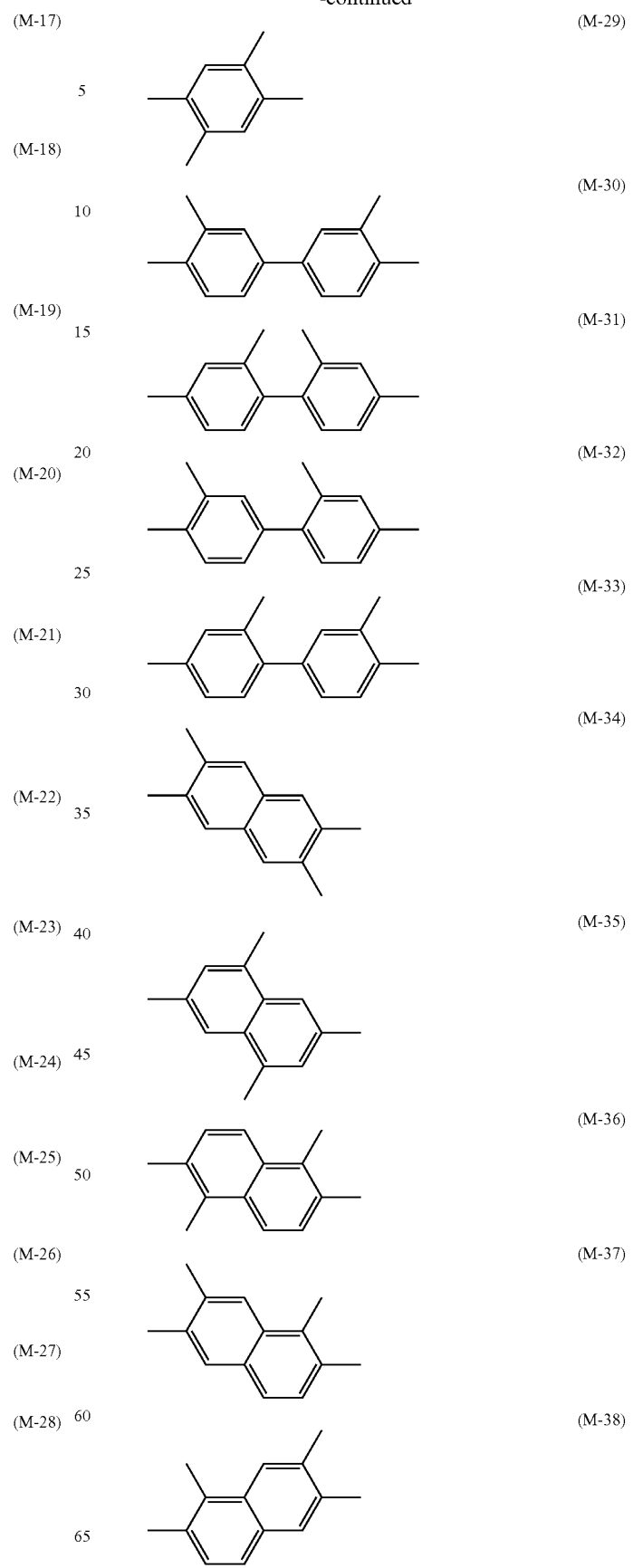

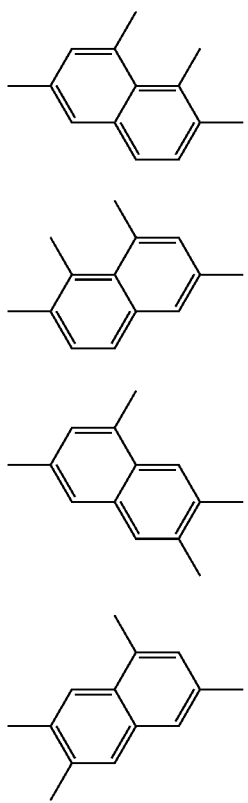
wherein, in the formula described above, c is an integer from 0 to 16.
Item 5. The compound according to item 1, 2 or 3, represented by any of formulas (1a) to (1s):
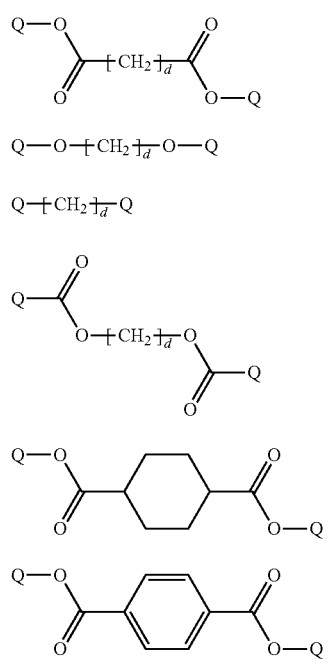
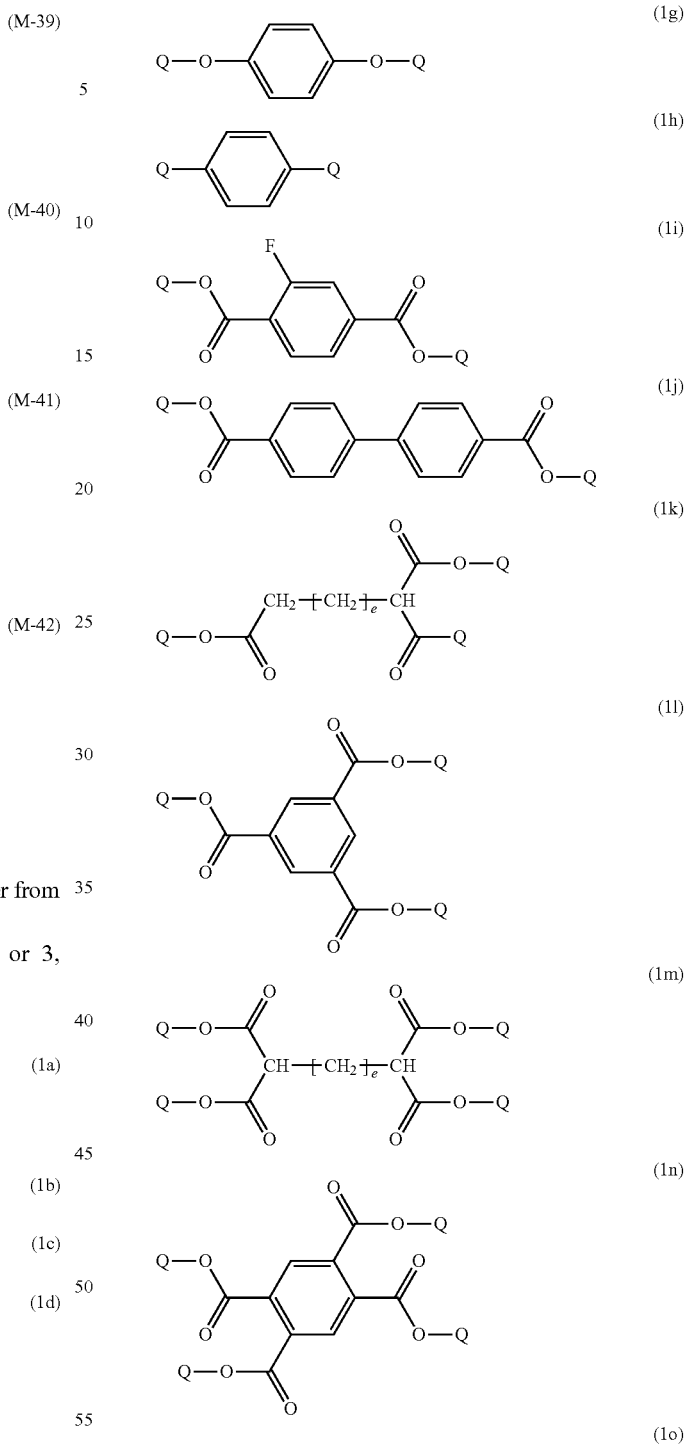
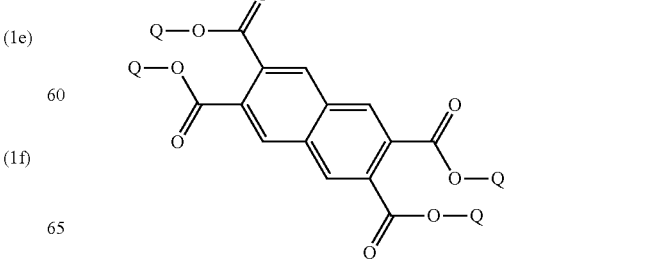

-continued

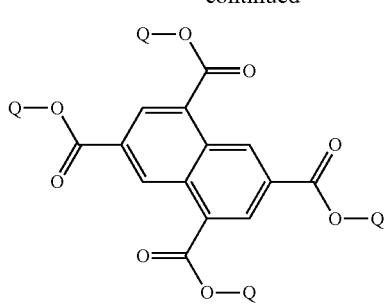
(1p)

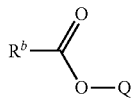
(1q)

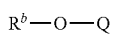
(1r)

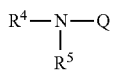
(1s)

wherein, in the formula described above,
d is an integer from 1 to 14;
e is an integer from 0 to 13;
Q is a monovalent group represented by formula (Q-1), (Q-2) or (Q-3), in which $R^a$ is hydrogen, —O., —OH or —$R^1$;

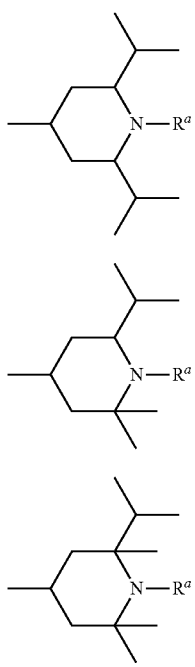
(Q-1)

(Q-2)

(Q-3)

$R^b$ is hydrogen or —$R^2$;
$R^1$ and $R^2$ are independently alkyl having 1 to 20 carbons, arylalkyl having 1 to 20 carbons or aryl having 1 to 20 carbons, and in the alkyl, at least one of —$CH_2$— may be replaced by —O—; and $R^4$ and $R^5$ are independently alkyl having 1 to 10 carbons.

Item 6. The compound according to item 5, wherein, in formulas (1a) to (1s) according to item 5, $R^a$ in formulas (Q-1) to (Q-3) is hydrogen, —O., —OH, alkyl having 1 to 10 carbons or alkoxy having 1 to 10 carbons.

Item 7. The compound according to item 1, 2, 3 or 5, represented by any of formulas (1a-1), (1f), (1h) and (1n):

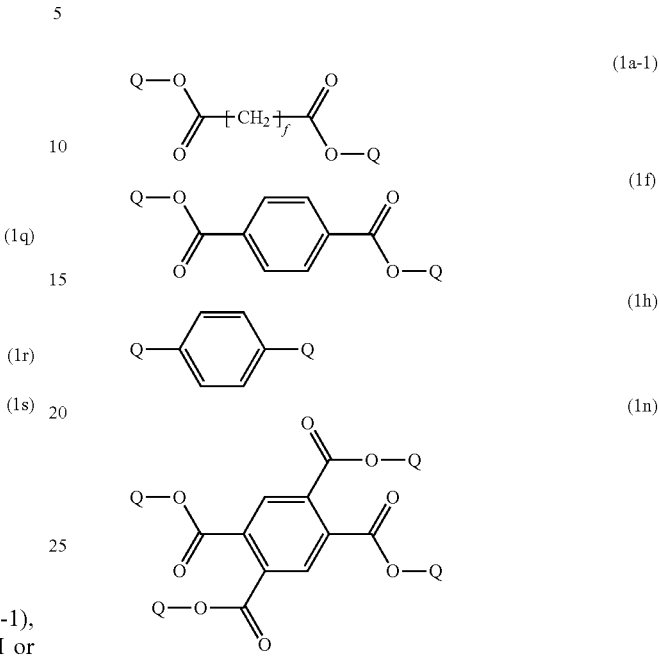

wherein, in formulas (1a-1), (1f-1), (1h) and (1n),
f is an integer from 1 to 12; and
Q is a monovalent group represented by any of formula (Q-1), (Q-2) or (Q-3), in which $R^a$ is hydrogen or alkyl having 1 to 15 carbons:

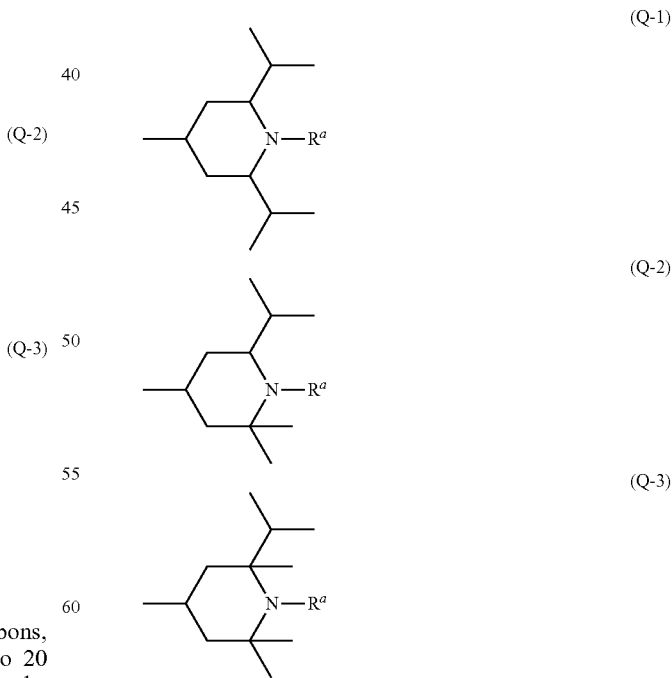

Item 8. The compound according to item 1, 2, 3, 5 or 7, represented by any of formulas (1a-1-1) to (1a-1-6), formulas (1f-1-1) to (1f-1-6) and formulas (1n-1-1) to (1n-1-3):

(1a-1-1)
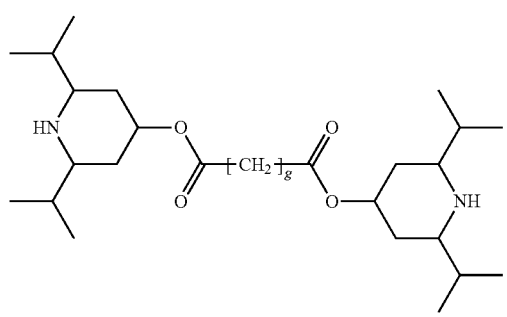
(1a-1-2)
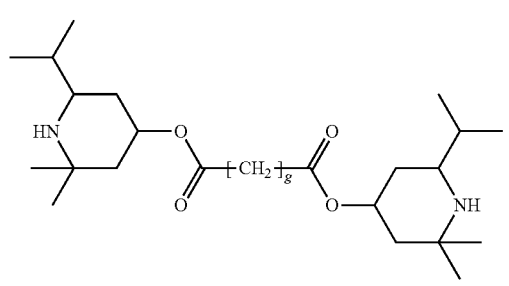
(1a-1-3)
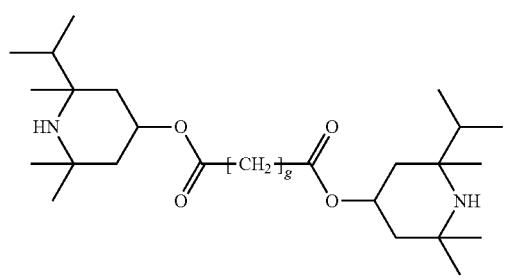
(1a-1-4)
(1a-1-5)
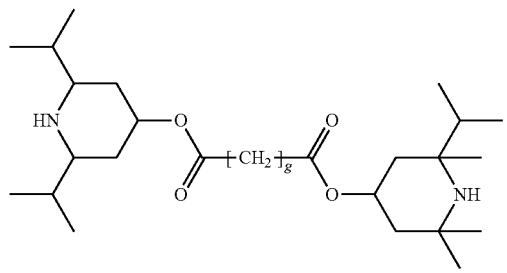
-continued
(1a-1-6)
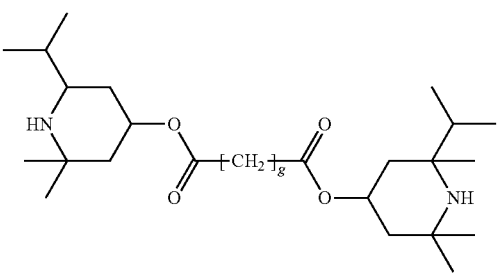
(1f-1-1)
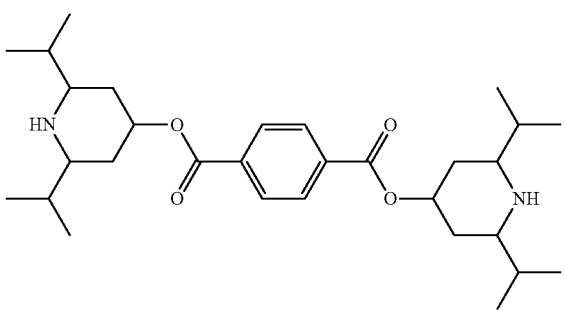
(1f-1-2)
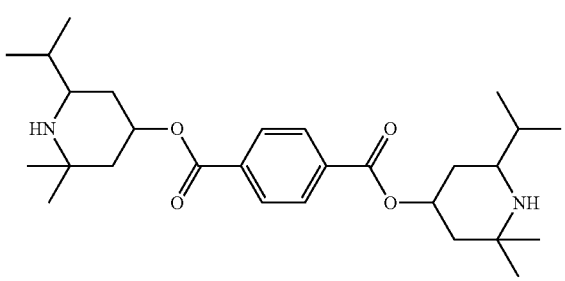
(1f-1-3)
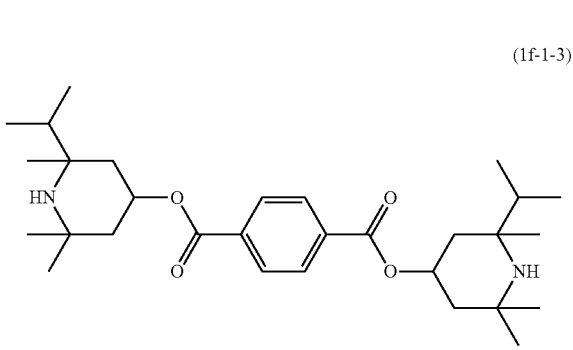
(1f-1-4)
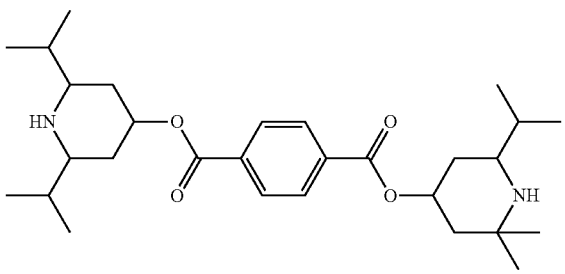

(1f-1-5)
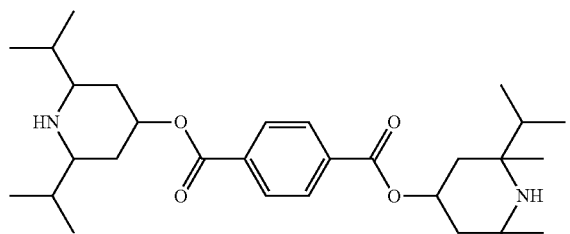

(1f-1-6)

(1n-1-1)
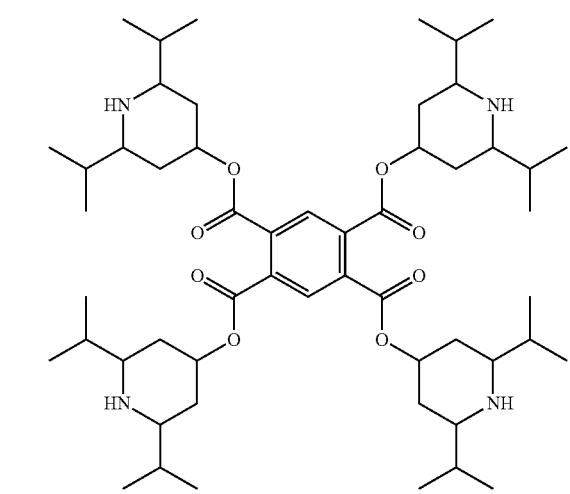

(1n-1-2)
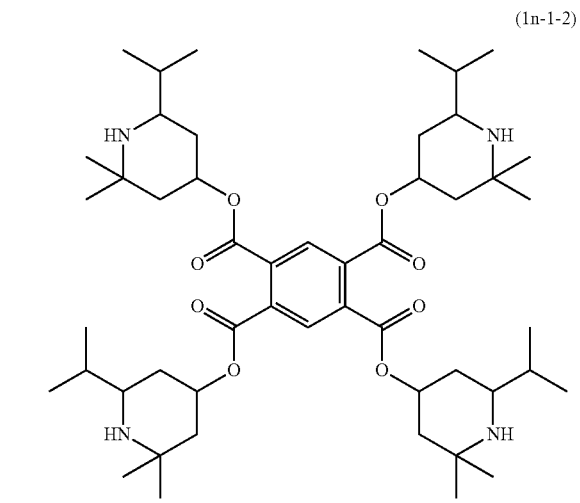

(1n-1-3)
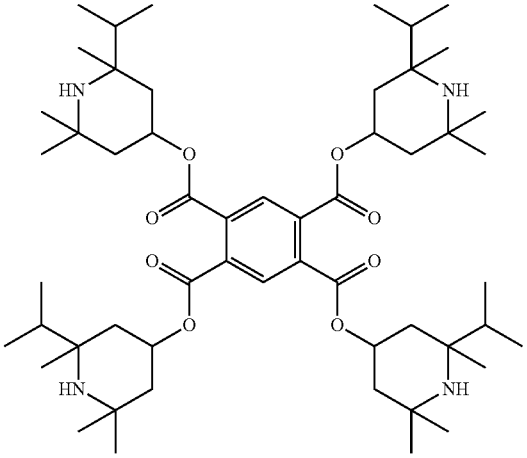

wherein, in formulas (1a-1-1) to (1a-1-6), g is an integer from 1 to 10.

Item 9. A liquid crystal composition, containing at least one compound according to any one of items 1 to 8.

Item 10. The liquid crystal composition according to item 9, further containing at least one compound selected from the group of compounds represented by formulas (2) to (4):

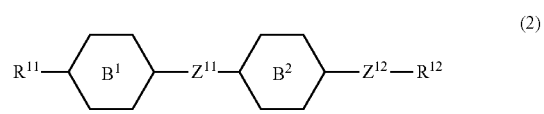
(2)

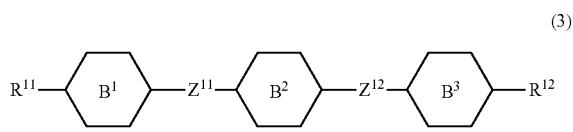
(3)

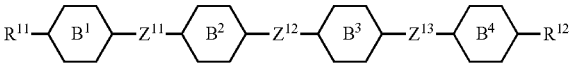
(4)

wherein, in formulas (2) to (4), $R^{11}$ and $R^{12}$ are independently alkyl having 1 to 10 carbons or alkenyl having 2 to 10 carbons, and in the alkyl or the alkenyl, at least one of —$CH_2$— may be replaced by —O—, and at least one of hydrogen may be replaced by fluorine;

ring $B^1$, $B^2$, $B^3$ and $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —$CH_2CH_2$—, —CH=CH—, —C≡C— or —COO—.

Item 11. The liquid crystal composition according to item 9 or 10, further containing at least one compound selected from the group of compounds represented by formulas (5) to (7):

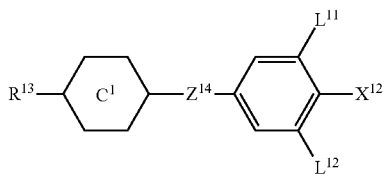
(5)

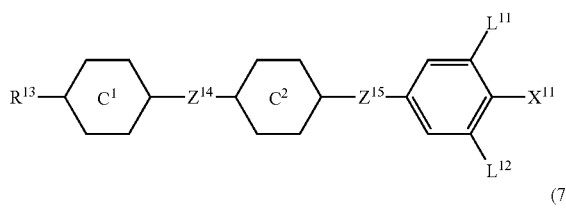
(6)

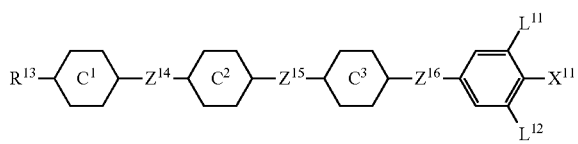
(7)

wherein, in formulas (5) to (7), $R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, $C^2$ and $C^3$ are independently 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 12. The liquid crystal composition according to item 9 or 10, further containing at least one compound selected from the group of compounds represented by formula (8):

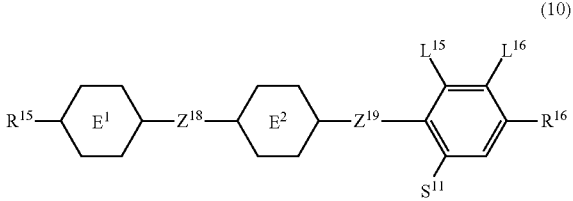
(8)

wherein, in formula (8), $R^{14}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$X^{12}$ is —C≡N or —C≡C—C≡N;

ring $D^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{17}$ is a single bond, —$CH_2CH_2$—, —C≡C—, —COO—, —$CF_2O$—, —$OCF_2$— or —$CH_2O$—;

$L^{13}$ and $L^{14}$ are independently hydrogen or fluorine; and i is 1, 2, 3 or 4.

Item 13. The liquid crystal composition according to item 9 or 10, further containing at least one compound selected from the group of compounds represented by formulas (9) to (15):

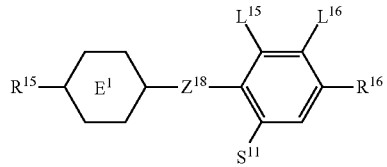
(9)

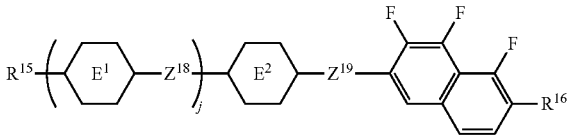
(10)

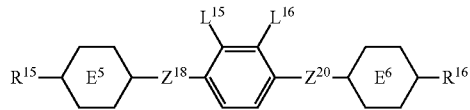
(11)

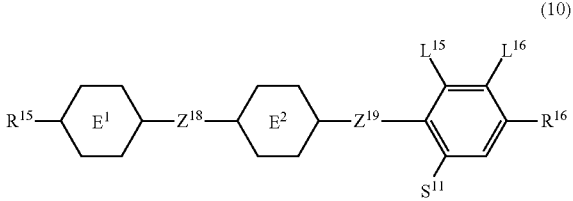
(12)

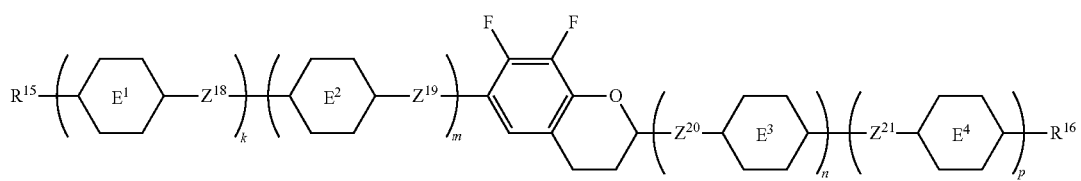
(13)

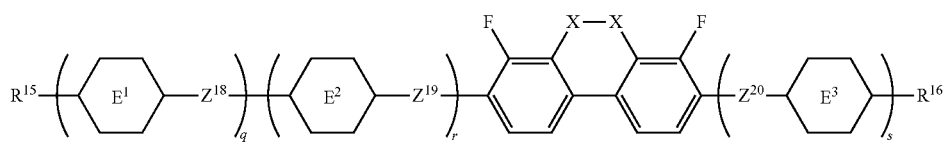
(14)

-continued

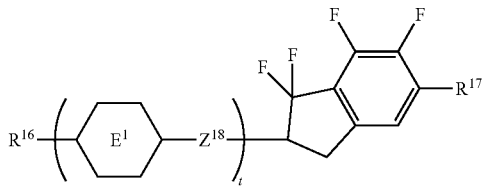

(15)

wherein, in formulas (9) to (15), $R^{15}$ and $R^{16}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

$R^{17}$ is hydrogen, fluorine, alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

rings $E^1$, $E^2$, $E^3$ and $E^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

rings $E^5$ and $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 14. The liquid crystal composition according to any one of items 9 to 13, further containing at least one of a polymerizable compound, a polymerization initiator, a polymerization inhibitor, an optically active compound, an antioxidant, an ultraviolet light absorber, a light stabilizer, a heat stabilizer and an antifoaming agent.

Item 15. A liquid crystal display device, including at least one liquid crystal composition according to any one of items 9 to 14.

The invention further includes the following items: (a) the liquid crystal composition, further containing at least two of additives such as a polymerizable compound, a polymerization initiator, a polymerization inhibitor, an optically active compound, an antioxidant, an ultraviolet light absorber, a light stabilizer or a heat stabilizer different from compound (1), and an antifoaming agent; (b) a polymerizable composition, prepared by adding the polymerizable compound to the liquid crystal composition; (c) a liquid crystal composite, prepared by polymerizing the polymerizable composition; (d) a liquid crystal display device, including the liquid crystal composite and having the polymer sustained alignment (PSA) mode; (e) use of compound (1) as a light stabilizer; (f) use of compound (1) as a heat stabilizer; (g) use in combination of a light stabilizer different from compound (1) with compound (1); and (h) use as an optically active composition by adding the optically active compound to the liquid crystal composition.

An aspect of compound (1), synthesis of compound (1), the liquid crystal composition and the liquid crystal display device will be described in the order.

1. Aspect of Compound (1)

Compound (1) of the invention has an isopropylpiperidine ring, and therefore is useful as a hindered amine light stabilizer. The compound has a feature of having a piperidine ring in which replacement is made by two isopropyl groups (or one of isopropyl and a plurality of methyl groups) in 2-position and 6-position. An amino group (NH) located between the groups is subjected to steric hindrance, and therefore reactivity is controlled. Accordingly, compound (1) is suitable for trapping a decomposition product formed by a photoreaction of a liquid crystal compound. The compound can be added to the liquid crystal composition. The reason is that the compound has a high solubility in the liquid crystal composition. The liquid crystal composition is a mixture of the liquid crystal compounds. Compound (1) is effective in preventing the liquid crystal compound from being decomposed by light from backlight or the sun. Compound (1) seems to be also effective as the heat stabilizer.

When the liquid crystal display device is used for a long period of time, the liquid crystal compound therein tends to be decomposed by light to produce a decomposition product. The product is an impurity, and thus is unfavorable for the device. The reason is that the impurity causes a phenomenon such as reduction of a contrast ratio, occurrence of display unevenness and image persistence. The phenomenon can be easily identified by visual observation, and also is significantly conspicuous even if a degree thereof is only a little. Accordingly, the light stabilizer that generates the impurity in an amount smaller even by 1% in comparison with a conventional light stabilizer is preferred. Compound (1) is such a light stabilizer.

Preferred examples of compound (1) are described. Preferred examples of organic group M, bonding group Z, monovalent group Q and $R^b$ in compound (1) are also applied to a subordinate formula of formula (1) for compound (1). In compound (1), characteristics can be arbitrarily adjusted by suitably combining kinds of the groups. Compound (1) may contain an isotope such as $^2H$ (deuterium) and $^{13}C$ in an amount larger than an amount of natural abundance because no significant difference exists in the characteristics of the compound.

$$M(Z-Q)_a(R^b)_b \qquad (1)$$

In formula (1), a is 1, 2, 3 or 4, and b is a numerical value: (4−a) obtained by subtracting a from 4. Subordinate formulas of the formula for the compound are represented by formulas (1-1) to (1-4) described in item 2.

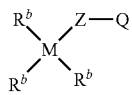 (1-1)

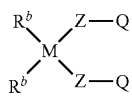 (1-2)

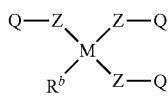 (1-3)

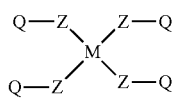 (1-4)

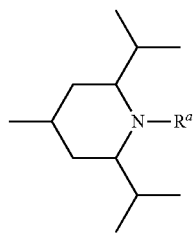 (Q-1)

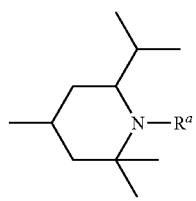 (Q-2)

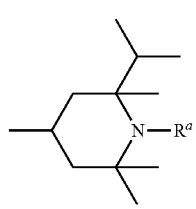 (Q-3)

In formula (1-1), three $R^b$ groups are bonded with M. Here, two groups represented by two of arbitrary $R^b$ may be identical or different. A same rule also applies to a symbol such as $R^a$, $R^b$, Z, Q and ring $B^1$ in any other formula.

From a viewpoint of the high solubility in the liquid crystal composition, compound (1-1) is preferred. From a viewpoint of ease of synthesis, compounds (1-1) and (1-2) are preferred. From a viewpoint of low volatility, compounds (1-1), (1-2) and (1-3) are preferred. From a viewpoint of an effect per unit weight, compounds (1-3) and (1-4) are preferred, and compound (1-4) is further preferred. From a viewpoint of a balance of physical properties, compounds (1-2) and (1-3) are preferred.

In formula (1), M is an organic group. A preferred organic group is an aliphatic hydrocarbon group having 1 to 20 carbons or an aromatic hydrocarbon group having 1 to 20 carbons, and in the groups, at least one of —CH$_2$— may be replaced by —O— or —S—, one or two of —CH=CH— may be replaced by —CH=N—, and at least one of hydrogen may be replaced by fluorine or chlorine. Preferred M is a tetravalent group derived by eliminating four of hydrogen from alkane (1 to 15 carbons), alkane (1 to 15 carbons) in which at least one of —CH$_2$— is replaced by —O—, cyclohexane, bicyclohexane, decahydronaphthalene, tetrahydropyran, dioxane, benzene, benzene in which at least one of hydrogen is replaced by fluorine, biphenyl, naphthalene, pyridine or pyrimidine. Further preferred M is groups (M-1) to (M-42) described in item 4. In divalent group (M-1), when c is 0, the group means a single bond.

In formula (1), Z is a single bond, —O—, —COO— or —OCO—. Preferred Z is a single bond, —O—, —COO— or —OCO—. Further preferred Z is —O—, —COO— or —OCO—. Most preferred Z is —COO— or —OCO—.

In formula (1), Q is a monovalent group represented by formula (Q-1), (Q-2) or (Q-3). Q is such a 4-piperidyl group having substituents in 2-, and 6-positions. From a viewpoint of ease of synthesis, a group represented by formula (Q-1) is preferred. From a viewpoint of an effect, groups represented by formulas (Q-2) and (Q-3) are preferred.

In formula (Q-1), (Q-2) or (Q-3), $R^a$ is hydrogen, —O. (oxygen radial), —OH or —R$^1$. Preferred $R^a$ is hydrogen, —O., —OH or —R$^1$. Further preferred $R^a$ is hydrogen, —O. or —R$^1$. Most preferred $R^a$ is hydrogen or —R$^1$.

In formula (1), $R^b$ is hydrogen, fluorine or —R$^2$. $R^1$ and $R^2$ are alkyl having 1 to 20 carbons, arylalkyl having 1 to 20 carbons or aryl having 1 to 20 carbons, and in the alkyl, at least one of —CH$_2$— may be replaced by —O—, —CO—, —COO—, —OCO— or —NHR$^3$—, and —CH$_3$ located at a terminal may be replaced by —NHR$^3$ or —NR$^4$R$^5$, in which $R^3$, $R^4$ and $R^5$ are alkyl having 1 to 10 carbons. Alkyl may be straight-chain alkyl, branched-chain alkyl or cyclic alkyl. Preferred alkyl is straight-chain alkyl.

Preferred $R^b$ is hydrogen or —R$^2$. Most preferred $R^b$ is hydrogen.

Preferred $R^1$ and $R^2$ are alkyl having 1 to 15 carbons, and in the alkyl, at least one of —CH$_2$— may be replaced by —O—, —CO—, —COO—, —OCO— or —NHR$^3$—, and —CH$_3$ located at a terminal may be replaced by —NHR$^3$ or —NR$^4$R$^5$. Further preferred $R^1$ and $R^2$ are alkyl, alkoxyalkyl, acyloxyalkyl, alkoxycarbonylalkyl, alkylaminoalkyl, dialkylaminoalkyl, alkoxy, alkoxyalkoxy, acyloxy, alkoxycarbonyl, alkylamino or dialkylamino. Particularly preferred $R^1$ and $R^2$ are alkyl, alkoxyalkyl, acyloxyalkyl, alkoxycarbonylalkyl or alkoxy. Most preferred $R^1$ and $R^2$ are alkyl.

Preferred $R^1$ and $R^2$ are also arylalkyl having 1 to 15 carbons, and in the alkyl, at least one of —CH$_2$— may be replaced by —O—, —CO—, —OCO—, —COO— or —NHR$^3$—. Further preferred $R^1$ and $R^2$ are also benzyl, styryl, cinnamyl, 3-phenylpropyl, cumyl or trityl. Most preferred $R^1$ and $R^2$ are also benzyl.

Preferred $R^1$ and $R^2$ are also aryl having 1 to 15 carbons. Further preferred $R^1$ and $R^2$ are also phenyl, tolyl, xylyl, cumenyl, mesityl, 1-naphthyl or 2-naphthyl. Most preferred $R^1$ and $R^2$ are also phenyl.

With referring to the preferred examples described above, compound (1) having objective characteristics can be obtained by suitably selecting a combination of organic group M, bonding group Z, monovalent group Q and $R^b$. Preferred examples of compound (1) include the compound described in item 5. Further specific examples are described in items 6 to 8.

2. Synthesis of Compound (1)

A method for preparing compound (1) is described. Compound (1) can be prepared by suitably combining methods in synthetic organic chemistry. A method for introducing objective organic group M, bonding group Z, monovalent group Q and monovalent group $R^b$ into a starting material is described in books such as Houben-Wyle, Methoden der Organische Chemie (Georg-Thieme Verlag, Stuttgart), Organic Syntheses (John Wily & Sons, Inc.), Organic Reactions (John Wily & Sons, Inc.), Comprehensive Organic Synthesis (Pergamon Press), New Experimental Chemistry Course (Shin Jikken Kagaku Koza in Japanese) (Maruzen Co., Ltd.) or the like.

2-1. Synthesis of Monovalent Group Q

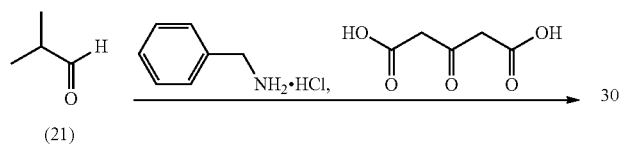

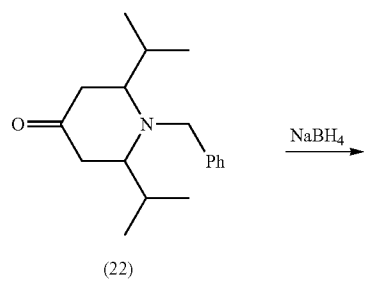

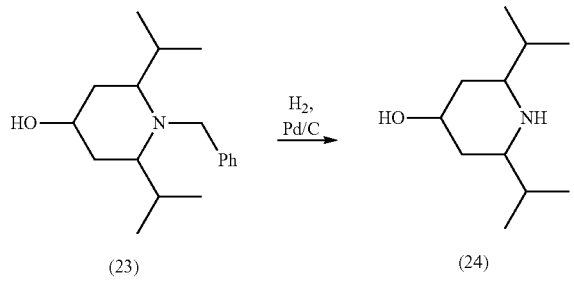

A structural unit of 2,6-diisopropylpiperidine is prepared as described below. Piperidinone form (22) is obtained by allowing benzylamine hydrochloride and acetonedicarboxylic acid to react with isobutyraldehyde (21). Subsequently, piperidinol form (23) is obtained by reducing the resulting piperidinone form (22) with sodium borohydride. Piperidinol form (24) is obtained by performing catalytic hydrogen reduction of the resulting piperidinol form (23) in the presence of palladium on carbon. The compound described above is converted into compound (1) by a technique in the synthetic organic chemistry.

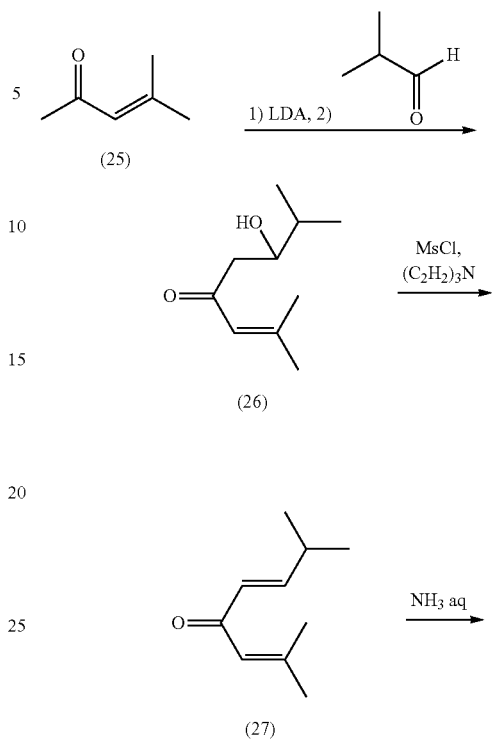

A unit structure of 6-isopropyl-2,2-dimethylpiperidine is prepared as described below. Enone form (26) is obtained by treating mesityl oxide (25) with lithium diisopropylamide (LDA), and then allowing the resulting product to react with isobutyraldehyde. Dienone form (27) is obtained by allowing the resulting enone form (26) to react with methanesulfonyl chloride in the presence of triethylamine. Subsequently, piperidinone form (28) is obtained by allowing the resulting dienone form (27) to react with an aqueous ammonia solution. Piperidinol form (29) is obtained by reducing the resulting piperidinone form (28) with sodium borohydride. The compound described above is converted into compound (1) by a technique in the synthetic organic chemistry.

2-2. Synthesis Examples

As an example of a method for preparing compound (1), methods for preparing compounds (1A), (1B), (1C), (1D), (1E), (1F), (1G) and (1H) are shown. A meaning of a symbol of $R^a$ in each compound is identical with a meaning of a symbol described in item 1.

(1) Compound (1A)

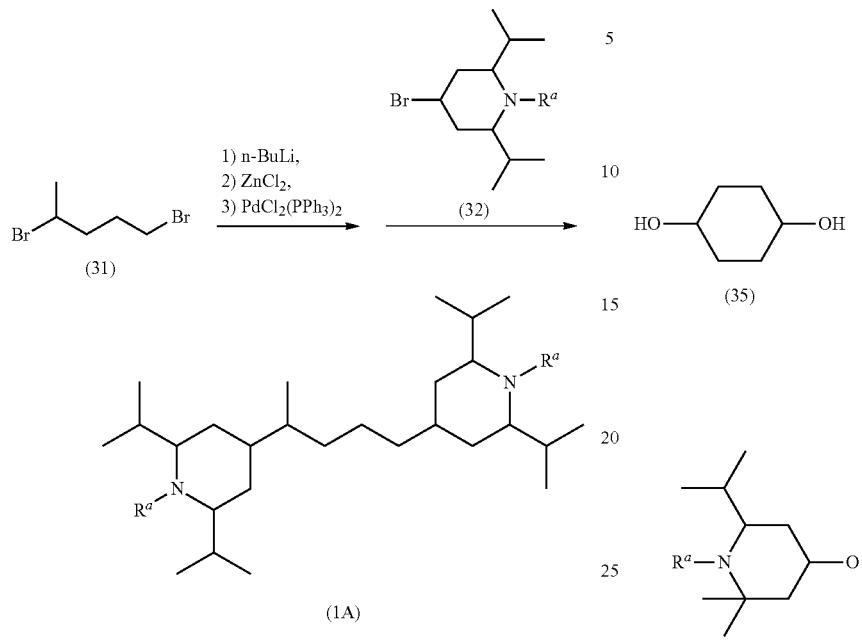

Then, 1,4-dibromopentane (31) is allowed to react with n-butyllithium, and then zinc chloride. Compound (1A) is prepared by allowing bromo form (32) to react with an intermediate thereof in the presence of a dichlorobis(triphenylphosphine) palladium catalyst.

(2) Compound (1B)

Then, 1,4-dibromobenzene (33) is allowed to react with n-butyllithium, and then zinc chloride. Compound (1B) is prepared by allowing bromo form (34) to react with an intermediate thereof in the presence of a dichlorobis(triphenylphosphine)palladium catalyst.

(3) Compound (1C)

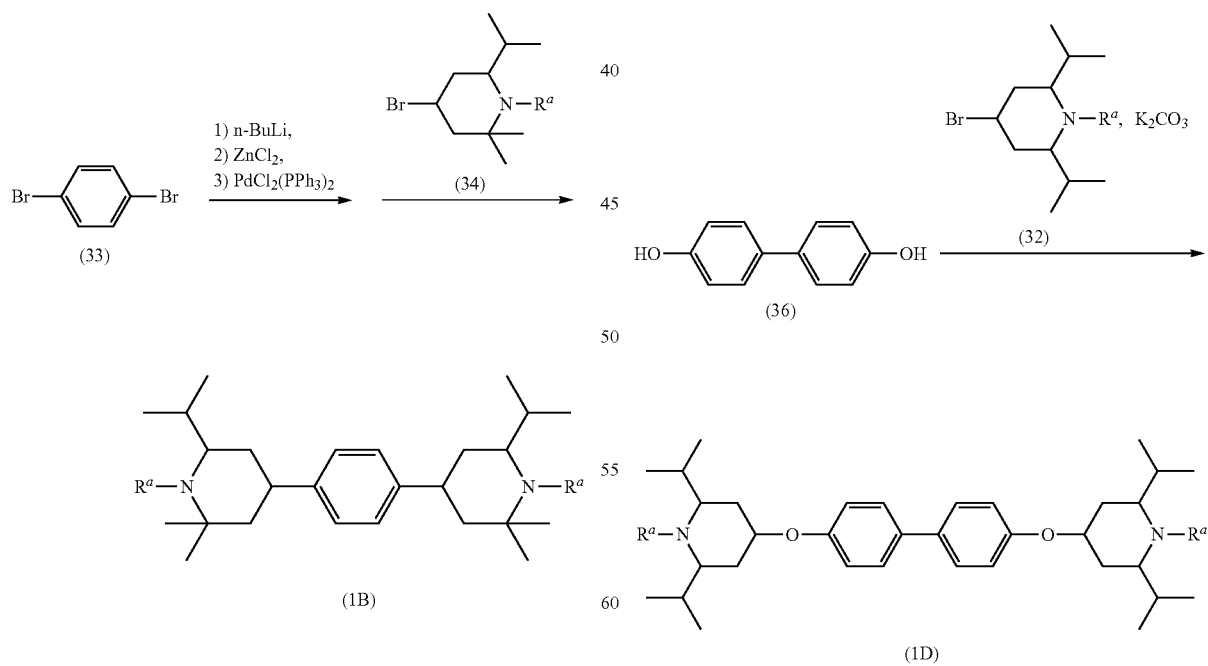

Compound (1C) is prepared by allowing 1,4-cyclohexanediol (35) to react with bromo form (34) in the presence of sodium hydride.

(4) Compound (1D)

Compound (1D) is prepared by allowing 4,4'-biphenol (36) to react with bromo form (32) in the presence of potassium carbonate.

(5) Compound (1E)

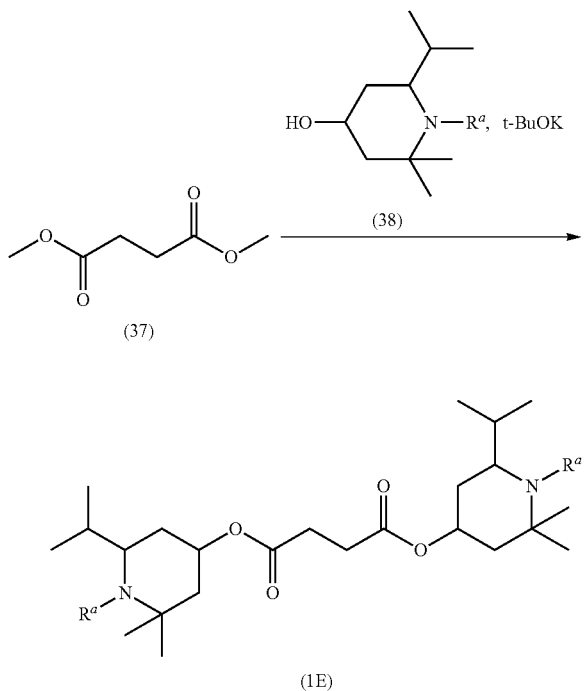

(1E)

Compound (1E) is prepared by allowing dimethyl succinate (37) to react with piperidinol form (38) and potassium t-butoxide.

(6) Compound (1F)

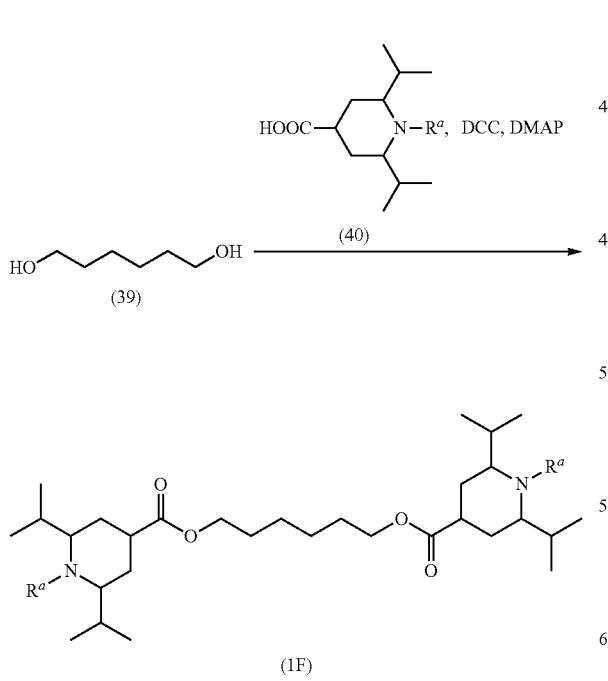

(1F)

Compound (1F) is prepared by dehydrating 1,6-hexanediol (39) and carboxylic acid (40) in the presence of 1,3-dicyclohexylcarbodiimide (DCC) and 4-dimethylaminopyridine (DMAP).

(7) Compound (1G)

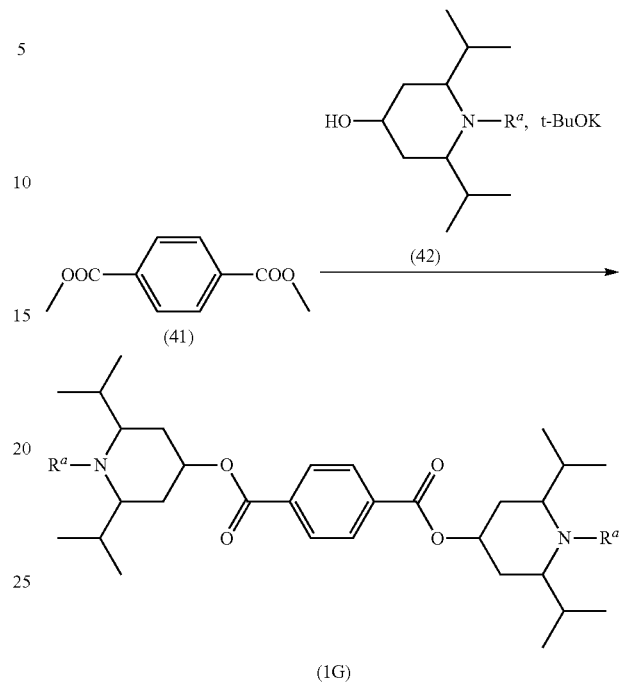

(1G)

Compound (1G) is prepared by allowing dimethyl terephthalate (41) to react with piperidinol form (42) in the presence of potassium t-butoxide.

(8) Compound (1H)

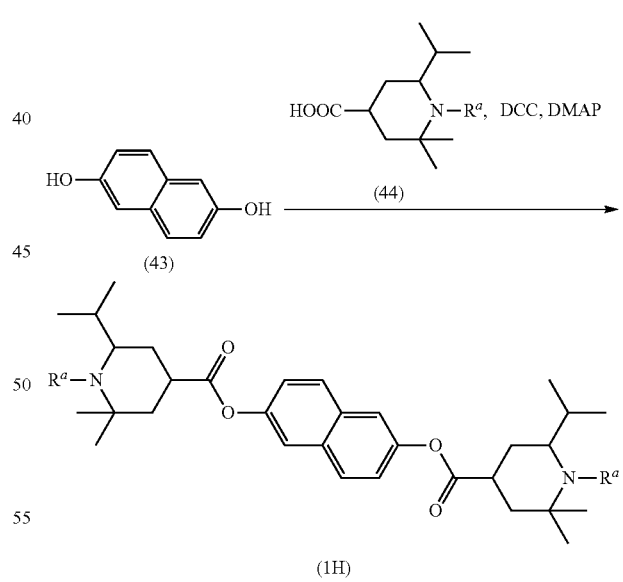

(1H)

Compound (1H) is prepared by dehydrating 2,6-naphthalenediol (43) and carboxylic acid (44) in the presence of 1,3-dicyclohexylcarbodiimide (DCC) and 4-dimethylaminopyridine (DMAP).

3. Liquid Crystal Composition

A liquid crystal composition of the invention contains compound (1) as component A. Compound (1) is suitable for preventing the liquid crystal composition from being decomposed by light and heat. The composition contains compound (1) as component A, and preferably further contains a liquid crystal compound selected from components B, C, D and E shown below. Component B includes compounds (2) to (4). Component C includes compounds (5) to (7). Component D includes compound (8). Component E includes compounds (9) to (15). The composition may contain other liquid crystal compounds different from compounds (2) to (15). Upon preparing the composition, components B, C, D and E are preferably selected in taking positive or negative dielectric anisotropy, magnitude of dielectric anisotropy, or the like into consideration. A composition in which the component is suitably selected has a high maximum temperature, a low minimum temperature, a small viscosity, a suitable optical anisotropy (more specifically, large optical anisotropy or small optical anisotropy), a large positive or negative dielectric anisotropy and a suitable elastic constant (more specifically, large elastic constant or small elastic constant).

A preferred ratio of compound (1) is in the range of approximately 0.01% by weight or more based on a weight of the liquid crystal composition in order to maintain a high stability to ultraviolet light, and in the range of approximately 5% by weight or less in order to dissolve compound (1) into the liquid crystal composition. A further preferred ratio is in the range of approximately 0.05% by weight to approximately 2% by weight. A most preferred ratio is in the range of approximately 0.05% by weight to approximately 1% by weight.

Component B is a compound in which two terminal groups are alkyl or the like. Specific preferred examples of component B include compounds (2-1) to (2-11), compounds (3-1) to (3-19) and compounds (4-1) to (4-7). In the compound of component B, $R^{11}$ and $R^{12}$ are independently alkyl having 1 to 10 carbons or alkenyl having 2 to 10 carbons, and in the alkyl or the alkenyl, at least one of —$CH_2$— may be replaced by —O— and at least one of hydrogen may be replaced by fluorine.

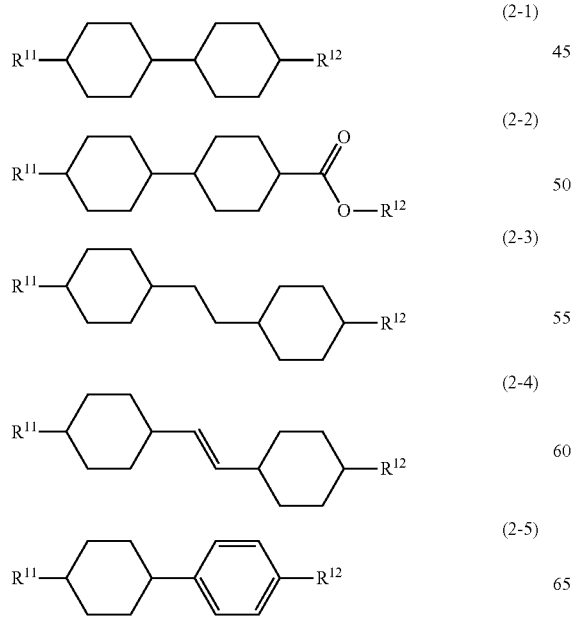

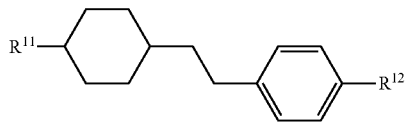

(2-6)

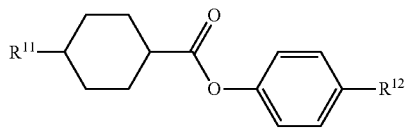

(2-7)

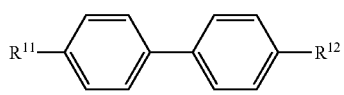

(2-8)

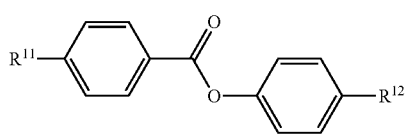

(2-9)

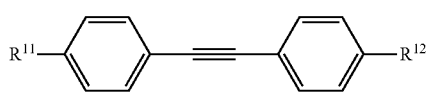

(2-10)

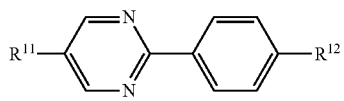

(2-11)

(3-1)

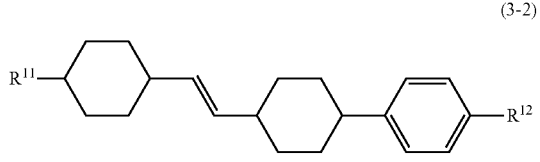

(3-2)

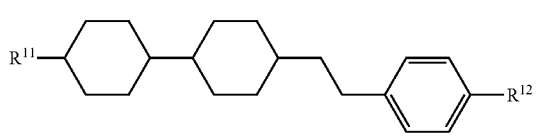

(3-3)

(3-4)

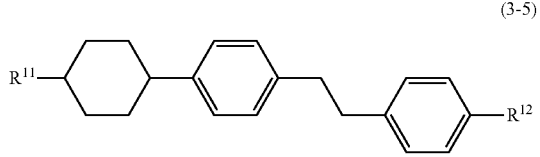

(3-5)

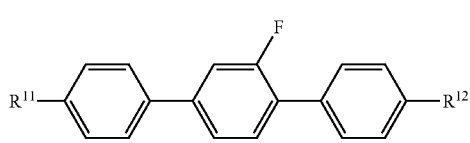

(3-6)

(3-7) 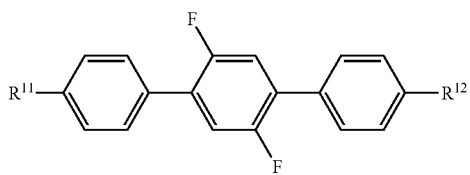

(3-8) 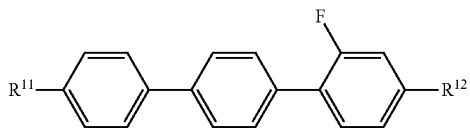

(3-9) 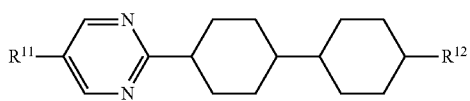

(3-10) 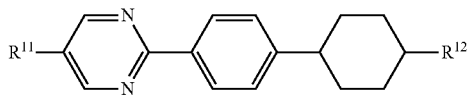

(3-11) 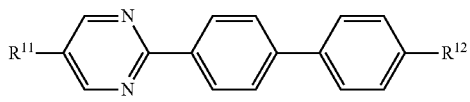

(3-12) 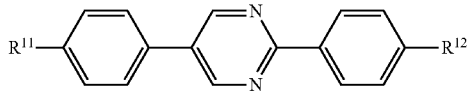

(3-13) 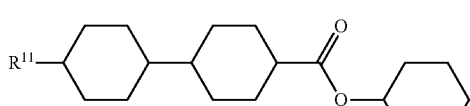

(3-14) 

(3-15) 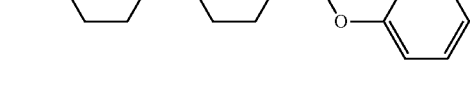

(3-16) 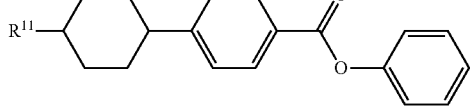

(3-17) 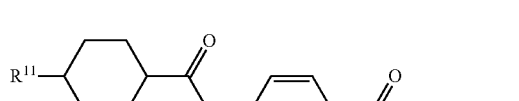

(3-18) 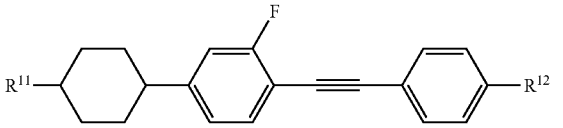

(3-19) 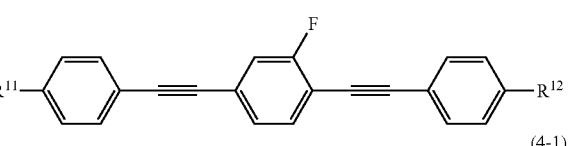

(4-1) 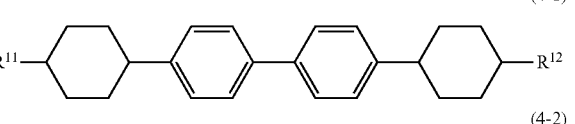

(4-2) 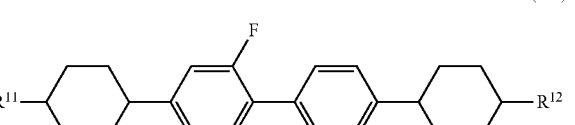

(4-3) 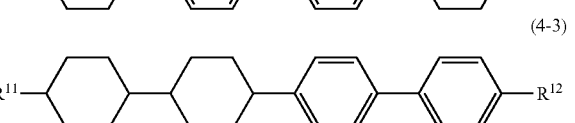

(4-4) 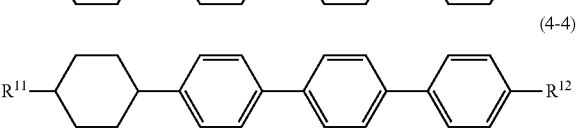

(4-5) 

(4-6) 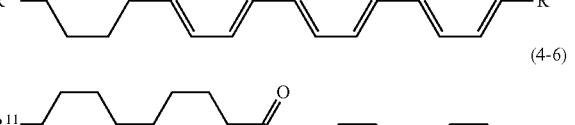

(4-7) 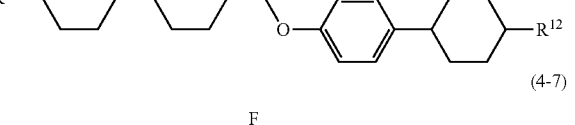

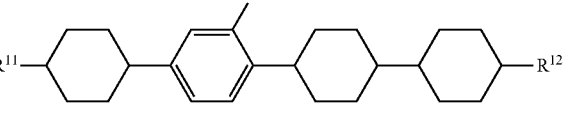

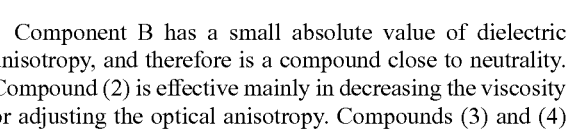

Component B has a small absolute value of dielectric anisotropy, and therefore is a compound close to neutrality. Compound (2) is effective mainly in decreasing the viscosity or adjusting the optical anisotropy. Compounds (3) and (4) are effective in extending the temperature range of the nematic phase by increasing the maximum temperature, or effective in adjusting the optical anisotropy.

Accordingly as a content of component B is increased, the dielectric anisotropy of the composition is decreased, but the viscosity decreases. Thus, as long as a desired value of threshold voltage of the device is met, the content is preferably as large as possible. When a composition for a mode such as IPS and VA is prepared, the content of component B is preferably in the range of approximately 30% by weight or more, and further preferably in the range of approximately 40% by weight or more, based on the weight of the liquid crystal composition.

Component C is a compound having a halogen-containing group or a fluorine-containing group at a right terminal. Specific preferred examples of component C include compounds (5-1) to (5-16), compounds (6-1) to (6-113) and compounds (7-1) to (7-57). In the compound of component C, $R^{13}$ is alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine; and $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

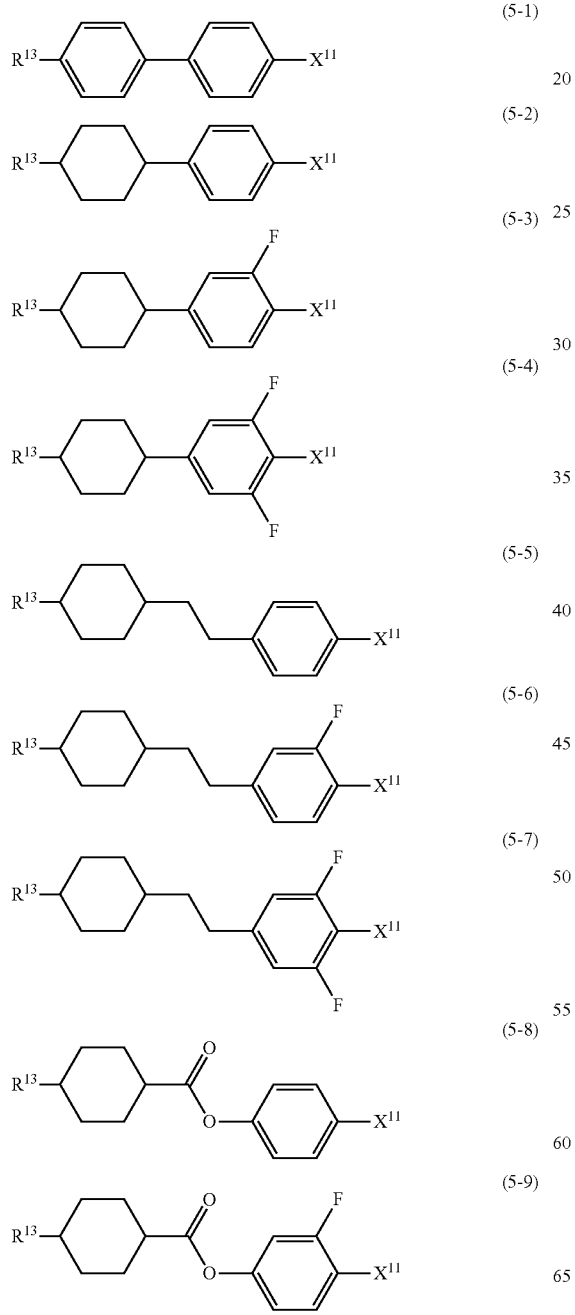

(6-4) 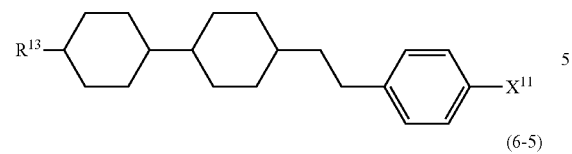
(6-5) 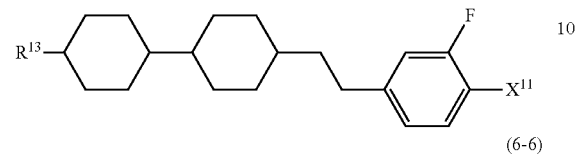
(6-6) 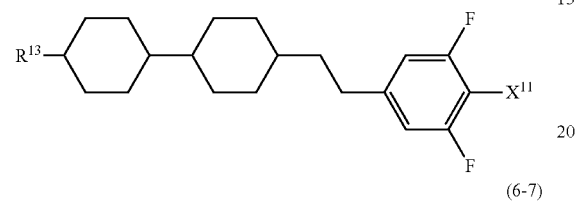
(6-7) 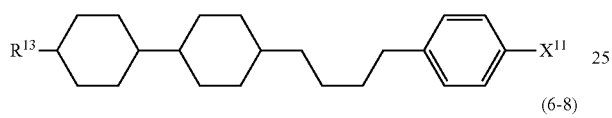
(6-8) 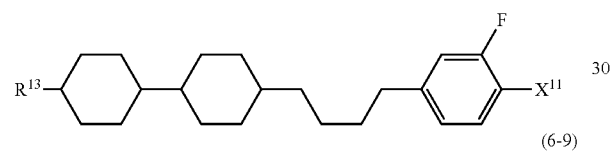
(6-9) 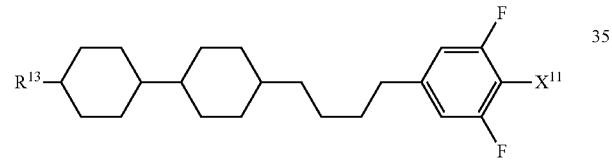
(6-10) 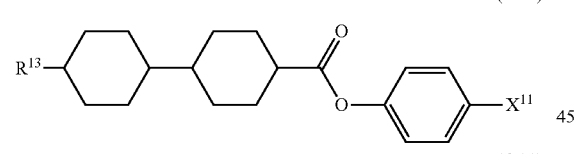
(6-11) 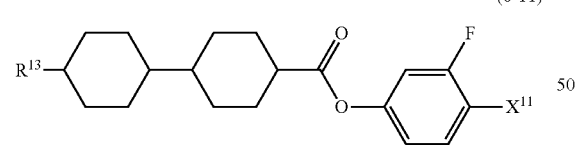
(6-12) 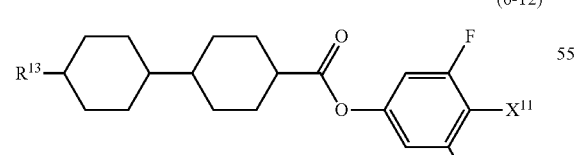
(6-13) 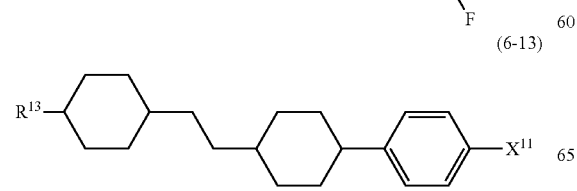
(6-14) 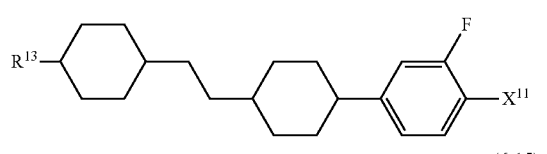
(6-15) 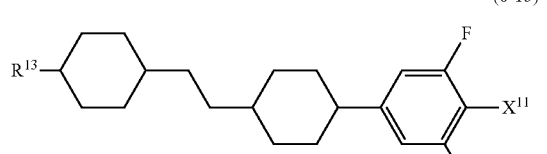
(6-16) 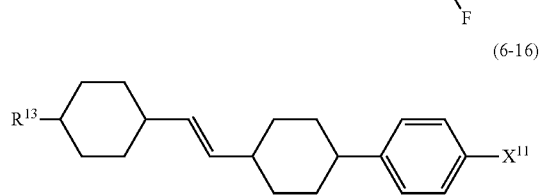
(6-17) 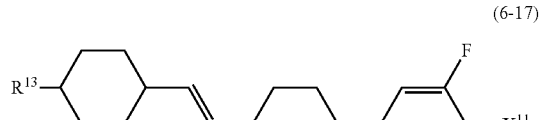
(6-18) 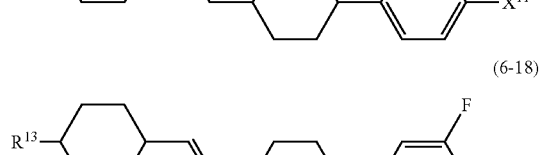
(6-19) 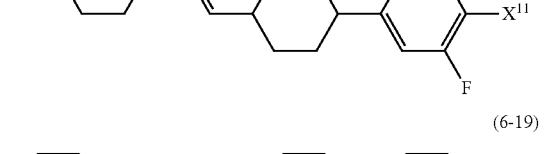
(6-20) 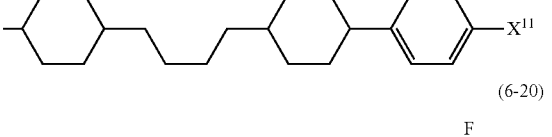
(6-21) 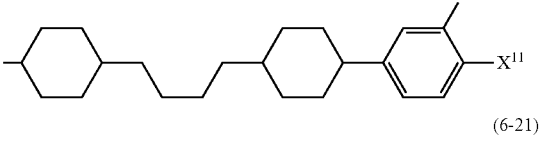
(6-22) 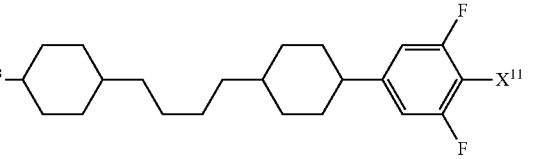
(6-23) 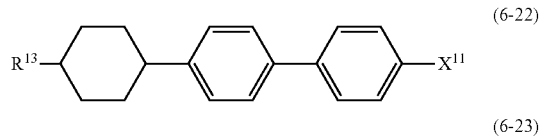

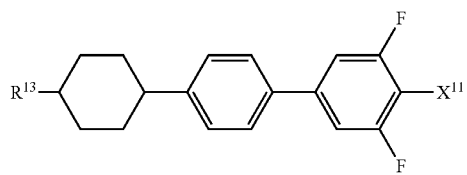
(6-24)
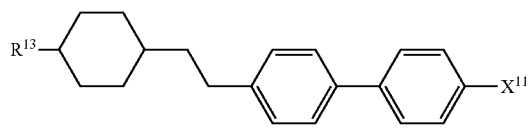
(6-25)
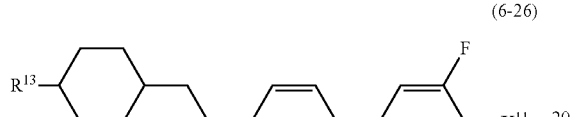
(6-26)
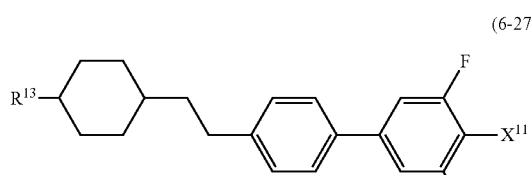
(6-27)
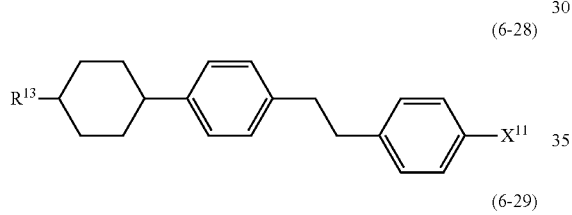
(6-28)
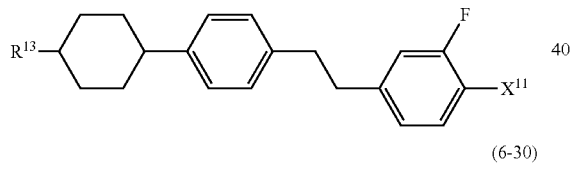
(6-29)
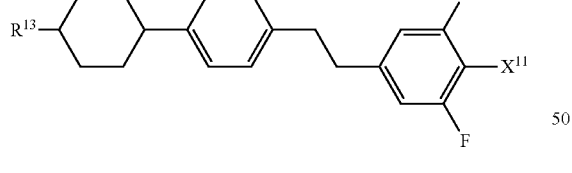
(6-30)
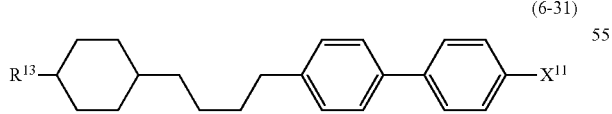
(6-31)
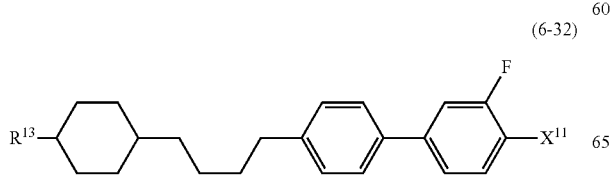
(6-32)
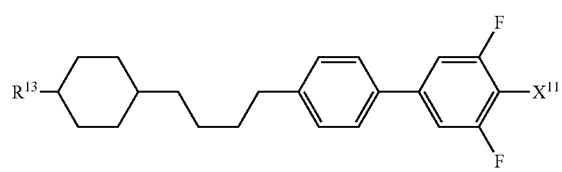
(6-33)
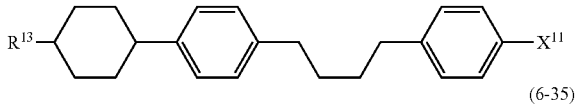
(6-34)
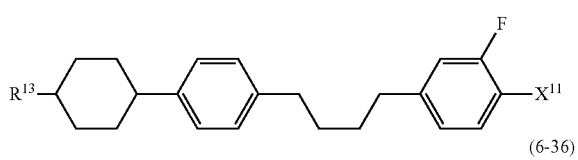
(6-35)
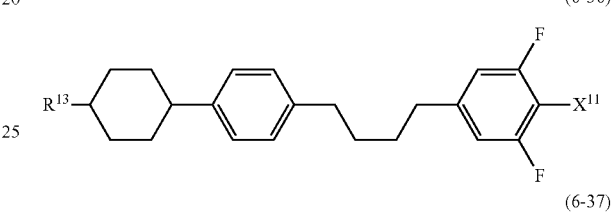
(6-36)
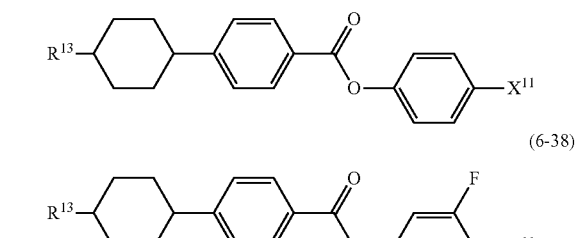
(6-37)
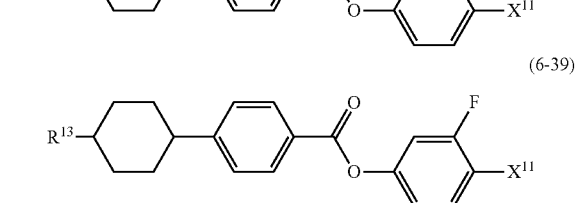
(6-38)
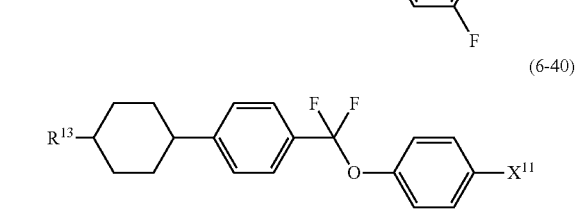
(6-39)
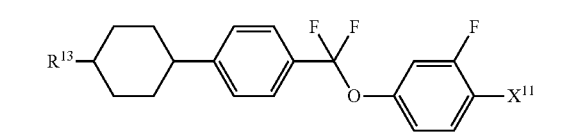
(6-40)
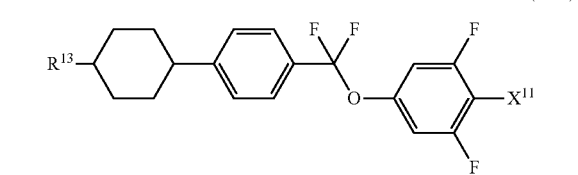
(6-41)
(6-42)

(6-43)
(6-44)
(6-45)
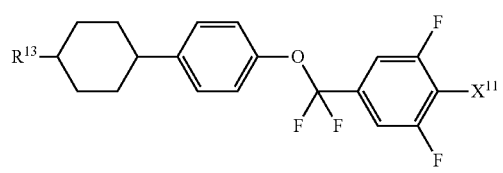
(6-46)
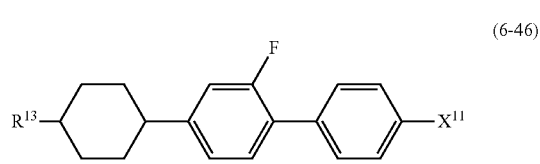
(6-47)
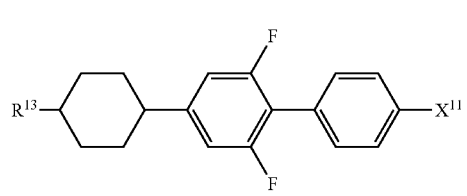
(6-48)
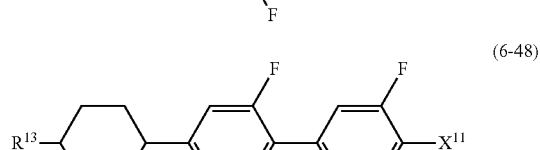
(6-49)

(6-50)
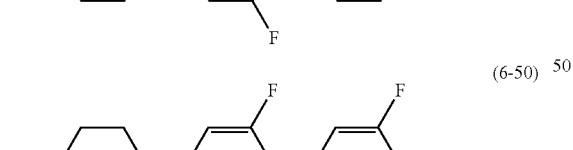
(6-51)

(6-52)
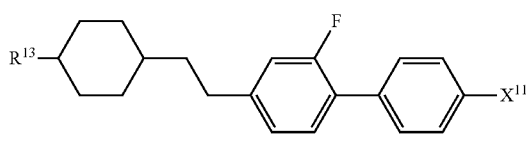
(6-53)
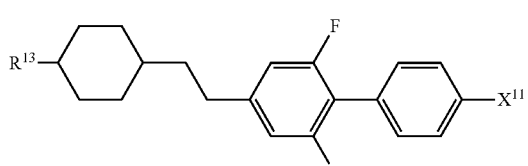
(6-54)
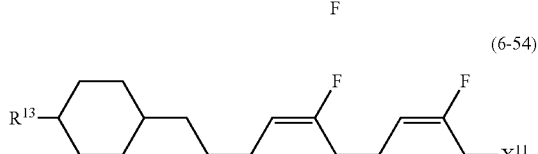
(6-55)
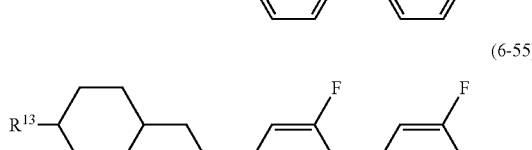
(6-56)
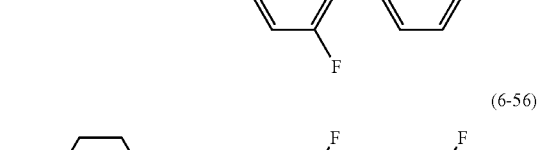
(6-57)
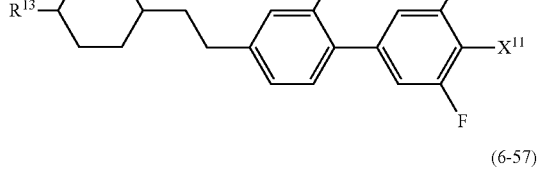
(6-58)
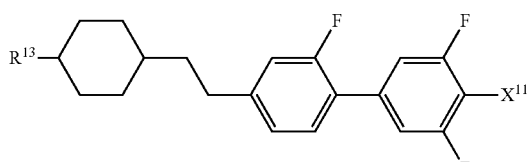
(6-59)
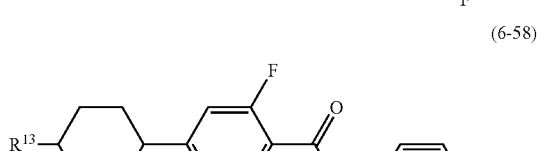

(6-60) 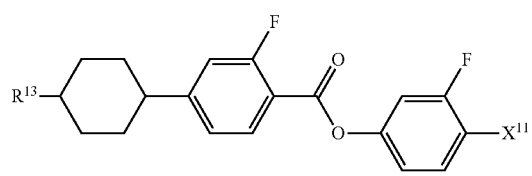
(6-61) 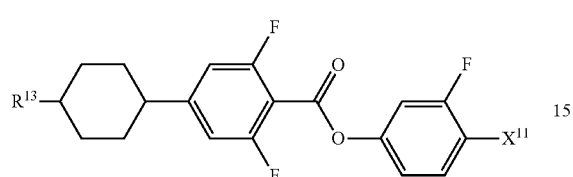
(6-62) 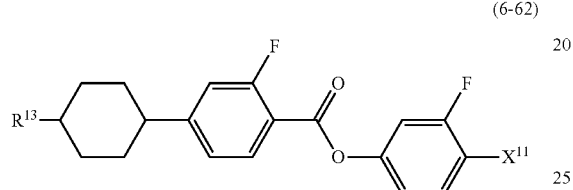
(6-63) 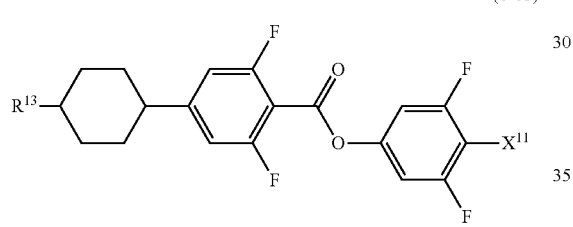
(6-64) 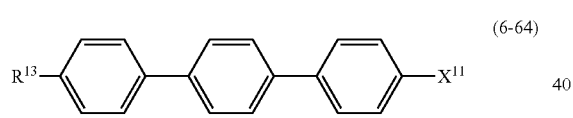
(6-65) 
(6-66) 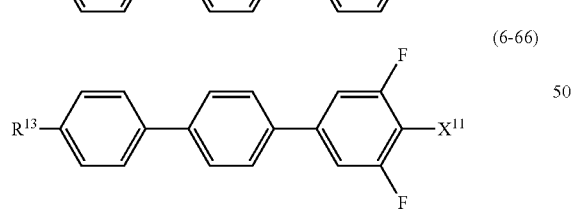
(6-67) 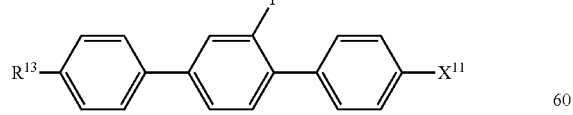
(6-68) 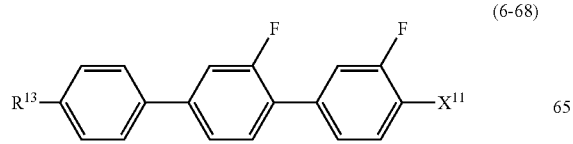
(6-69) 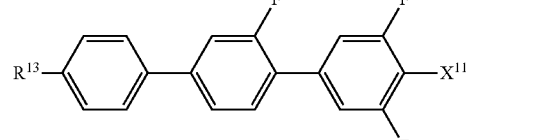
(6-70) 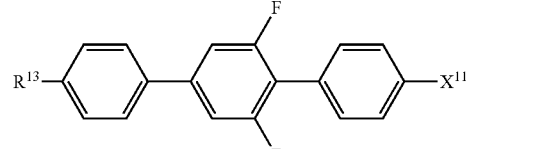
(6-71) 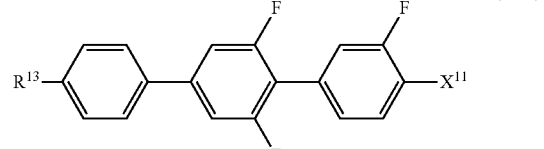
(6-72) 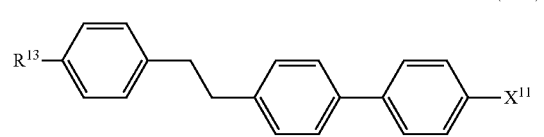
(6-73) 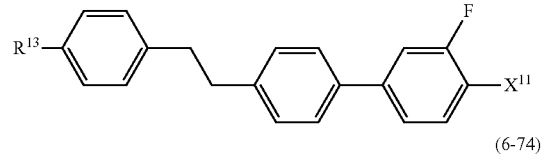
(6-74) 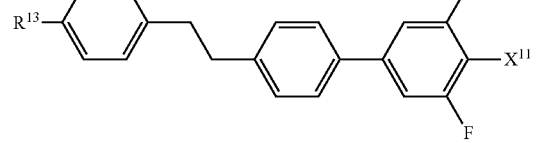
(6-75) 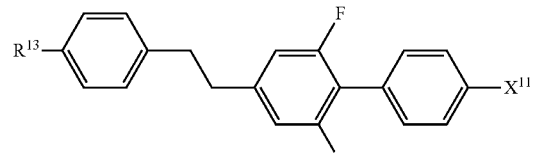
(6-76) 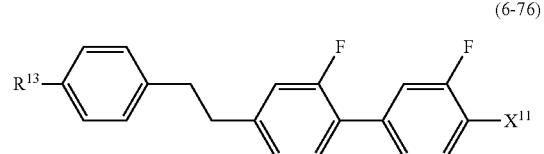
(6-77) 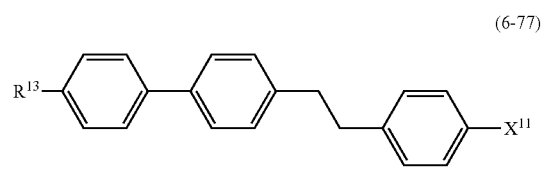

(6-78) 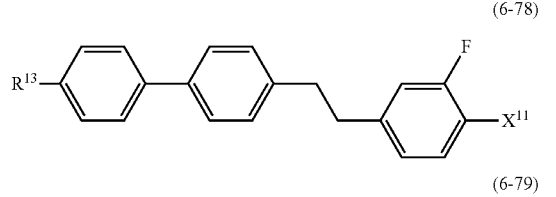
(6-79) 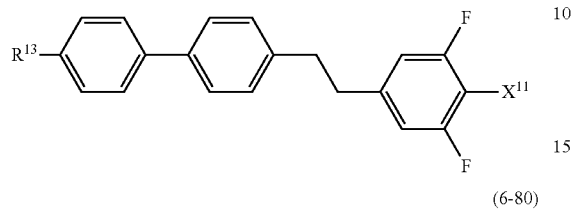
(6-80) 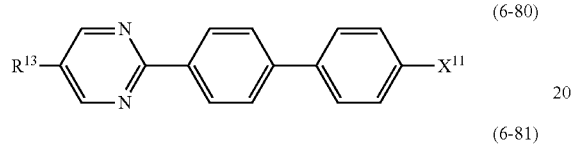
(6-81) 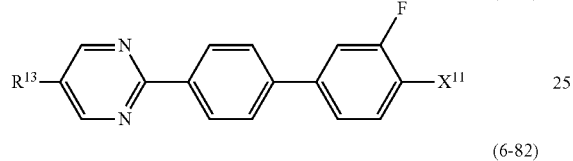
(6-82) 
(6-83) 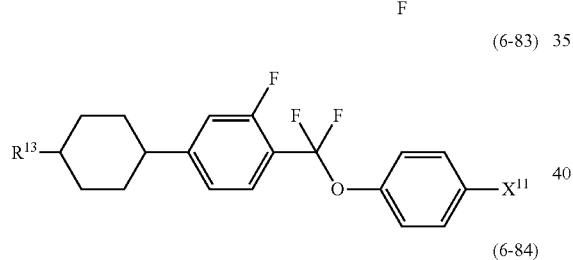
(6-84) 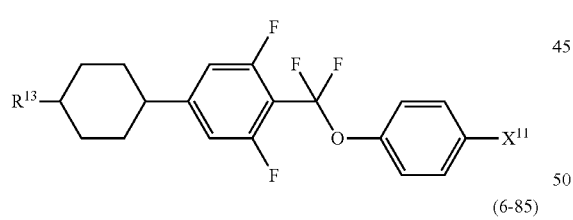
(6-85) 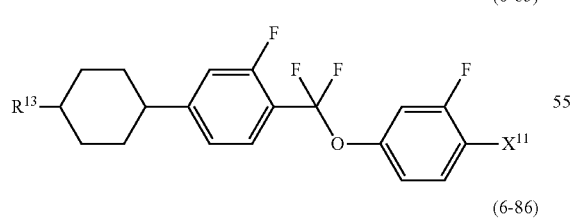
(6-86) 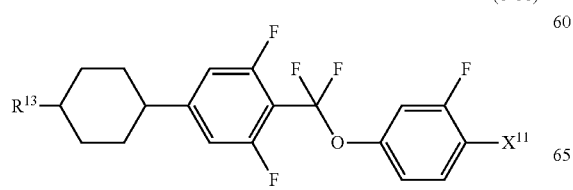
(6-87) 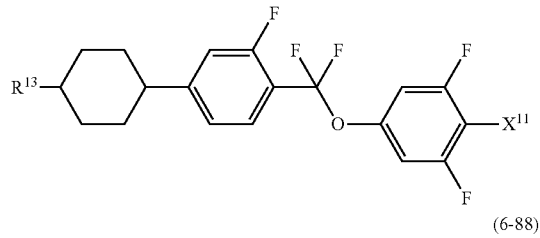
(6-88) 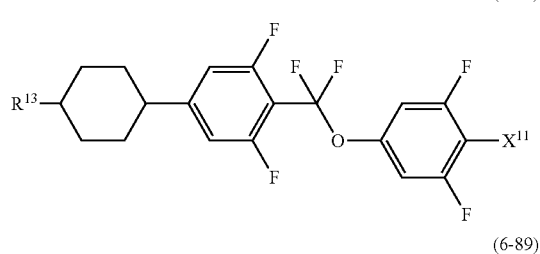
(6-89) 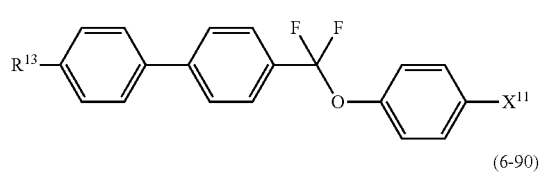
(6-90) 
(6-91) 
(6-92) 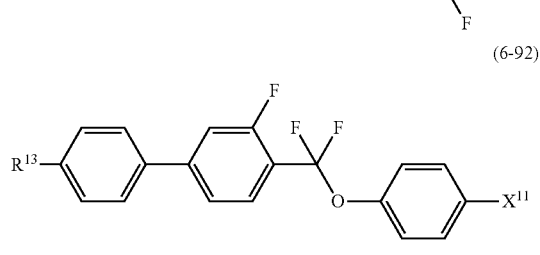
(6-93) 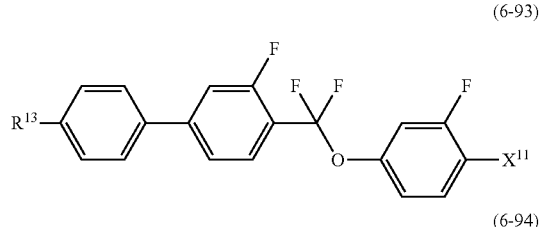
(6-94) 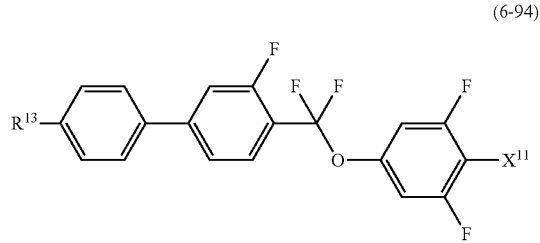

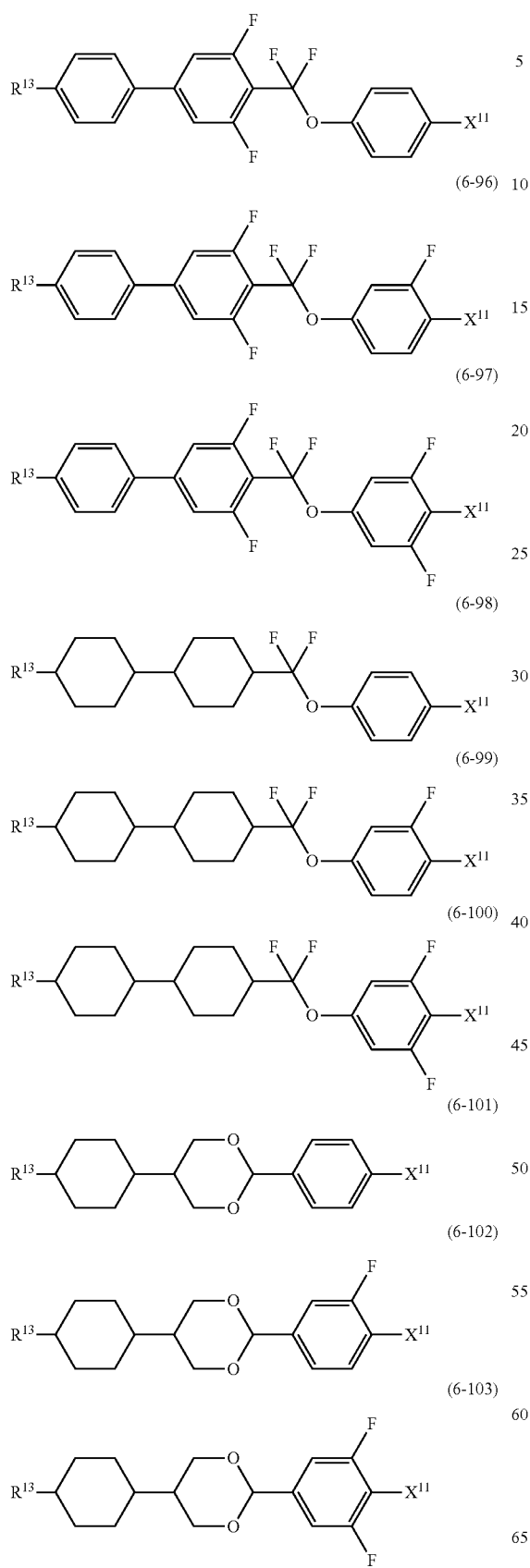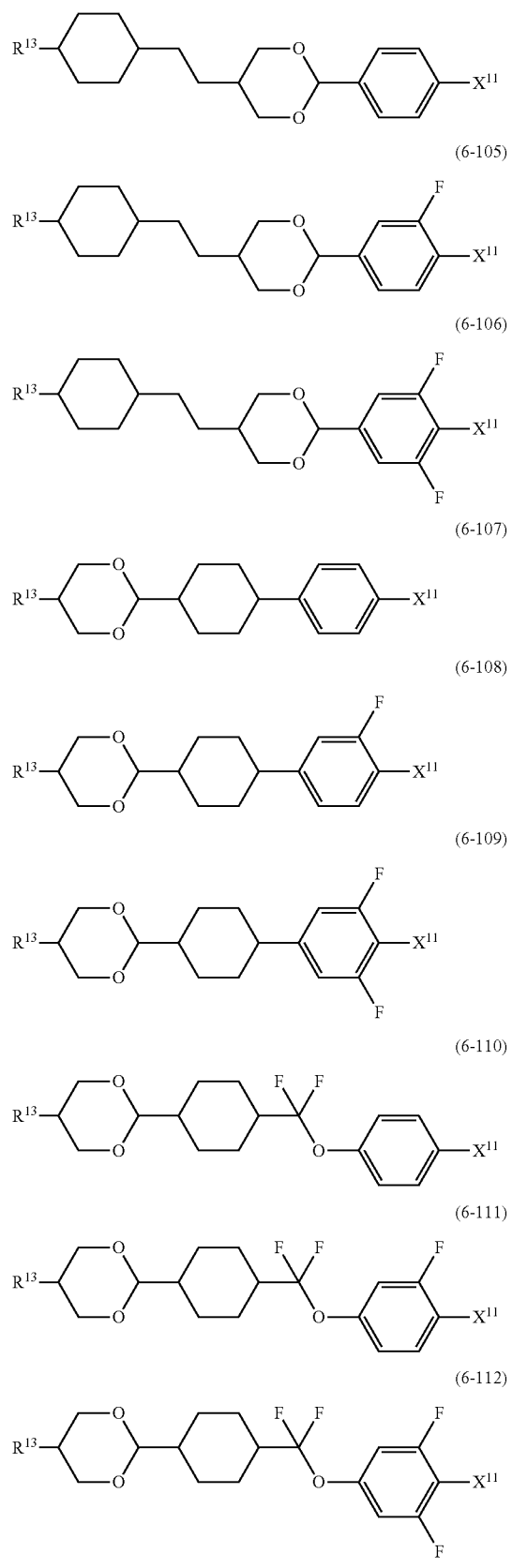

(6-113)
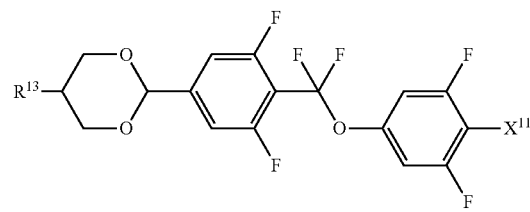
(7-1)
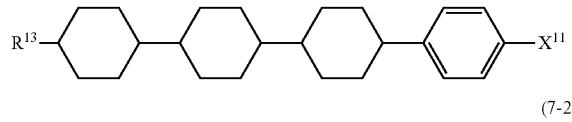
(7-2)
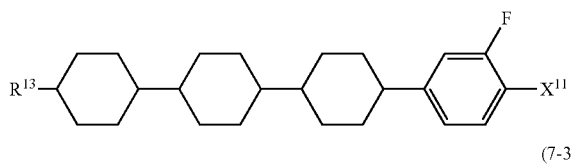
(7-3)
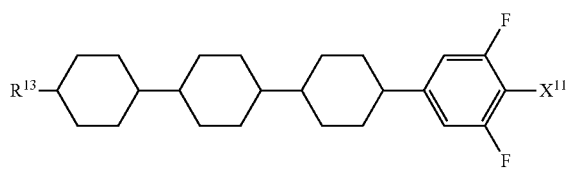
(7-4)
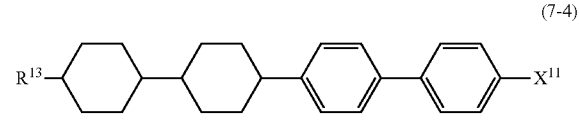
(7-5)
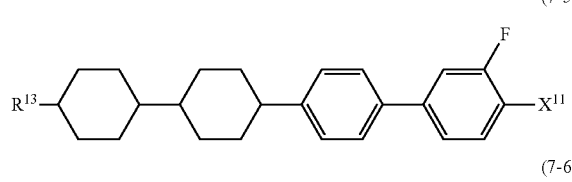
(7-6)
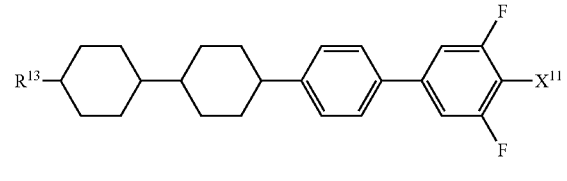
(7-7)
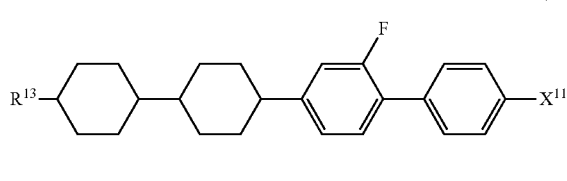
(7-8)
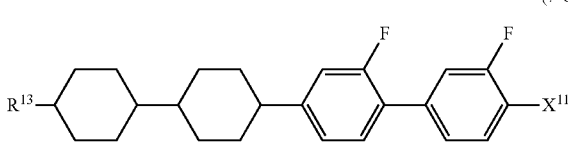
(7-9)
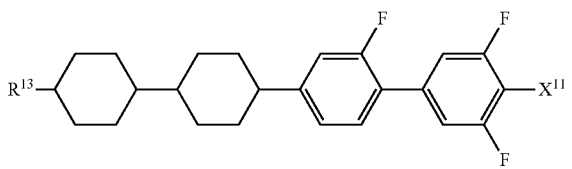
(7-10)
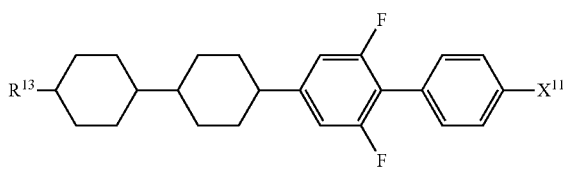
(7-11)
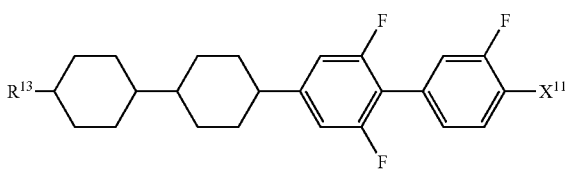
(7-12)
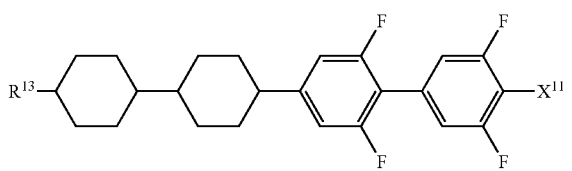
(7-13)
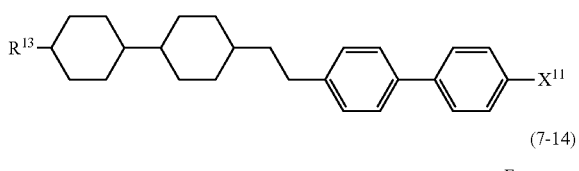
(7-14)
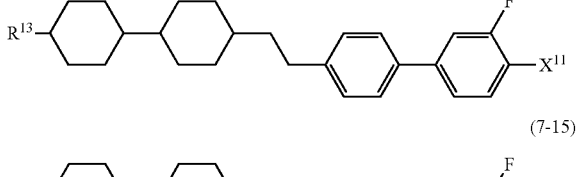
(7-15)
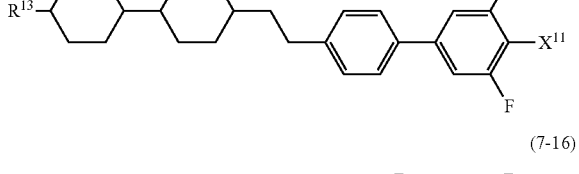
(7-16)
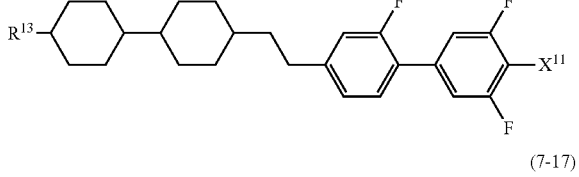
(7-17)
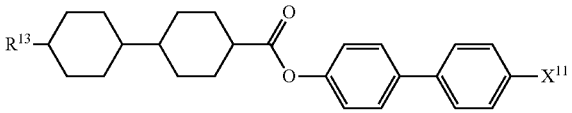

-continued
(7-18)
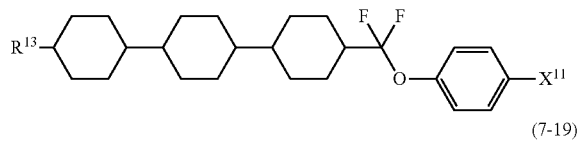
(7-19)
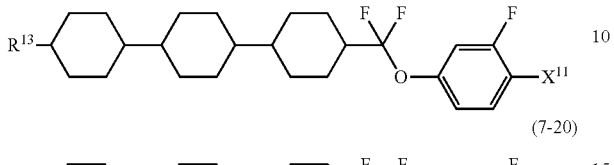
(7-20)
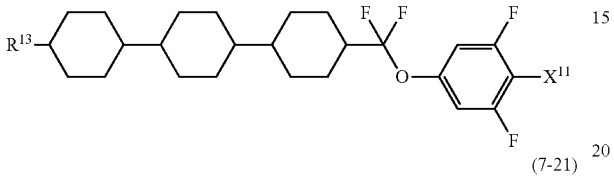
(7-21)
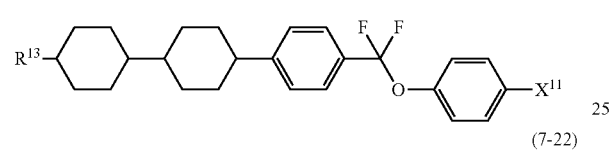
(7-22)
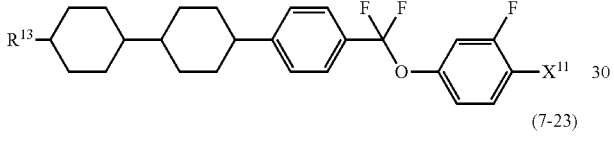
(7-23)
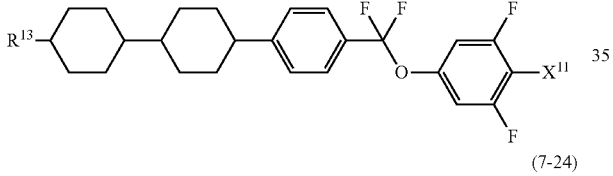
(7-24)
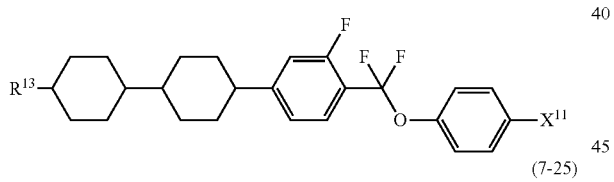
(7-25)
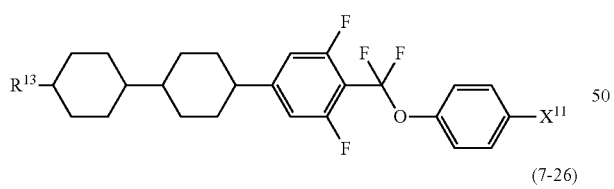
(7-26)
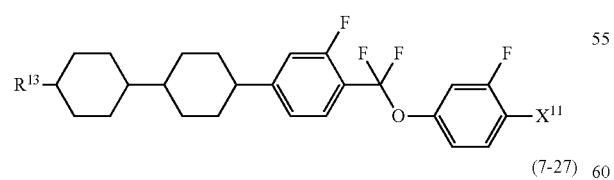
(7-27)
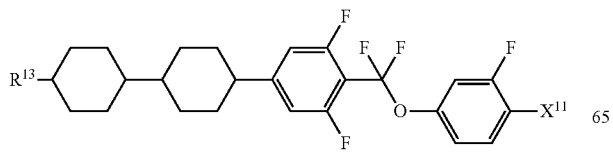
-continued
(7-28)
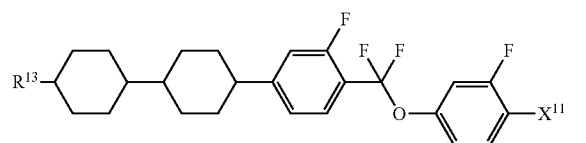
(7-29)
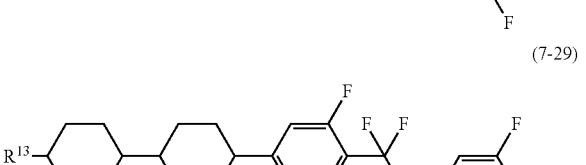
(7-30)
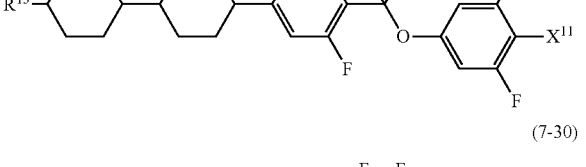
(7-31)
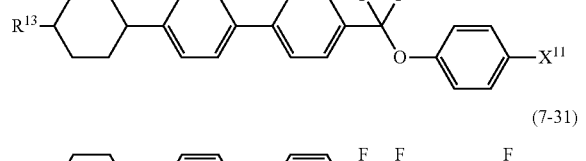
(7-32)
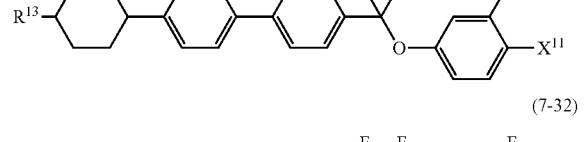
(7-33)
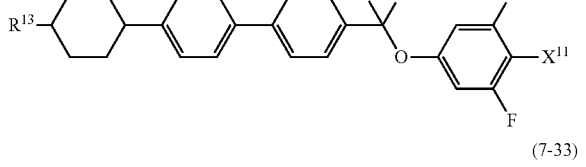
(7-34)
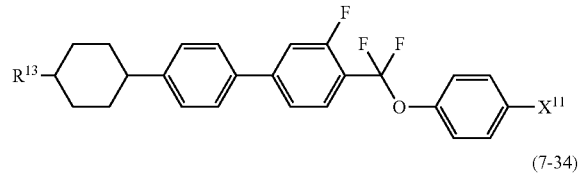
(7-35)
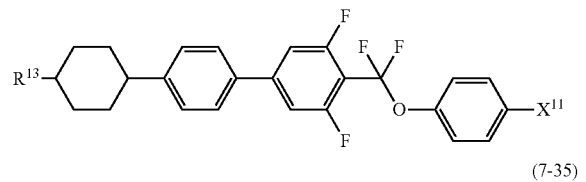
(7-36)
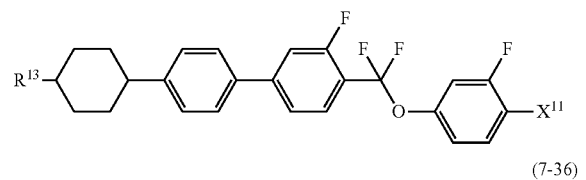
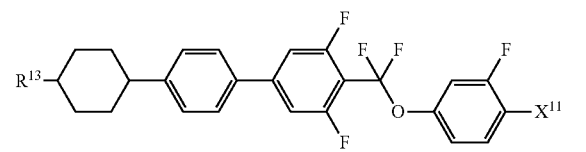

(7-37) through (7-52): chemical structure diagrams

-continued

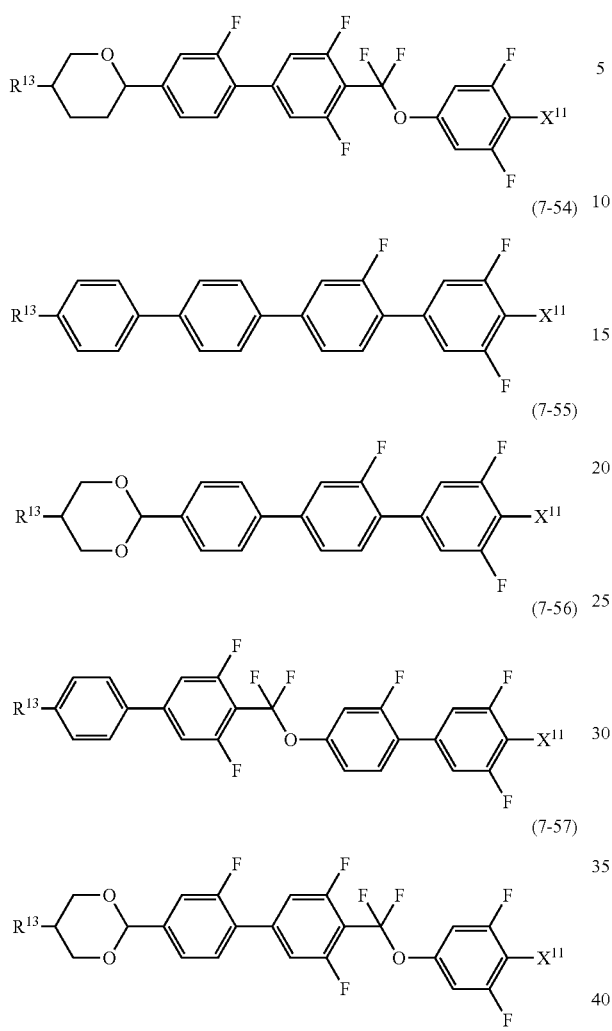

(7-53)
(7-54)
(7-55)
(7-56)
(7-57)

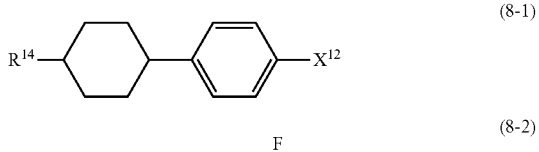
(8-1)

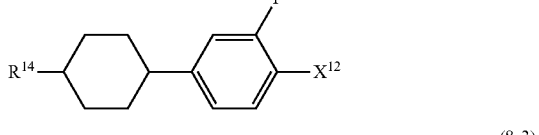
(8-2)

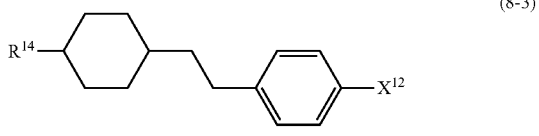
(8-3)

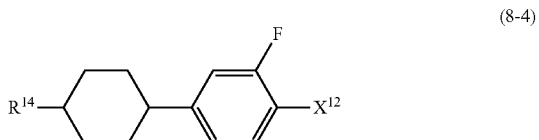
(8-4)

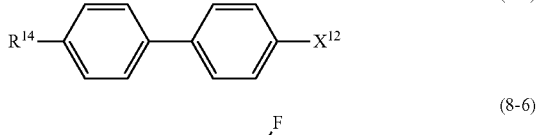
(8-5)

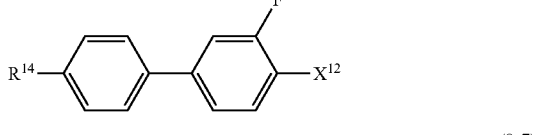
(8-6)

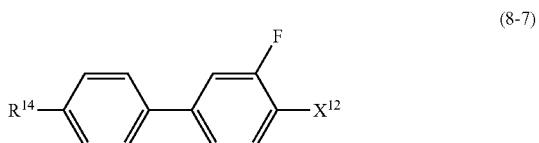
(8-7)

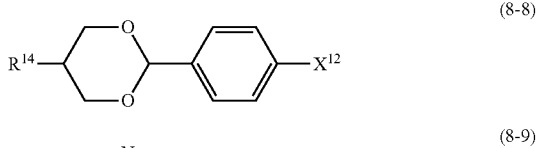
(8-8)

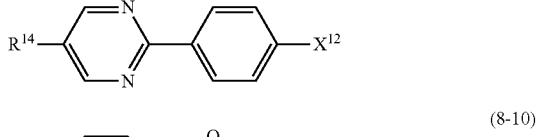
(8-9)

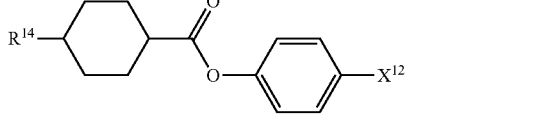
(8-10)

(8-11)

Component C has the positive dielectric anisotropy, and superb stability to heat, light and so forth, and thus is used for preparing a composition for a mode such as IPS, FFS and OCB. A content of component C is suitably in the range of approximately 1% by weight to approximately 99% by weight, preferably in the range of approximately 10% by weight to approximately 97% by weight, and further preferably in the range of approximately 40% by weight to approximately 95% by weight, based on the weight of the liquid crystal composition. When component C is added to a composition having negative dielectric anisotropy, a content of component C is preferably in the range of approximately 30% by weight or less based on the weight of the liquid crystal composition. Addition of component C allows adjustment of the elastic constant of the composition and adjustment of a voltage-transmittance curve of the device.

Component D is compound (8) in which a right-terminal group is —C≡N or —C≡C—C≡N. Specific preferred examples of component D include compounds (8-1) to (8-64). In the compound of component D, $R^{14}$ is alkyl having 1 to 10 carbons or alkenyl having 2 to 10 carbons, and in the alkyl and the alkenyl, at least one of —CH$_2$— may be replaced by —O—, and at least one of hydrogen may be replaced by fluorine; and $X^{12}$ is —C≡N or —C≡C—C≡N.

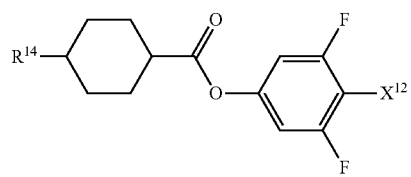 (8-12)
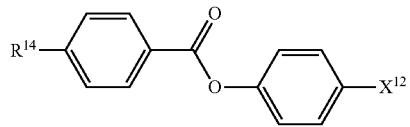 (8-13)
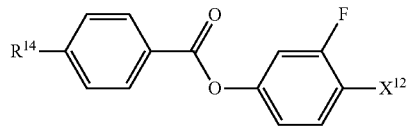 (8-14)
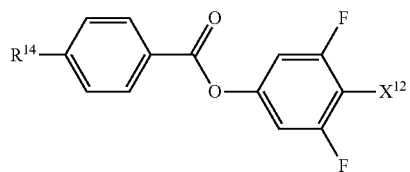 (8-15)
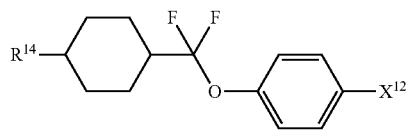 (8-16)
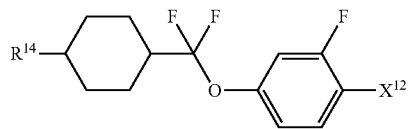 (8-17)
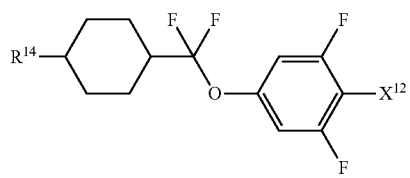 (8-18)
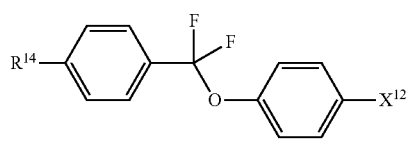 (8-19)
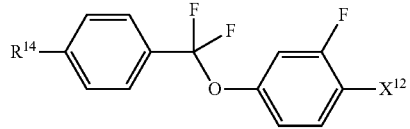 (8-20)
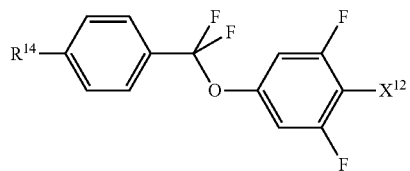 (8-21)
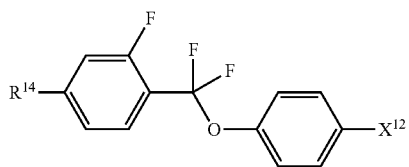 (8-22)
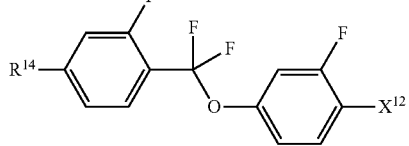 (8-23)
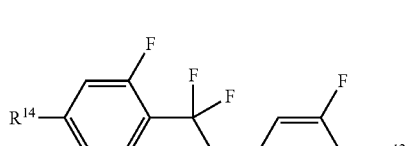 (8-24)
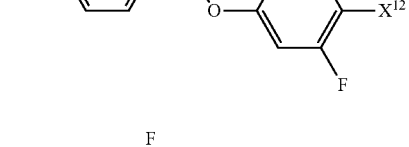 (8-25)
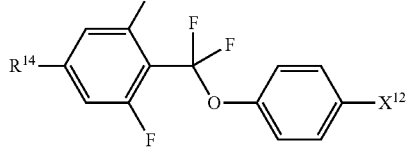 (8-26)
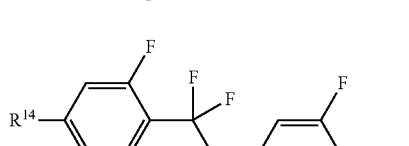 (8-27)
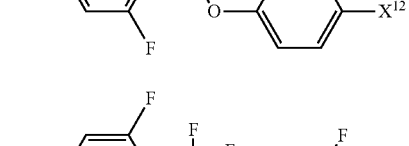 (8-28)
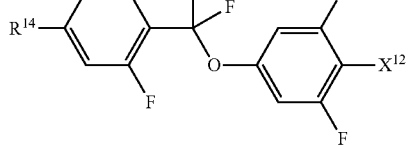 (8-29)
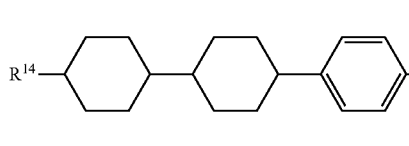 (8-30)

-continued
 (8-31)
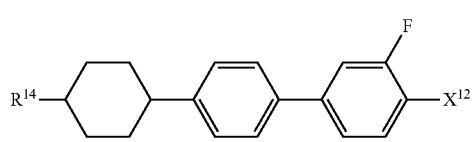 (8-32)
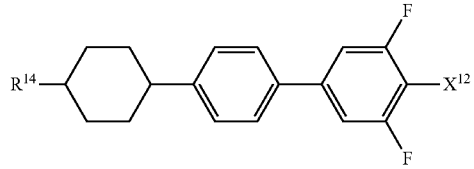 (8-33)
 (8-34)
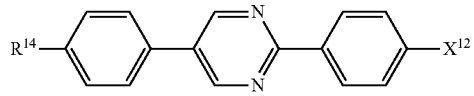 (8-35)
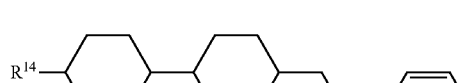 (8-36)
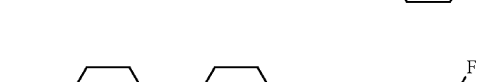 (8-37)
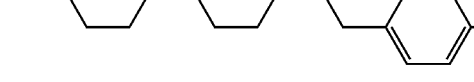 (8-38)
 (8-39)
 (8-40)
-continued
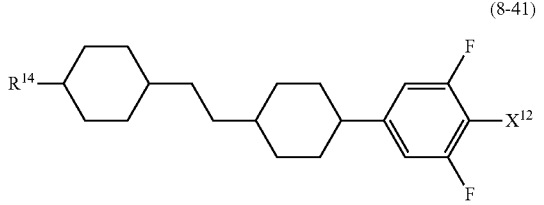 (8-41)
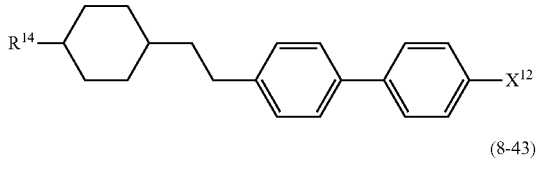 (8-42)
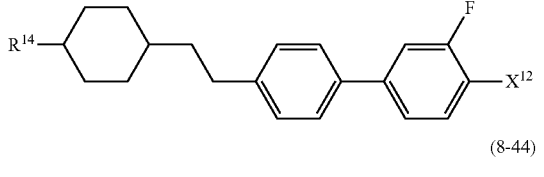 (8-43)
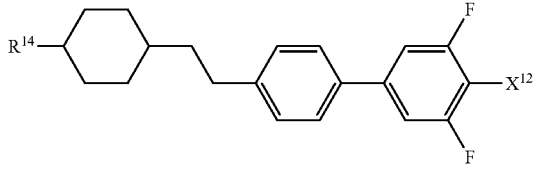 (8-44)
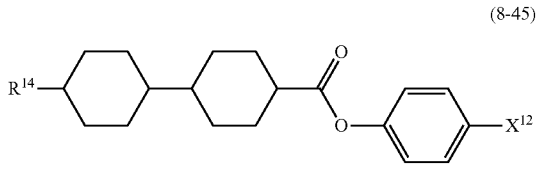 (8-45)
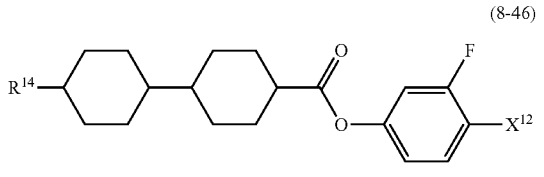 (8-46)
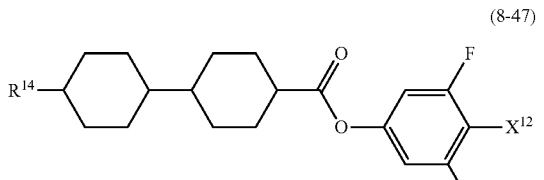 (8-47)
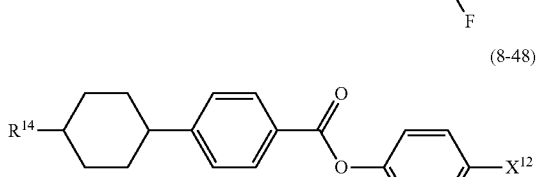 (8-48)
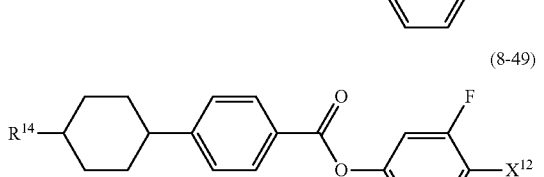 (8-49)

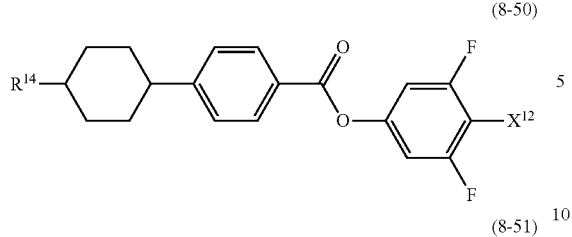
(8-50)

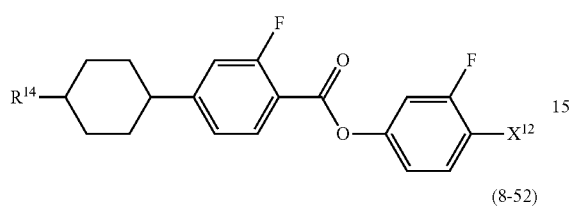
(8-51)

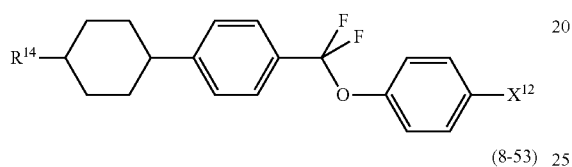
(8-52)

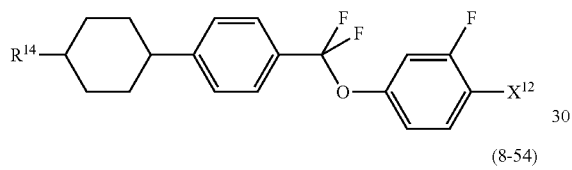
(8-53)

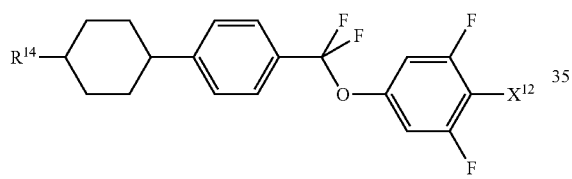
(8-54)

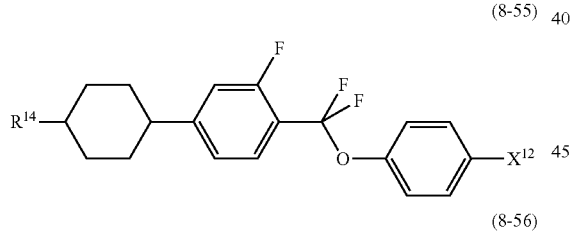
(8-55)

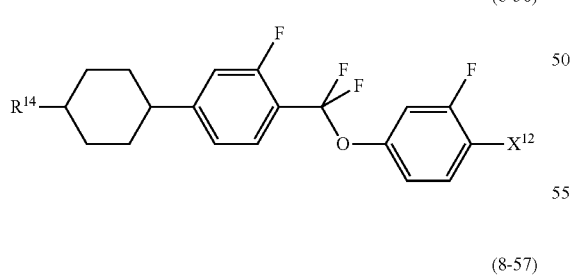
(8-56)

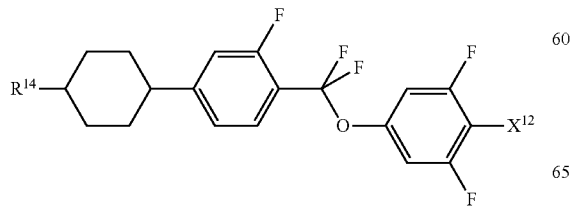
(8-57)

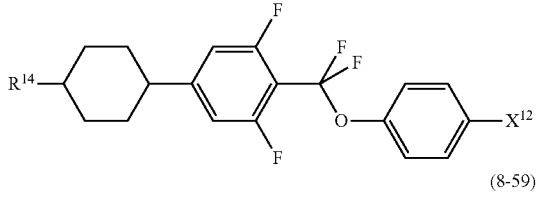
(8-58)

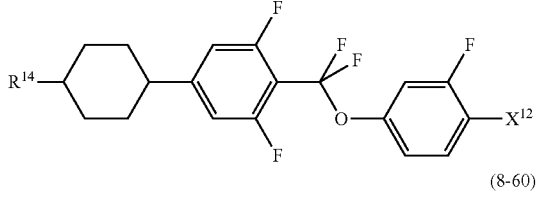
(8-59)

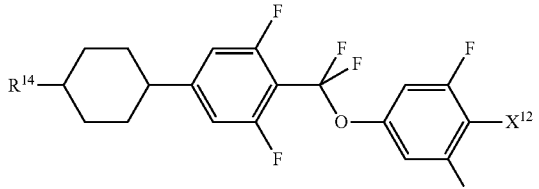
(8-60)

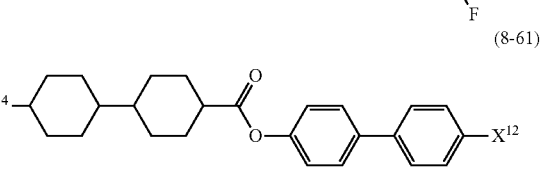
(8-61)

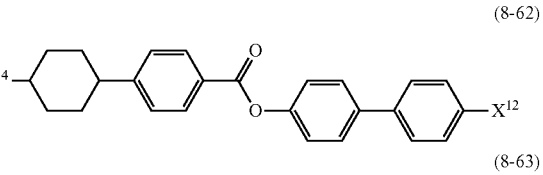
(8-62)

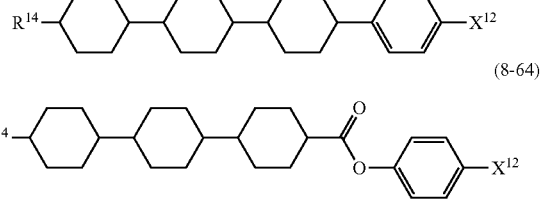
(8-63)

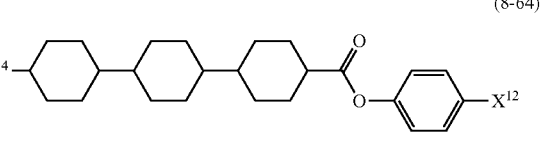
(8-64)

Component D has the positive dielectric anisotropy and a value thereof is large Component D has a large value of positive dielectric anisotropy, and therefore is used as a main component when a composition used for a mode such as the TN mode is prepared. The dielectric anisotropy of the composition can be increased by adding component D thereto. Component D is effective in extending the temperature range of the liquid crystal phase, adjusting the viscosity or adjusting optical anisotropy. Component D is also useful for adjustment of the voltage-transmittance curve of the device.

When the composition used for the mode such as the TN mode is prepared, a content of component D is suitably in the range of approximately 1% by weight to approximately 99% by weight, preferably in the range of approximately 10% by weight to approximately 97% by weight, and further preferably in the range of approximately 40% by weight to approximately 95% by weight, based on the total weight of the liquid crystal composition. When component D is added to a composition having the negative dielectric anisotropy, the content of component D is preferably in the range of 30% by weight or less based on the total weight of the liquid crystal composition. Addition of component D allows adjustment of the elastic constant of the composition and the voltage-transmittance curve of the device.

Component E has phenylene in which two of hydrogen in lateral positions is replaced by two of halogen, such as 2,3-difluoro-1,4-phenylene. Specific preferred examples of the compound include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compound, $R^{15}$ and $R^{16}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine; and $R^{17}$ is hydrogen, fluorine, alkyl having 1 to 10 carbons, or alkenyl having 2 to 10 carbons, and in the alkyl and the alkenyl, at least one of —$CH_2$— may be replaced by —O—, and at least one of hydrogen may be replaced by fluorine.

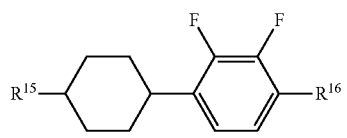

(9-1)

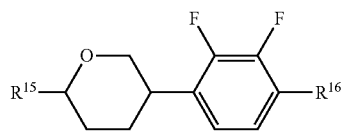

(9-2)

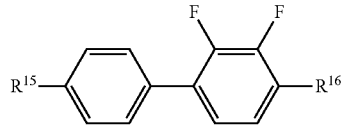

(9-3)

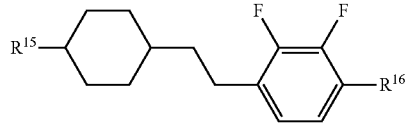

(9-4)

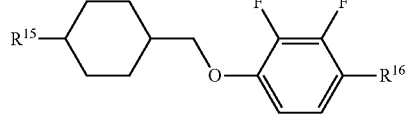

(9-5)

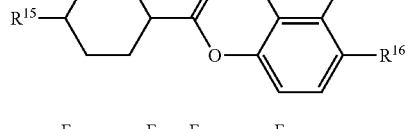

(9-6)

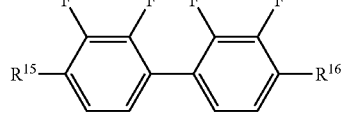

(9-7)

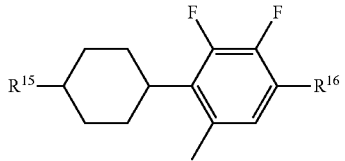

(9-8)

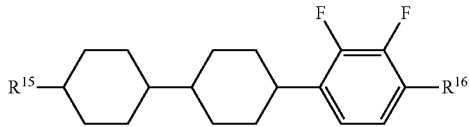

(10-1)

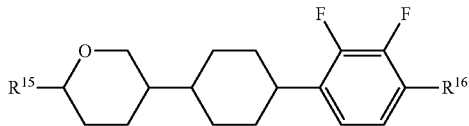

(10-2)

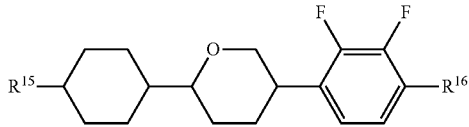

(10-3)

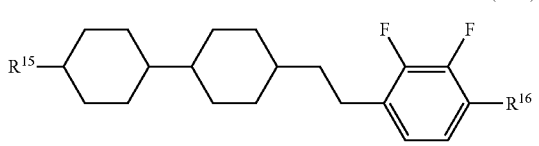

(10-4)

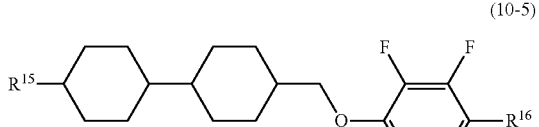

(10-5)

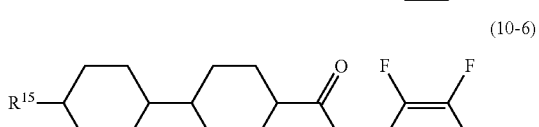

(10-6)

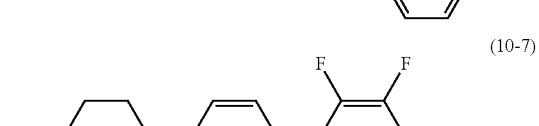

(10-7)

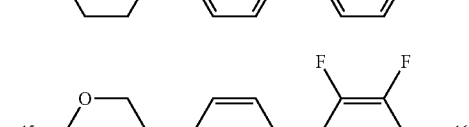

(10-8)

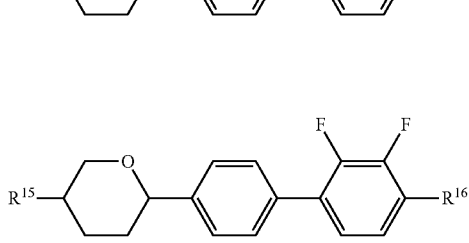

(10-9)

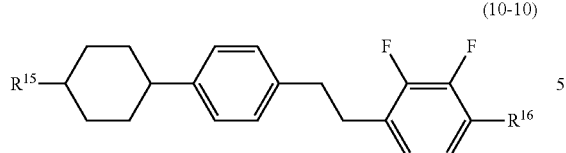 (10-10)
 (10-11)
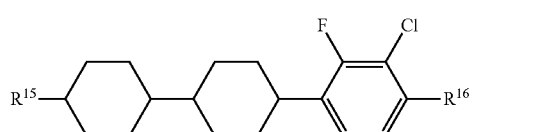 (10-12)
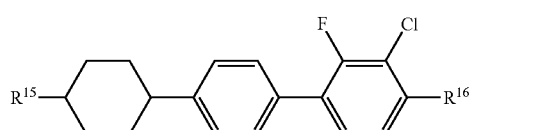 (10-13)
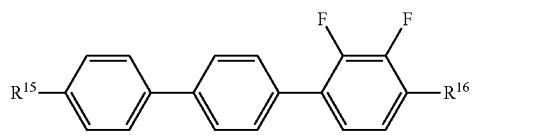 (10-14)
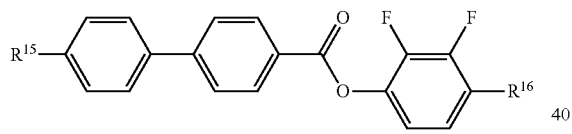 (10-15)
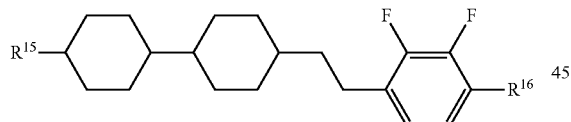 (10-16)
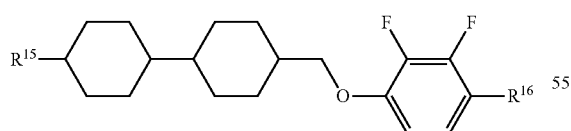 (10-17)
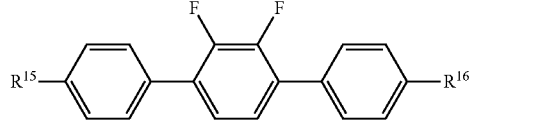 (11-1)
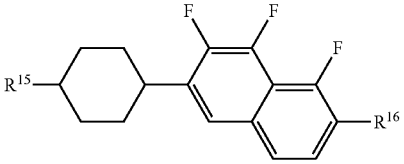 (12-1)
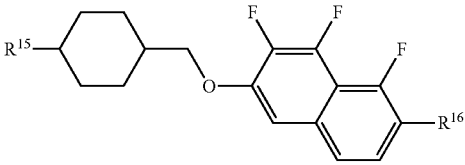 (12-2)
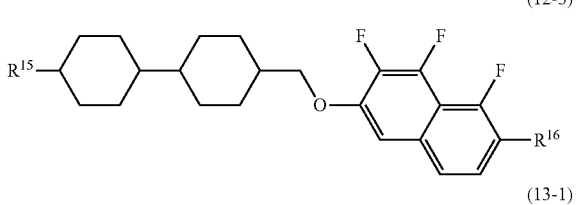 (12-3)
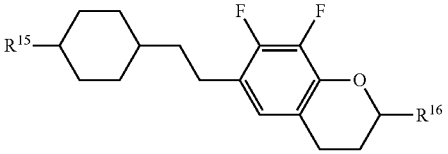 (13-1)
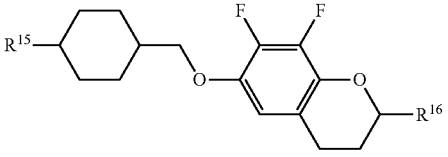 (13-2)
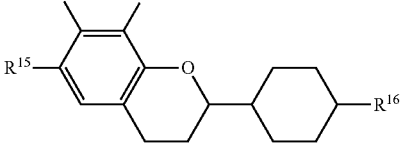 (13-3)
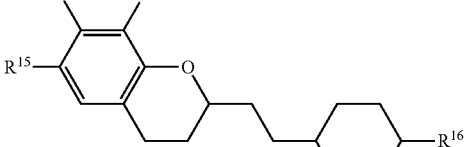 (13-4)
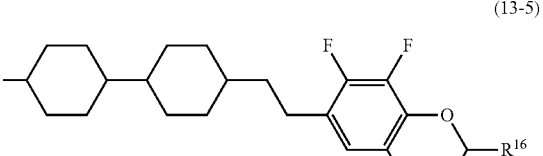 (13-5)
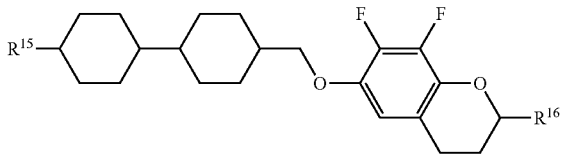 (13-6)

-continued (13-7)
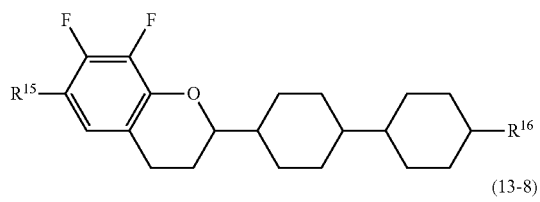

(13-8)
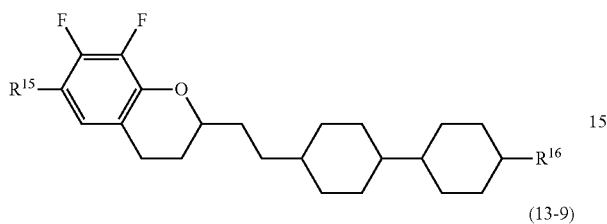

(13-9)
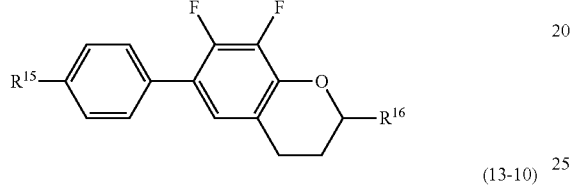

(13-10)

(13-11)
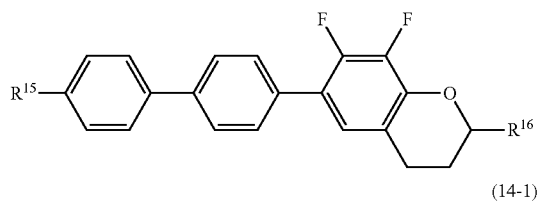

(14-1)
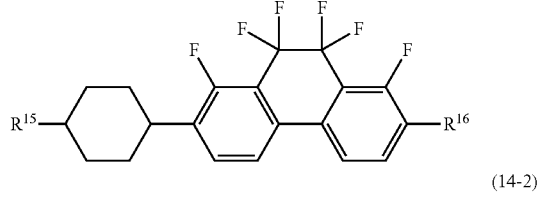

(14-2)
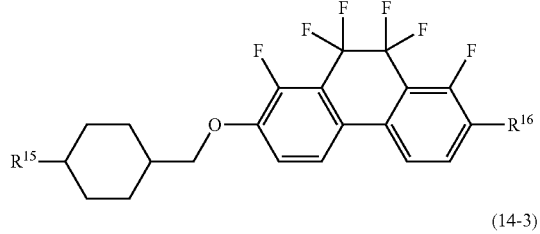

(14-3)
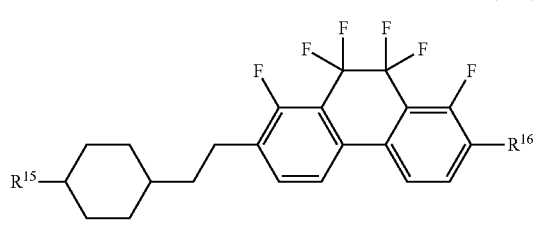

-continued (15-1)
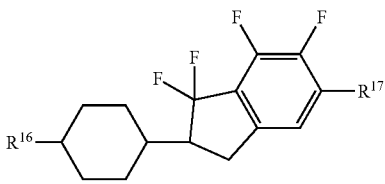

(15-2)
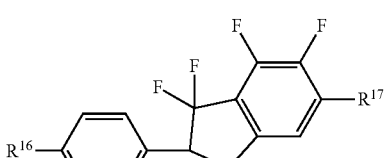

(15-3)
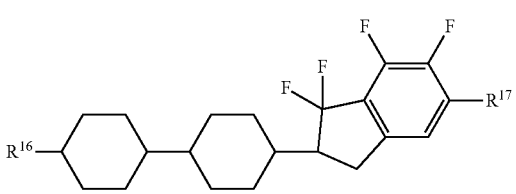

Component E has a large negative dielectric anisotropy. The compounds are used when a composition for the mode such as IPS, VA and PSA is prepared. Accordingly as a content of the compounds is increased, the dielectric anisotropy of the composition negatively increases, but the viscosity increases. Thus, as long as the desired value of threshold voltage of the device is met, the content is preferably as small as possible. In consideration of approximately −5 of the dielectric anisotropy, the content is preferably in the range of approximately 40% by weight or more in order to allow sufficient voltage driving.

Among the compounds, compound (9) is a bicyclic compound, and therefore effective mainly in decreasing the viscosity, adjusting the optical anisotropy or increasing the dielectric anisotropy. Compounds (10) and (11) are a tricyclic compound, and therefore effective in increasing the maximum temperature, the optical anisotropy or the dielectric anisotropy. Compounds (12) to (15) are effective in increasing the dielectric anisotropy.

When a composition for the mode such as IPS, VA and PSA is prepared, a content of compounds (9) to (15) is preferably in the range of approximately 40% by weight or more, and further preferably in the range of approximately 50% by weight to approximately 95% by weight, based on the weight of the liquid crystal composition. When compounds (9) to (15) are added to a composition having the positive dielectric anisotropy, a content of the compound is preferably in the range of approximately 30% by weight or less based on the weight of the liquid crystal composition. Addition of the compound allows adjustment of the elastic constant of the composition and the voltage-transmittance curve of the device.

The liquid crystal composition satisfying at least one of characteristics such as the high maximum temperature, the low minimum temperature, the small viscosity, the suitable optical anisotropy, the large dielectric anisotropy, the suitable elastic constant and the large specific resistance by suitably combining components B, C, D and E described above. When necessary, a liquid crystal compound different from components B, C, D and E may be added.

A liquid crystal composition that is stable to light can be prepared by adding compound (1) to a mixture of such components. Preparation of the liquid crystal composition is performed by a method of dissolving required components at temperature higher than room temperature, or the like. According to an application, an additive may be added to the composition. Specific examples of the additive include a polymerizable compound, a polymerization initiator, a polymerization inhibitor, an optically active compound, an antioxidant, an ultraviolet light absorber, any other light stabilizer, a heat stabilizer and an antifoaming agent. Such additives are well known to those skilled in the art, and described in literature.

The polymerizable compound is added to the liquid crystal composition for the purpose of forming a polymer in the liquid crystal composition. The polymer is formed in the liquid crystal composition by irradiating the polymerizable compound with ultraviolet light in a state in which voltage is applied between electrodes to polymerize the polymerizable compound. A suitable pretilt can be obtained by the method, and therefore the liquid crystal display device can be obtained in which the response time is shortened and the image persistence is improved. Preferred examples of the polymerizable compound include an acrylate, a methacrylate, a vinyl compound, a vinyloxy compound, a propenyl ether, an epoxy compound (oxirane, oxetane) and a vinyl ketone. Further preferred examples include a compound having at least one of acryloyloxy and a compound having at least one of methacryloyloxy. Still further preferred examples also include a compound having both acryloyloxy and methacryloyloxy.

Further preferred examples include compounds (RM-1) to (RM-12). In compounds (RM-1) to (RM-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

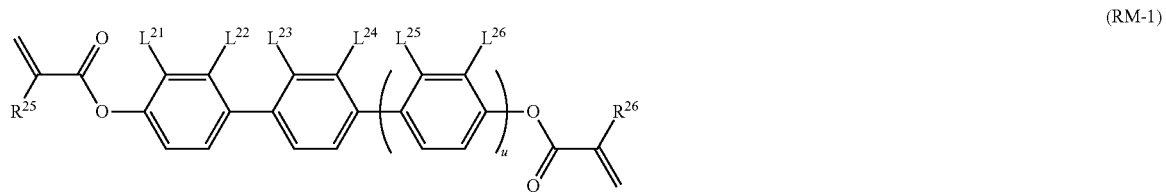
(RM-1)

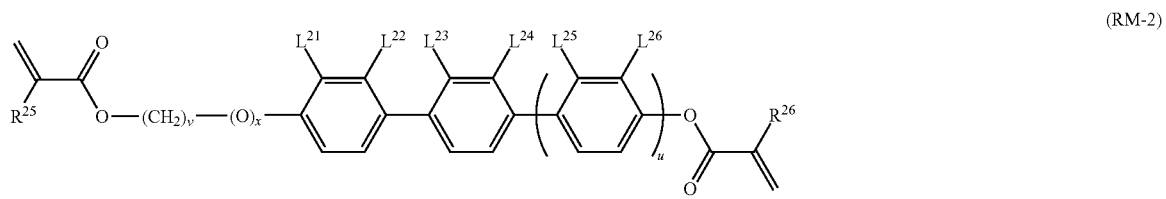
(RM-2)

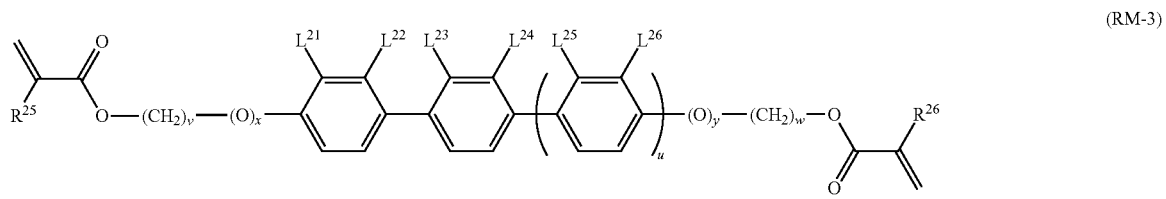
(RM-3)

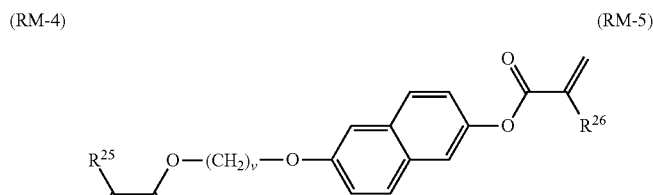
(RM-4) (RM-5)

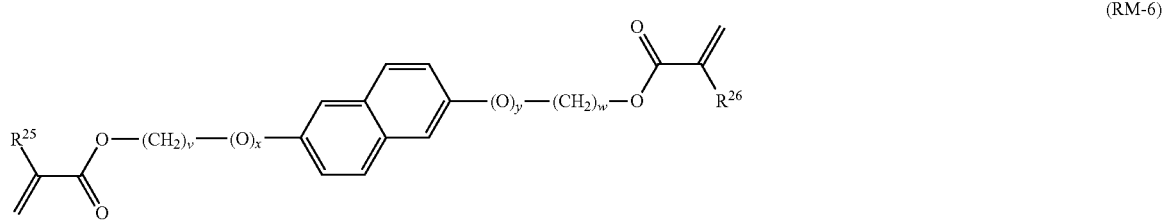
(RM-6)

-continued

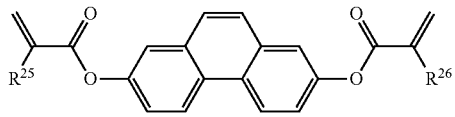
(RM-7)

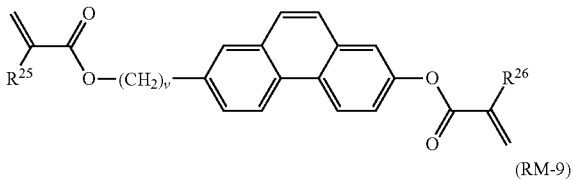
(RM-8)

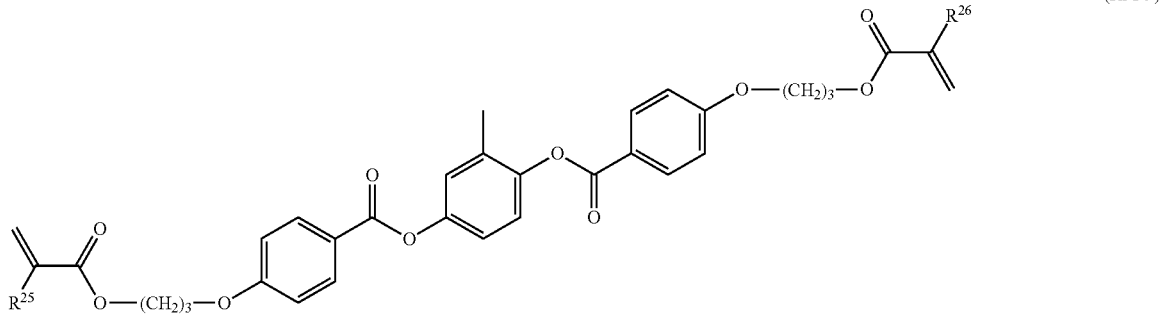
(RM-9)

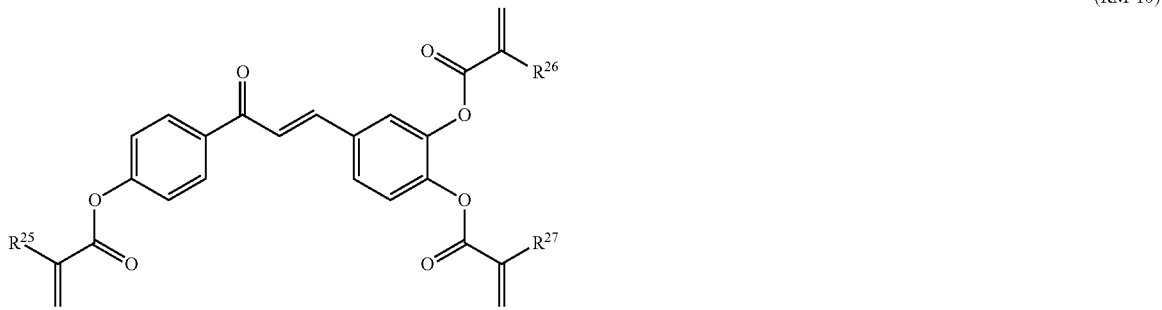
(RM-10)

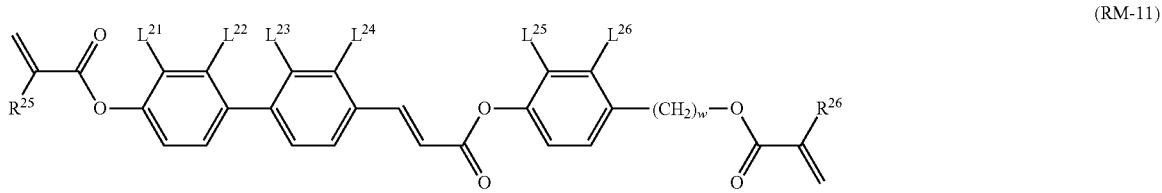
(RM-11)

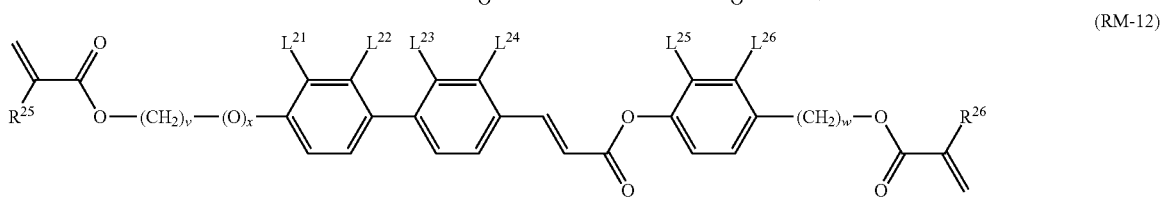
(RM-12)

The polymerizable compound can be rapidly polymerized by adding the polymerization initiator. An amount of a remaining polymerizable compound can be decreased by optimizing reaction temperature. Examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2- morpholinopropane-1-one, a 2,4-diethylxanthone-methyl p-dimethylaminobenzoate mixture and a benzophenone-methyltriethanolamine mixture.

The polymerization can be performed by adding the photoradical polymerization initiator to the liquid crystal composition, and then irradiating the resulting mixture with ultraviolet light in a state in which an electric field is applied. However, an unreacted polymerization initiator or a decomposition product of the polymerization initiator might cause poor display to the device, such as the image persistence. In order to prevent such poorness, photopolymerization may be performed without adding the polymerization initiator. A preferred wavelength of light to be irradiated is in the range of approximately 150 nanometers to approximately 500 nanometers. A further preferred wavelength is in the range of approximately 250 nanometers to approximately 450 nanometers, and a most preferred wavelength is in the range of approximately 300 nanometers to approximately 400 nanometers.

Upon storing the polymerizable compound, the polymerization inhibitor may be added thereto in order to prevent polymerization. The polymerizable compound is ordinarily added to the composition without eliminating the polymerization inhibitor. Examples of the polymerization inhibitor include hydroquinone, a hydroquinone derivative such as methylhydroquinone, 4-tert-butylcatechol, 4-methoxyphenol and phenothiazine.

The optically active compound is effective in inducing helical structure in liquid crystal molecules to give a required twist angle, thereby being effective in preventing a reverse twist. Addition of the optically active compound allows adjustment of a helical pitch. Two or more optically active compounds may be added for the purpose of adjusting temperature dependence of the helical pitch. Specific preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

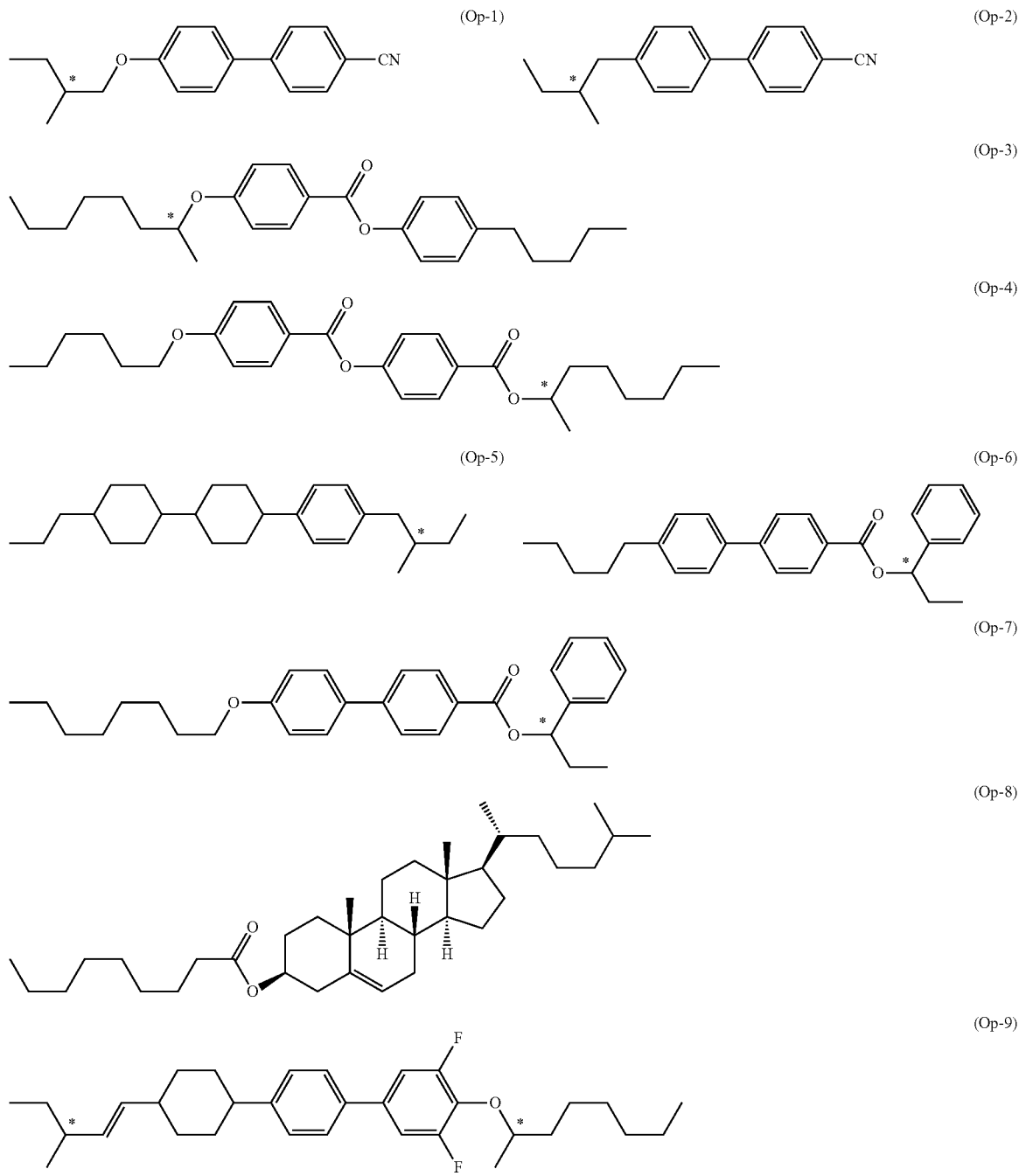

-continued
(Op-10)
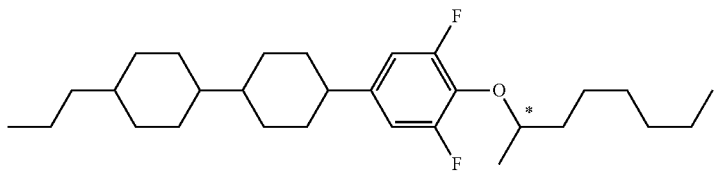
(Op-11)
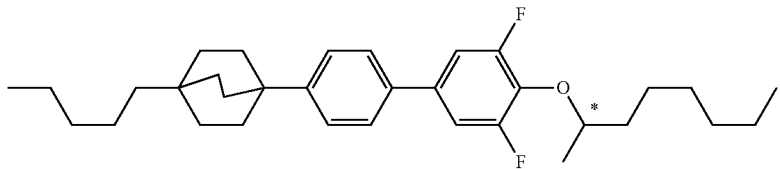
(Op-12)
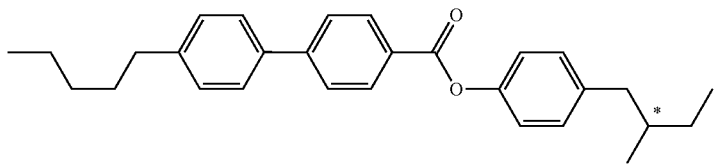
(Op-13)
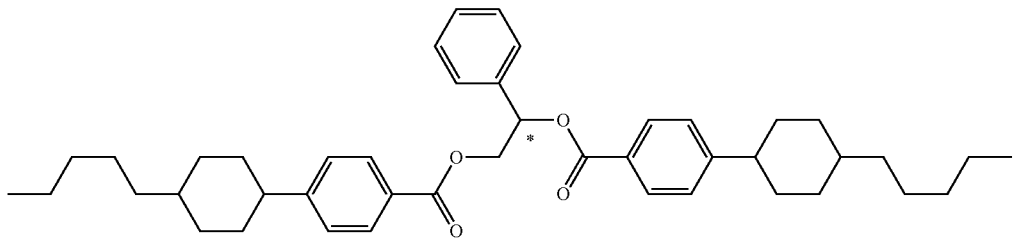
(Op-14)
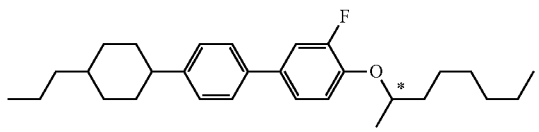
(Op-15)
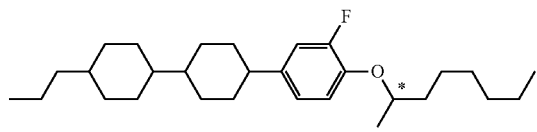
(Op-16)
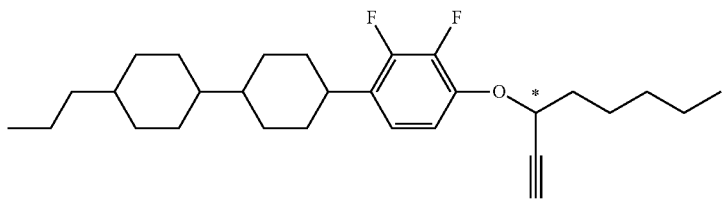
(Op-17)
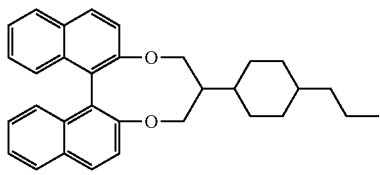
(Op-18)
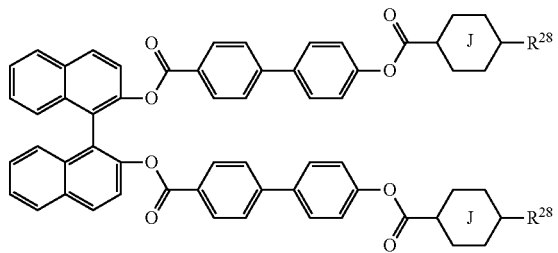

The antioxidant is effective for maintaining a large voltage holding ratio. Specific preferred examples of the antioxidant include compounds (AO-1) and (AO-2) described below; and IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease in the maximum temperature. Preferred examples of the ultraviolet light absorber include a benzophenone derivative, a benzoate derivative and a triazole derivative. Specific examples include compounds (AO-3) and (AO-4) described below; TINUVIN329, TINUVIN P, TINUVIN 326, TINUVIN 234, TINUVIN 213, TINUVIN 400, TINUVIN 328 and TINUVIN 99-2 (trade names: BASF SE); and 1,4-diazabicyclo[2.2.2]octane (DABCO).

A light stabilizer such as an amine having steric hindrance is preferred for maintaining the large voltage holding ratio. Preferred examples of the light stabilizer include compounds (AO-5) and (AO-6) described below; and TINUVIN 144, TINUVIN 765 and TINUVIN 770DF (trade names: BASF SE). Further preferred examples of the light stabilizer include compound (1). The heat stabilizer is also effective for maintaining the large voltage holding ratio, and specific preferred examples include Irgafos 168 (trade name: BASF SE). The antifoaming agent is effective for preventing foam formation. Preferred examples of the antifoaming agent include dimethyl silicone oil and methylphenyl silicone oil.

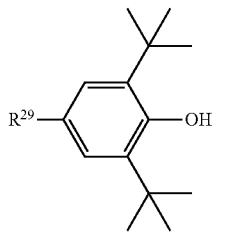
(AO-1)

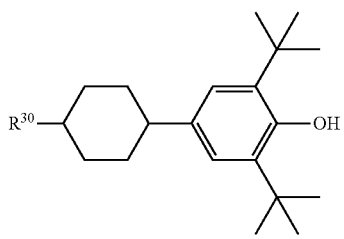
(AO-2)

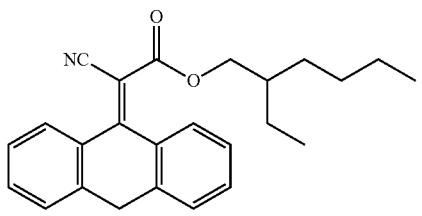
(AO-3)

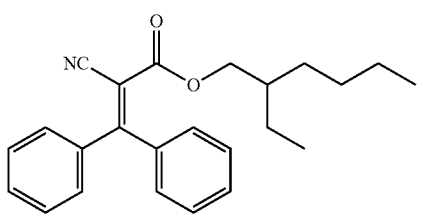
(AO-4)

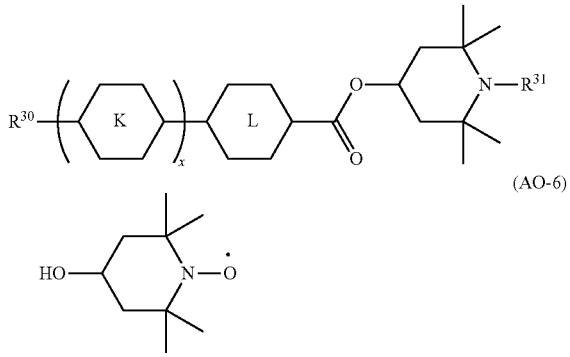
(AO-5)
(AO-6)

In compound (AO-1), $R^{29}$ is alkyl having 1 to 20 carbons, alkoxy having 1 to 20 carbons, $-COOR^{32}$ or $-CH_2CH_2COOR^{32}$, in which $R^{32}$ is alkyl having 1 to 20 carbons. In compounds (AO-2) and (AO-5), $R^{30}$ is alkyl having 1 to 20 carbons. In compound (AO-5), $R^{31}$ is hydrogen, methyl or O. (oxygen radical), ring K and ring L are 1,4-cyclohexylene or 1,4-phenylene, and x is 0, 1 or 2.

4. Liquid Crystal Display Device

A liquid crystal composition can be used for a liquid crystal display device having an operating mode such as PC, TN, STN, OCB and PSA, and driven by an active matrix (AM mode). The composition can also be used for a liquid crystal display device having the operating mode such as PC, TN, STN, OCB, VA and IPS, and driven by a passive matrix (PM) mode. The devices driven by the AM mode and the PM mode can be applied to any of a reflective type, a transmissive type and a transflective type.

The composition can also be used for a nematic curvilinear aligned phase (NCAP) device prepared by microencapsulating a nematic liquid crystal, and a polymer dispersed liquid crystal display device (PDLCD) and a polymer network liquid crystal display device (PNLCD), in which a three-dimensional network polymer is formed in the liquid crystal. When an amount of addition of the polymerizable compound is in the range of approximately 10% by weight or less based on the weight of the liquid crystal composition, the liquid crystal display device having the PSA mode is prepared. A preferred ratio is in the range of approximately 0.1% by weight to approximately 2% by weight. A further preferred ratio is in the range of approximately 0.2% by weight to approximately 1.0% by weight. The device having the PSA mode can be driven by the driving mode such as the active matrix and the passive matrix. Such a device can be applied to any of the reflective type, the transmissive type and the transflective type. An increase in the amount of addition of the polymerizable compound also allows preparation of a device having a polymer dispersed mode.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in more detail by way of Examples (including Use Examples). The invention includes a mixture of a composition in Use Example 1 and a composition in Use Example 2. The invention also includes a composition prepared by mixing at least two compositions in Use Examples. The invention is not limited by the Examples.

1. Example of Compound (1)

Compound (1) was prepared according to procedures described in Examples. Unless otherwise described, a reaction was performed under a nitrogen atmosphere. Compound (1) was prepared according to procedures described in Example 1 or the like. A compound prepared was identified by a method such as an NMR analysis. Characteristics of the compound were measured by methods described below.

NMR Analysis

For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using $CFCl_3$ as an internal standard. In the explanation of nuclear magnetic resonance spectrum, s, d, t, q, quin, sex and m stand for a singlet, a doublet, a triplet, a quartet, a quintet, a sextet and a multiplet, respectively, and br means being broad.

Gas Chromatographic Analysis

For measurement, GC-2010 Gas Chromatograph made by Shimadzu Corporation was used. As a column, a capillary column DB-1 (length 60 m, bore 0.25 mm, film thickness 0.25 μm) made by Agilent Technologies, Inc. was used. Helium was used as a carrier gas, and a flow rate was adjusted to 1 milliliter per minute. A temperature in a sample injector and a detector (FID) part were set to 300° C. and 300° C., respectively. A sample was dissolved in acetone to prepare a solution having 1% by weight, and 1 microliter of the solution obtained was injected into the sample injector. As a recorder, GCSolution System made by Shimadzu Corporation or the like was used.

HPLC Analysis

For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector and a CORONA detector or the like was appropriately used. When the UV detector was used, a detection wavelength was set at 254 nanometers. A sample was dissolved in acetonitrile to prepare a solution having 0.1% by weight, and 1 microliter of the solution obtained was introduced into a sample injector. As a recorder, C-R7A plus made by Shimadzu Corporation was used.

Ultraviolet-Visible Spectrophotometry

For measurement, PharmaSpec UV-1700 made by Shimadzu Corporation was used. A detection wavelength was adjusted in the range of 190 nanometers to 700 nanometers. A sample was dissolved in acetonitrile and prepared to be a solution having 0.01 millimole per liter, and measurement was carried out by putting the solution in a quartz cell (optical path length 1 cm).

Sample for Measurement

Upon measuring phase structure and transition temperature (a clearing point, a melting point, polymerization starting temperature, or the like), a compound itself was used as a sample. Upon measuring characteristics such as a maximum temperature of a nematic phase, viscosity, optical anisotropy and dielectric anisotropy, a mixture of a compound and a base liquid crystal was used as a sample.

Measurement Methods

Characteristics were measured by methods described below. Most of the methods are applied as described in the Standard of Japan Electronics and Information Technology Industries Association (hereinafter, abbreviated as JEITA) discussed and established in JEITA (JEITA ED-2521B), or as modified thereon. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a scanning calorimeter, Diamond DSC System, made by PerkinElmer, Inc., or a high-sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A melting point and a polymerization starting temperature of a compound were also measured using the apparatus. Temperature at which a compound undergoes transition from a solid to a liquid crystal phase such as a smectic phase and the nematic phase may be occasionally abbreviated as "minimum temperature of the liquid crystal phase." Temperature at which a compound undergoes transition from the liquid crystal phase to a liquid may be occasionally abbreviated as a "clearing point."

Crystals were expressed as C. When kinds of the crystals were distinguishable, each of the crystals was expressed as $C_1$ or $C_2$. A smectic phase and a nematic phase were expressed as S and N, respectively. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from a crystal to a nematic phase is 50.0° C., and a transition temperature from the nematic phase to a liquid is 100.0° C.

(3) Maximum Temperature of Nematic Phase ($T_{NI}$ or NI; ° C.)

A sample was placed on a hot plate of a melting point apparatus equipped with a polarizing microscope and was heated at a rate of 1° C. per minute. Temperature when part of the sample began to change from a nematic phase to an isotropic liquid was measured. A higher limit of a temperature range of the nematic phase may be occasionally abbreviated as "maximum temperature." When the sample was a mixture of compound (1) and the base liquid crystal, the maximum temperature was expressed using a symbol $T_{NI}$.

When the sample was a mixture of compound (1) and a compound such as components B, C and D, the maximum temperature was expressed using a symbol NI.

(4) Minimum Temperature of Nematic Phase ($T_C$; ° C.)

Samples each having a nematic phase were kept in freezers at temperatures of 0° C., −10° C., −20° C., −30° C. and −40° C. for 10 days, and then the liquid crystal phases were observed. For example, when the sample maintained the nematic phase at −20° C. and changed to the crystals or the smectic phase at −30° C., $T_c$ was expressed as $T_c \leq -20°$ C. A lower limit of the temperature range of the nematic phase may be occasionally abbreviated as "minimum temperature."

(5) Viscosity (Bulk Viscosity; η; Measured at 20° C.; mPa·s)

A cone-plate (E type) rotational viscometer made by TOKYO KEIKI INC. was used for measurement.

(6) Optical Anisotropy (Refractive Index Anisotropy; Measured at 25° C.; Δn)

Measurement was carried out by an Abbe refractometer with a polarizing plate mounted on an ocular by using light at a wavelength of 589 nanometers. A surface of a main prism was rubbed in one direction, and then a sample was added dropwise onto the main prism. A refractive index (n∥) was measured when a direction of polarized light was parallel to the direction of the rubbing. A refractive index (n⊥) was measured when a direction of polarized light was perpendicular to the direction of the rubbing. A value of optical anisotropy (Δn) was calculated from an equation: Δn=n∥−n⊥.

(7) Specific Resistance (ρ; Measured at 25° C.; Ωcm)

Into a vessel provided with electrodes, 1.0 milliliter of sample was injected. Direct current voltage (10 V) was applied to the vessel, and a direct current after 10 seconds was measured. The specific resistance was calculated from an expression described below: (Specific resistance)={(voltage)×(electric capacity of a vessel)}/{(direct current)×(dielectric constant of a vacuum)}.

(8) Voltage Holding Ratio (VHR-1; Measured at 25° C.; %)

A TN device used for measurement had a polyimide alignment film and a distance (cell gap) between two glass substrates was 5 micrometers. A sample was put in the device, and then the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was obtained. Area B was an area without decay. A voltage holding ratio is expressed in terms of a percentage of area A to area B.

(9) Voltage Holding Ratio (VHR-2; Measured at 80° C.; %)

A voltage holding ratio was measured in procedures identical with the procedures described above except that the voltage holding ratio was measured at 80° C. in place of 25° C. The results obtained were expressed using a symbol VHR-2.

Methods for measuring characteristics may be occasionally different between a sample having positive dielectric anisotropy and a sample having negative dielectric anisotropy. The measurement method in positive dielectric anisotropy was described in sections (10a) to (14a). The measurement method in negative dielectric anisotropy was described in sections (10b) to (14b).

(10a) Viscosity (Rotational Viscosity; γ1; Measured at 25° C.; mPa·s)

Positive dielectric anisotropy: Measurement was carried out according to a method described in M. Imai et al., Molecular Crystals and Liquid Crystals, Vol. 259, 37 (1995). A sample was put in a TN device in which a twist angle was 0 degrees and a distance (cell gap) between two glass substrates was 5 micrometers. A voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. A value of dielectric anisotropy required for the calculation was determined using the device by which the rotational viscosity was measured and by a method described below.

(10b) Viscosity (Rotational Viscosity; γ1; Measured at 25° C.; mPa·s)

Negative dielectric anisotropy: Measurement was carried out according to a method described in M. Imai et al., Molecular Crystals and Liquid Crystals, Vol. 259, 37 (1995). A sample was put in a VA device in which a distance (cell gap) between two glass substrates was 20 micrometers. A voltage was applied stepwise to the device in the range of 39 V to 50 V at an increment of 1.0 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. As a value of dielectric anisotropy necessary for the calculation, a value measured in the section of dielectric anisotropy described below was used.

(11a) Dielectric Anisotropy (Δ∈; Measured at 25° C.)

Positive dielectric anisotropy: A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (∈∥) in a major axis direction of liquid crystal molecules was measured. Sine waves (0.5 V, 1 kHz) were applied to the device, and after 2 seconds, a dielectric constant (∈⊥) in a minor axis direction of the liquid crystal molecules was measured. A value of dielectric anisotropy was calculated from an equation: Δ∈=∈∥−∈⊥.

(11b) Dielectric Anisotropy (Δ∈; Measured at 25° C.)

Negative dielectric anisotropy: A value of dielectric anisotropy was calculated from an equation: Δ∈=∈∥−∈⊥. A dielectric constant (∈∥ and ∈⊥) was measured as described below. (1) Measurement of dielectric constant (∈∥): An ethanol (20 mL) solution of octadecyl triethoxysilane (0.16 mL) was applied to a well-cleaned glass substrate. The glass substrate was rotated with a spinner, and then heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈∥) in a major axis direction of liquid crystal molecules was measured. (2) Measurement of dielectric constant (∈⊥): A polyimide solution was applied to a well-cleaned glass substrate. After calcining the glass substrate, rubbing treatment was applied to an alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in a minor axis direction of the liquid crystal molecules was measured.

(12a) Elastic Constant (K; Measured at 25° C.; pN)

Positive dielectric anisotropy: HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.), and the values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K was expressed using a mean value of thus determined $K_{11}$, $K_{22}$ and $K_{33}$.

(12b) Elastic Constant ($K_{11}$ and $K_{33}$; Measured at 25° C.; pN)

Negative dielectric anisotropy: Elastic Constant Measurement System Model EC-1 made by TOYO Corporation was used for measurement. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(13a) Threshold Voltage (Vth; Measured at 25° C.; V)

Positive dielectric anisotropy: An LCD-5100 luminance meter made by Otsuka Electronics Co., Ltd. was used for measurement. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a perpendicular direction, and an amount of light transmitted through the device was measured. A voltage-transmittance curve was prepared, in which the maximum value of the amount of light corresponded to 100% transmittance and the minimum value of an amount of light corresponded to 0% transmittance. A threshold voltage is expressed in terms of a voltage at 90% transmittance.

(13b) Threshold Voltage (Vth; Measured at 25° C.; V)

Negative dielectric anisotropy: An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) applied to the device was increased stepwise from 0 V to 20 V at an increment of 0.02 V. On the occasion, the device was irradiated with light from a perpendicular direction, and an amount of light transmitted through the device was measured. A voltage-transmittance curve was prepared, in which the maximum value of the amount of light corresponded to 100% transmittance and the minimum value of the amount of light corresponded to 0% transmittance. A threshold voltage was expressed by a voltage at 10% transmittance.

(14a) Response Time (T; Measured at 25° C.; ms)

Positive dielectric anisotropy: An LCD-5100 luminance meter made by Otsuka Electronics Co., Ltd. was used for measurement. A light source was a halogen lamp. A low-pass filter was set to 5 kHz. A sample was put in a normally white mode TN device in which a distance (cell gap) between two glass substrates was 5.0 micrometers and a twist angle was 80 degrees. Rectangular waves (60 Hz, 5 v, 0.5 second) were applied to the device. On the occasion, the device was irradiated with light from a perpendicular direction, and an amount of light transmitted through the device was measured. The maximum amount of light corresponded to 100% transmittance, and the minimum amount of light corresponded to 0% transmittance. A rise time (τr: rise time; millisecond) is a period of time required for a change in transmittance from 90% to 10%. A fall time (τf: fall time; millisecond) is a period of time required for a change in transmittance from 10% to 90%. A response time was expressed by a sum of the rise time and the fall time thus obtained.

(14b) Response Time (τ; Measured at 25° C.; ms)

Negative dielectric anisotropy: An LCD-5100 luminance meter made by Otsuka Electronics Co., Ltd. was used for measurement. A light source was a halogen lamp. A low-pass filter was set to 5 kHz. A sample was put in a normally black mode PVA device in which a distance (cell gap) between two glass substrates was 3.2 micrometers and a rubbing direction was anti-parallel. The device was sealed using an ultraviolet-curable adhesive. A voltage having a degree a little over a threshold voltage was applied to the device for 1 minute, and then the device was irradiated with ultraviolet light having 23.5 mW/cm$^2$ for 8 minutes while applying a voltage of 5.6 V. Rectangular waves (60 Hz, 10 V, 0.5 second) were applied to the device. On the occasion, the device was irradiated with light from a perpendicular direction, and an amount of light transmitted through the device was measured. The maximum amount of light corresponded to 100% transmittance, and the minimum amount of light corresponded to 0% transmittance. A response time was expressed by a period of time required for a change from 90% transmittance to 10% transmittance (fall time; millisecond).

Example 1

Synthesis of Compound (No. 37)

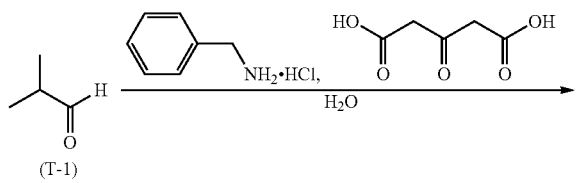

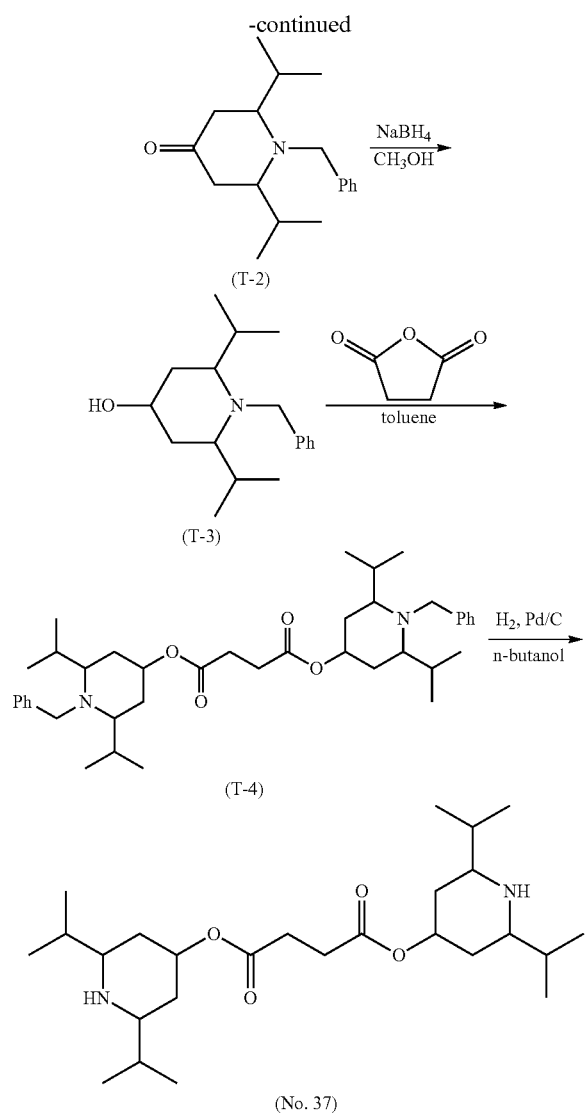

(T-2)

(T-3)

(T-4)

(No. 37)

First step

In a 300-mL Erlenmeyer flask, isobutyraldehyde (T-1) (24.50 g, 0.34 mol) and 130 g of water were put, and the resulting mixture was cooled to 4° C. Benzylamine hydrochloride (31.60 g, 0.22 mol) was added thereto, and the resulting mixture was stirred for 30 minutes, and then acetonedicarboxylic acid (24.80 g, 0.17 mol) and a sodium acetate aqueous solution (sodium acetate (6.4 g, 0.078 mol), water 50 g) were added thereto. The resulting reaction mixture was slowly heated to room temperature, and stirred at room temperature for 30 hours. Deposited crystals were obtained by filtration to obtain piperidinone form (T-2) (12.25 g, yield 26.4%).

Second Step

In a 1-L beaker, piperidinone form (T-2) (20.49 g, 0.074 mol) and 375 mL of methanol were put, and sodium borohydride (5.67 g, 0.150 mol) was slowly added at 20° C. The resulting reaction mixture was stirred for 1 hour, and then a solvent was distilled off, and 95 mL of a saturated ammonium chloride aqueous solution was added thereto. The resulting mixture was subjected to extraction with 150 mL of toluene, an organic layer was washed with 500 mL of saturated brine, and dried over anhydrous magnesium sulfate, and a solvent was distilled off. The residue was recrystallized from hexane to obtain piperidinol form (T-3) (10.64 g, yield 52.0%).

Third Step

In a 200-mL three-necked flask, piperidinol form (T-3) (3.30 g, 0.012 mol), succinic anhydride (0.60 g, 0.006 mol) and 100 mL of toluene were put, and the resulting mixture was refluxed for 1 hour. The resulting mixture was cooled to 40° C., and then p-toluenesulfonic acid monohydrate (3.42 g, 0.018 mol) was added thereto, and the resulting mixture was refluxed again for 45 hours. The resulting reaction mixture was allowed to cool to room temperature, and a 15 wt % sodium hydrogencarbonate aqueous solution was added thereto, and an organic layer was separated and taken. An organic layer was washed with 500 mL of saturated brine, and dried over anhydrous magnesium sulfate, and a solvent was distilled off. The residue was purified by silica gel column chromatography using heptane to obtain ester form (T-4) (2.20 g, yield 29.2%).

Fourth Step

In a 500-mL four-necked flask, ester form (T-4) (5.06 g, 0.008 mol) and 200 mL of n-butanol were put, and the resulting mixture was decompressed, and an atmosphere was replaced by argon. Then, 10% palladium on carbon (0.46 g, 9% by weight) was added thereto, and the resulting mixture was decompressed again, and an atmosphere was replaced by hydrogen. The resulting mixture was stirred at 50° C. for 40 hours, and then the resulting reaction mixture was filtrated and a solvent of a filtrate was distilled off. The residue was purified by silica gel column chromatography using heptane and further recrystallized from hexane to obtain compound (No. 37) (1.93 g, yield 53.8%).

$^1$H-NMR (CDCl$_3$; δ ppm): 4.97 (tt, J=10.5, 4.5 Hz, 2H), 2.64-2.56 (m, 6H), 2.48-2.44 (m, 2H), 2.05-1.95 (m, 4H), 1.93-1.87 (m, 2H), 1.65-1.53 (m, 6H), 1.25 (ddd, J=11.8, 10.5, 10.5 Hz, 2H), 0.93-0.89 (m, 24H).

Example 2

Synthesis of Compound (No. 38)

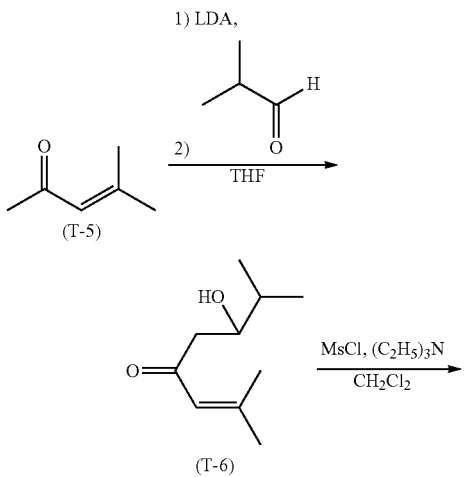

(T-5)

(T-6)

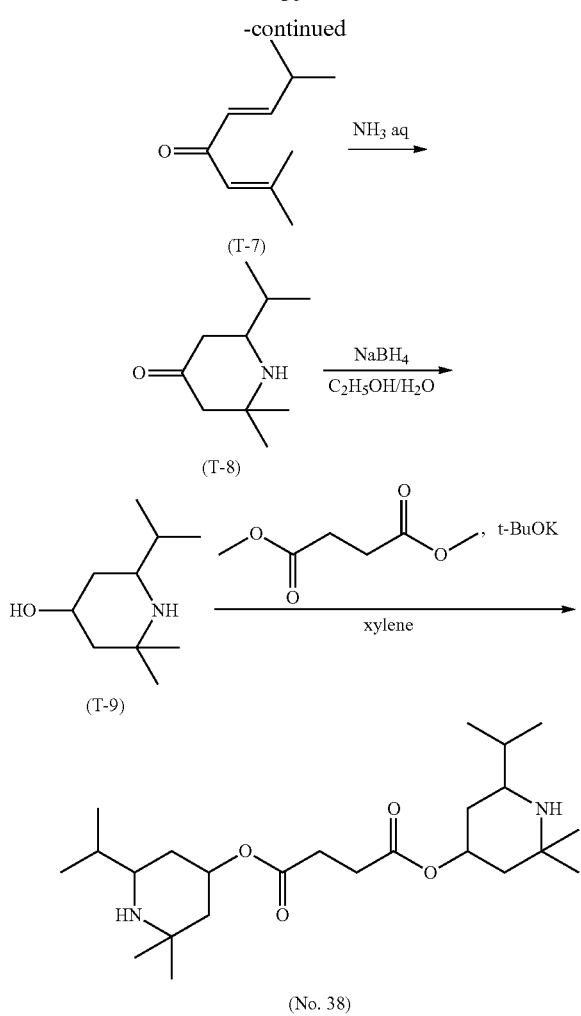

First Step

In a 1-L four-necked flask, 800 mL of THF was put, and then an atmosphere inside a system was replaced by argon. The resulting mixture was cooled to −15° C., and lithium diisopropylamide (2.00 mol/1,100 mL, 0.20 mol) was added thereto. The resulting mixture was cooled to −65° C., mesityl oxide (T-5) (19.05 g, 0.20 mol) was added thereto, and the resulting mixture was stirred for 1 hour. Subsequently, a THF solution (80 mL) of isobutyraldehyde (12.62 g, 0.17 mol) was added dropwise thereto for 30 minutes. The resulting reaction mixture was stirred for 1 hour, and then heated to 0° C., 800 mL of saturated ammonium chloride aqueous solution was added thereto, and the resulting mixture was stirred. The resulting mixture was subjected to extraction with 100 mL of ethyl acetate three times, and an organic layer was washed with 800 mL of saturated brine, and dried over anhydrous magnesium sulfate, and then a solvent was distilled off to obtain enone form (T-6) (30.7 g). Enone form (T-6) was used for the following step without purification.

Second Step

In a 1-L four-necked flask, enone form (T-6) (30.7 g, 0.18 mol), triethylamine (44.2 g, 0.43 mol) and 750 mL of dichloromethane were put, and an atmosphere was replaced by argon and the resulting mixture was cooled to 0° C. Methanesulfonyl chloride (24.2 g, 0.21 mol) was added thereto, and the resulting mixture was heated to 18° C. for 20 minutes, and stirred for 8 hours. Then, 500 mL of saturated sodium hydrogencarbonate aqueous solution was added to the resulting reaction mixture, the resulting mixture was stirred, subjected to extraction with 100 mL of dichloromethane three times, and an organic layer was washed with 1,000 mL of saturated brine, and dried over anhydrous magnesium sulfate, and then a solvent was distilled off. The residue was purified by silica gel column chromatography using heptane to obtain dienone form (T-7) (18.1 g, yield 70.6% (based on isobutyraldehyde)).

Third Step

In a 300-mL pressure-resistant vessel, dienone form (T-7) (18.1 g, 0.12 mol) and a 28% ammonia aqueous solution (47.2 g, 0.78 mol) were put, and the resulting mixture was stirred at room temperature for 2 days. Then, 10 wt % dilute hydrochloric acid was added to an organic layer until pH was adjusted to 1, and the resultant mixture was subjected to extraction with 100 mL of dichloromethane two times, and unreacted dienone form (T-7) was removed. Potassium carbonate was added to an aqueous layer until pH was adjusted to 8, and the resulting mixture was subjected to extraction with 150 mL of dichloromethane three times. An organic layer was dried over anhydrous magnesium sulfate, and then a solvent was distilled off. The residue was purified by silica gel column chromatography using heptane to obtain piperidinone form (T-8) (5.63 g, yield 27.5%).

Fourth Step

In a 300-mL four-necked flask, piperidinone form (T-8) (15.7 g, 0.093 mol) and 200 mL of a mixed solvent of ethanol/water (1/1 in a volume ratio) were put, and the resulting mixture was cooled to 10° C. Sodium borohydride (1.78 g, 0.047 mol) was added thereto, and the resulting mixture was stirred for 1 hour. Then, 20 g of sodium chloride was added to the resulting reaction mixture, and then the resulting mixture was subjected to extraction with 100 mL of toluene two times. An organic layer was washed with 100 mL of saturated brine, and dried over potassium carbonate, and then a solvent was distilled off. The residue was purified by silica gel column chromatography using n-heptane and further by recrystallization from hexane to obtain piperidinol form (T-9) (3.00 g, yield 18.3%).

Fifth Step

Under a nitrogen flow, in a 100-mL three-necked flask on which a Dean-Stark condenser was mounted, piperidinol form (T-9) (3.00 g, 0.018 mol), dimethyl succinate (1.41 g, 0.0096 mol) and 15 mL of xylene were put. A THF solution (2.75 mL, 0.0028 mol) of 12% potassium t-butoxide was added thereto, and the resulting mixture was refluxed for 11 hours while methanol collected in the Dean-Stark condenser was distilled off. The resulting reaction mixture was allowed to cool to room temperature, and subjected to extraction with 20 mL of toluene. An organic layer was washed with 20 mL of saturated brine, and dried over anhydrous magnesium sulfate, and then a solvent was distilled off. The residue was purified by silica gel column chromatography using heptane to obtain compound (No. 38) (0.84 g, yield 22.6%).

$^1$H-NMR (CDCl$_3$; δ ppm): 5.18 (br, 2H), 2.73 (ddd, J=11.4, 6.6, 1.6 Hz, 2H), 2.69-2.58 (m, 6H), 1.83-1.73 (m, 4H), 1.52 (dq, J=13.6, 6.8 Hz, 2H), 1.44 (dd, J=14.7, 3.4 Hz, 2H), 1.26-1.20 (m, 8H), 1.09 (s, 6H), 0.93 (d, J=6.7, 6H), 0.90 (d, J=6.8, 6H).

Example 3

Synthesis of Compound (No. 167)

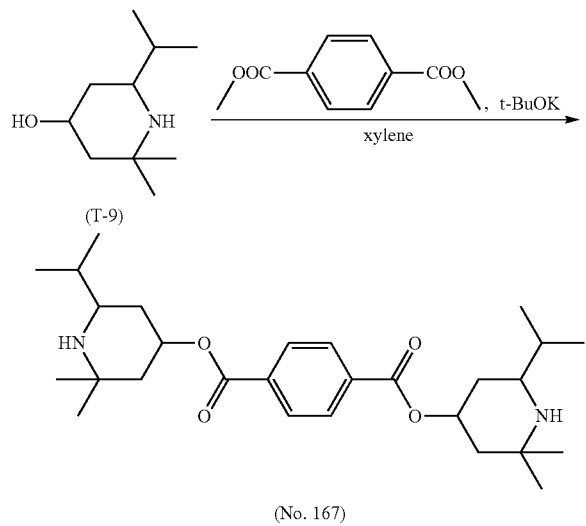

Under a nitrogen flow, in a 100-mL three-necked flask on which a Dean-Stark condenser was mounted, piperidinol form (T-9) (2.00 g, 0.012 mol), dimethyl terephthalate (1.13 g, 0.0058 mol) and 10 mL of xylene were put. A THF solution (12%; 1.17 ml, 0.0012 mol) of potassium t-butoxide was added thereto, and the resulting mixture was refluxed for 2 hours while methanol collected in the Dean-Stark condenser was distilled off. The resulting reaction mixture was allowed to cool to room temperature, and subjected to extraction with 25 mL of toluene. An organic layer was washed with 100 mL of water, and dried over anhydrous magnesium sulfate, and then a solvent was distilled off. The residue was purified by recrystallization from acetone to obtain compound (No. 167) (0.70 g, yield 27.6%).

$^1$H-NMR (CDCl$_3$; δ ppm): 8.13 (s, 4H), 5.47-5.45 (m, 2H), 2.85 (ddd, J=11.5, 6.5, 2.1 Hz, 2H), 2.00-1.96 (m, 4H), 1.60-1.55 (m, 4H), 1.37 (ddd, J=14.6, 11.9, 3.4 Hz, 2H), 1.33 (s, 6H), 1.14 (s, 6H), 0.97 (br, 2H), 0.95 (d, J=6.7, 6H), 0.92 (d, J=6.7, 6H).

Compounds (No. 1) to (No. 376) and so forth shown below can be prepared according to the synthesis methods described in Examples 1 to 3.

| No. | |
|---|---|
| 1 | 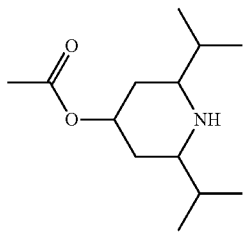 [SMILES: CC(=O)OC1CC(C(C)C)NC(C(C)C)C1] |
| 2 | 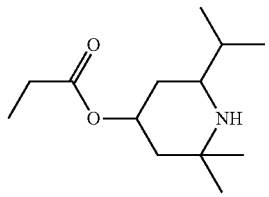 [SMILES: CCC(=O)OC1CC(C(C)C)NC(C)(C)C1] |
| 3 | 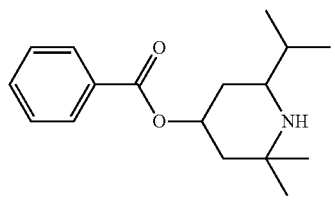 [SMILES: CC(C)C1CC(OC(=O)c2ccccc2)CC(C)(C)N1] |

| No. | |
|---|---|
| 4 | 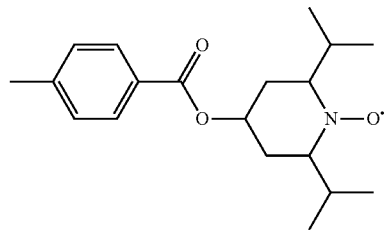 |
| 5 | 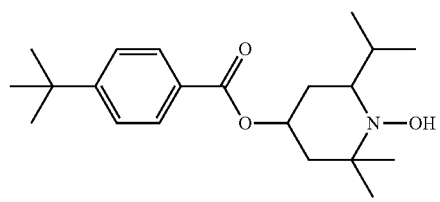 [SMILES: CC(C)C1CC(OC(=O)c2ccc(C(C)(C)C)cc2)CC(C)(C)N1O] |
| 6 | 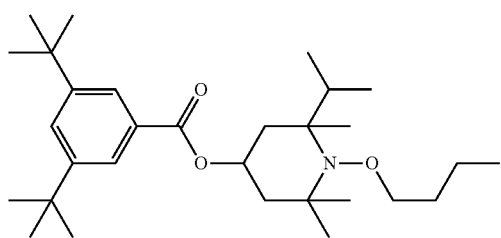 [SMILES: CCCCON1C(C)(C)CC(OC(=O)c2cc(C(C)(C)C)cc(C(C)(C)C)c2)CC1(C)C(C)C] |
| 7 | 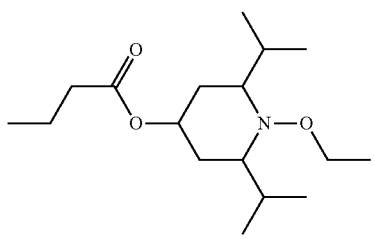 [SMILES: CCCC(=O)OC1CC(C(C)C)N(OCC)C(C(C)C)C1] |
| 8 | 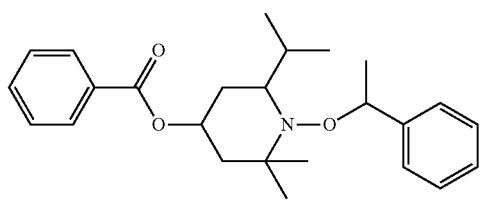 [SMILES: CC(ON1C(C(C)C)CC(OC(=O)c2ccccc2)CC1(C)C)c1ccccc1] |
| 9 | 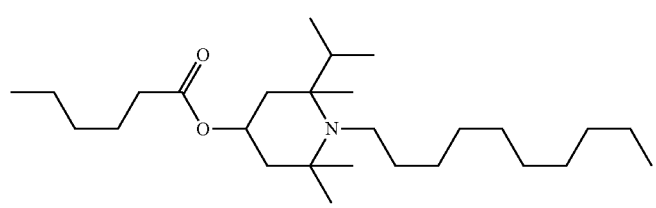 [SMILES: CCCCCCCCCCN1C(C)(C)CC(OC(=O)CCCCC)CC1(C)C(C)C] |

| No. | |
|---|---|
| 10 | 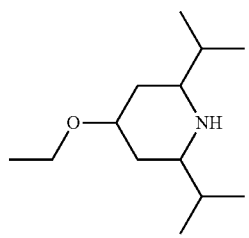 |
| 11 | 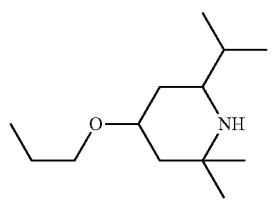 |
| 12 | 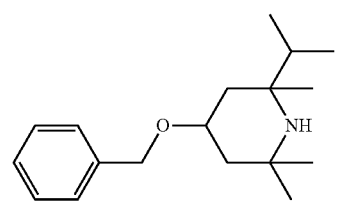 [SMILES: CC(C)C1(C)CC(OCc2ccccc2)CC(C)(C)N1] |
| 13 | 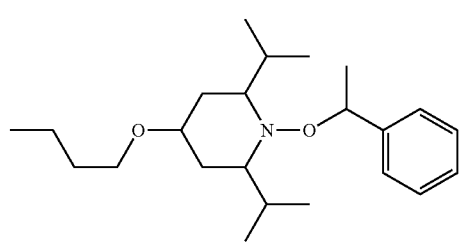 [SMILES: CCCCOC1CC(C(C)C)N(OC(C)c2ccccc2)C(C(C)C)C1] |
| 14 | 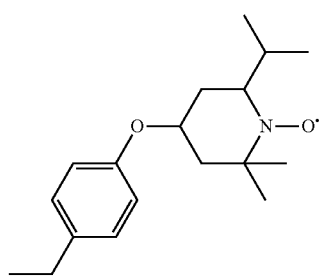 |
| 15 |  |

| No. | |
|---|---|
| 16 | 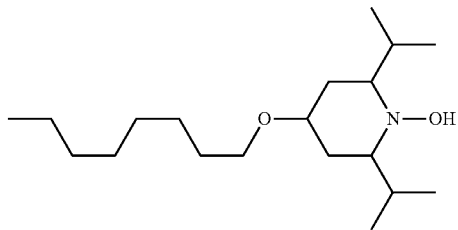 [SMILES: CCCCCCCCOC1CC(C(C)C)N(O)C(C(C)C)C1] |
| 17 | 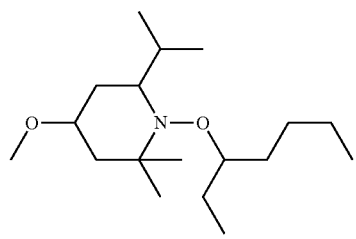 [SMILES: CCCCC(CC)ON1C(C(C)C)CC(OC)CC1(C)C] |
| 18 | 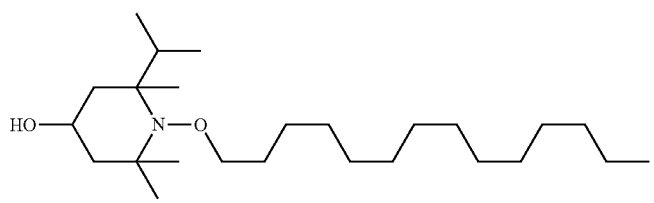 [SMILES: CCCCCCCCCCCCCCON1C(C)(C)CC(O)CC1(C)C(C)C] |
| 19 | 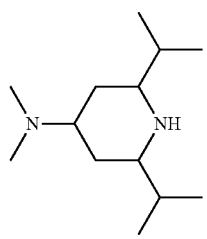 |
| 20 | 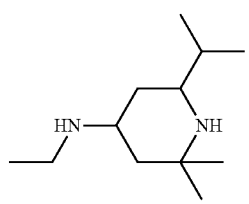 |
| 21 | 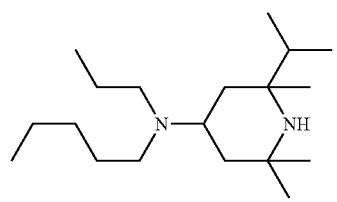 [SMILES: CCCCCN(CCC)C1CC(C)(C)NC(C)(C(C)C)C1] |

| No. | |
|---|---|
| 22 | 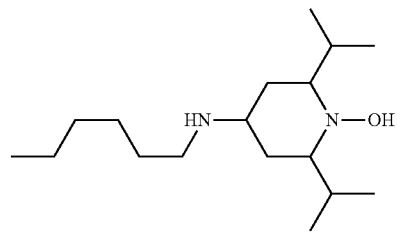 [SMILES: CCCCCCNC1CC(C(C)C)N(O)C(C(C)C)C1] |
| 23 | 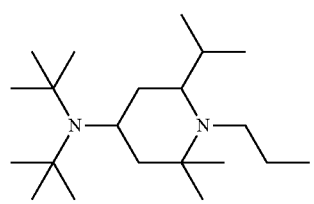 [SMILES: CCCN1C(C(C)C)CC(N(C(C)(C)C)C(C)(C)C)CC1(C)C] |
| 24 | 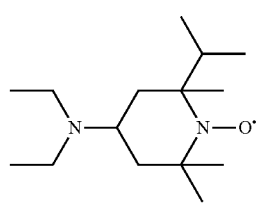 |
| 25 | 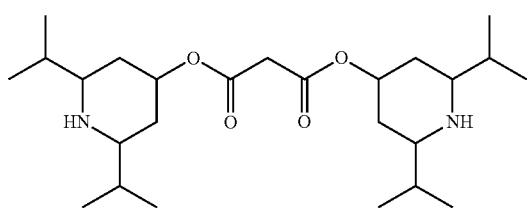 [SMILES: CC(C)C1CC(OC(=O)CC(=O)OC2CC(C(C)C)NC(C(C)C)C2)CC(C(C)C)N1] |
| 26 | 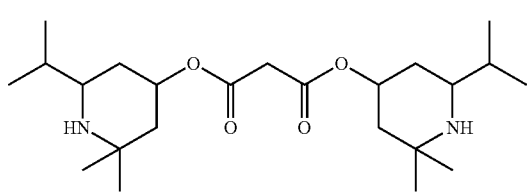 [SMILES: CC(C)C1CC(OC(=O)CC(=O)OC2CC(C(C)C)NC(C)(C)C2)CC(C)(C)N1] |
| 27 | 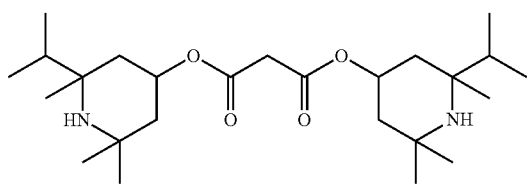 [SMILES: CC(C)C1(C)CC(OC(=O)CC(=O)OC2CC(C)(C)NC(C)(C(C)C)C2)CC(C)(C)N1] |
| 28 | 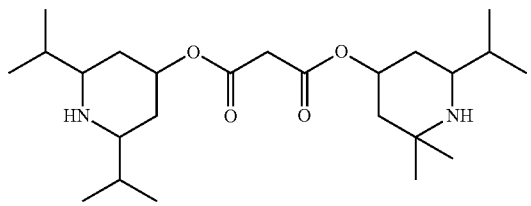 [SMILES: CC(C)C1CC(OC(=O)CC(=O)OC2CC(C(C)C)NC(C)(C)C2)CC(C(C)C)N1] |

| No. | |
|---|---|
| 29 | 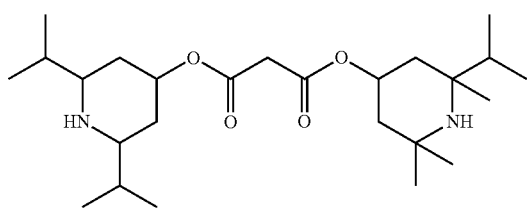 [SMILES: CC(C)C1CC(OC(=O)CC(=O)OC2CC(C)(C)NC(C)(C(C)C)C2)CC(C(C)C)N1] |
| 30 | 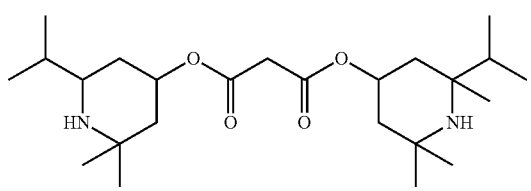 [SMILES: CC(C)C1CC(OC(=O)CC(=O)OC2CC(C)(C)NC(C)(C(C)C)C2)CC(C)(C)N1] |
| 31 | 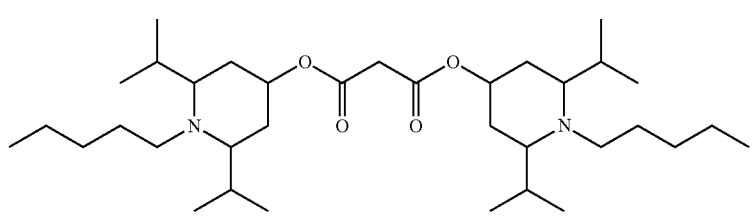 [SMILES: CCCCCN1C(C(C)C)CC(OC(=O)CC(=O)OC2CC(C(C)C)N(CCCCC)C(C(C)C)C2)CC1C(C)C] |
| 32 | 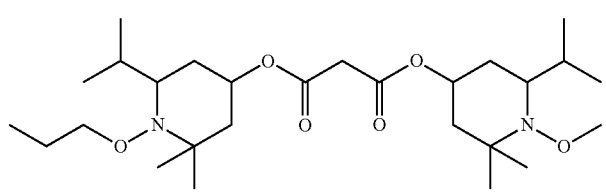 [SMILES: CCCON1C(C(C)C)CC(OC(=O)CC(=O)OC2CC(C(C)C)N(OC)C(C)(C)C2)CC1(C)C] |
| 33 |  |
| 34 | 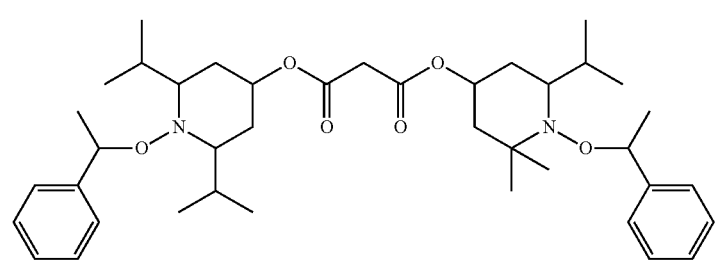 [SMILES: CC(ON1C(C(C)C)CC(OC(=O)CC(=O)OC2CC(C(C)C)N(OC(C)c3ccccc3)C(C)(C)C2)CC1C(C)C)c1ccccc1] |
| 35 | 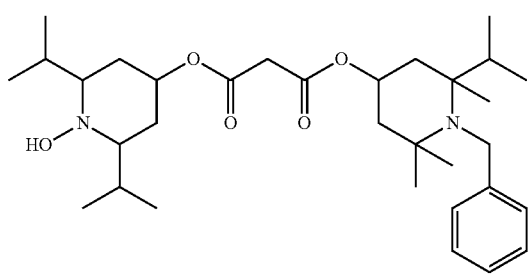 [SMILES: CC(C)C1CC(OC(=O)CC(=O)OC2CC(C)(C)N(Cc3ccccc3)C(C)(C(C)C)C2)CC(C(C)C)N1O] |

| No. | |
|---|---|
| 36 | 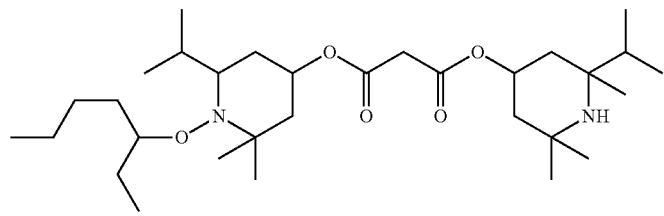 [SMILES: CCCCC(CC)ON1C(C(C)C)CC(OC(=O)CC(=O)OC2CC(C)(C)NC(C)(C(C)C)C2)CC1(C)C] |
| 37 | 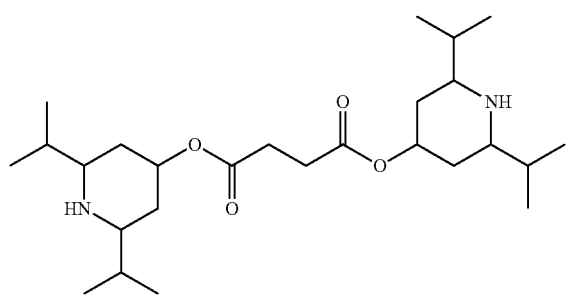 [SMILES: CC(C)C1CC(OC(=O)CCC(=O)OC2CC(C(C)C)NC(C(C)C)C2)CC(C(C)C)N1] |
| 38 | 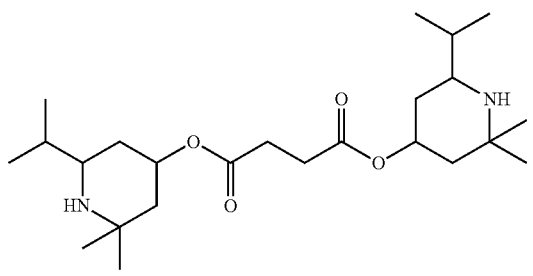 [SMILES: CC(C)C1CC(OC(=O)CCC(=O)OC2CC(C(C)C)NC(C)(C)C2)CC(C)(C)N1] |
| 39 | 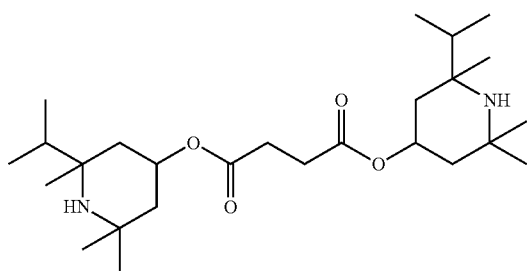 [SMILES: CC(C)C1(C)CC(OC(=O)CCC(=O)OC2CC(C)(C)NC(C)(C(C)C)C2)CC(C)(C)N1] |
| 40 | 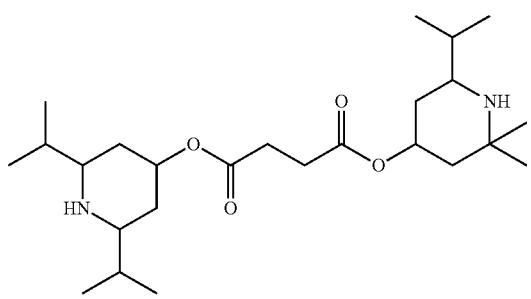 [SMILES: CC(C)C1CC(OC(=O)CCC(=O)OC2CC(C(C)C)NC(C)(C)C2)CC(C(C)C)N1] |

| No. | |
|---|---|
| 41 | 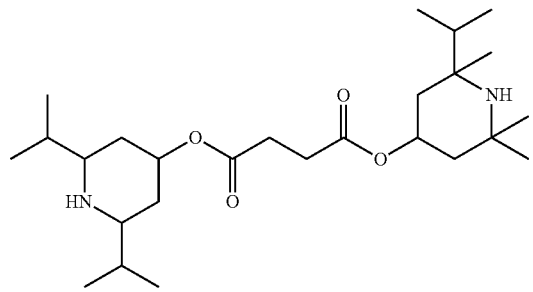 [SMILES: CC(C)C1CC(OC(=O)CCC(=O)OC2CC(C)(C)NC(C)(C(C)C)C2)CC(C(C)C)N1] |
| 42 | 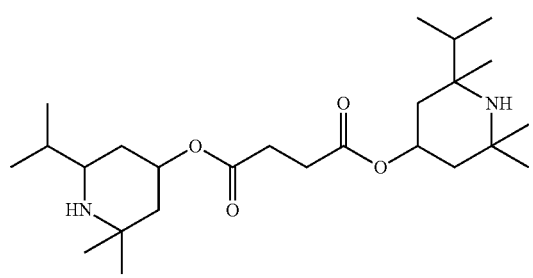 [SMILES: CC(C)C1CC(OC(=O)CCC(=O)OC2CC(C)(C)NC(C)(C(C)C)C2)CC(C)(C)N1] |
| 43 | 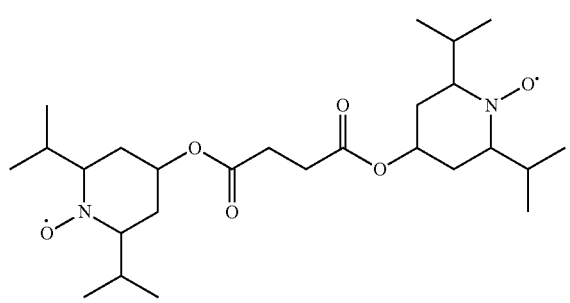 |
| 44 | 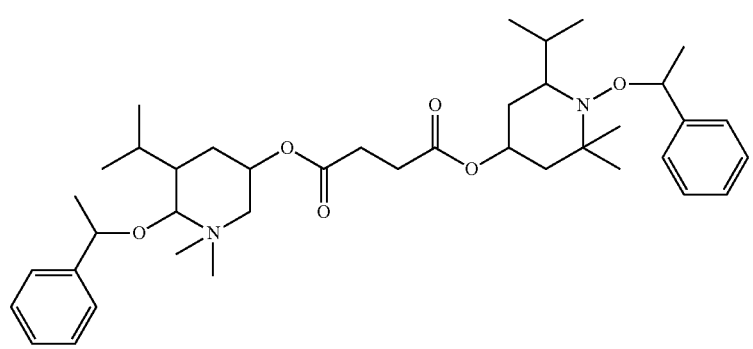 |
| 45 | 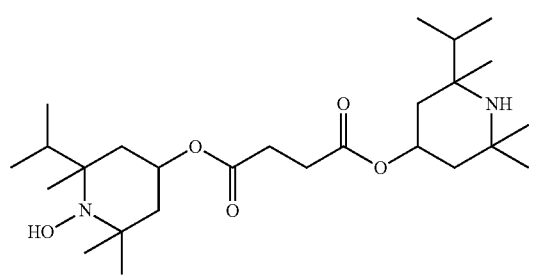 [SMILES: CC(C)C1(C)CC(OC(=O)CCC(=O)OC2CC(C)(C)N(O)C(C)(C(C)C)C2)CC(C)(C)N1] |

| No. | |
|---|---|
| 46 | 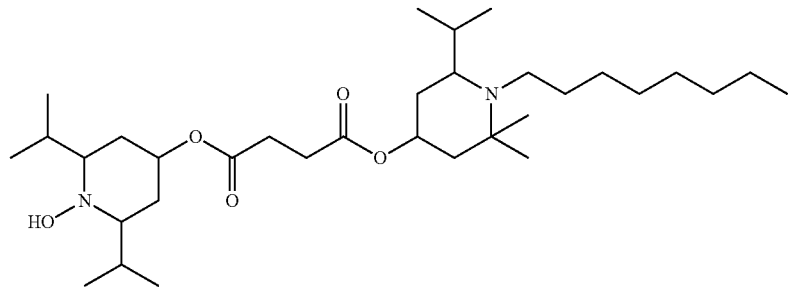 [SMILES: CCCCCCCCN1C(C(C)C)CC(OC(=O)CCC(=O)OC2CC(C(C)C)N(O)C(C(C)C)C2)CC1(C)C] |
| 47 | 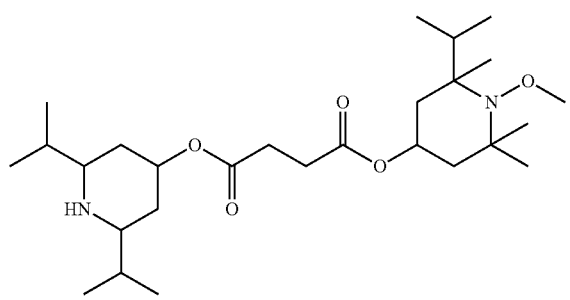 [SMILES: CON1C(C)(C)CC(OC(=O)CCC(=O)OC2CC(C(C)C)NC(C(C)C)C2)CC1(C)C(C)C] |
| 48 | 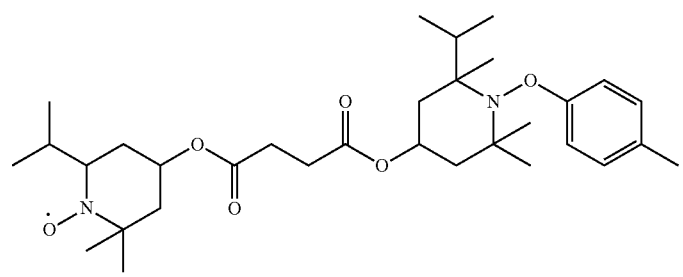 [SMILES: Cc1ccc(ON2C(C)(C)CC(OC(=O)CCC(=O)OC3CC(C(C)C)N(O)C(C)(C)C3)CC2(C)C(C)C)cc1] |
| 49 | 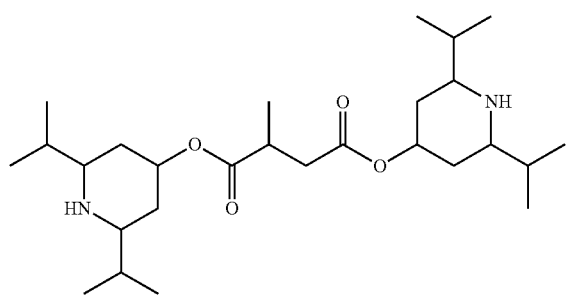 [SMILES: CC(CC(=O)OC1CC(C(C)C)NC(C(C)C)C1)C(=O)OC1CC(C(C)C)NC(C(C)C)C1] |
| 50 | 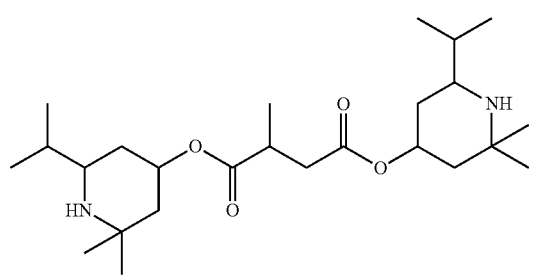 [SMILES: CC(CC(=O)OC1CC(C(C)C)NC(C)(C)C1)C(=O)OC1CC(C(C)C)NC(C)(C)C1] |

| No. | |
|---|---|
| 51 | 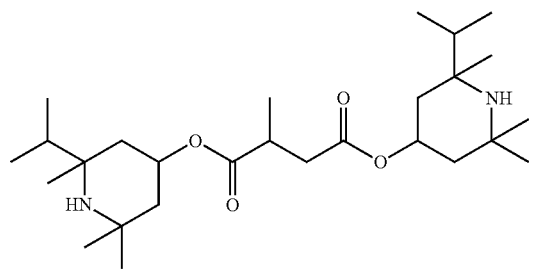 [SMILES: CC(CC(=O)OC1CC(C)(C)NC(C)(C(C)C)C1)C(=O)OC1CC(C)(C)NC(C)(C(C)C)C1] |
| 52 | 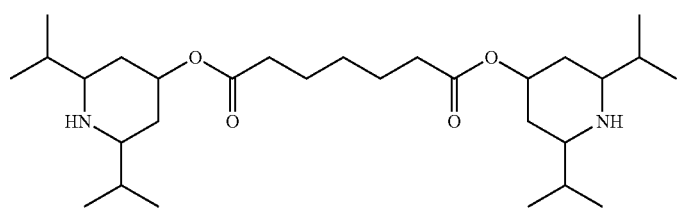 [SMILES: CC(C)C1CC(OC(=O)CCCCCC(=O)OC2CC(C(C)C)NC(C(C)C)C2)CC(C(C)C)N1] |
| 53 | 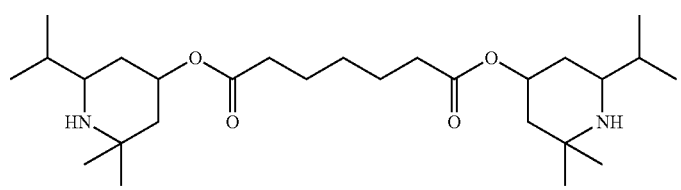 [SMILES: CC(C)C1CC(OC(=O)CCCCCC(=O)OC2CC(C(C)C)NC(C)(C)C2)CC(C)(C)N1] |
| 54 | 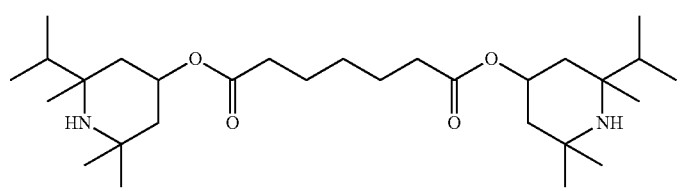 [SMILES: CC(C)C1(C)CC(OC(=O)CCCCCC(=O)OC2CC(C)(C)NC(C)(C(C)C)C2)CC(C)(C)N1] |
| 55 | 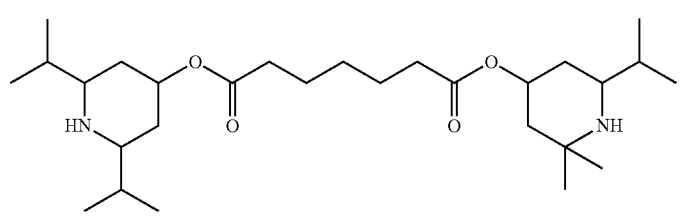 [SMILES: CC(C)C1CC(OC(=O)CCCCCC(=O)OC2CC(C(C)C)NC(C)(C)C2)CC(C(C)C)N1] |
| 56 | 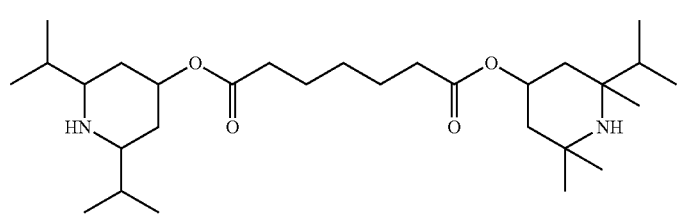 [SMILES: CC(C)C1CC(OC(=O)CCCCCC(=O)OC2CC(C)(C)NC(C)(C(C)C)C2)CC(C(C)C)N1] |
| 57 | 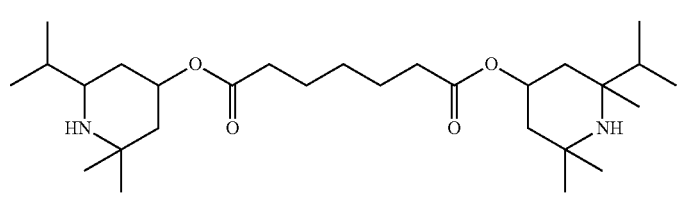 [SMILES: CC(C)C1CC(OC(=O)CCCCCC(=O)OC2CC(C)(C)NC(C)(C(C)C)C2)CC(C)(C)N1] |

-continued
| No. | |
|---|---|
| 58 | 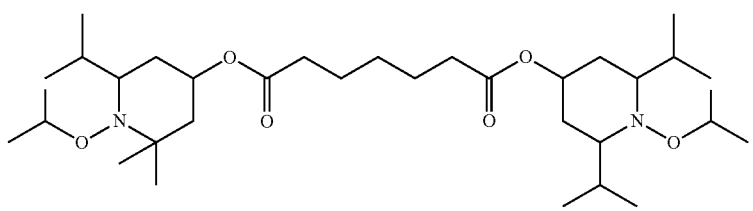 [SMILES: CC(C)ON1C(C(C)C)CC(OC(=O)CCCCCC(=O)OC2CC(C(C)C)N(OC(C)C)C(C)(C)C2)CC1C(C)C] |
| 59 | 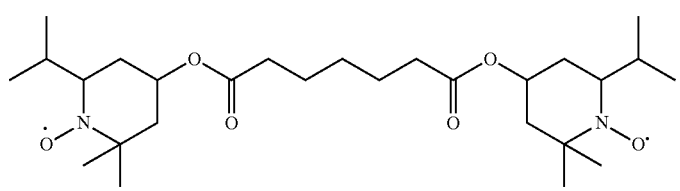 |
| 60 | 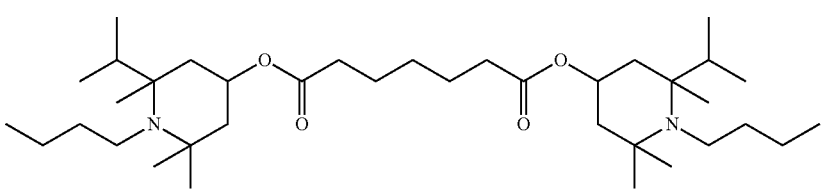 [SMILES: CCCCN1C(C)(C)CC(OC(=O)CCCCCC(=O)OC2CC(C)(C)N(CCCC)C(C)(C(C)C)C2)CC1(C)C(C)C] |
| 61 | 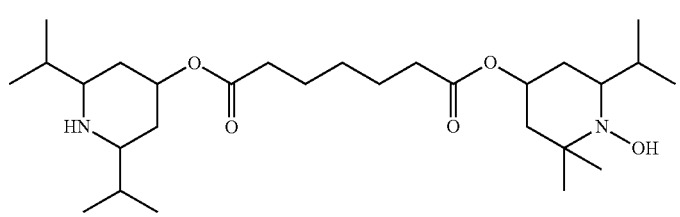 [SMILES: CC(C)C1CC(OC(=O)CCCCCC(=O)OC2CC(C(C)C)N(O)C(C)(C)C2)CC(C(C)C)N1] |
| 62 | 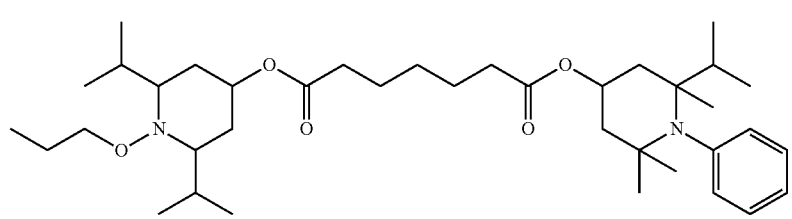 [SMILES: CCCON1C(C(C)C)CC(OC(=O)CCCCCC(=O)OC2CC(C)(C)N(c3ccccc3)C(C)(C(C)C)C2)CC1C(C)C] |
| 63 | 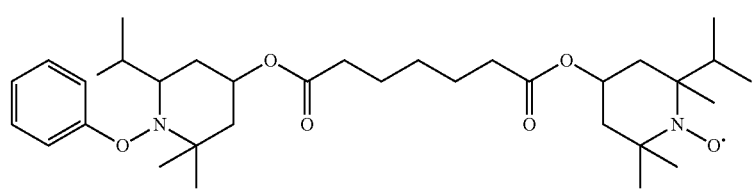 |
| 64 | 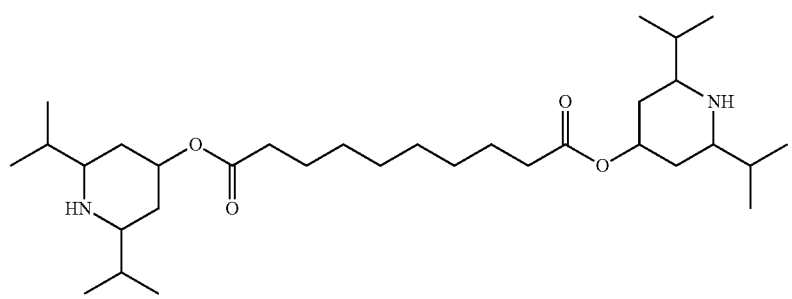 [SMILES: CC(C)C1CC(OC(=O)CCCCCCCCC(=O)OC2CC(C(C)C)NC(C(C)C)C2)CC(C(C)C)N1] |

-continued
| No. | |
|---|---|
| 65 | 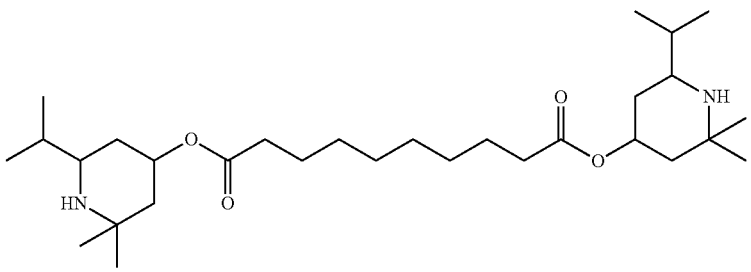 [SMILES: CC(C)C1CC(OC(=O)CCCCCCCCC(=O)OC2CC(C(C)C)NC(C)(C)C2)CC(C)(C)N1] |
| 66 | 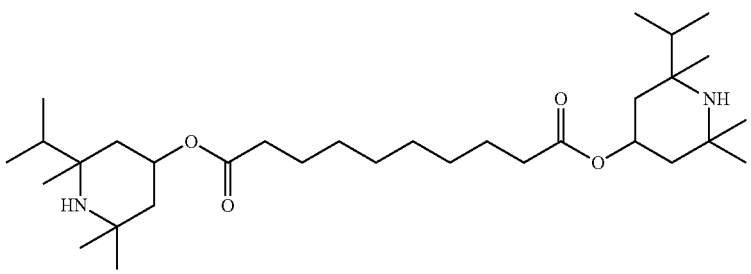 [SMILES: CC(C)C1(C)CC(OC(=O)CCCCCCCCC(=O)OC2CC(C)(C)NC(C)(C(C)C)C2)CC(C)(C)N1] |
| 67 | 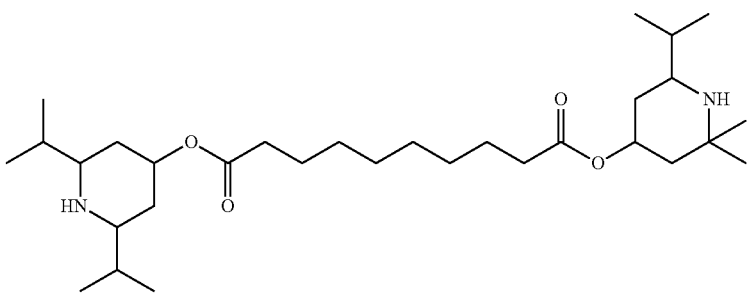 [SMILES: CC(C)C1CC(OC(=O)CCCCCCCCC(=O)OC2CC(C(C)C)NC(C)(C)C2)CC(C(C)C)N1] |
| 68 | 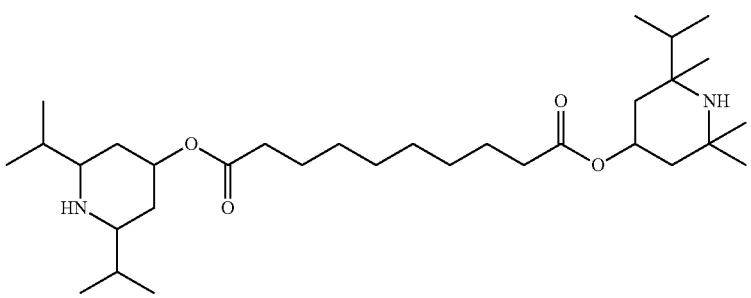 [SMILES: CC(C)C1CC(OC(=O)CCCCCCCCC(=O)OC2CC(C)(C)NC(C)(C(C)C)C2)CC(C(C)C)N1] |
| 69 | 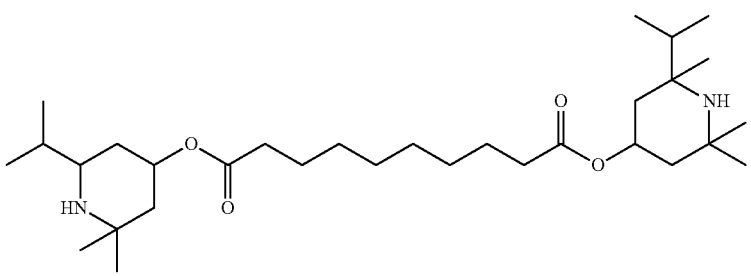 [SMILES: CC(C)C1CC(OC(=O)CCCCCCCCC(=O)OC2CC(C)(C)NC(C)(C(C)C)C2)CC(C)(C)N1] |

| No. |
|---|
| 70 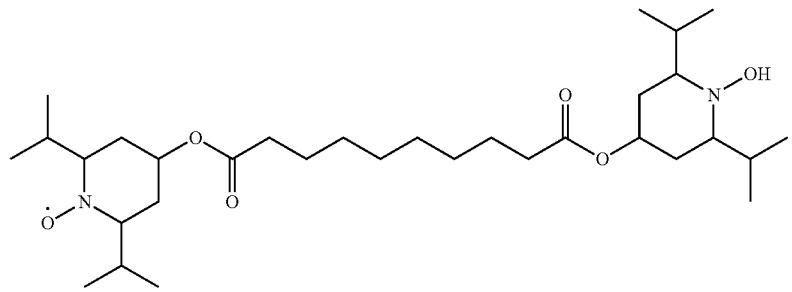 [SMILES: CC(C)C1CC(OC(=O)CCCCCCCCC(=O)OC2CC(C(C)C)N(O)C(C(C)C)C2)CC(C(C)C)N1O] |
| 71 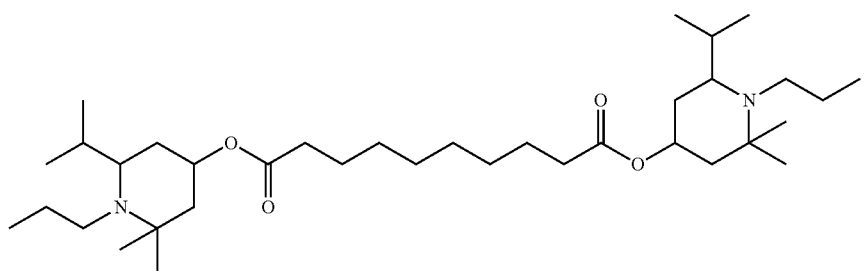 [SMILES: CCCN1C(C(C)C)CC(OC(=O)CCCCCCCCC(=O)OC2CC(C(C)C)N(CCC)C(C)(C)C2)CC1(C)C] |
| 72 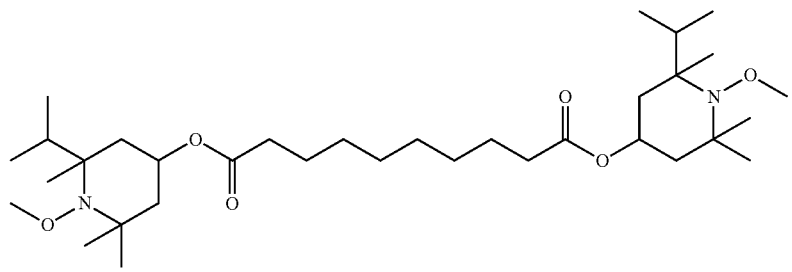 [SMILES: CON1C(C)(C)CC(OC(=O)CCCCCCCCC(=O)OC2CC(C)(C)N(OC)C(C)(C(C)C)C2)CC1(C)C(C)C] |
| 73 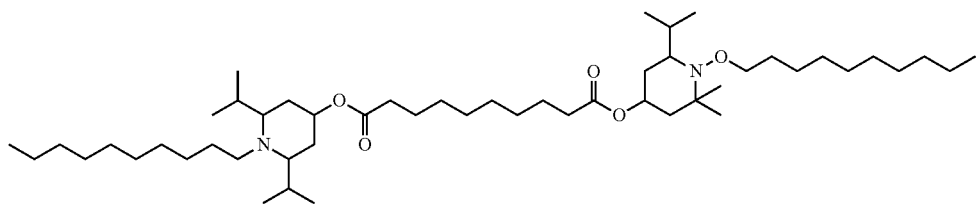 [SMILES: CCCCCCCCCCON1C(C(C)C)CC(OC(=O)CCCCCCCCC(=O)OC2CC(C(C)C)N(CCCCCCCCCC)C(C(C)C)C2)CC1(C)C] |
| 74 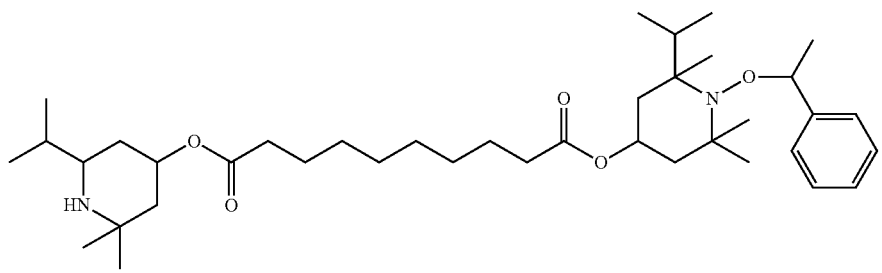 [SMILES: CC(ON1C(C)(C)CC(OC(=O)CCCCCCCCC(=O)OC2CC(C(C)C)NC(C)(C)C2)CC1(C)C(C)C)c1ccccc1] |

-continued
| No. |
|---|
| 75 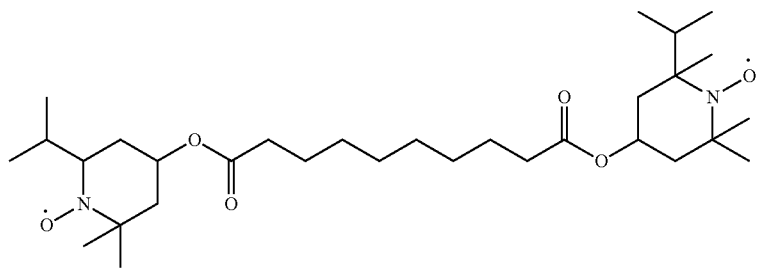 [SMILES: CC(C)C1CC(OC(=O)CCCCCCCCC(=O)OC2CC(C)(C)N(O)C(C)(C(C)C)C2)CC(C)(C)N1O] |
| 76 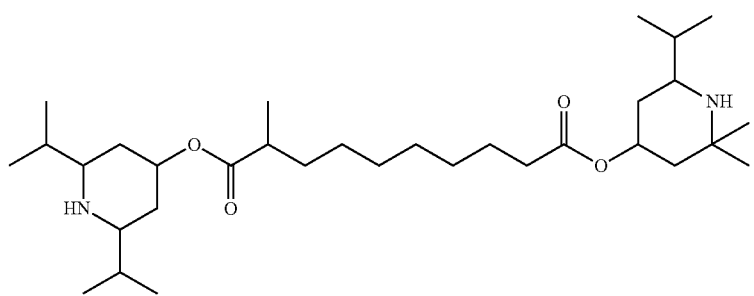 [SMILES: CC(CCCCCCCC(=O)OC1CC(C(C)C)NC(C)(C)C1)C(=O)OC1CC(C(C)C)NC(C(C)C)C1] |
| 77 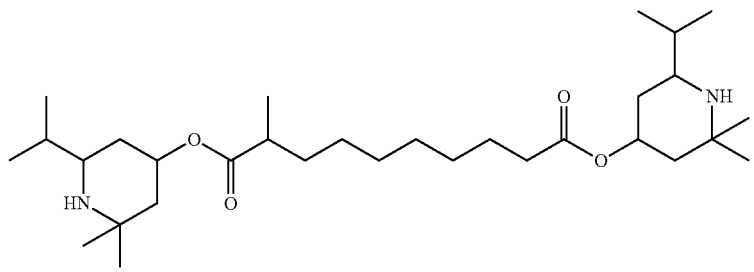 [SMILES: CC(CCCCCCCC(=O)OC1CC(C(C)C)NC(C)(C)C1)C(=O)OC1CC(C(C)C)NC(C)(C)C1] |
| 78 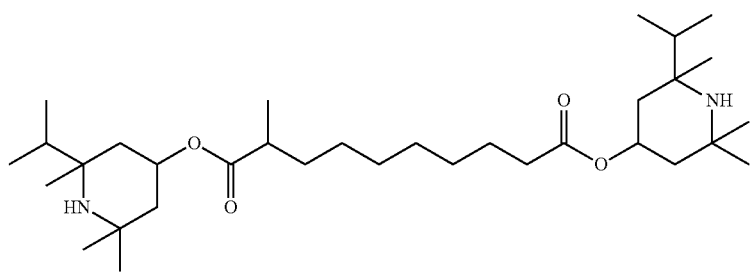 [SMILES: CC(CCCCCCCC(=O)OC1CC(C)(C)NC(C)(C(C)C)C1)C(=O)OC1CC(C)(C)NC(C)(C(C)C)C1] |
| 79 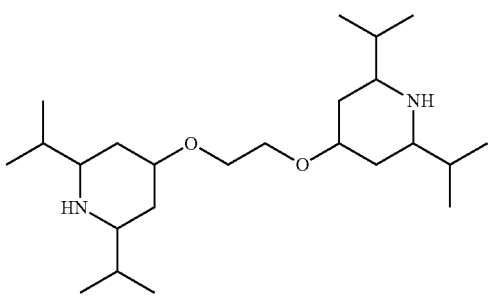 [SMILES: CC(C)C1CC(OCCOC2CC(C(C)C)NC(C(C)C)C2)CC(C(C)C)N1] |

-continued
| No. | |
|---|---|
| 80 | 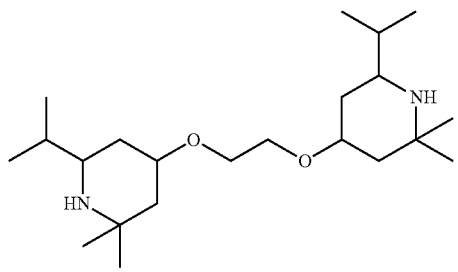 [SMILES: CC(C)C1CC(OCCOC2CC(C(C)C)NC(C)(C)C2)CC(C)(C)N1] |
| 81 | 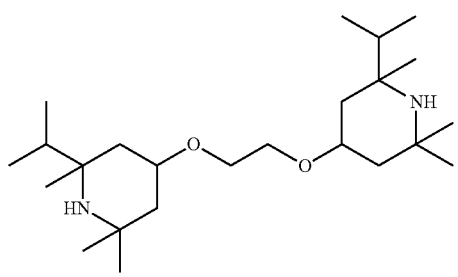 [SMILES: CC(C)C1(C)CC(OCCOC2CC(C)(C)NC(C)(C(C)C)C2)CC(C)(C)N1] |
| 82 | 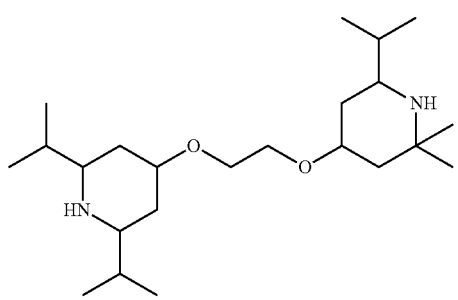 [SMILES: CC(C)C1CC(OCCOC2CC(C(C)C)NC(C)(C)C2)CC(C(C)C)N1] |
| 83 | 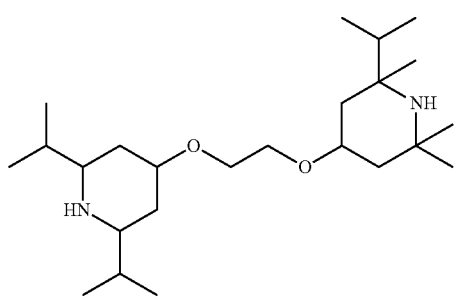 [SMILES: CC(C)C1CC(OCCOC2CC(C)(C)NC(C)(C(C)C)C2)CC(C(C)C)N1] |
| 84 | 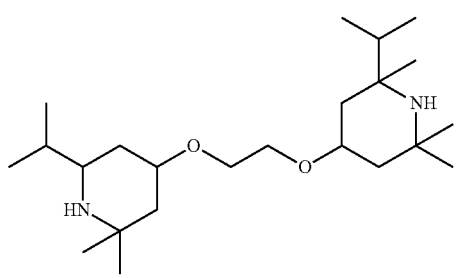 [SMILES: CC(C)C1CC(OCCOC2CC(C)(C)NC(C)(C(C)C)C2)CC(C)(C)N1] |

-continued
| No. |
|---|
| 85 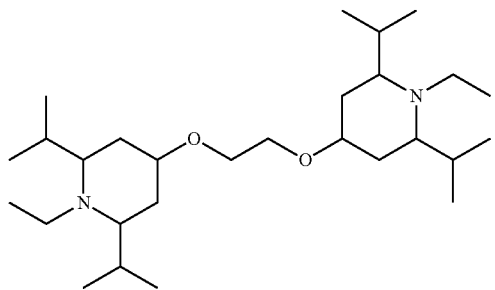 [SMILES: CCN1C(C(C)C)CC(OCCOC2CC(C(C)C)N(CC)C(C(C)C)C2)CC1C(C)C] |
| 86 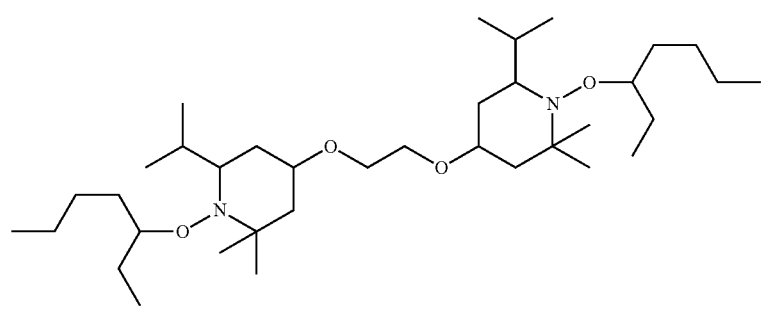 [SMILES: CCCCC(CC)ON1C(C(C)C)CC(OCCOC2CC(C(C)C)N(OC(CC)CCCC)C(C)(C)C2)CC1(C)C] |
| 87 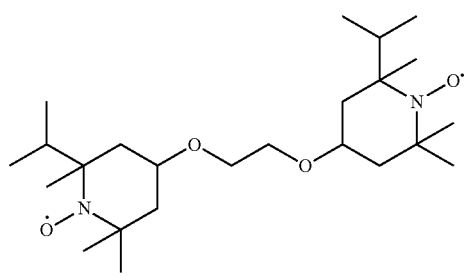 |
| 88 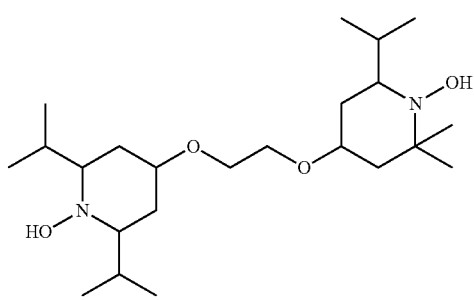 [SMILES: CC(C)C1CC(OCCOC2CC(C(C)C)N(O)C(C)(C)C2)CC(C(C)C)N1O] |
| 89 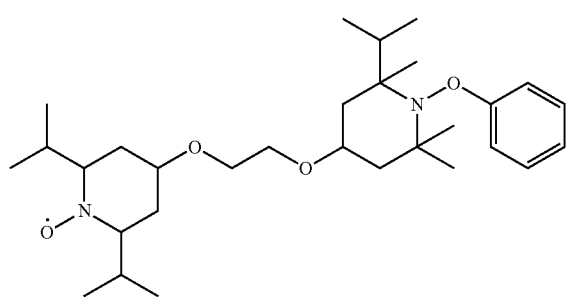 [SMILES: CC(C)C1CC(OCCOC2CC(C)(C)N(Oc3ccccc3)C(C)(C(C)C)C2)CC(C(C)C)N1O] |

| No. | |
|---|---|
| 90 | 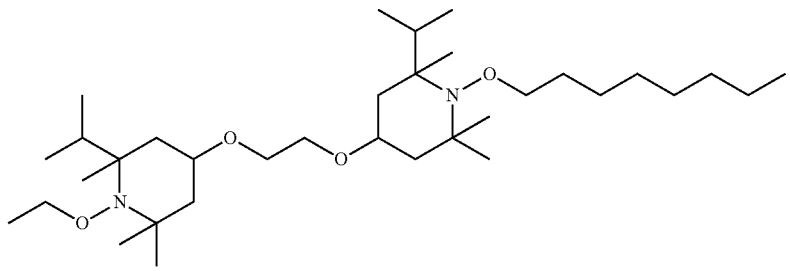 [SMILES: CCCCCCCCON1C(C)(C)CC(OCCOC2CC(C)(C)N(OCC)C(C)(C(C)C)C2)CC1(C)C(C)C] |
| 91 | 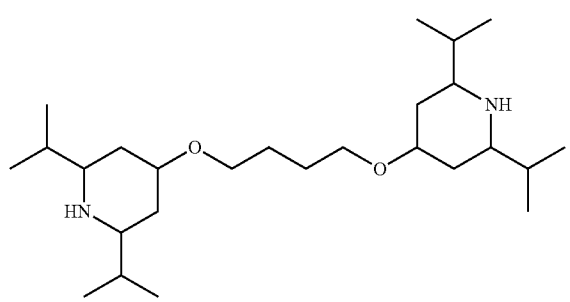 [SMILES: CC(C)C1CC(OCCCCOC2CC(C(C)C)NC(C(C)C)C2)CC(C(C)C)N1] |
| 92 | 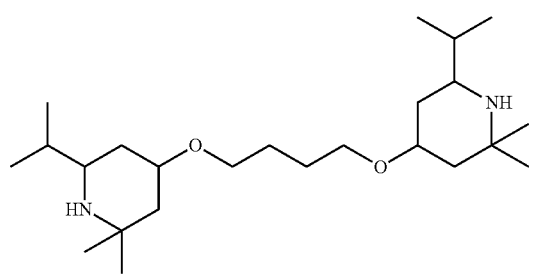 [SMILES: CC(C)C1CC(OCCCCOC2CC(C(C)C)NC(C)(C)C2)CC(C)(C)N1] |
| 93 | 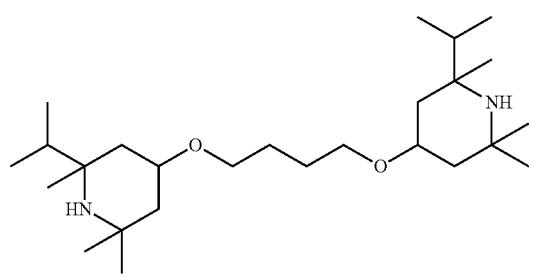 [SMILES: CC(C)C1(C)CC(OCCCCOC2CC(C)(C)NC(C)(C(C)C)C2)CC(C)(C)N1] |
| 94 | 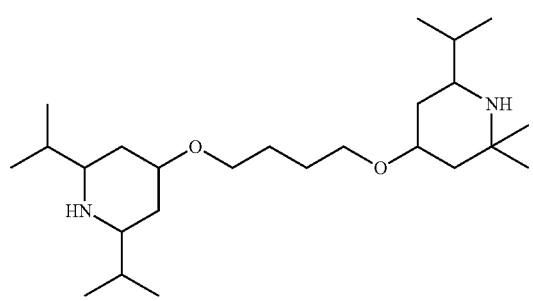 [SMILES: CC(C)C1CC(OCCCCOC2CC(C(C)C)NC(C)(C)C2)CC(C(C)C)N1] |

| No. |
|---|
| 95 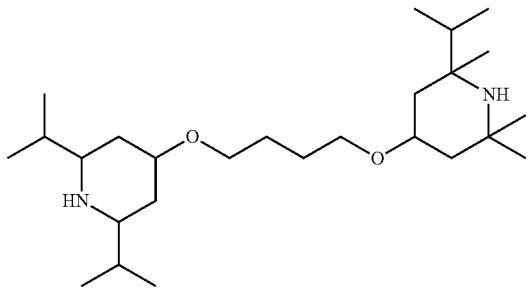 [SMILES: CC(C)C1CC(OCCCCOC2CC(C)(C)NC(C)(C(C)C)C2)CC(C(C)C)N1] |
| 96 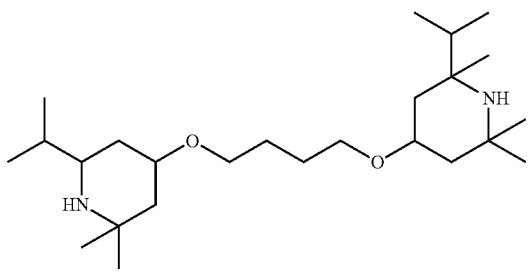 [SMILES: CC(C)C1CC(OCCCCOC2CC(C)(C)NC(C)(C(C)C)C2)CC(C)(C)N1] |
| 97 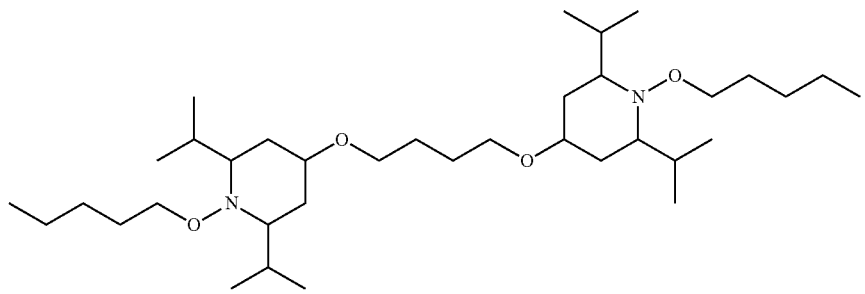 [SMILES: CCCCCON1C(C(C)C)CC(OCCCCOC2CC(C(C)C)N(OCCCCC)C(C(C)C)C2)CC1C(C)C] |
| 98 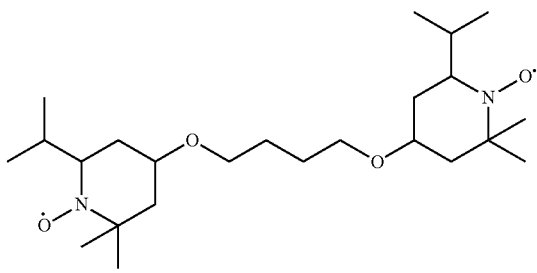 |
| 99 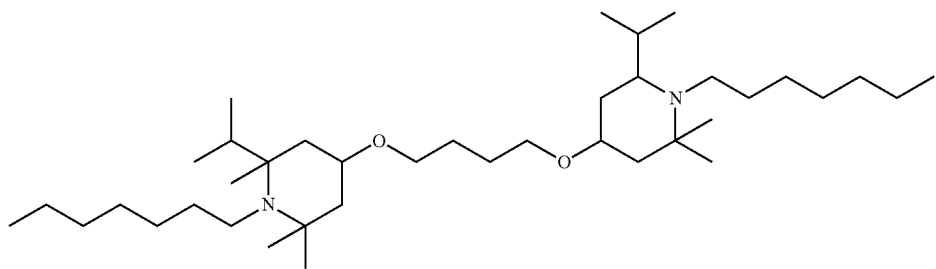 [SMILES: CCCCCCCN1C(C(C)C)CC(OCCCCOC2CC(C)(C)N(CCCCCCC)C(C)(C(C)C)C2)CC1(C)C] |

| No. |
|---|
| 100 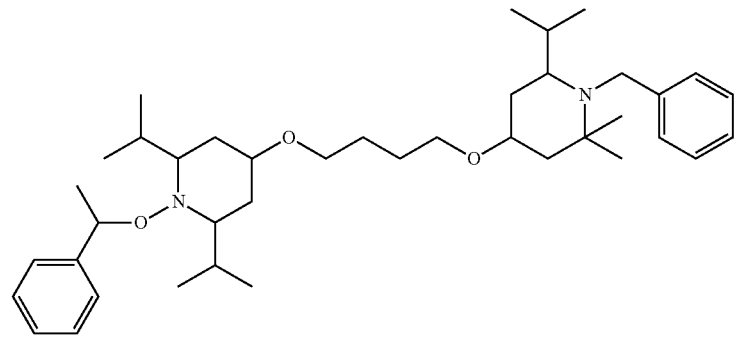 [SMILES: CC(ON1C(C(C)C)CC(OCCCCOC2CC(C(C)C)N(Cc3ccccc3)C(C)(C)C2)CC1C(C)C)c1ccccc1] |
| 101 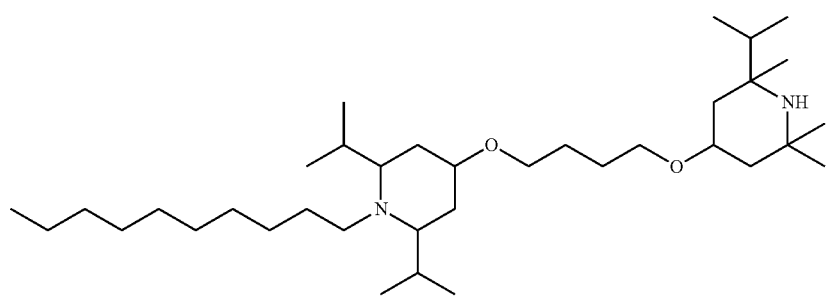 [SMILES: CCCCCCCCCCN1C(C(C)C)CC(OCCCCOC2CC(C)(C)NC(C)(C(C)C)C2)CC1C(C)C] |
| 102 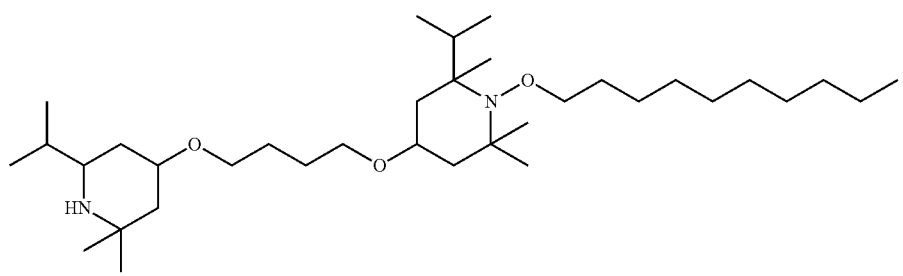 [SMILES: CCCCCCCCCCON1C(C)(C)CC(OCCCCOC2CC(C(C)C)NC(C)(C)C2)CC1(C)C(C)C] |
| 103 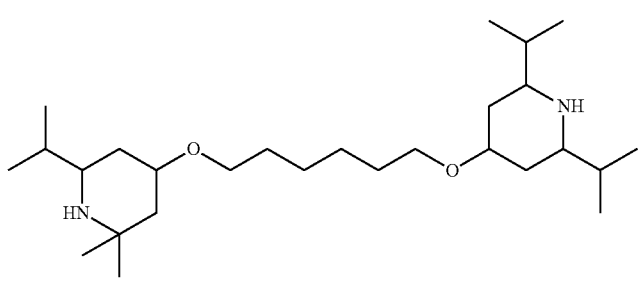 [SMILES: CC(C)C1CC(OCCCCCCOC2CC(C(C)C)NC(C)(C)C2)CC(C(C)C)N1] |
| 104 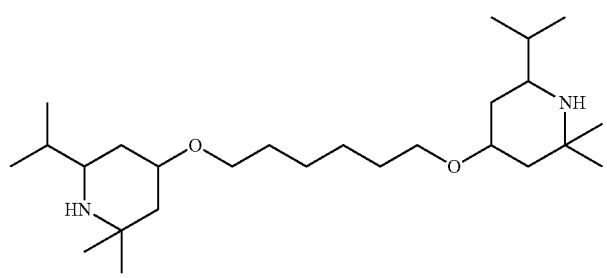 [SMILES: CC(C)C1CC(OCCCCCCOC2CC(C(C)C)NC(C)(C)C2)CC(C)(C)N1] |

| No. |
|---|
| 105 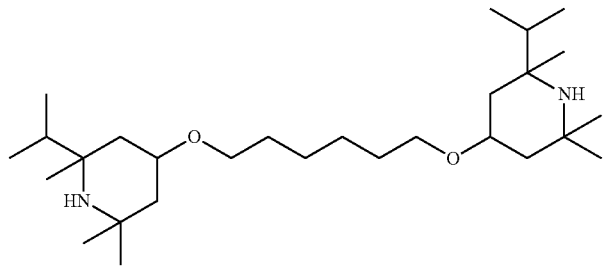 [SMILES: CC(C)C1(C)CC(OCCCCCCOC2CC(C)(C)NC(C)(C(C)C)C2)CC(C)(C)N1] |
| 106 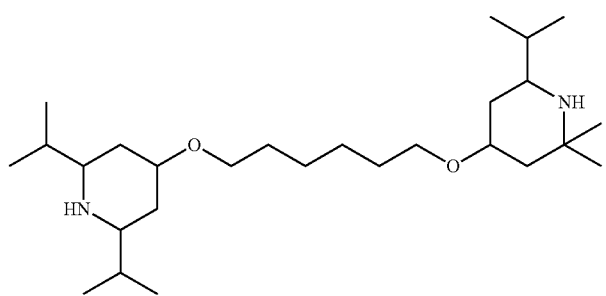 [SMILES: CC(C)C1CC(OCCCCCCOC2CC(C(C)C)NC(C)(C)C2)CC(C(C)C)N1] |
| 107 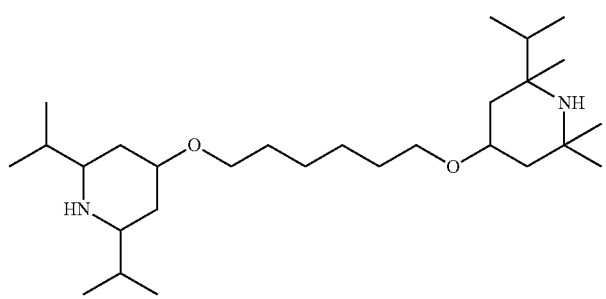 [SMILES: CC(C)C1CC(OCCCCCCOC2CC(C)(C)NC(C)(C(C)C)C2)CC(C(C)C)N1] |
| 108 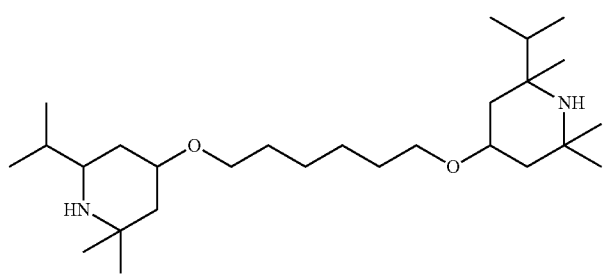 [SMILES: CC(C)C1CC(OCCCCCCOC2CC(C)(C)NC(C)(C(C)C)C2)CC(C)(C)N1] |
| 109 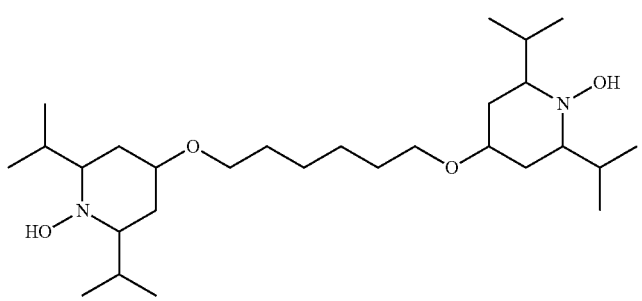 [SMILES: CC(C)C1CC(OCCCCCCOC2CC(C(C)C)N(O)C(C(C)C)C2)CC(C(C)C)N1O] |

| No. | |
|---|---|
| 110 | 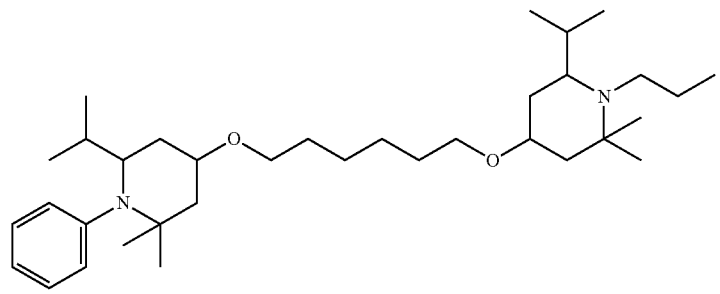 [SMILES: CCCN1C(C(C)C)CC(OCCCCCCOC2CC(C(C)C)N(c3ccccc3)C(C)(C)C2)CC1(C)C] |
| 111 | 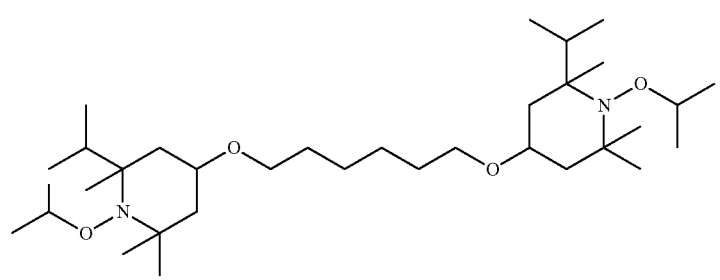 [SMILES: CC(C)ON1C(C)(C)CC(OCCCCCCOC2CC(C)(C)N(OC(C)C)C(C)(C(C)C)C2)CC1(C)C(C)C] |
| 112 | 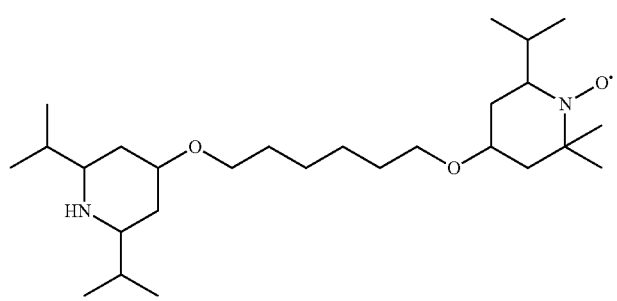 |
| 113 | 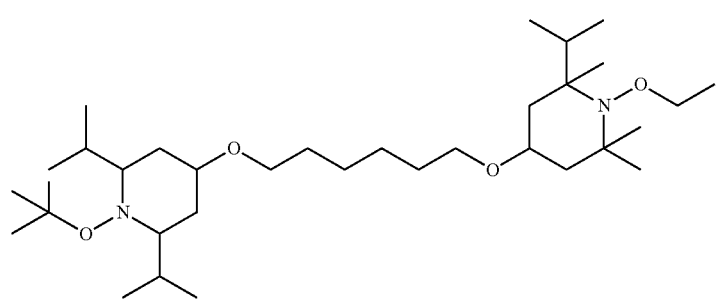 [SMILES: CCON1C(C)(C)CC(OCCCCCCOC2CC(C(C)C)N(OC(C)(C)C)C(C(C)C)C2)CC1(C)C(C)C] |
| 114 | 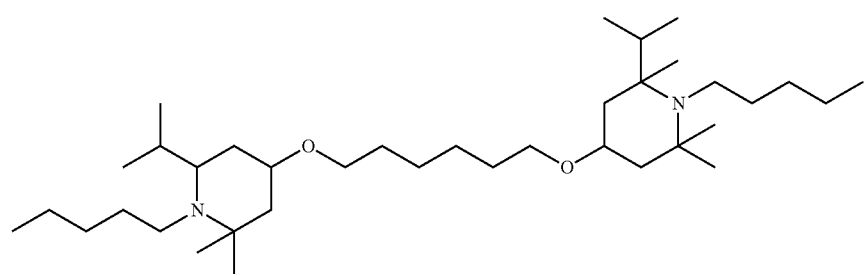 [SMILES: CCCCCN1C(C(C)C)CC(OCCCCCCOC2CC(C)(C)N(CCCCC)C(C)(C(C)C)C2)CC1(C)C] |

| No. | |
|---|---|
| 115 | 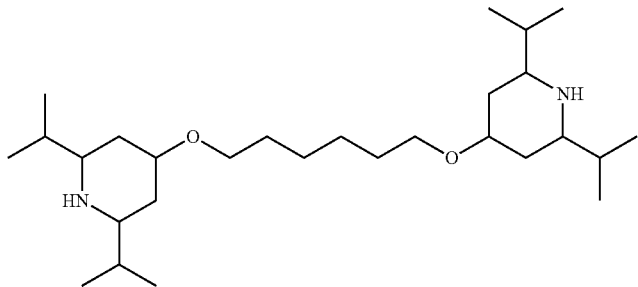 [SMILES: CC(C)C1CC(OCCCCCCOC2CC(C(C)C)NC(C(C)C)C2)CC(C(C)C)N1] |
| 116 | 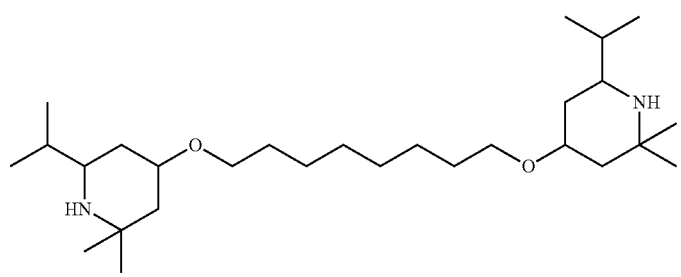 [SMILES: CC(C)C1CC(OCCCCCCCCOC2CC(C(C)C)NC(C)(C)C2)CC(C)(C)N1] |
| 117 | 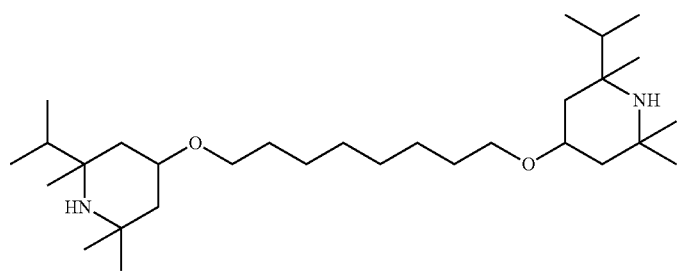 [SMILES: CC(C)C1(C)CC(OCCCCCCCCOC2CC(C)(C)NC(C)(C(C)C)C2)CC(C)(C)N1] |
| 118 | 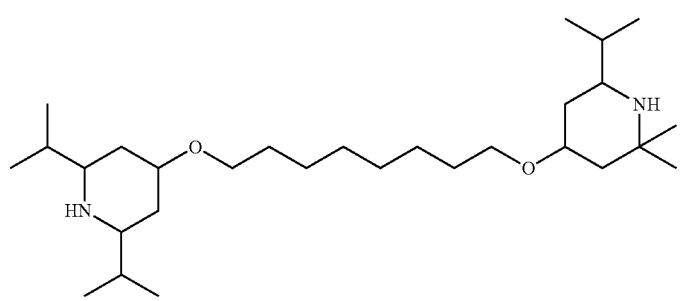 [SMILES: CC(C)C1CC(OCCCCCCCCOC2CC(C(C)C)NC(C)(C)C2)CC(C(C)C)N1] |
| 119 | 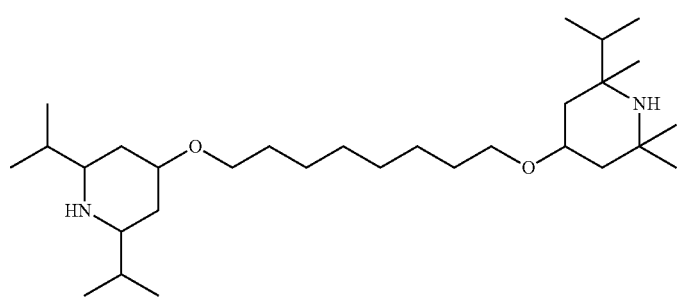 [SMILES: CC(C)C1CC(OCCCCCCCCOC2CC(C)(C)NC(C)(C(C)C)C2)CC(C(C)C)N1] |

-continued
| No. | |
|---|---|
| 120 | 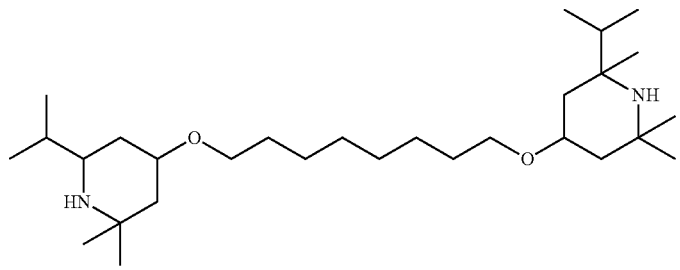 [SMILES: CC(C)C1CC(OCCCCCCCCOC2CC(C)(C)NC(C)(C(C)C)C2)CC(C)(C)N1] |
| 121 | 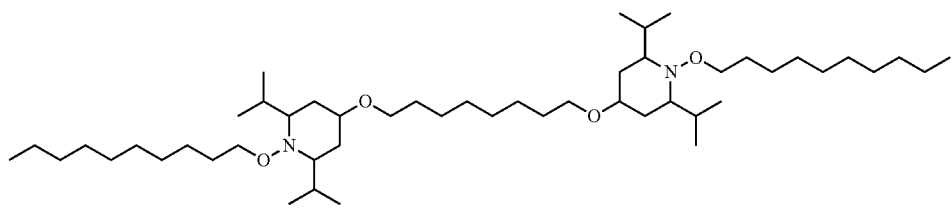 [SMILES: CCCCCCCCCCON1C(C(C)C)CC(OCCCCCCCCOC2CC(C(C)C)N(OCCCCCCCCCC)C(C(C)C)C2)CC1C(C)C] |
| 122 | 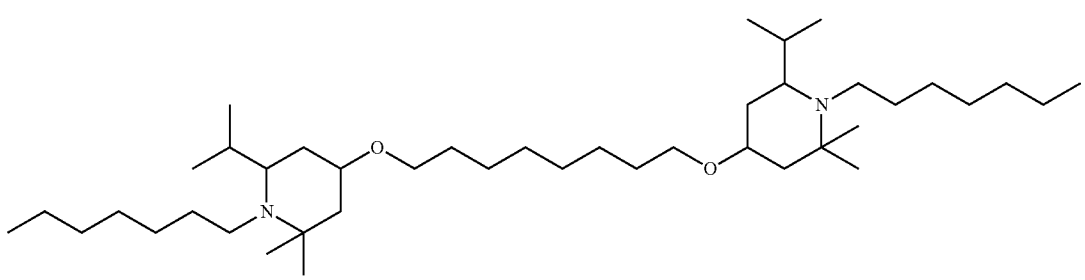 [SMILES: CCCCCCCN1C(C(C)C)CC(OCCCCCCCCOC2CC(C(C)C)N(CCCCCCC)C(C)(C)C2)CC1(C)C] |
| 123 | 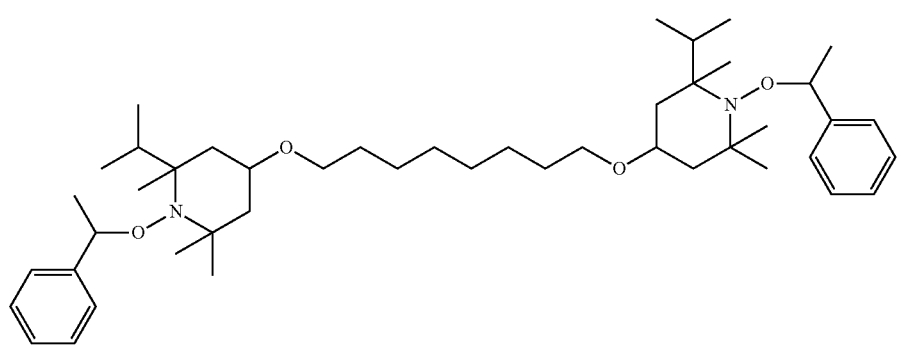 [SMILES: CC(ON1C(C)(C)CC(OCCCCCCCCOC2CC(C)(C)N(OC(C)c3ccccc3)C(C)(C(C)C)C2)CC1(C)C(C)C)c1ccccc1] |
| 124 | 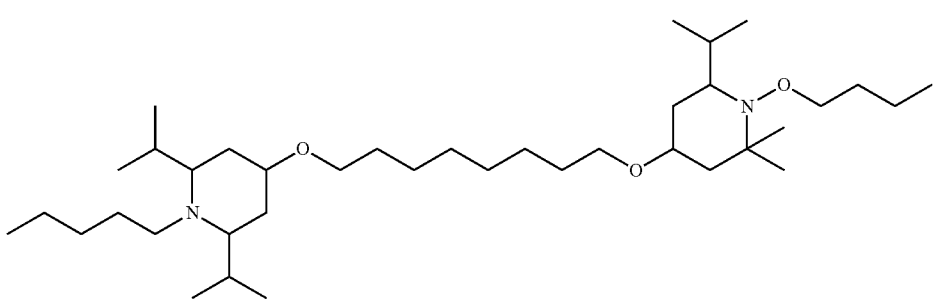 [SMILES: CCCCCN1C(C(C)C)CC(OCCCCCCCCOC2CC(C(C)C)N(OCCCC)C(C)(C)C2)CC1C(C)C] |

| No. |
|---|
| 125 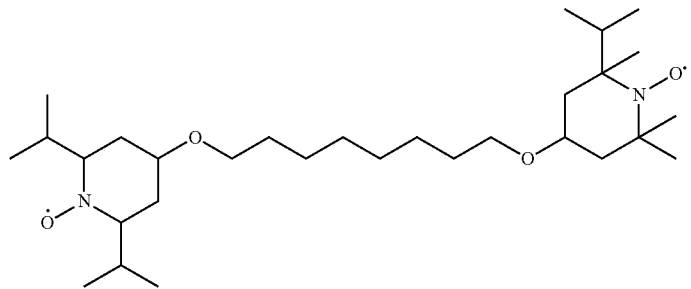 |
| 126 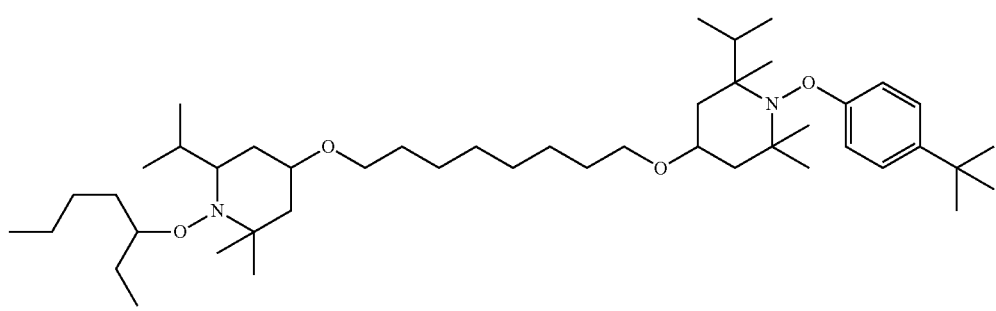 [SMILES: CCCCC(CC)ON1C(C(C)C)CC(OCCCCCCCCOC2CC(C)(C)N(Oc3ccc(C(C)(C)C)cc3)C(C)(C(C)C)C2)CC1(C)C] |
| 127 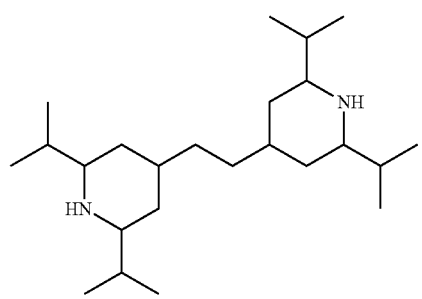 [SMILES: CC(C)C1CC(CCC2CC(C(C)C)NC(C(C)C)C2)CC(C(C)C)N1] |
| 128 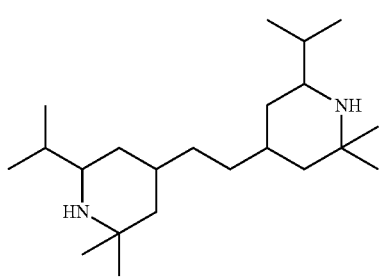 [SMILES: CC(C)C1CC(CCC2CC(C(C)C)NC(C)(C)C2)CC(C)(C)N1] |
| 129 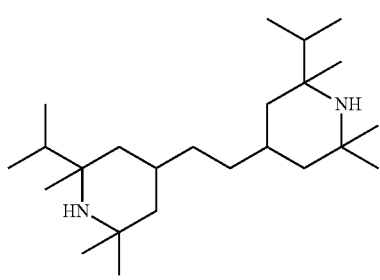 [SMILES: CC(C)C1(C)CC(CCC2CC(C)(C)NC(C)(C(C)C)C2)CC(C)(C)N1] |

-continued
| No. | |
|---|---|
| 130 | 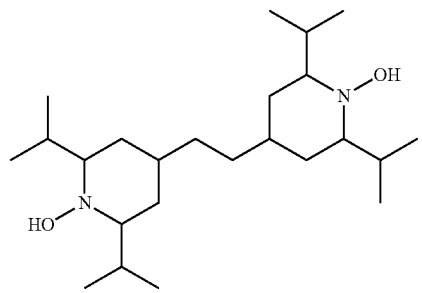 [SMILES: CC(C)C1CC(CCC2CC(C(C)C)N(O)C(C(C)C)C2)CC(C(C)C)N1O] |
| 131 | 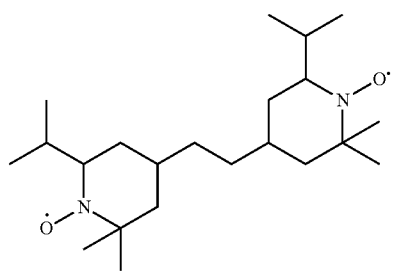 |
| 132 | 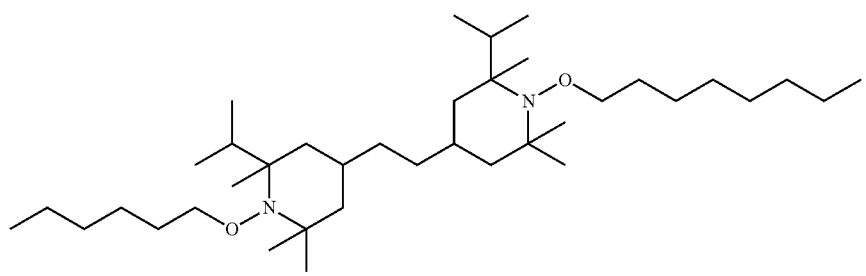 [SMILES: CCCCCCCCON1C(C)(C)CC(CCC2CC(C)(C)N(OCCCCCC)C(C)(C(C)C)C2)CC1(C)C(C)C] |
| 133 | 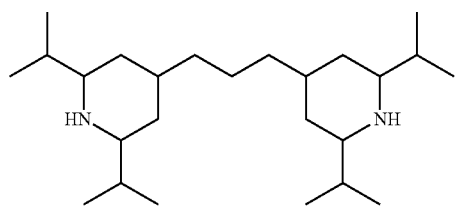 [SMILES: CC(C)C1CC(CCCC2CC(C(C)C)NC(C(C)C)C2)CC(C(C)C)N1] |
| 134 | 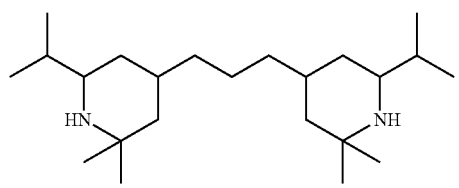 [SMILES: CC(C)C1CC(CCCC2CC(C(C)C)NC(C)(C)C2)CC(C)(C)N1] |
| 135 | 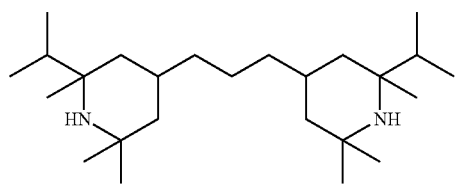 [SMILES: CC(C)C1(C)CC(CCCC2CC(C)(C)NC(C)(C(C)C)C2)CC(C)(C)N1] |

-continued
| No. | |
|---|---|
| 136 | 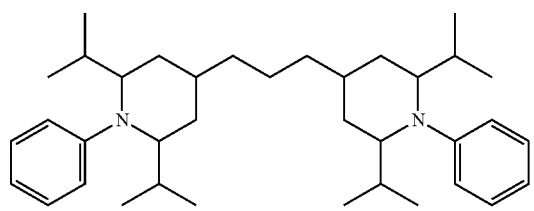 [SMILES: CC(C)C1CC(CCCC2CC(C(C)C)N(c3ccccc3)C(C(C)C)C2)CC(C(C)C)N1c1ccccc1] |
| 137 | 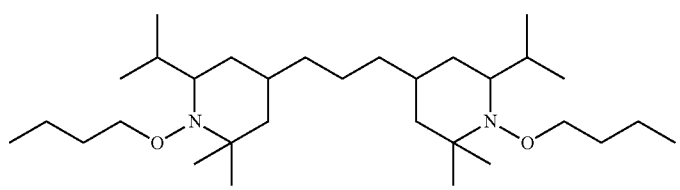 [SMILES: CCCCON1C(C(C)C)CC(CCCC2CC(C(C)C)N(OCCCC)C(C)(C)C2)CC1(C)C] |
| 138 | 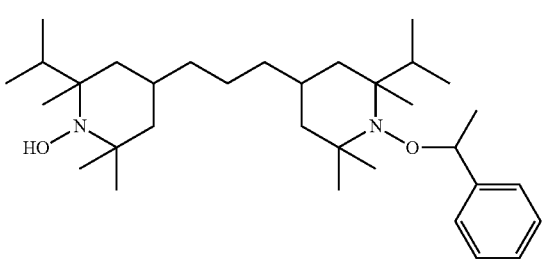 [SMILES: CC(ON1C(C)(C)CC(CCCC2CC(C)(C)N(O)C(C)(C(C)C)C2)CC1(C)C(C)C)c1ccccc1] |
| 139 | 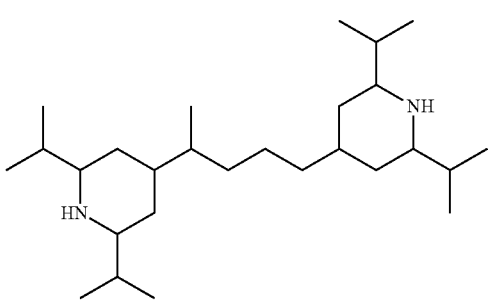 [SMILES: CC(C)C1CC(CCCC(C)C2CC(C(C)C)NC(C(C)C)C2)CC(C(C)C)N1] |
| 140 | 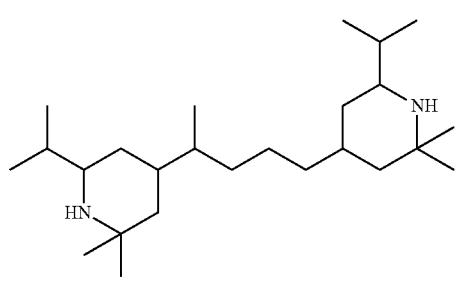 [SMILES: CC(C)C1CC(CCCC(C)C2CC(C(C)C)NC(C)(C)C2)CC(C)(C)N1] |
| 141 | 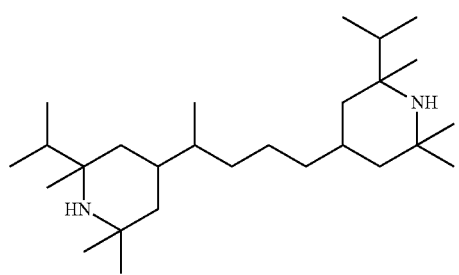 [SMILES: CC(CCCC1CC(C)(C)NC(C)(C(C)C)C1)C1CC(C)(C)NC(C)(C(C)C)C1] |

| No. | |
|---|---|
| 142 | 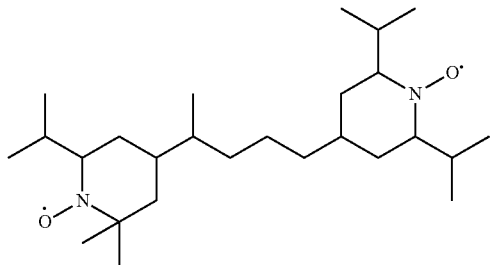 |
| 143 | 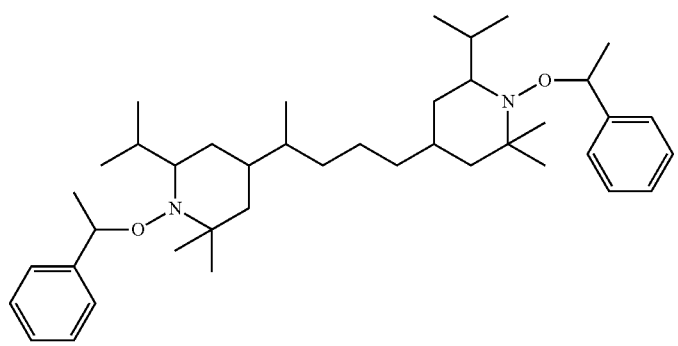 [SMILES: CC(ON1C(C(C)C)CC(CCCC(C)C2CC(C(C)C)N(OC(C)c3ccccc3)C(C)(C)C2)CC1(C)C)c1ccccc1] |
| 144 | 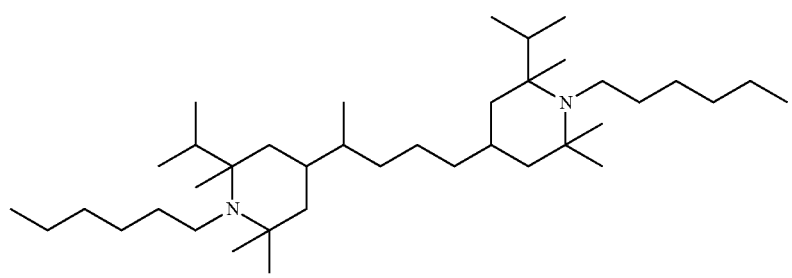 [SMILES: CCCCCCN1C(C)(C)CC(CCCC(C)C2CC(C)(C)N(CCCCCC)C(C)(C(C)C)C2)CC1(C)C(C)C] |
| 145 | 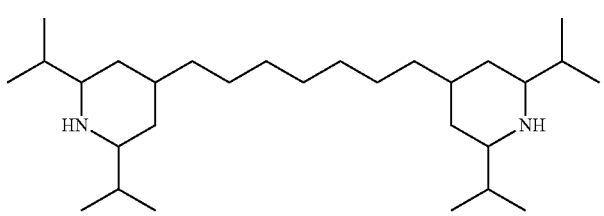 [SMILES: CC(C)C1CC(CCCCCCCC2CC(C(C)C)NC(C(C)C)C2)CC(C(C)C)N1] |
| 146 | 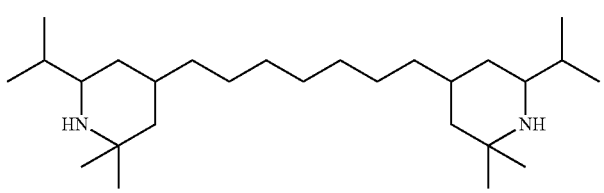 [SMILES: CC(C)C1CC(CCCCCCCC2CC(C(C)C)NC(C)(C)C2)CC(C)(C)N1] |
| 147 | 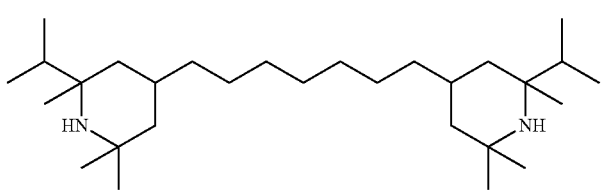 [SMILES: CC(C)C1(C)CC(CCCCCCCC2CC(C)(C)NC(C)(C(C)C)C2)CC(C)(C)N1] |

-continued
| No. | |
|---|---|
| 148 | 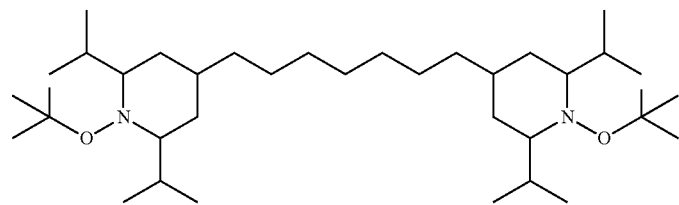 [SMILES: CC(C)C1CC(CCCCCCCC2CC(C(C)C)N(OC(C)(C)C)C(C(C)C)C2)CC(C(C)C)N1OC(C)(C)C] |
| 149 | 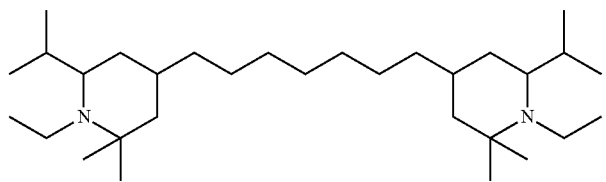 [SMILES: CCN1C(C(C)C)CC(CCCCCCCC2CC(C(C)C)N(CC)C(C)(C)C2)CC1(C)C] |
| 150 | 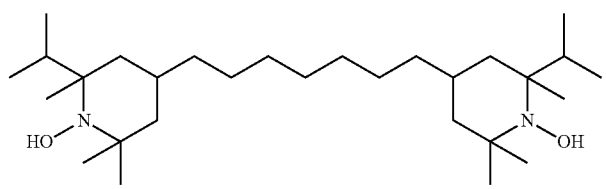 [SMILES: CC(C)C1(C)CC(CCCCCCCC2CC(C)(C)N(O)C(C)(C(C)C)C2)CC(C)(C)N1O] |
| 151 | 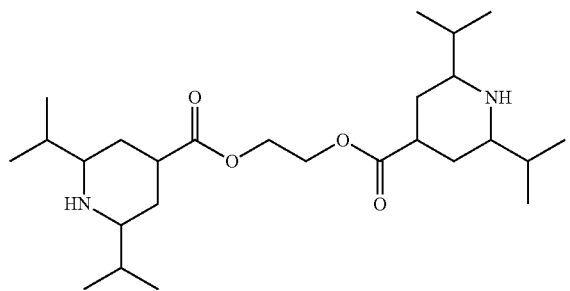 [SMILES: CC(C)C1CC(C(=O)OCCOC(=O)C2CC(C(C)C)NC(C(C)C)C2)CC(C(C)C)N1] |
| 152 | 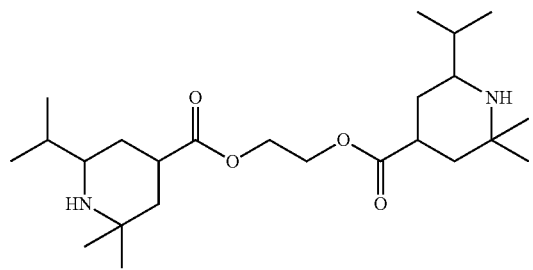 [SMILES: CC(C)C1CC(C(=O)OCCOC(=O)C2CC(C(C)C)NC(C)(C)C2)CC(C)(C)N1] |
| 153 | 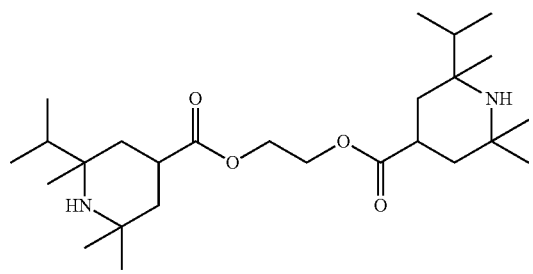 [SMILES: CC(C)C1(C)CC(C(=O)OCCOC(=O)C2CC(C)(C)NC(C)(C(C)C)C2)CC(C)(C)N1] |

| No. |
|---|
| 154 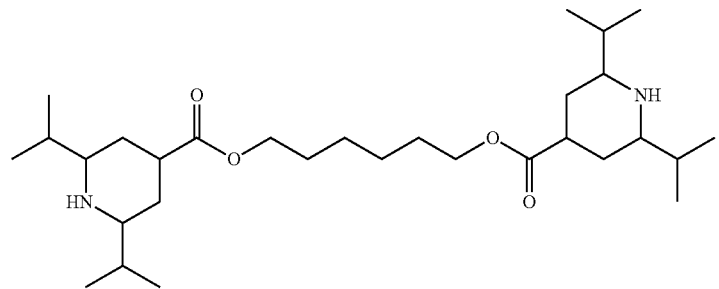 [SMILES: CC(C)C1CC(C(=O)OCCCCCCOC(=O)C2CC(C(C)C)NC(C(C)C)C2)CC(C(C)C)N1] |
| 155 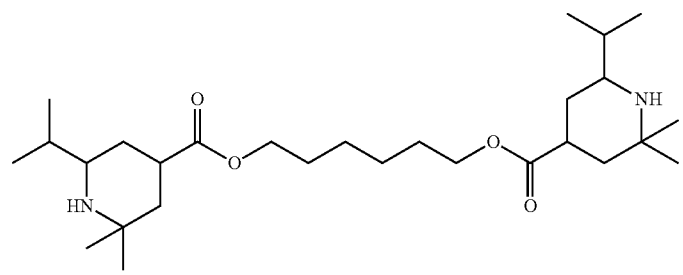 [SMILES: CC(C)C1CC(C(=O)OCCCCCCOC(=O)C2CC(C(C)C)NC(C)(C)C2)CC(C)(C)N1] |
| 156 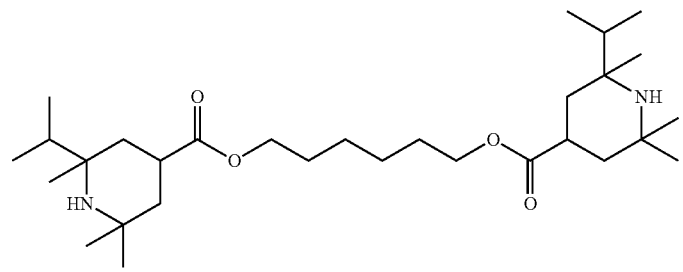 [SMILES: CC(C)C1(C)CC(C(=O)OCCCCCCOC(=O)C2CC(C)(C)NC(C)(C(C)C)C2)CC(C)(C)N1] |
| 157 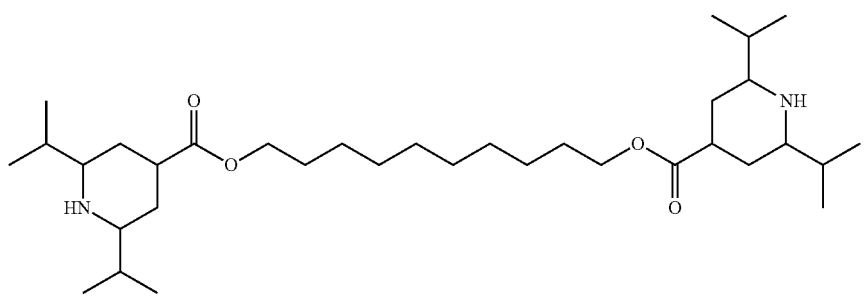 [SMILES: CC(C)C1CC(C(=O)OCCCCCCCCCCOC(=O)C2CC(C(C)C)NC(C(C)C)C2)CC(C(C)C)N1] |
| 158 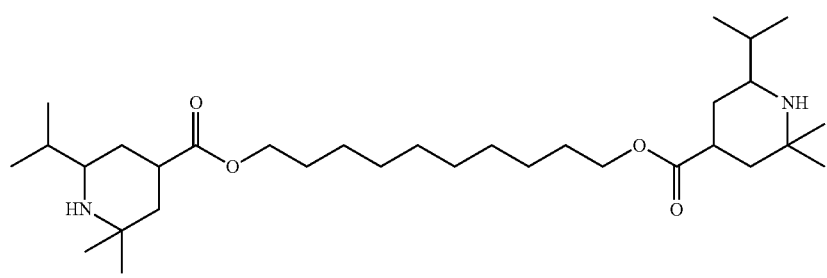 [SMILES: CC(C)C1CC(C(=O)OCCCCCCCCCCOC(=O)C2CC(C(C)C)NC(C)(C)C2)CC(C)(C)N1] |

| No. |
|---|
| 159 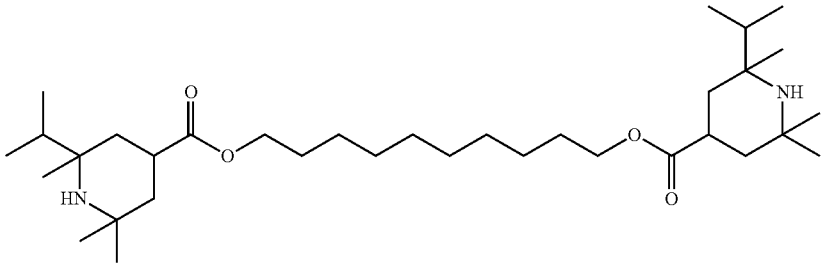 [SMILES: CC(C)C1(C)CC(C(=O)OCCCCCCCCCCOC(=O)C2CC(C)(C)NC(C)(C(C)C)C2)CC(C)(C)N1] |
| 160 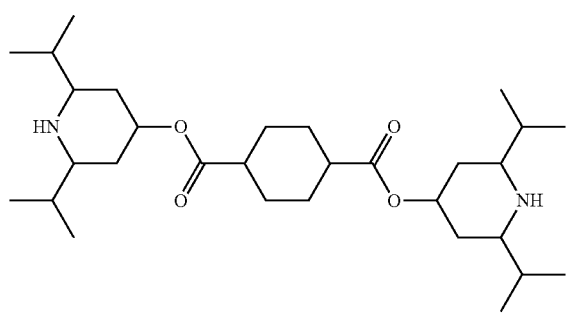 [SMILES: CC(C)C1CC(OC(=O)C2CCC(C(=O)OC3CC(C(C)C)NC(C(C)C)C3)CC2)CC(C(C)C)N1] |
| 161 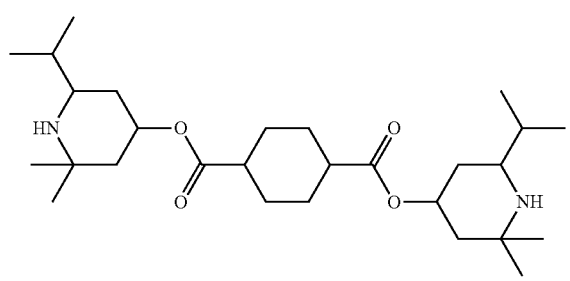 [SMILES: CC(C)C1CC(OC(=O)C2CCC(C(=O)OC3CC(C(C)C)NC(C)(C)C3)CC2)CC(C)(C)N1] |
| 162 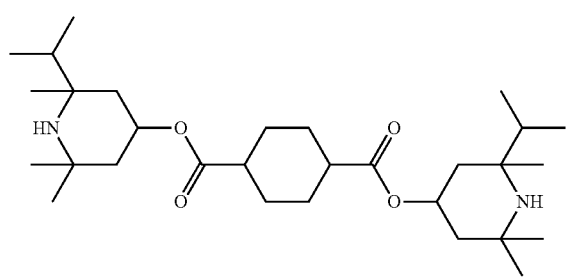 |
| 163 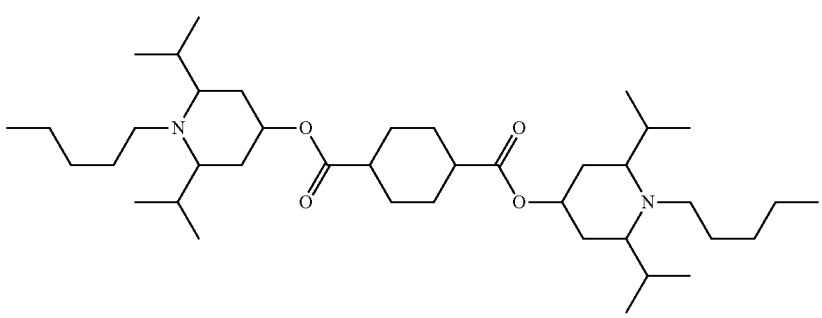 [SMILES: CCCCCN1C(C(C)C)CC(OC(=O)C2CCC(C(=O)OC3CC(C(C)C)N(CCCCC)C(C(C)C)C3)CC2)CC1C(C)C] |

| No. | |
|---|---|
| 164 | 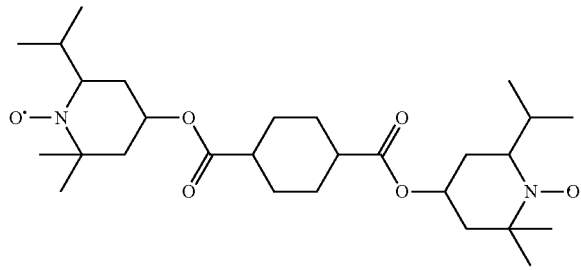 |
| 165 | 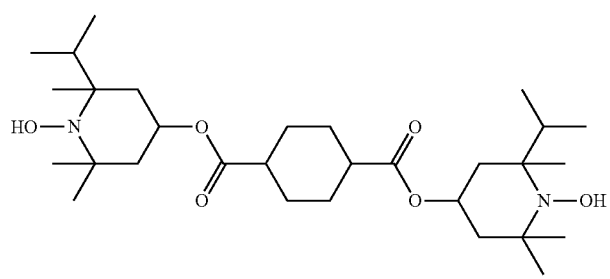 [SMILES: CC(C)C1(C)CC(OC(=O)C2CCC(C(=O)OC3CC(C)(C)N(O)C(C)(C(C)C)C3)CC2)CC(C)(C)N1O] |
| 166 | 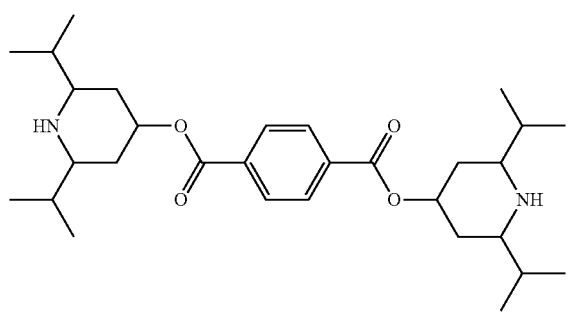 [SMILES: CC(C)C1CC(OC(=O)c2ccc(C(=O)OC3CC(C(C)C)NC(C(C)C)C3)cc2)CC(C(C)C)N1] |
| 167 | 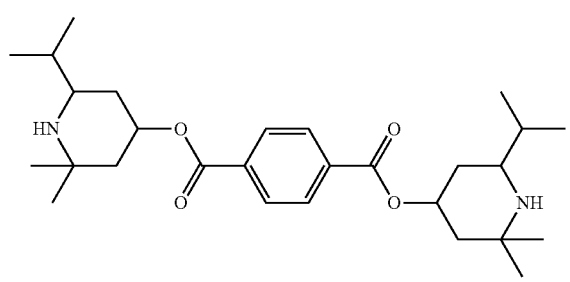 [SMILES: CC(C)C1CC(OC(=O)c2ccc(C(=O)OC3CC(C(C)C)NC(C)(C)C3)cc2)CC(C)(C)N1] |
| 168 | 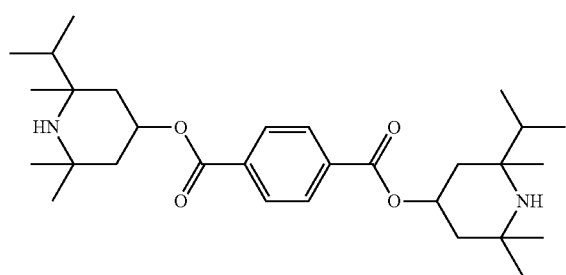 [SMILES: CC(C)C1(C)CC(OC(=O)c2ccc(C(=O)OC3CC(C)(C)NC(C)(C(C)C)C3)cc2)CC(C)(C)N1] |

| No. | |
|---|---|
| 169 | 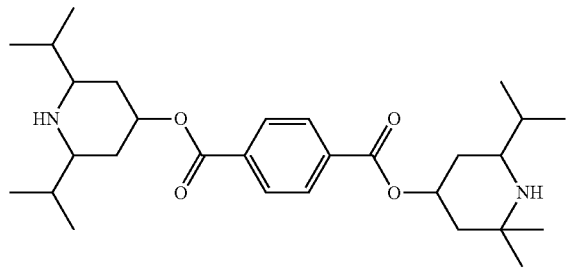 [SMILES: CC(C)C1CC(OC(=O)c2ccc(C(=O)OC3CC(C(C)C)NC(C)(C)C3)cc2)CC(C(C)C)N1] |
| 170 | 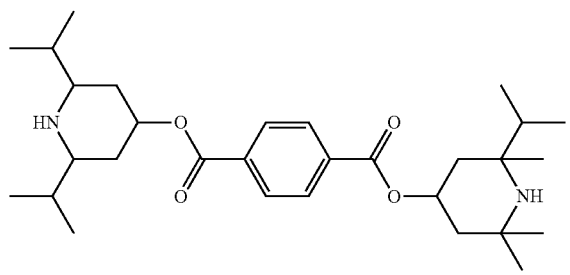 [SMILES: CC(C)C1CC(OC(=O)c2ccc(C(=O)OC3CC(C)(C)NC(C)(C(C)C)C3)cc2)CC(C(C)C)N1] |
| 171 | 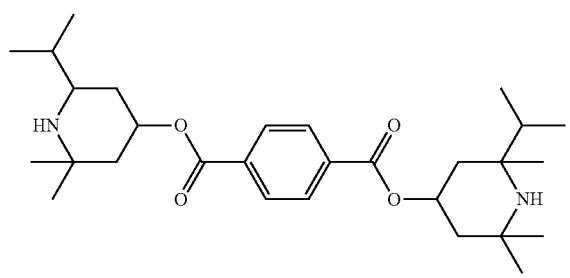 [SMILES: CC(C)C1CC(OC(=O)c2ccc(C(=O)OC3CC(C)(C)NC(C)(C(C)C)C3)cc2)CC(C)(C)N1] |
| 172 | 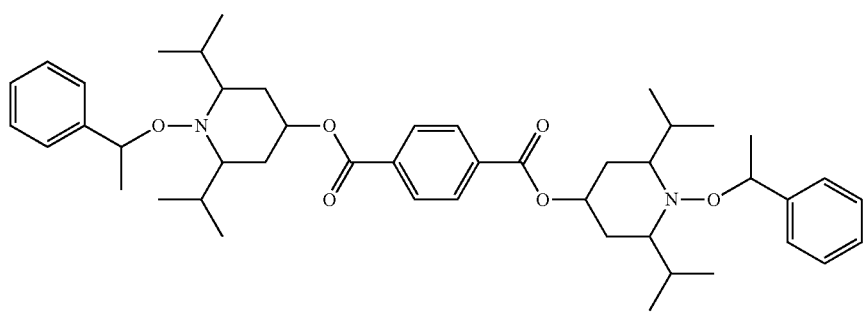 [SMILES: CC(ON1C(C(C)C)CC(OC(=O)c2ccc(C(=O)OC3CC(C(C)C)N(OC(C)c4ccccc4)C(C(C)C)C3)cc2)CC1C(C)C)c1ccccc1] |
| 173 | 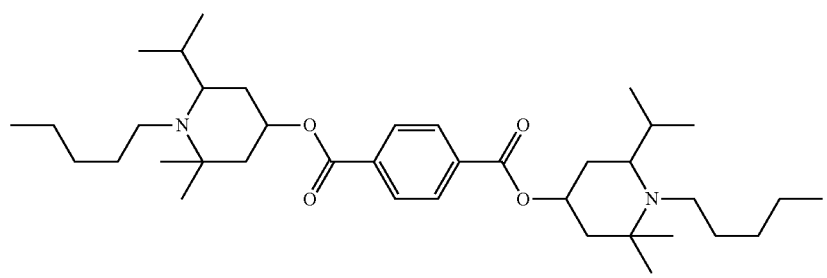 [SMILES: CCCCCN1C(C(C)C)CC(OC(=O)c2ccc(C(=O)OC3CC(C(C)C)N(CCCCC)C(C)(C)C3)cc2)CC1(C)C] |

| No. |
|---|
| 174 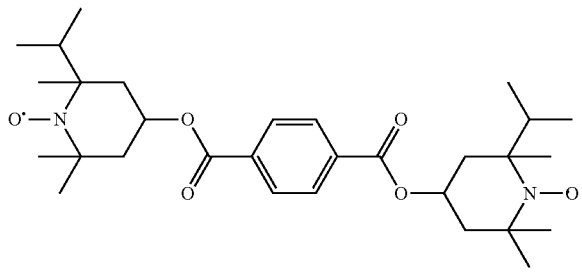 |
| 175 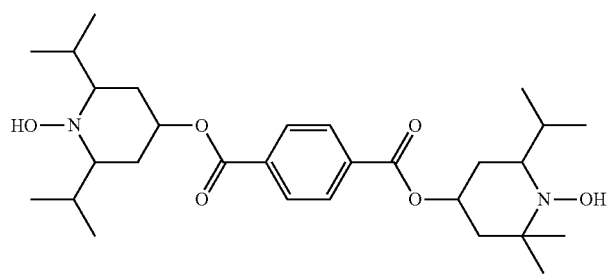 [SMILES: CC(C)C1CC(OC(=O)c2ccc(C(=O)OC3CC(C(C)C)N(O)C(C)(C)C3)cc2)CC(C(C)C)N1O] |
| 176 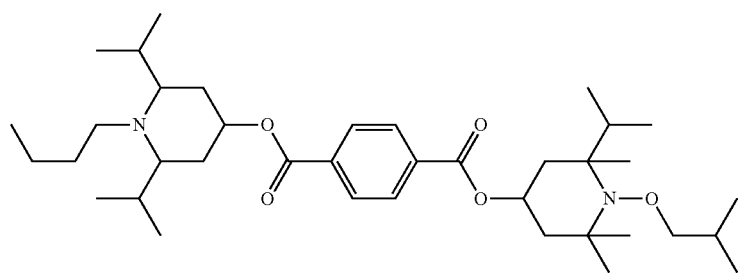 [SMILES: CCCCN1C(C(C)C)CC(OC(=O)c2ccc(C(=O)OC3CC(C)(C)N(OCC(C)C)C(C)(C(C)C)C3)cc2)CC1C(C)C] |
| 177 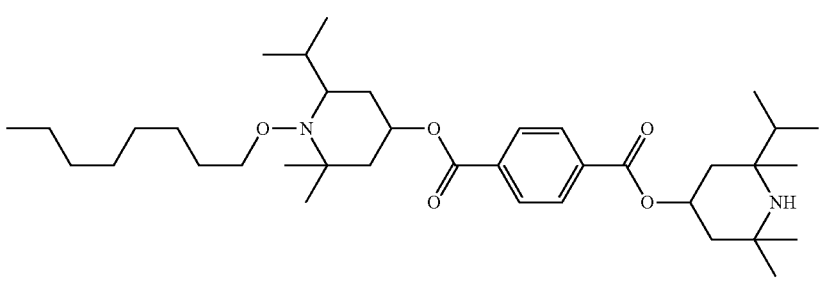 [SMILES: CCCCCCCCON1C(C(C)C)CC(OC(=O)c2ccc(C(=O)OC3CC(C)(C)NC(C)(C(C)C)C3)cc2)CC1(C)C] |
| 178 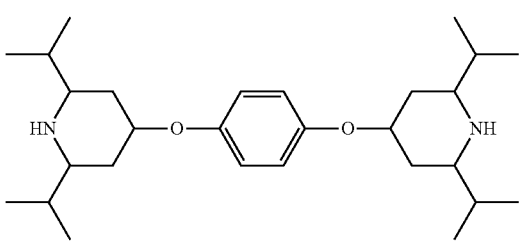 [SMILES: CC(C)C1CC(Oc2ccc(OC3CC(C(C)C)NC(C(C)C)C3)cc2)CC(C(C)C)N1] |

| No. | |
|---|---|
| 179 | 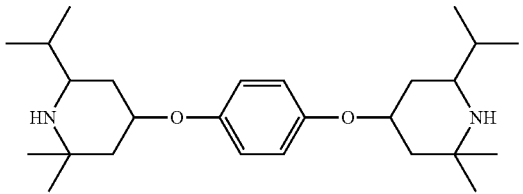 [SMILES: CC(C)C1CC(Oc2ccc(OC3CC(C(C)C)NC(C)(C)C3)cc2)CC(C)(C)N1] |
| 180 | 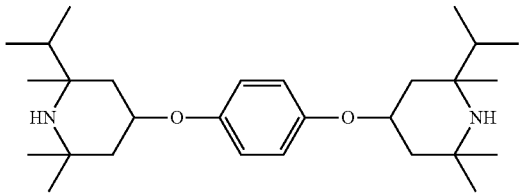 [SMILES: CC(C)C1(C)CC(Oc2ccc(OC3CC(C)(C)NC(C)(C(C)C)C3)cc2)CC(C)(C)N1] |
| 181 | 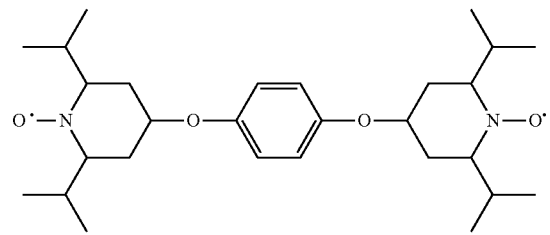 |
| 182 | 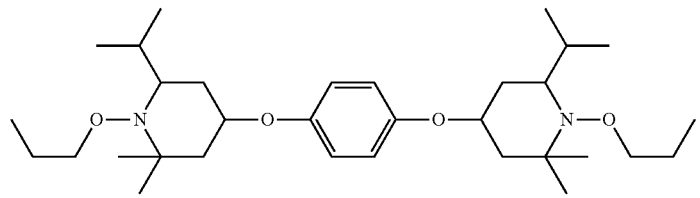 [SMILES: CCCON1C(C(C)C)CC(Oc2ccc(OC3CC(C(C)C)N(OCCC)C(C)(C)C3)cc2)CC1(C)C] |
| 183 | 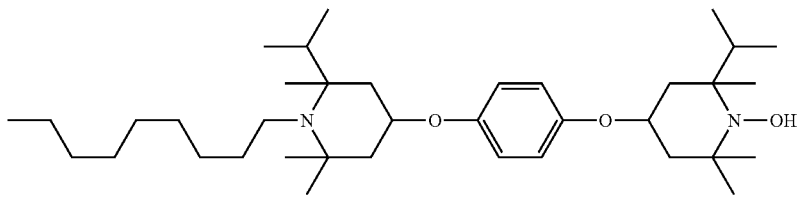 [SMILES: CCCCCCCCCN1C(C)(C)CC(Oc2ccc(OC3CC(C)(C)N(O)C(C)(C(C)C)C3)cc2)CC1(C)C(C)C] |
| 184 | 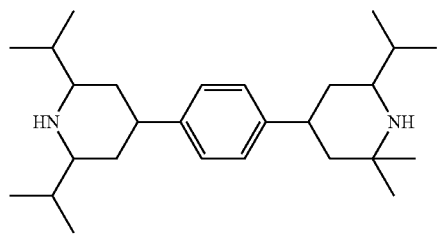 |
| 185 | 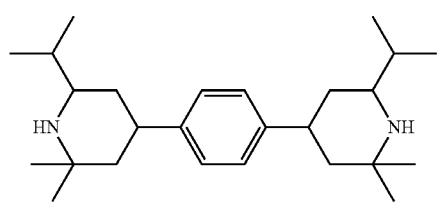 [SMILES: CC(C)C1CC(c2ccc(C3CC(C(C)C)NC(C)(C)C3)cc2)CC(C)(C)N1] |

| No. | |
|---|---|
| 186 | 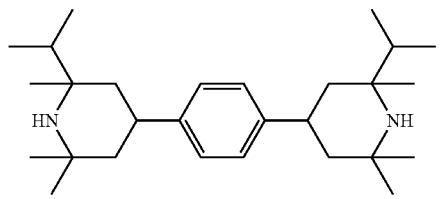 [SMILES: CC(C)C1(C)CC(c2ccc(C3CC(C)(C)NC(C)(C(C)C)C3)cc2)CC(C)(C)N1] |
| 187 | 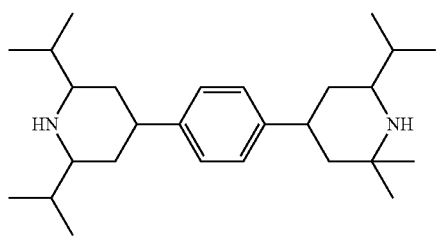 [SMILES: CC(C)C1CC(c2ccc(C3CC(C(C)C)NC(C)(C)C3)cc2)CC(C(C)C)N1] |
| 188 | 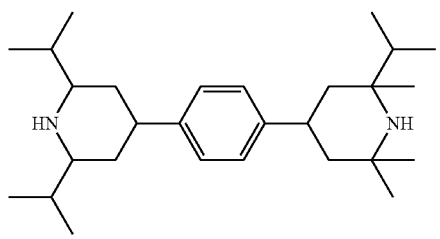 [SMILES: CC(C)C1CC(c2ccc(C3CC(C)(C)NC(C)(C(C)C)C3)cc2)CC(C(C)C)N1] |
| 189 | 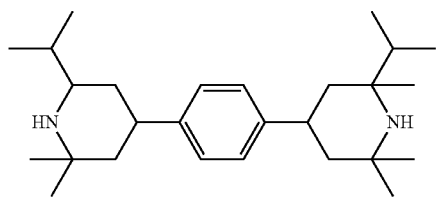 [SMILES: CC(C)C1CC(c2ccc(C3CC(C)(C)NC(C)(C(C)C)C3)cc2)CC(C)(C)N1] |
| 190 | 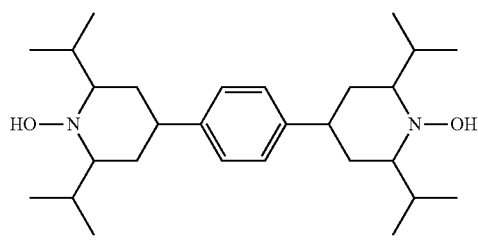 |
| 191 | 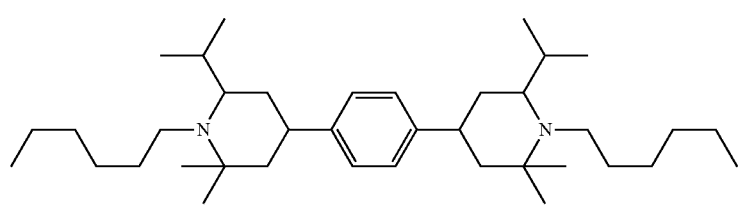 [SMILES: CCCCCCN1C(C(C)C)CC(c2ccc(C3CC(C(C)C)N(CCCCCC)C(C)(C)C3)cc2)CC1(C)C] |

| No. |
|---|
| 192 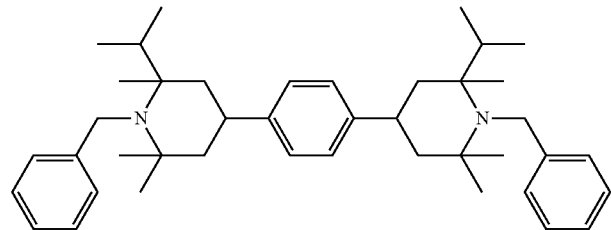 [SMILES: CC(C)C1(C)CC(c2ccc(C3CC(C)(C)N(Cc4ccccc4)C(C)(C(C)C)C3)cc2)CC(C)(C)N1Cc1ccccc1] |
| 193 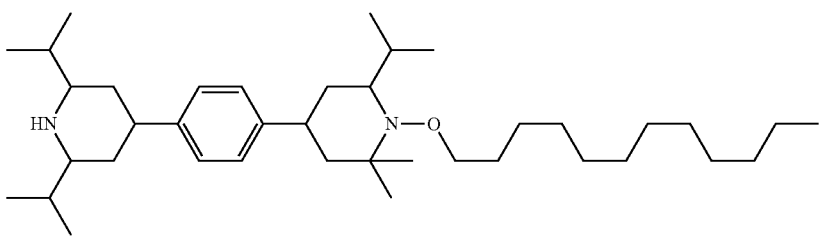 [SMILES: CCCCCCCCCCCCON1C(C(C)C)CC(c2ccc(C3CC(C(C)C)NC(C(C)C)C3)cc2)CC1(C)C] |
| 194 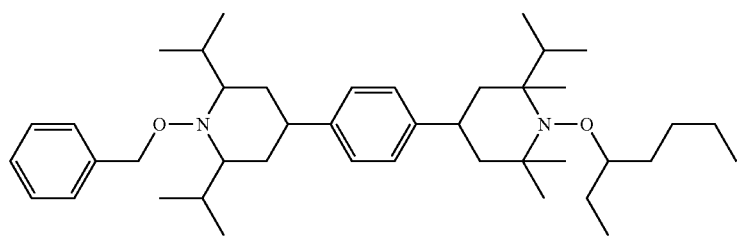 [SMILES: CCCCC(CC)ON1C(C)(C)CC(c2ccc(C3CC(C(C)C)N(OCc4ccccc4)C(C(C)C)C3)cc2)CC1(C)C(C)C] |
| 195 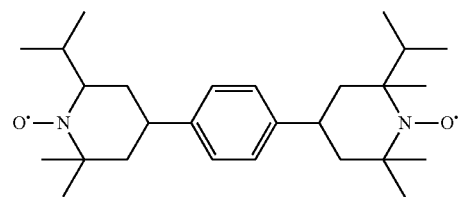 |
| 196 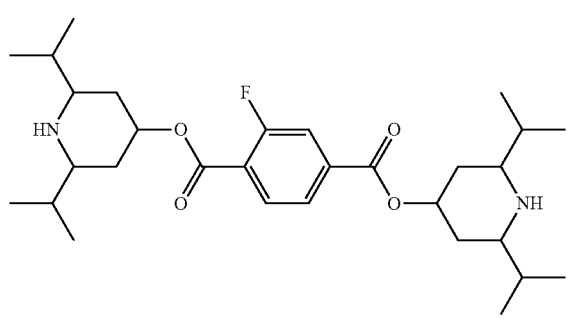 |
| 197 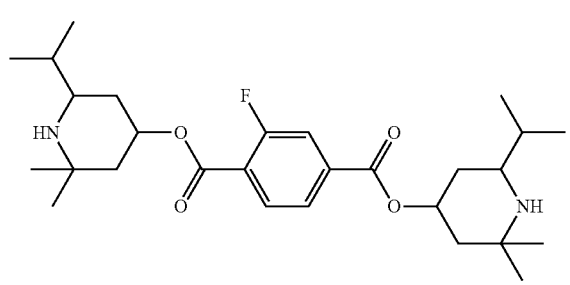 [SMILES: CC(C)C1CC(OC(=O)c2ccc(C(=O)OC3CC(C(C)C)NC(C)(C)C3)c(F)c2)CC(C)(C)N1] |

| No. | |
|---|---|
| 198 | 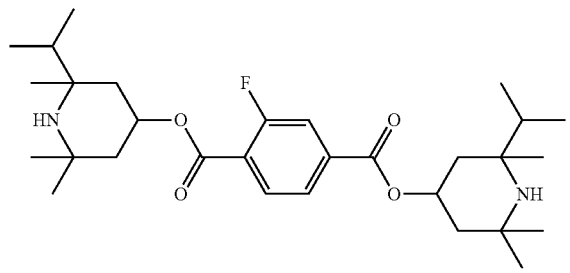 [SMILES: CC(C)C1(C)CC(OC(=O)c2ccc(C(=O)OC3CC(C)(C)NC(C)(C(C)C)C3)c(F)c2)CC(C)(C)N1] |
| 199 | 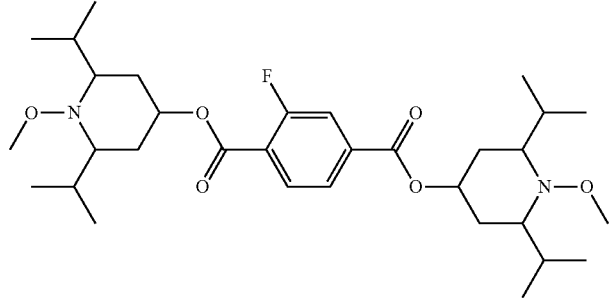 |
| 200 | 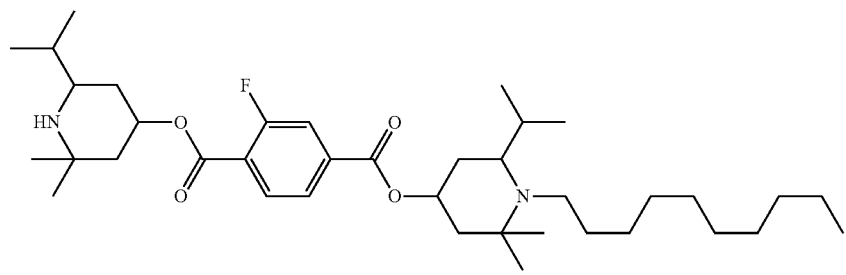 [SMILES: CCCCCCCCCCN1C(C(C)C)CC(OC(=O)c2ccc(C(=O)OC3CC(C(C)C)NC(C)(C)C3)c(F)c2)CC1(C)C] |
| 201 | 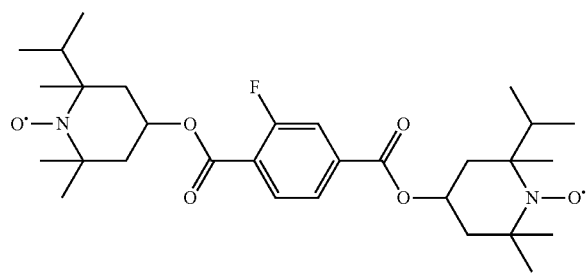 |
| 202 | 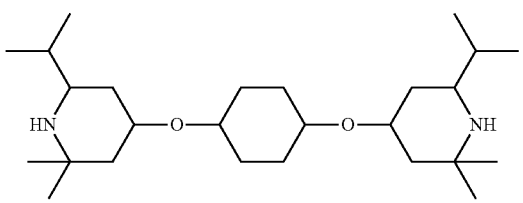 [SMILES: CC(C)C1CC(OC2CCC(OC3CC(C(C)C)NC(C)(C)C3)CC2)CC(C)(C)N1] |

-continued
| No. | |
|---|---|
| 203 | 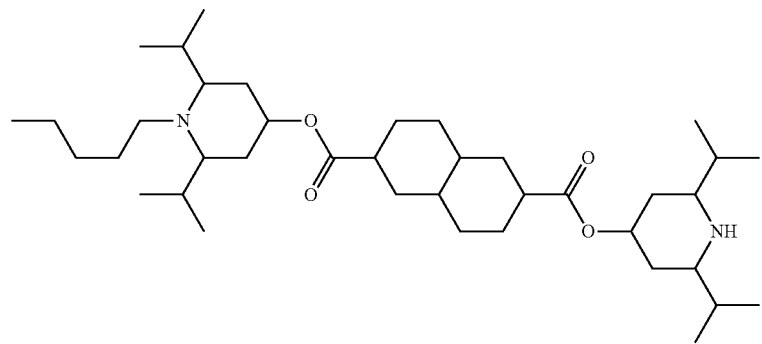 [SMILES: CCCCCN1C(C(C)C)CC(OC(=O)C2CCC3CC(C(=O)OC4CC(C(C)C)NC(C(C)C)C4)CCC3C2)CC1C(C)C] |
| 204 | 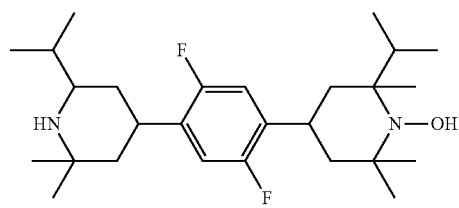 [SMILES: CC(C)C1CC(c2cc(F)c(C3CC(C)(C)N(O)C(C)(C(C)C)C3)cc2F)CC(C)(C)N1] |
| 205 | 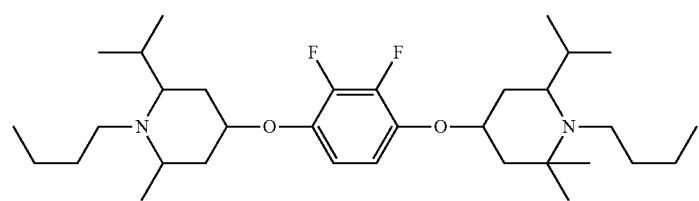 [SMILES: CCCCN1C(C)CC(Oc2ccc(OC3CC(C(C)C)N(CCCC)C(C)(C)C3)c(F)c2F)CC1C(C)C] |
| 206 | 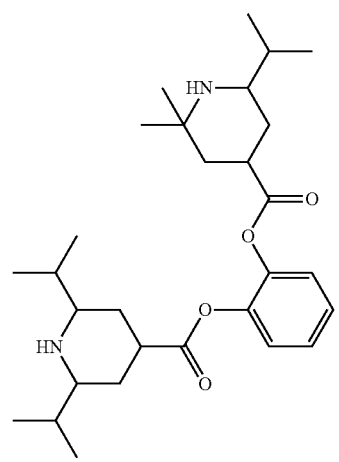 [SMILES: CC(C)C1CC(C(=O)Oc2ccccc2OC(=O)C2CC(C(C)C)NC(C)(C)C2)CC(C(C)C)N1] |

| No. |
|---|
| 207 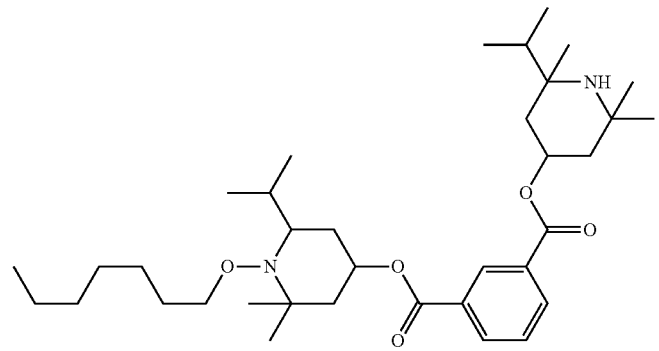 [SMILES: CCCCCCCON1C(C(C)C)CC(OC(=O)c2cccc(C(=O)OC3CC(C)(C)NC(C)(C(C)C)C3)c2)CC1(C)C] |
| 208 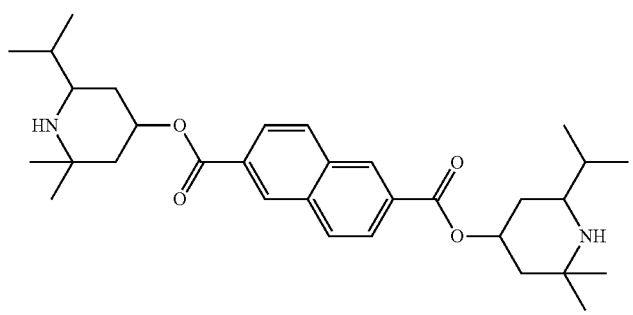 [SMILES: CC(C)C1CC(OC(=O)c2ccc3cc(C(=O)OC4CC(C(C)C)NC(C)(C)C4)ccc3c2)CC(C)(C)N1] |
| 209 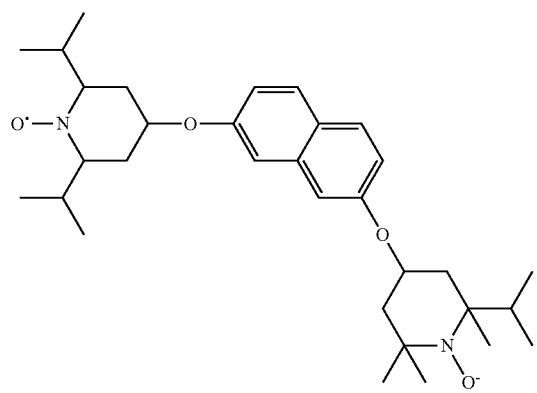 |
| 210 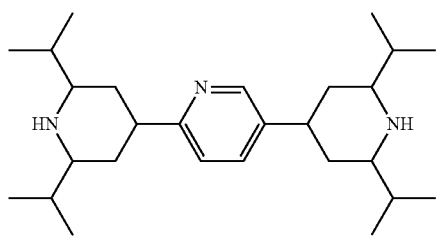 [SMILES: CC(C)C1CC(c2ccc(C3CC(C(C)C)NC(C(C)C)C3)nc2)CC(C(C)C)N1] |

| No. | |
|---|---|
| 211 | 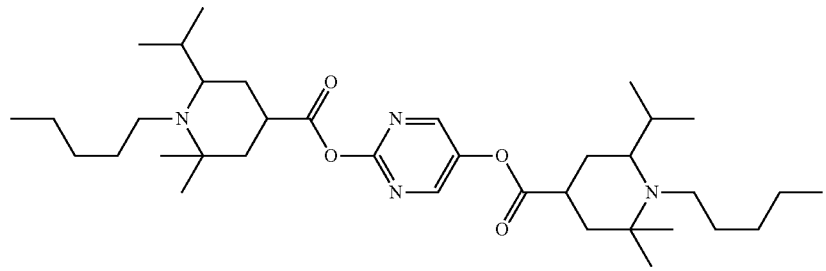 [SMILES: CCCCCN1C(C(C)C)CC(C(=O)Oc2cnc(OC(=O)C3CC(C(C)C)N(CCCCC)C(C)(C)C3)nc2)CC1(C)C] |
| 212 | 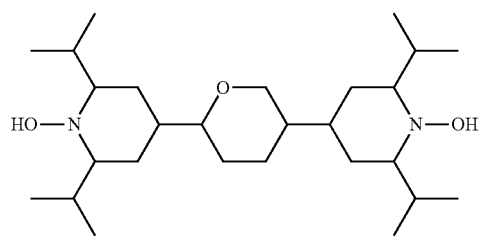 [SMILES: CC(C)C1CC(C2CCC(C3CC(C(C)C)N(O)C(C(C)C)C3)OC2)CC(C(C)C)N1O] |
| 213 | 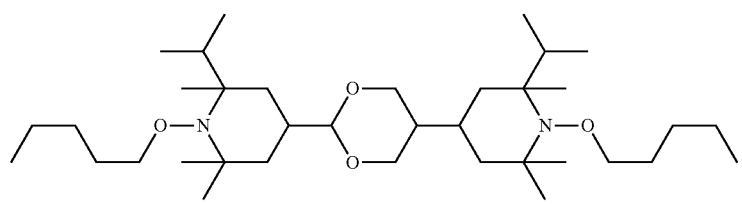 [SMILES: CCCCCON1C(C)(C)CC(C2COC(C3CC(C)(C)N(OCCCCC)C(C)(C(C)C)C3)OC2)CC1(C)C(C)C] |
| 214 | 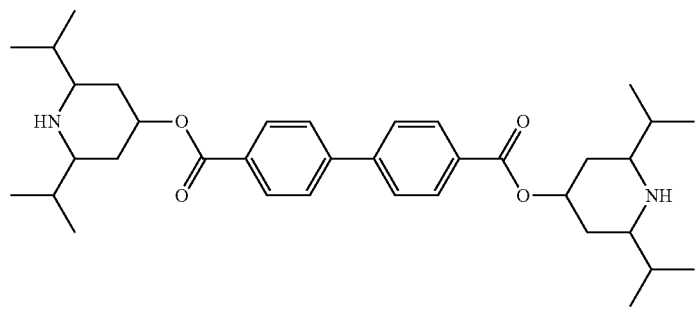 [SMILES: CC(C)C1CC(OC(=O)c2ccc(-c3ccc(C(=O)OC4CC(C(C)C)NC(C(C)C)C4)cc3)cc2)CC(C(C)C)N1] |
| 215 | 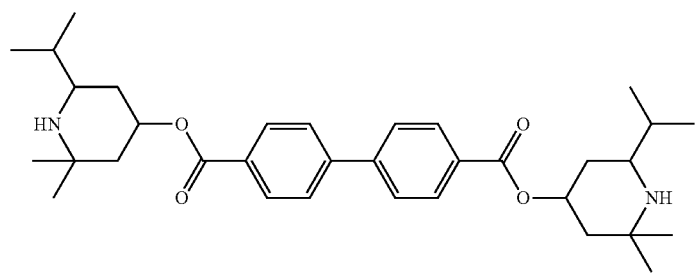 [SMILES: CC(C)C1CC(OC(=O)c2ccc(-c3ccc(C(=O)OC4CC(C(C)C)NC(C)(C)C4)cc3)cc2)CC(C)(C)N1] |

| No. | |
|---|---|
| 216 | 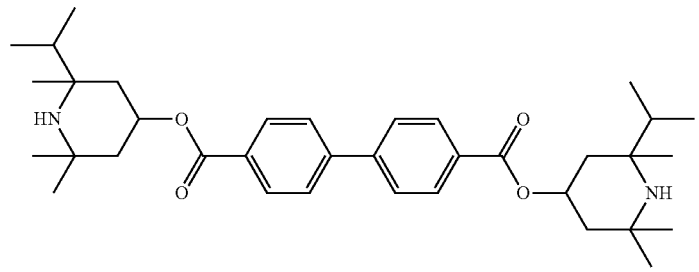 [SMILES: CC(C)C1(C)CC(OC(=O)c2ccc(-c3ccc(C(=O)OC4CC(C)(C)NC(C)(C(C)C)C4)cc3)cc2)CC(C)(C)N1] |
| 217 | 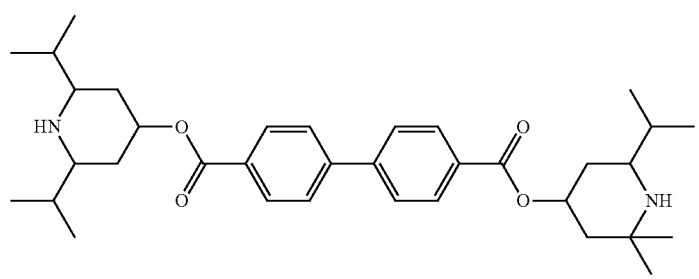 |
| 218 | 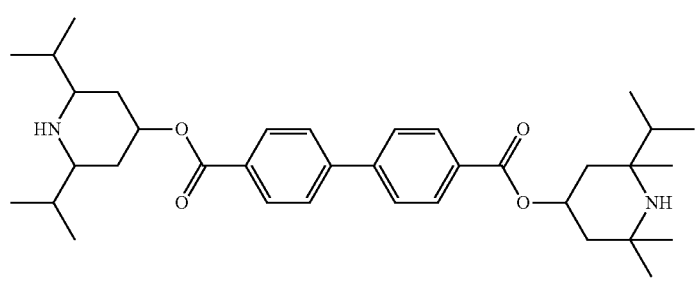 [SMILES: CC(C)C1CC(OC(=O)c2ccc(-c3ccc(C(=O)OC4CC(C(C)C)NC(C)(C)C4)cc3)cc2)CC(C(C)C)N1] |
| 219 | 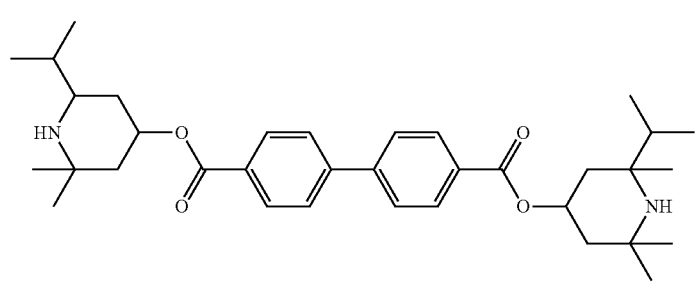 [SMILES: CC(C)C1CC(OC(=O)c2ccc(-c3ccc(C(=O)OC4CC(C)(C)NC(C)(C(C)C)C4)cc3)cc2)CC(C)(C)N1] |
| 220 | 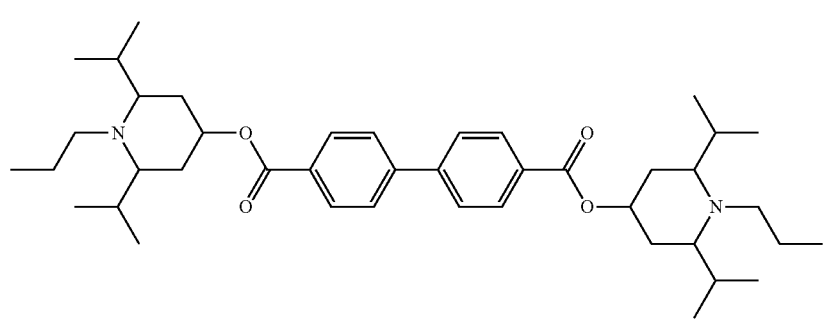 [SMILES: CCCN1C(C(C)C)CC(OC(=O)c2ccc(-c3ccc(C(=O)OC4CC(C(C)C)N(CCC)C(C(C)C)C4)cc3)cc2)CC1C(C)C] |

| No. | |
|---|---|
| 221 | 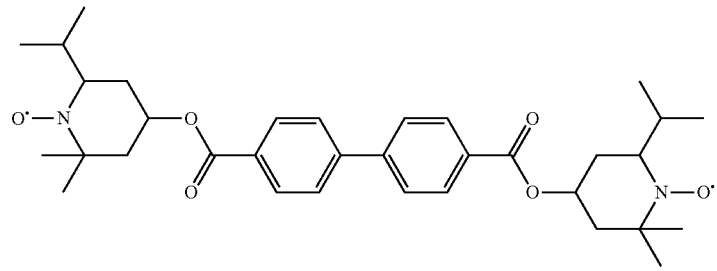 |
| 222 | 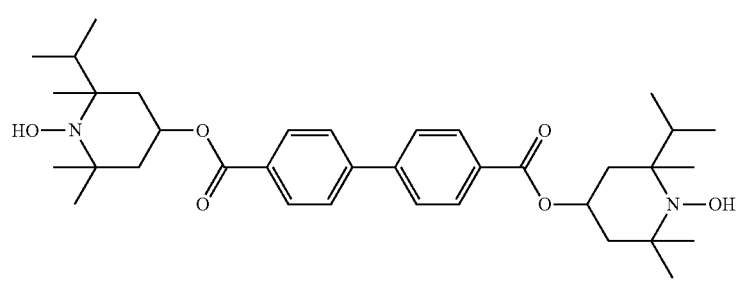 [SMILES: CC(C)C1(C)CC(OC(=O)c2ccc(-c3ccc(C(=O)OC4CC(C)(C)N(O)C(C)(C(C)C)C4)cc3)cc2)CC(C)(C)N1O] |
| 223 | 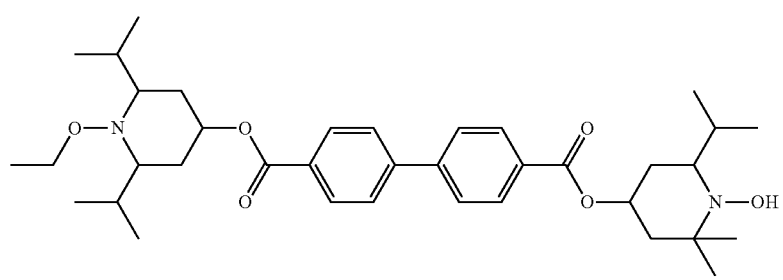 [SMILES: CCON1C(C(C)C)CC(OC(=O)c2ccc(-c3ccc(C(=O)OC4CC(C(C)C)N(O)C(C)(C)C4)cc3)cc2)CC1C(C)C] |
| 224 | 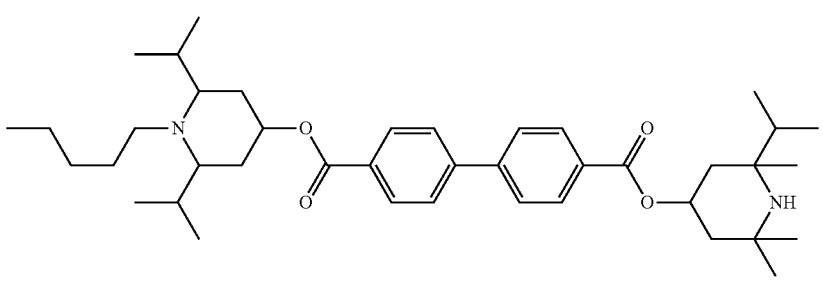 [SMILES: CCCCCN1C(C(C)C)CC(OC(=O)c2ccc(-c3ccc(C(=O)OC4CC(C)(C)NC(C)(C(C)C)C4)cc3)cc2)CC1C(C)C] |
| 225 | 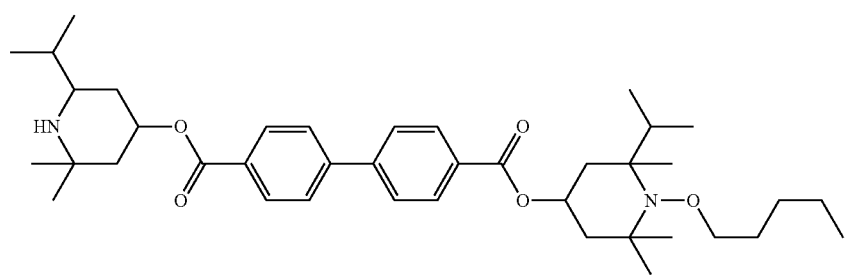 [SMILES: CCCCCON1C(C)(C)CC(OC(=O)c2ccc(-c3ccc(C(=O)OC4CC(C(C)C)NC(C)(C)C4)cc3)cc2)CC1(C)C(C)C] |

| No. |
| --- |
| 226 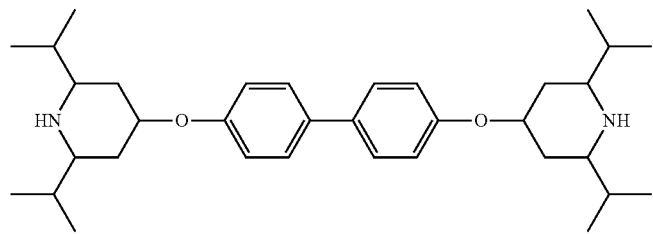 [SMILES: CC(C)C1CC(Oc2ccc(-c3ccc(OC4CC(C(C)C)NC(C(C)C)C4)cc3)cc2)CC(C(C)C)N1] |
| 227 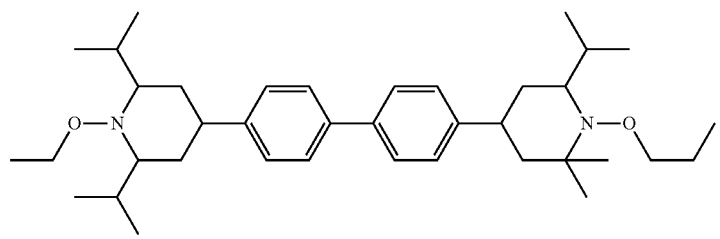 [SMILES: CCCON1C(C(C)C)CC(c2ccc(-c3ccc(C4CC(C(C)C)N(OCC)C(C(C)C)C4)cc3)cc2)CC1(C)C] |
| 228 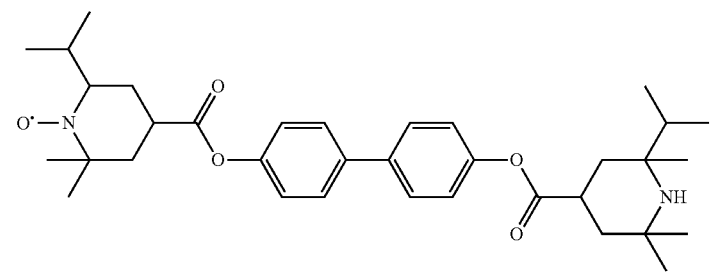 |
| 229 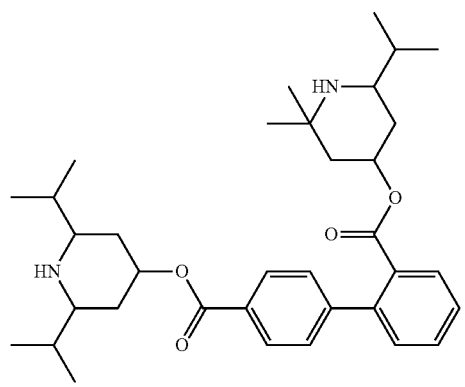 [SMILES: CC(C)C1CC(OC(=O)c2ccc(-c3ccccc3C(=O)OC3CC(C(C)C)NC(C)(C)C3)cc2)CC(C(C)C)N1] |
| 230 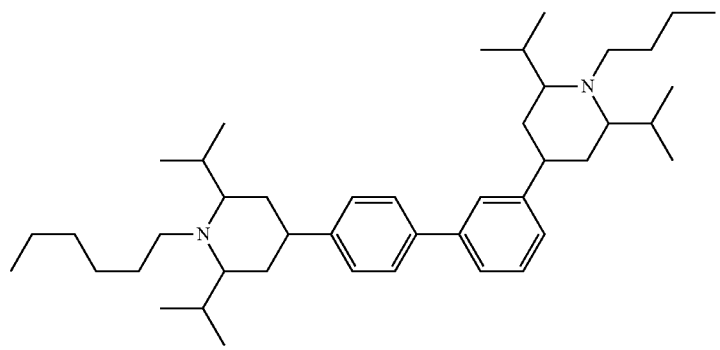 [SMILES: CCCCCCN1C(C(C)C)CC(c2ccc(-c3cccc(C4CC(C(C)C)N(CCCC)C(C(C)C)C4)c3)cc2)CC1C(C)C] |

| No. | |
|---|---|
| 231 | 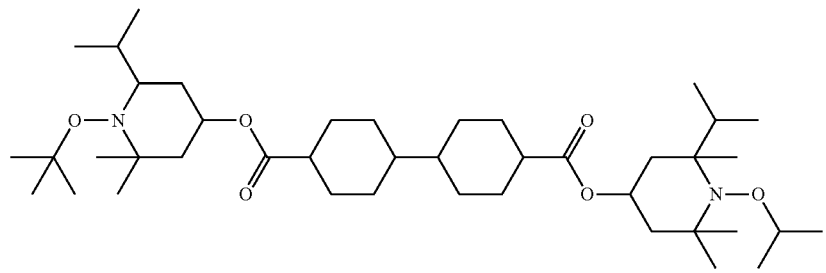 [SMILES: CC(C)ON1C(C)(C)CC(OC(=O)C2CCC(C3CCC(C(=O)OC4CC(C(C)C)N(OC(C)(C)C)C(C)(C)C4)CC3)CC2)CC1(C)C(C)C] |
| 232 | 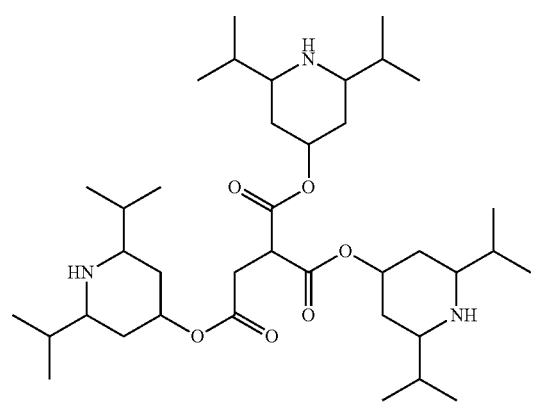 [SMILES: CC(C)C1CC(OC(=O)CC(C(=O)OC2CC(C(C)C)NC(C(C)C)C2)C(=O)OC2CC(C(C)C)NC(C(C)C)C2)CC(C(C)C)N1] |
| 233 | 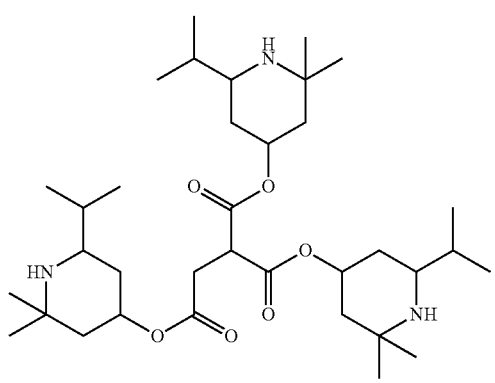 [SMILES: CC(C)C1CC(OC(=O)CC(C(=O)OC2CC(C(C)C)NC(C)(C)C2)C(=O)OC2CC(C(C)C)NC(C)(C)C2)CC(C)(C)N1] |
| 234 | 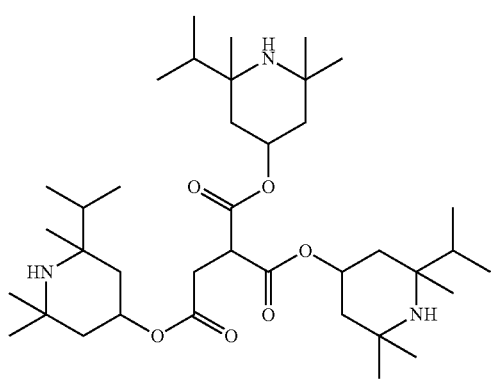 [SMILES: CC(C)C1(C)CC(OC(=O)CC(C(=O)OC2CC(C)(C)NC(C)(C(C)C)C2)C(=O)OC2CC(C)(C)NC(C)(C(C)C)C2)CC(C)(C)N1] |

| No. |
|---|
| 235 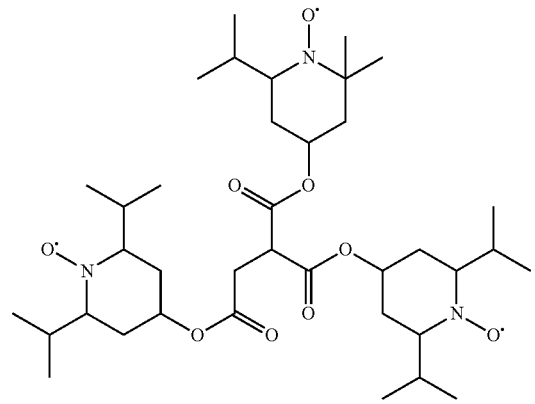 |
| 236 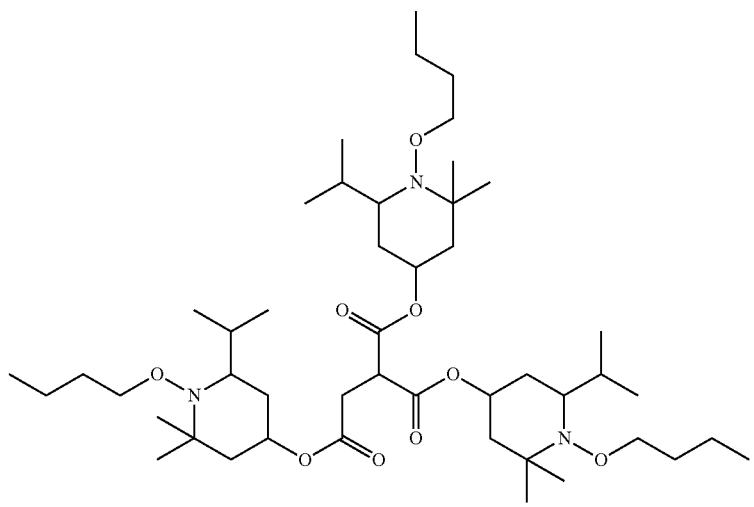 [SMILES: CCCCON1C(C(C)C)CC(OC(=O)CC(C(=O)OC2CC(C(C)C)N(OCCCC)C(C)(C)C2)C(=O)OC2CC(C(C)C)N(OCCCC)C(C)(C)C2)CC1(C)C] |
| 237 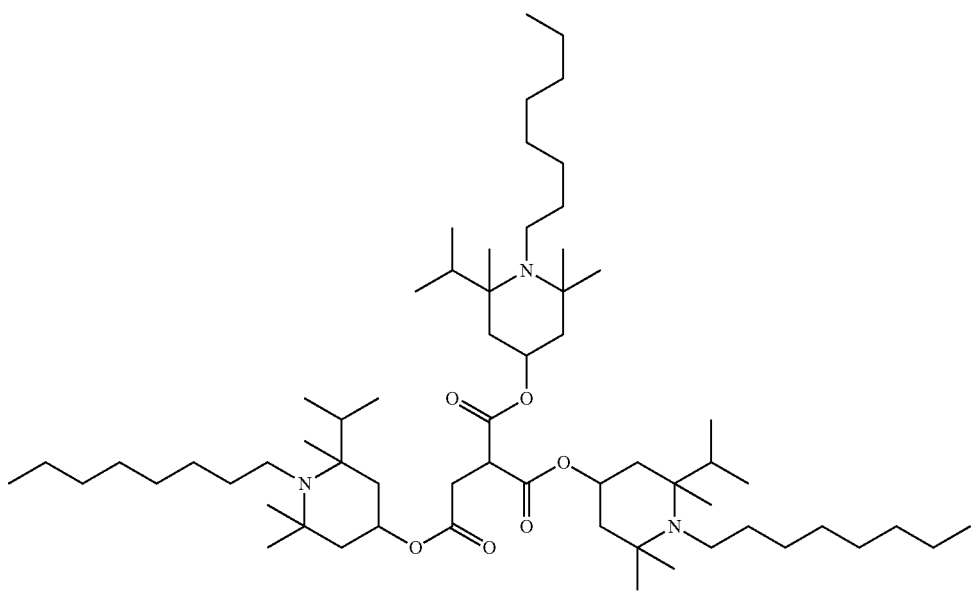 [SMILES: CCCCCCCCN1C(C)(C)CC(OC(=O)CC(C(=O)OC2CC(C)(C)N(CCCCCCCC)C(C)(C(C)C)C2)C(=O)OC2CC(C)(C)N(CCCCCCCC)C(C)(C(C)C)C2)CC1(C)C(C)C] |

| No. |
|---|
| 238 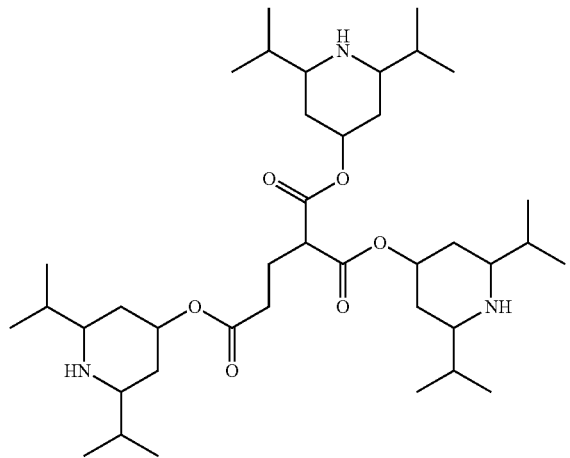 [SMILES: CC(C)C1CC(OC(=O)CCC(C(=O)OC2CC(C(C)C)NC(C(C)C)C2)C(=O)OC2CC(C(C)C)NC(C(C)C)C2)CC(C(C)C)N1] |
| 239 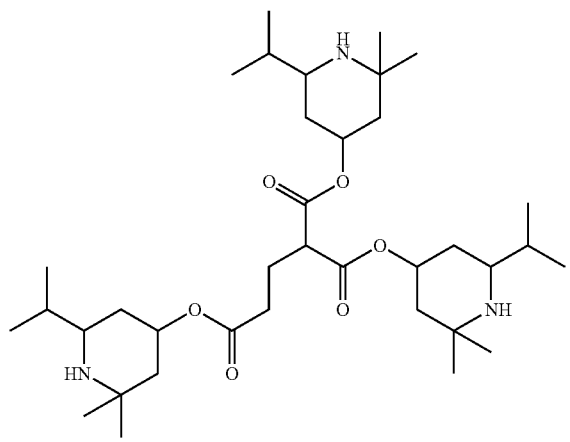 [SMILES: CC(C)C1CC(OC(=O)CCC(C(=O)OC2CC(C(C)C)NC(C)(C)C2)C(=O)OC2CC(C(C)C)NC(C)(C)C2)CC(C)(C)N1] |
| 240 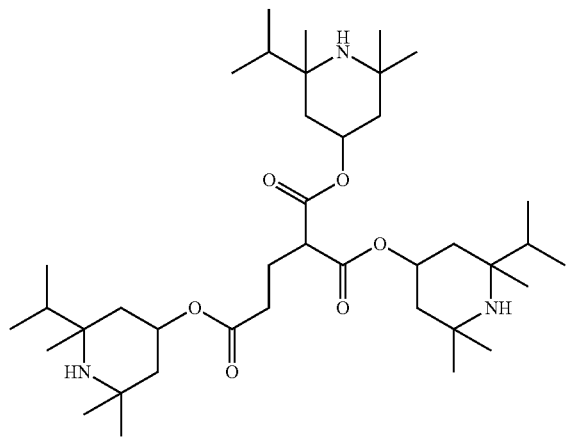 [SMILES: CC(C)C1(C)CC(OC(=O)CCC(C(=O)OC2CC(C)(C)NC(C)(C(C)C)C2)C(=O)OC2CC(C)(C)NC(C)(C(C)C)C2)CC(C)(C)N1] |

| No. |
|---|
| 241 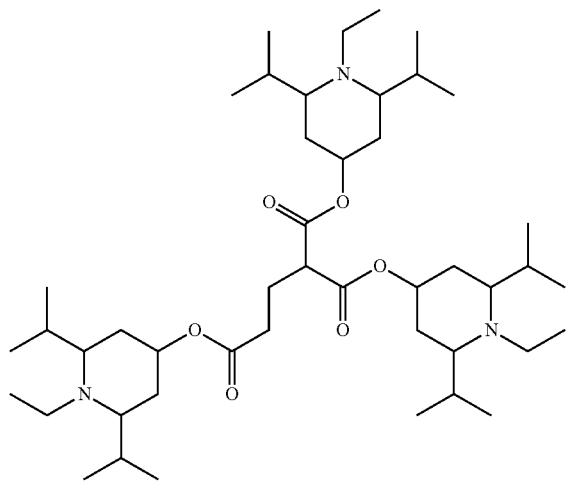 [SMILES: CCN1C(C(C)C)CC(OC(=O)CCC(C(=O)OC2CC(C(C)C)N(CC)C(C(C)C)C2)C(=O)OC2CC(C(C)C)N(CC)C(C(C)C)C2)CC1C(C)C] |
| 242 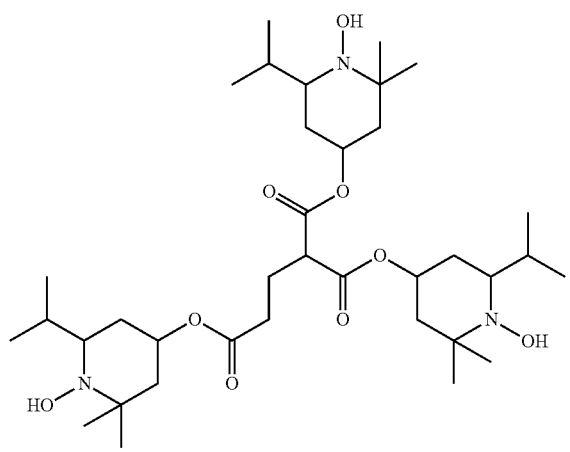 [SMILES: CC(C)C1CC(OC(=O)CCC(C(=O)OC2CC(C(C)C)N(O)C(C)(C)C2)C(=O)OC2CC(C(C)C)N(O)C(C)(C)C2)CC(C)(C)N1O] |

| No. |
|---|
| 243 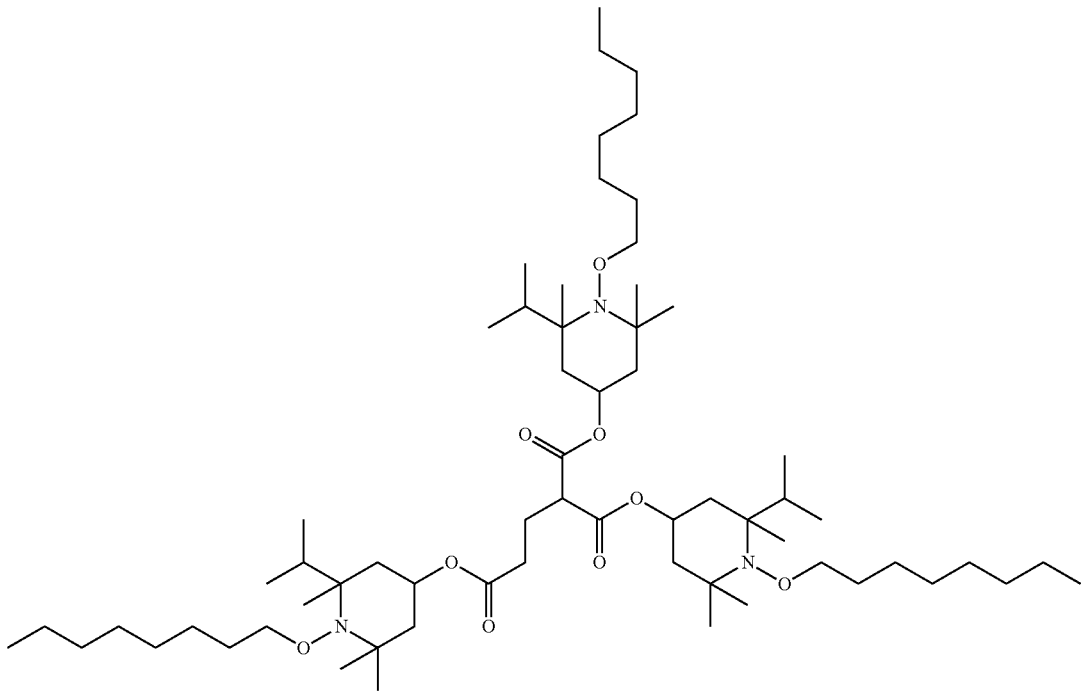 [SMILES: CCCCCCCCON1C(C)(C)CC(OC(=O)CCC(C(=O)OC2CC(C)(C)N(OCCCCCCCC)C(C)(C(C)C)C2)C(=O)OC2CC(C)(C)N(OCCCCCCCC)C(C)(C(C)C)C2)CC1(C)C(C)C] |
| 244 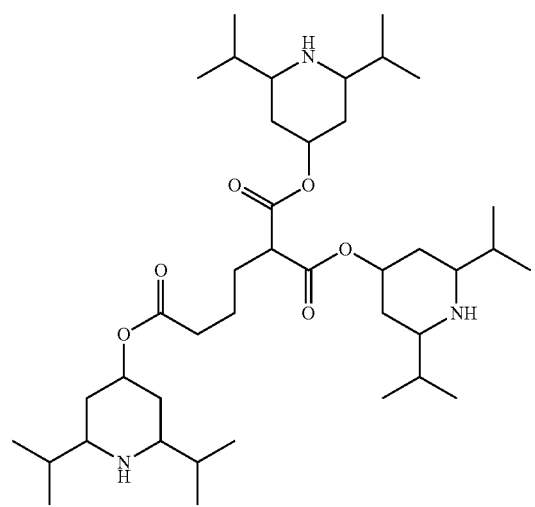 [SMILES: CC(C)C1CC(OC(=O)CCCC(C(=O)OC2CC(C(C)C)NC(C(C)C)C2)C(=O)OC2CC(C(C)C)NC(C(C)C)C2)CC(C(C)C)N1] |

| No. |
|---|
| 245 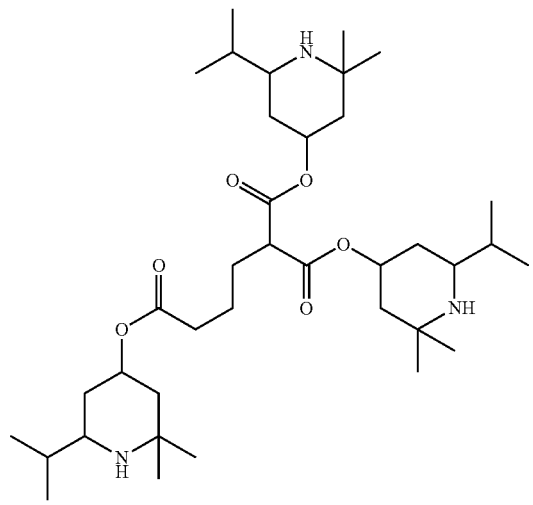 [SMILES: CC(C)C1CC(OC(=O)CCCC(C(=O)OC2CC(C(C)C)NC(C)(C)C2)C(=O)OC2CC(C(C)C)NC(C)(C)C2)CC(C)(C)N1] |
| 246 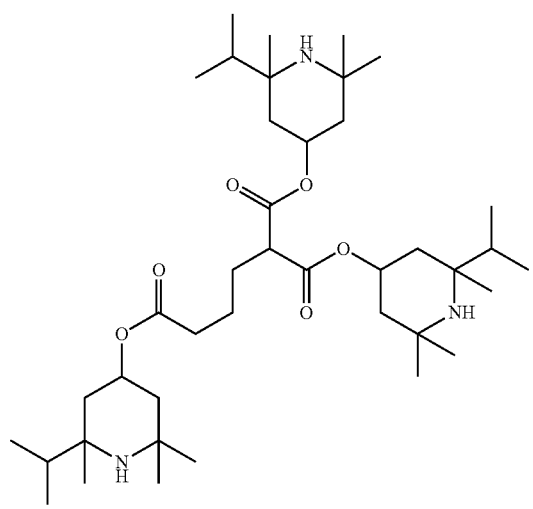 [SMILES: CC(C)C1(C)CC(OC(=O)CCCC(C(=O)OC2CC(C)(C)NC(C)(C(C)C)C2)C(=O)OC2CC(C)(C)NC(C)(C(C)C)C2)CC(C)(C)N1] |
| 247 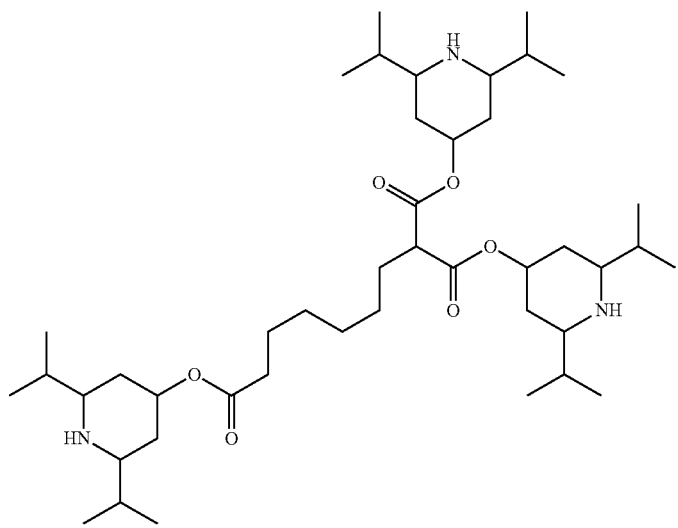 [SMILES: CC(C)C1CC(OC(=O)CCCCCCC(C(=O)OC2CC(C(C)C)NC(C(C)C)C2)C(=O)OC2CC(C(C)C)NC(C(C)C)C2)CC(C(C)C)N1] |

| No. |
|---|
| 248 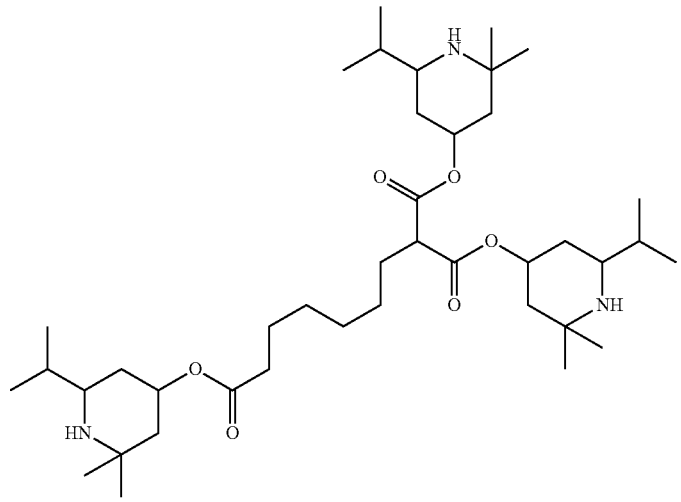 [SMILES: CC(C)C1CC(OC(=O)CCCCCCC(C(=O)OC2CC(C(C)C)NC(C)(C)C2)C(=O)OC2CC(C(C)C)NC(C)(C)C2)CC(C)(C)N1] |
| 249 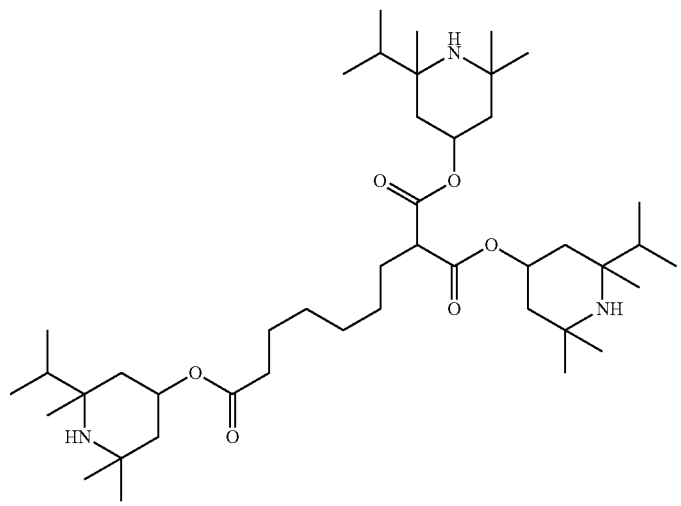 [SMILES: CC(C)C1(C)CC(OC(=O)CCCCCCC(C(=O)OC2CC(C)(C)NC(C)(C(C)C)C2)C(=O)OC2CC(C)(C)NC(C)(C(C)C)C2)CC(C)(C)N1] |
| 250 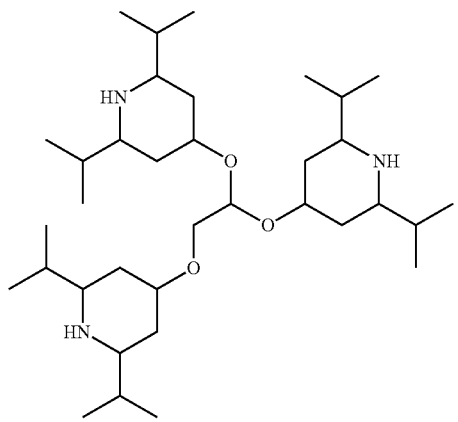 [SMILES: CC(C)C1CC(OCC(OC2CC(C(C)C)NC(C(C)C)C2)OC2CC(C(C)C)NC(C(C)C)C2)CC(C(C)C)N1] |

| No. |
|---|
| 251 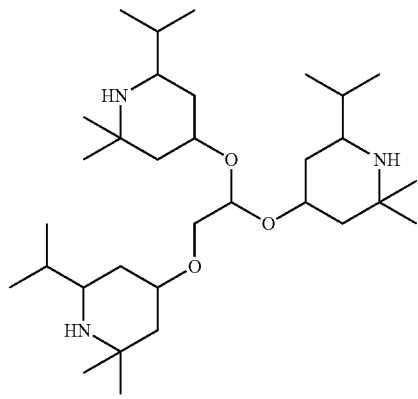 [SMILES: CC(C)C1CC(OCC(OC2CC(C(C)C)NC(C)(C)C2)OC2CC(C(C)C)NC(C)(C)C2)CC(C)(C)N1] |
| 252 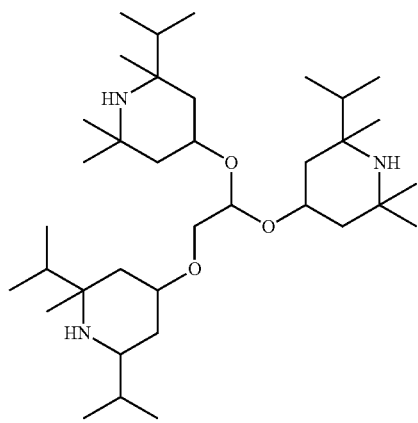 [SMILES: CC(C)C1CC(OCC(OC2CC(C)(C)NC(C)(C(C)C)C2)OC2CC(C)(C)NC(C)(C(C)C)C2)CC(C)(C(C)C)N1] |
| 253 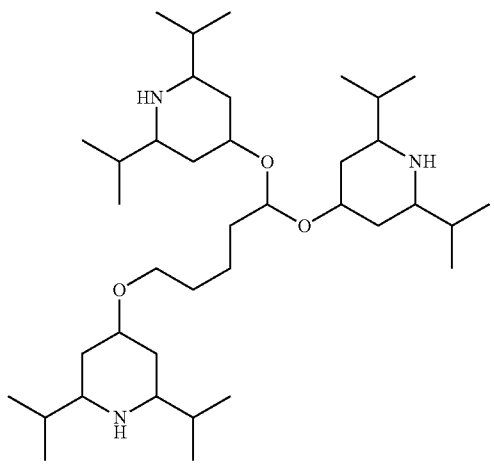 [SMILES: CC(C)C1CC(OCCCCC(OC2CC(C(C)C)NC(C(C)C)C2)OC2CC(C(C)C)NC(C(C)C)C2)CC(C(C)C)N1] |

| No. | |
|---|---|
| 254 | 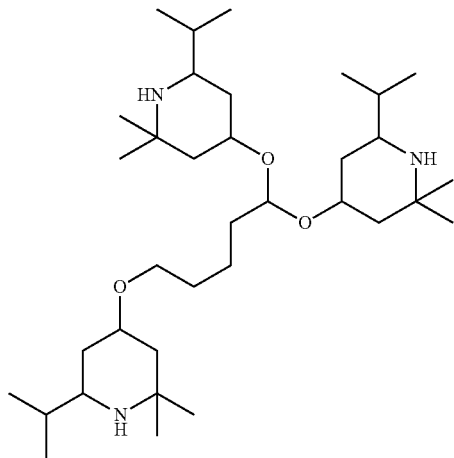 [SMILES: CC(C)C1CC(OCCCCC(OC2CC(C(C)C)NC(C)(C)C2)OC2CC(C(C)C)NC(C)(C)C2)CC(C)(C)N1] |
| 255 | 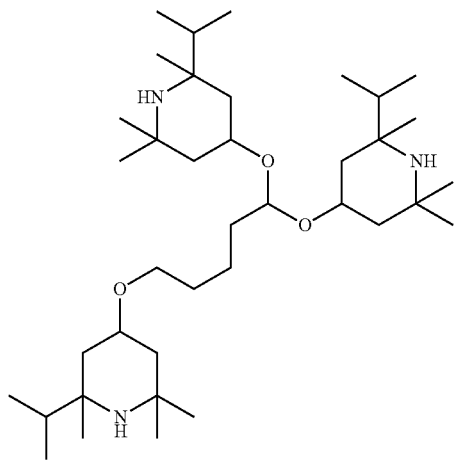 [SMILES: CC(C)C1(C)CC(OCCCCC(OC2CC(C)(C)NC(C)(C(C)C)C2)OC2CC(C)(C)NC(C)(C(C)C)C2)CC(C)(C)N1] |
| 256 | 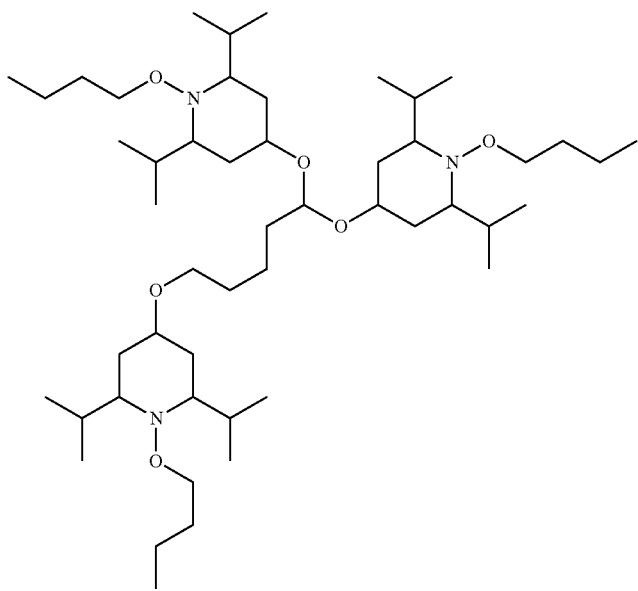 [SMILES: CCCCON1C(C(C)C)CC(OCCCCC(OC2CC(C(C)C)N(OCCCC)C(C(C)C)C2)OC2CC(C(C)C)N(OCCCC)C(C(C)C)C2)CC1C(C)C] |

| No. |
|---|
| 257 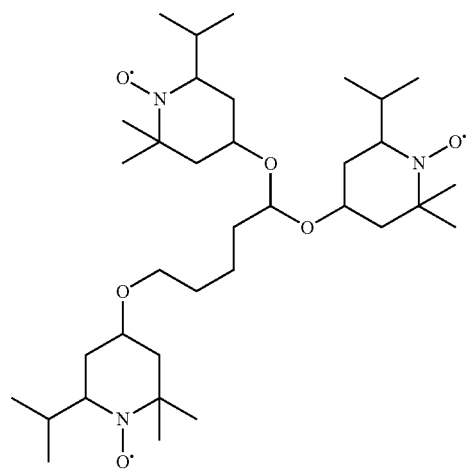 |
| 258 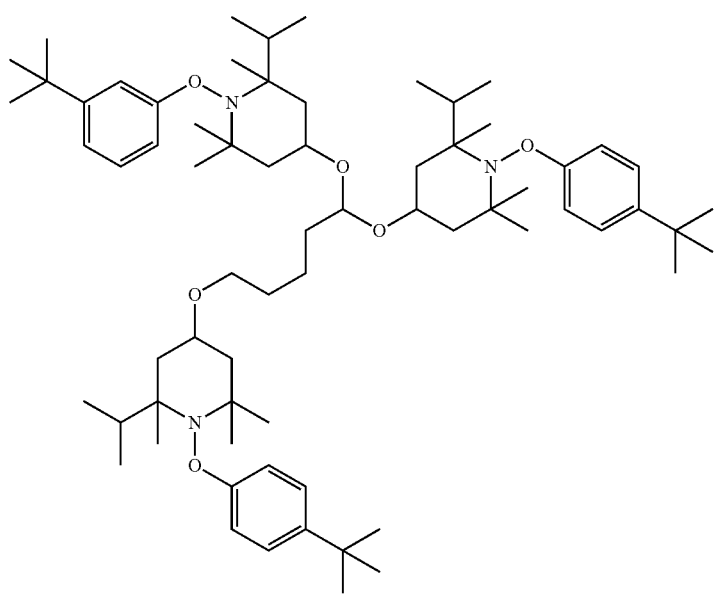 [SMILES: CC(C)C1(C)CC(OCCCCC(OC2CC(C)(C)N(Oc3ccc(C(C)(C)C)cc3)C(C)(C(C)C)C2)OC2CC(C)(C)N(Oc3cccc(C(C)(C)C)c3)C(C)(C(C)C)C2)CC(C)(C)N1Oc1ccc(C(C)(C)C)cc1] |
| 259 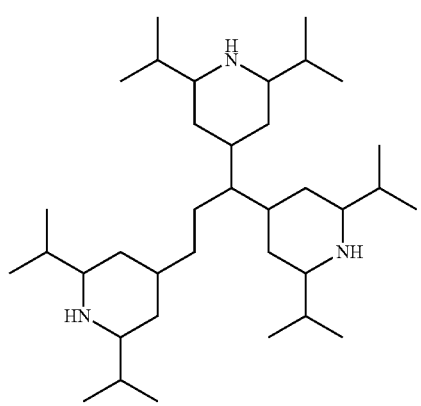 [SMILES: CC(C)C1CC(CCC(C2CC(C(C)C)NC(C(C)C)C2)C2CC(C(C)C)NC(C(C)C)C2)CC(C(C)C)N1] |

| No. |
|---|
| 260 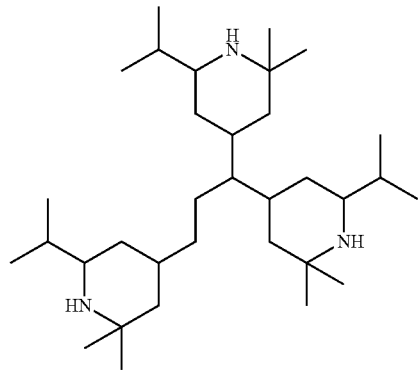 [SMILES: CC(C)C1CC(CCC(C2CC(C(C)C)NC(C)(C)C2)C2CC(C(C)C)NC(C)(C)C2)CC(C)(C)N1] |
| 261 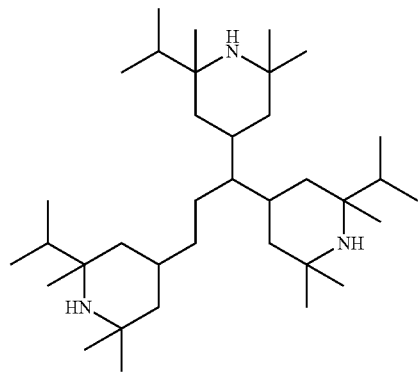 [SMILES: CC(C)C1(C)CC(CCC(C2CC(C)(C)NC(C)(C(C)C)C2)C2CC(C)(C)NC(C)(C(C)C)C2)CC(C)(C)N1] |
| 262 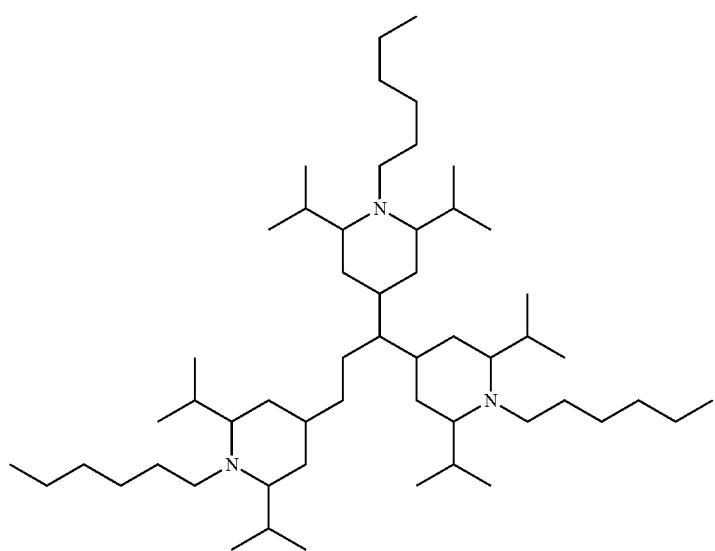 [SMILES: CCCCCCN1C(C(C)C)CC(CCC(C2CC(C(C)C)N(CCCCCC)C(C(C)C)C2)C2CC(C(C)C)N(CCCCCC)C(C(C)C)C2)CC1C(C)C] |

| No. | |
|---|---|
| 263 | 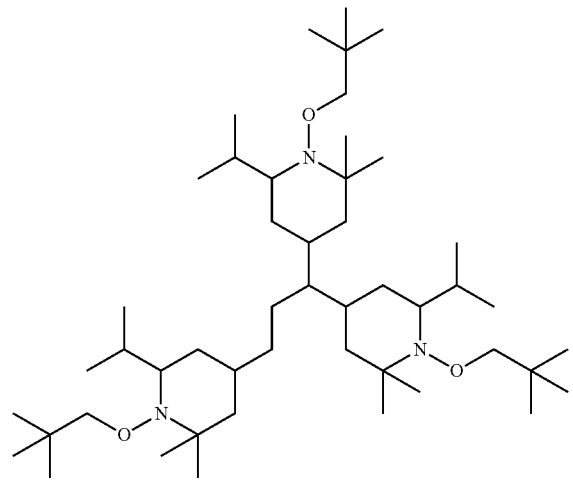 [SMILES: CC(C)C1CC(CCC(C2CC(C(C)C)N(OCC(C)(C)C)C(C)(C)C2)C2CC(C(C)C)N(OCC(C)(C)C)C(C)(C)C2)CC(C)(C)N1OCC(C)(C)C] |
| 264 | 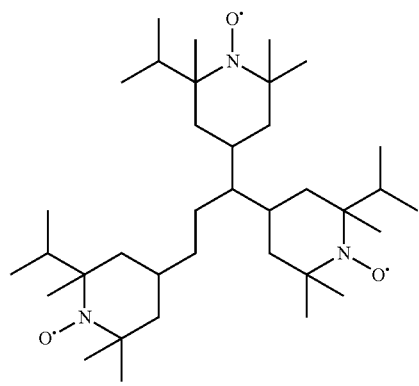 |
| 265 | 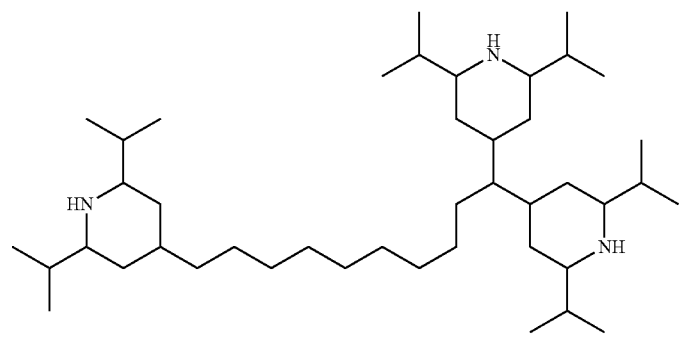 [SMILES: CC(C)C1CC(CCCCCCCCCC(C2CC(C(C)C)NC(C(C)C)C2)C2CC(C(C)C)NC(C(C)C)C2)CC(C(C)C)N1] |
| 266 | 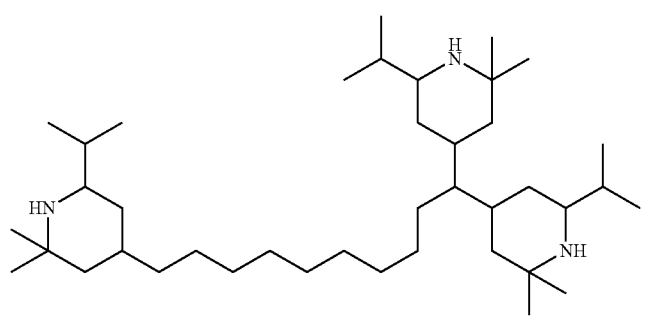 [SMILES: CC(C)C1CC(CCCCCCCCCC(C2CC(C(C)C)NC(C)(C)C2)C2CC(C(C)C)NC(C)(C)C2)CC(C)(C)N1] |

| No. | |
|---|---|
| 267 | 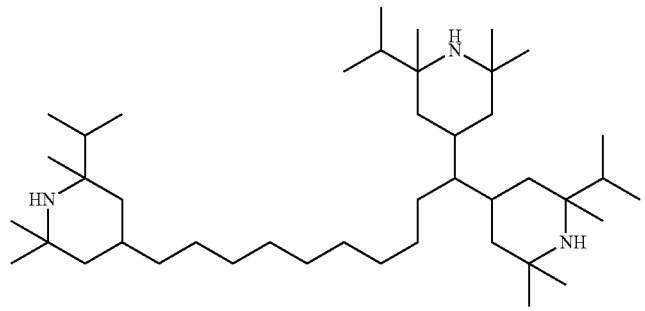 [SMILES: CC(C)C1(C)CC(CCCCCCCCCC(C2CC(C)(C)NC(C)(C(C)C)C2)C2CC(C)(C)NC(C)(C(C)C)C2)CC(C)(C)N1] |
| 268 | 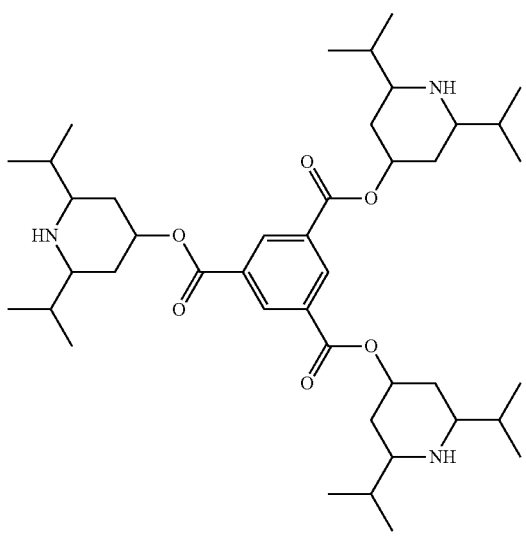 [SMILES: CC(C)C1CC(OC(=O)c2cc(C(=O)OC3CC(C(C)C)NC(C(C)C)C3)cc(C(=O)OC3CC(C(C)C)NC(C(C)C)C3)c2)CC(C(C)C)N1] |
| 269 | 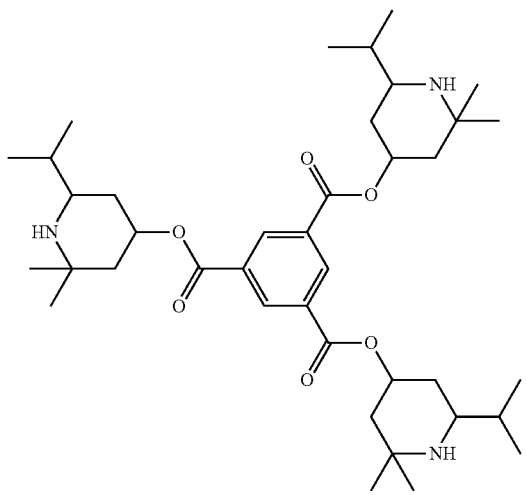 [SMILES: CC(C)C1CC(OC(=O)c2cc(C(=O)OC3CC(C(C)C)NC(C)(C)C3)cc(C(=O)OC3CC(C(C)C)NC(C)(C)C3)c2)CC(C)(C)N1] |

| No. |
|---|
| 270 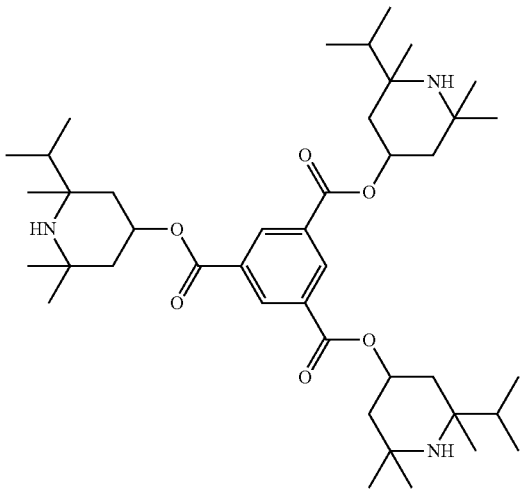 [SMILES: CC(C)C1(C)CC(OC(=O)c2cc(C(=O)OC3CC(C)(C)NC(C)(C(C)C)C3)cc(C(=O)OC3CC(C)(C)NC(C)(C(C)C)C3)c2)CC(C)(C)N1] |
| 271 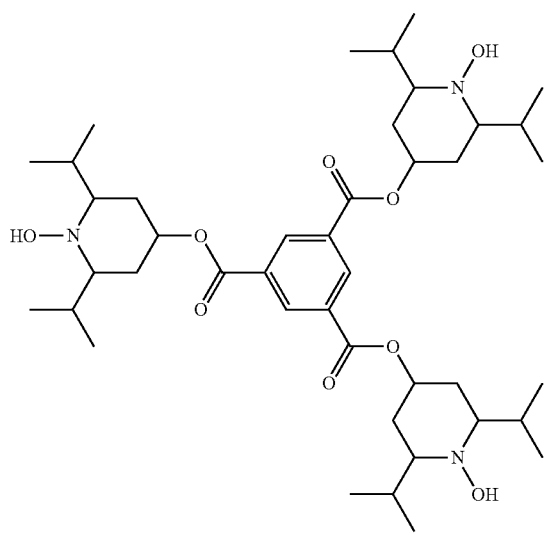 [SMILES: CC(C)C1CC(OC(=O)c2cc(C(=O)OC3CC(C(C)C)N(O)C(C(C)C)C3)cc(C(=O)OC3CC(C(C)C)N(O)C(C(C)C)C3)c2)CC(C(C)C)N1O] |

| No. |
|---|
| 272 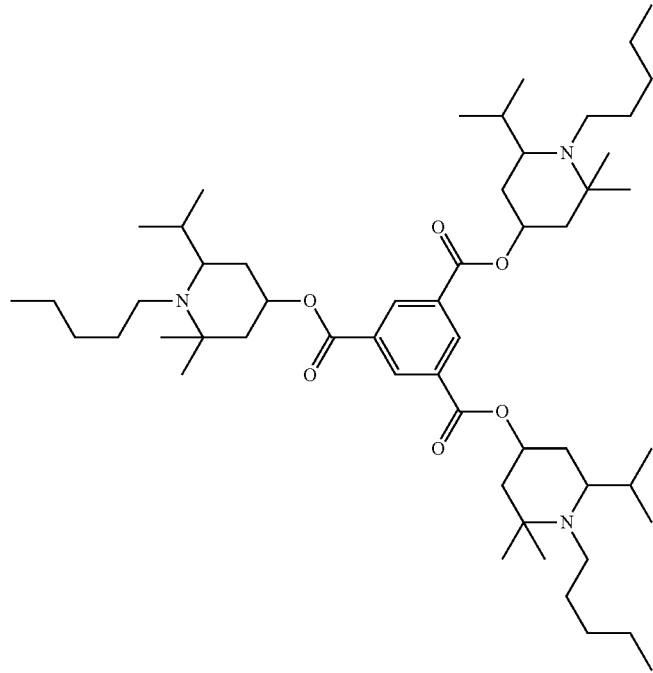 [SMILES: CCCCCN1C(C(C)C)CC(OC(=O)c2cc(C(=O)OC3CC(C(C)C)N(CCCCC)C(C)(C)C3)cc(C(=O)OC3CC(C(C)C)N(CCCCC)C(C)(C)C3)c2)CC1(C)C] |
| 273 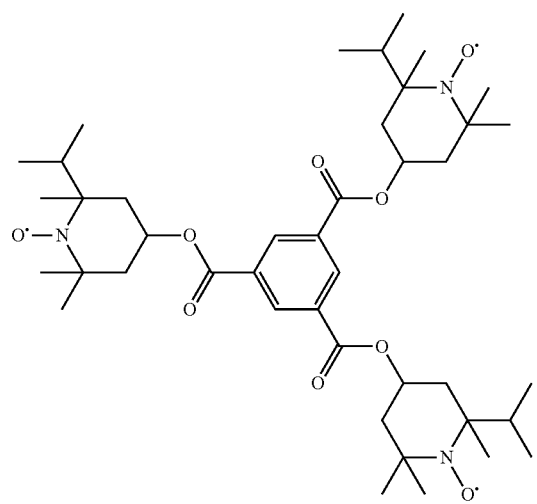 |

| No. | |
|---|---|
| 274 | 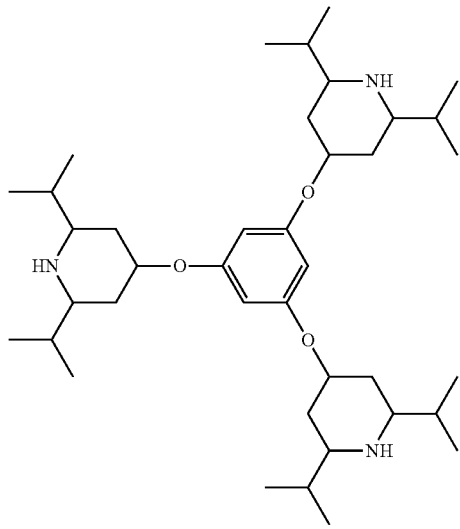 [SMILES: CC(C)C1CC(Oc2cc(OC3CC(C(C)C)NC(C(C)C)C3)cc(OC3CC(C(C)C)NC(C(C)C)C3)c2)CC(C(C)C)N1] |
| 275 | 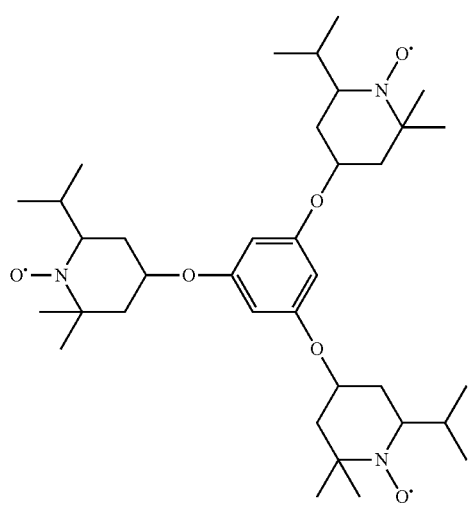 |

| No. |
|---|
| 276 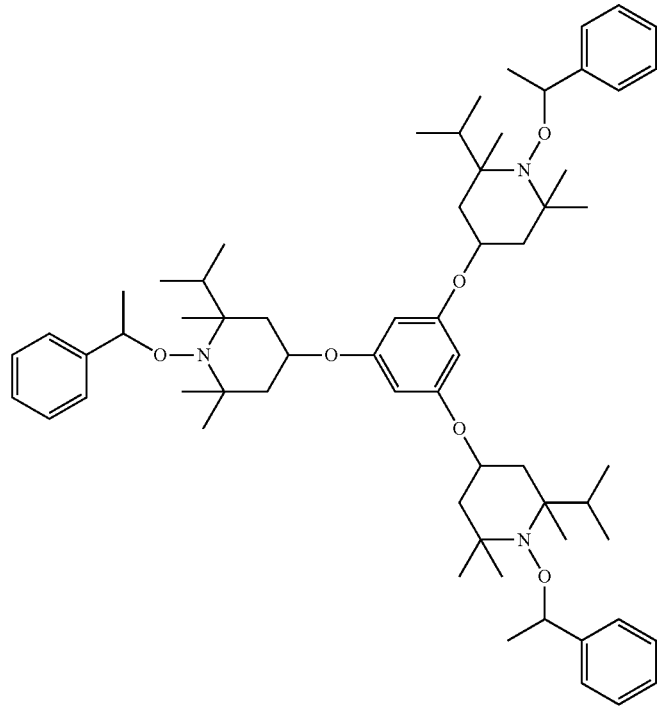 [SMILES: CC(ON1C(C)(C)CC(Oc2cc(OC3CC(C)(C)N(OC(C)c4ccccc4)C(C)(C(C)C)C3)cc(OC3CC(C)(C)N(OC(C)c4ccccc4)C(C)(C(C)C)C3)c2)CC1(C)C(C)C)c1ccccc1] |
| 277 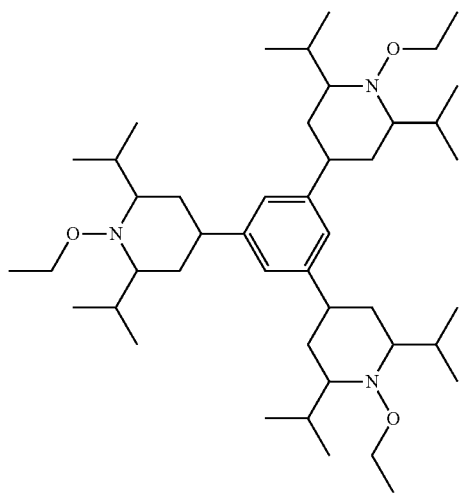 [SMILES: CCON1C(C(C)C)CC(c2cc(C3CC(C(C)C)N(OCC)C(C(C)C)C3)cc(C3CC(C(C)C)N(OCC)C(C(C)C)C3)c2)CC1C(C)C] |

| No. |
|---|
| 278 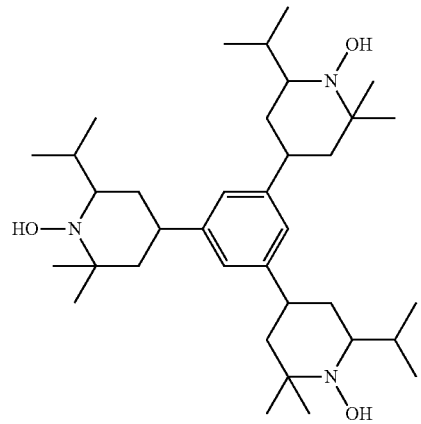 [SMILES: CC(C)C1CC(c2cc(C3CC(C(C)C)N(O)C(C)(C)C3)cc(C3CC(C(C)C)N(O)C(C)(C)C3)c2)CC(C)(C)N1O] |
| 279 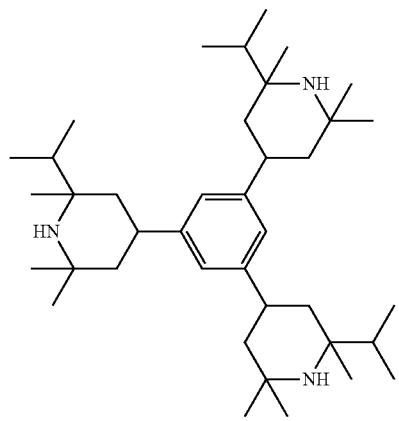 [SMILES: CC(C)C1(C)CC(c2cc(C3CC(C)(C)NC(C)(C(C)C)C3)cc(C3CC(C)(C)NC(C)(C(C)C)C3)c2)CC(C)(C)N1] |
| 280 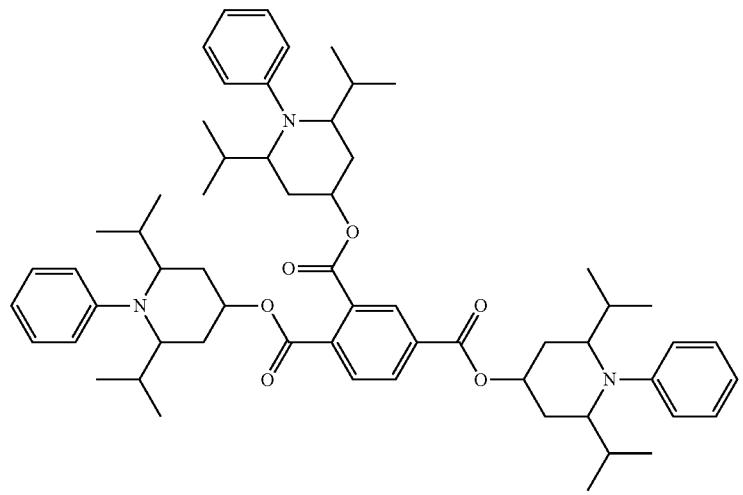 [SMILES: CC(C)C1CC(OC(=O)c2ccc(C(=O)OC3CC(C(C)C)N(c4ccccc4)C(C(C)C)C3)c(C(=O)OC3CC(C(C)C)N(c4ccccc4)C(C(C)C)C3)c2)CC(C(C)C)N1c1ccccc1] |

| No. |
|---|
| 281 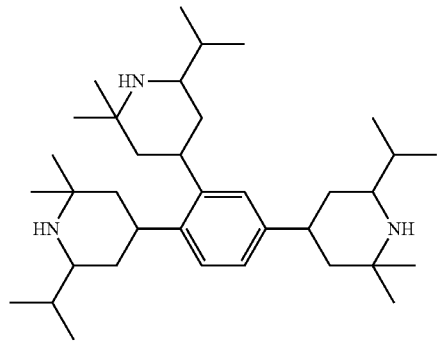 [SMILES: CC(C)C1CC(c2ccc(C3CC(C(C)C)NC(C)(C)C3)c(C3CC(C(C)C)NC(C)(C)C3)c2)CC(C)(C)N1] |
| 282 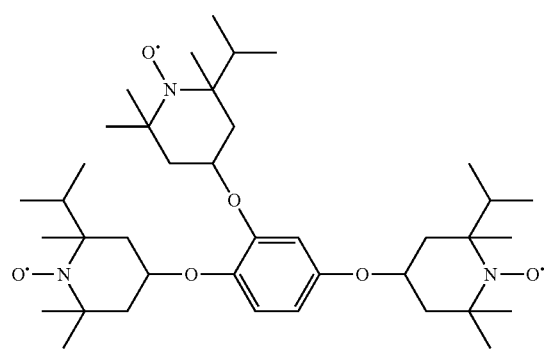 |
| 283 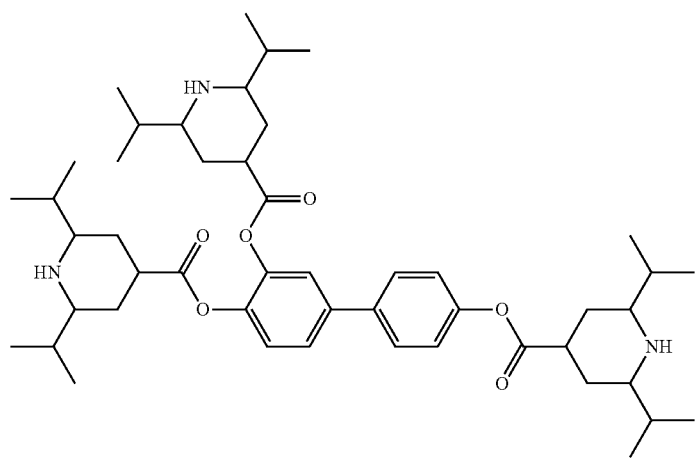 [SMILES: CC(C)C1CC(C(=O)Oc2ccc(-c3ccc(OC(=O)C4CC(C(C)C)NC(C(C)C)C4)c(OC(=O)C4CC(C(C)C)NC(C(C)C)C4)c3)cc2)CC(C(C)C)N1] |
| 284 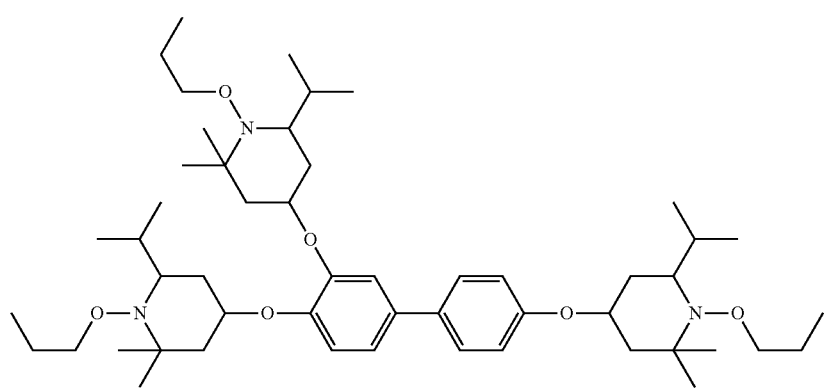 [SMILES: CCCON1C(C(C)C)CC(Oc2ccc(-c3ccc(OC4CC(C(C)C)N(OCCC)C(C)(C)C4)c(OC4CC(C(C)C)N(OCCC)C(C)(C)C4)c3)cc2)CC1(C)C] |

| No. |
|---|
| 285 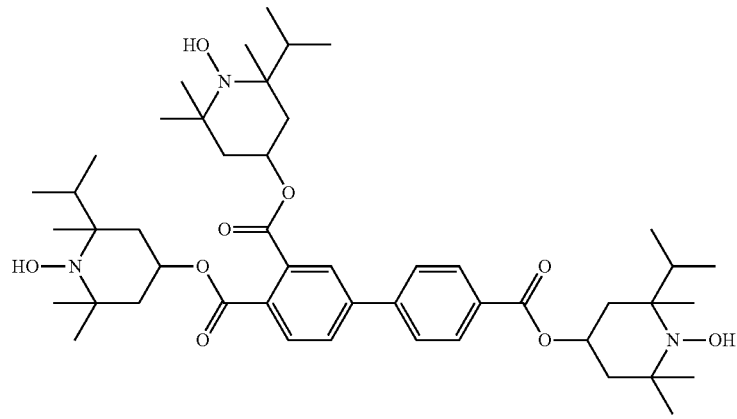 [SMILES: CC(C)C1(C)CC(OC(=O)c2ccc(-c3ccc(C(=O)OC4CC(C)(C)N(O)C(C)(C(C)C)C4)c(C(=O)OC4CC(C)(C)N(O)C(C)(C(C)C)C4)c3)cc2)CC(C)(C)N1O] |
| 286 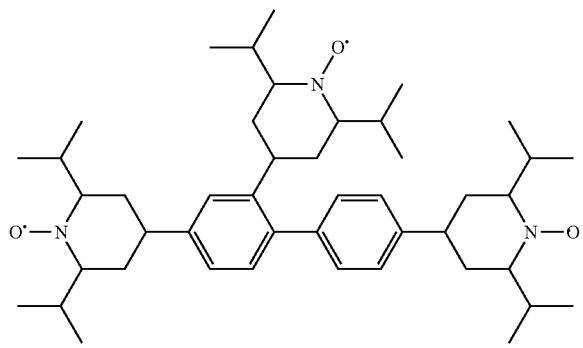 |
| 287 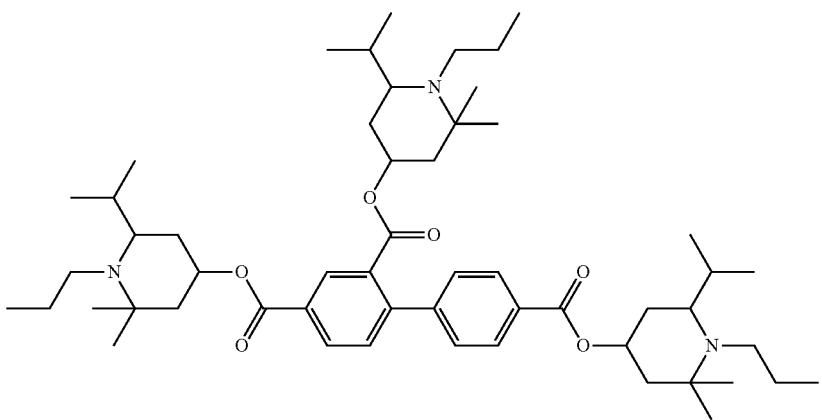 [SMILES: CCCN1C(C(C)C)CC(OC(=O)c2ccc(-c3ccc(C(=O)OC4CC(C(C)C)N(CCC)C(C)(C)C4)cc3C(=O)OC3CC(C(C)C)N(CCC)C(C)(C)C3)cc2)CC1(C)C] |

US 9,631,142 B2
| No. | |
|---|---|
| 288 | 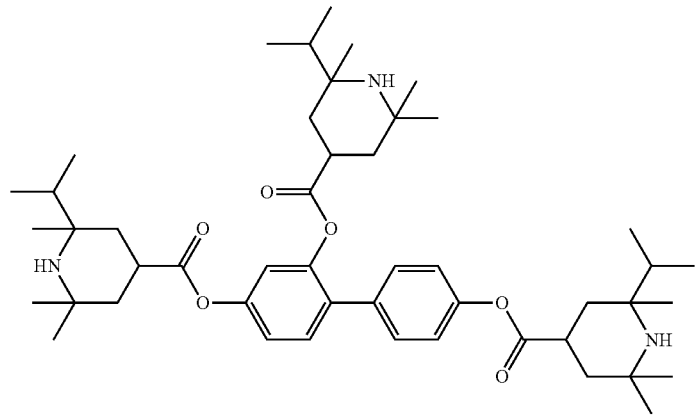 [SMILES: CC(C)C1(C)CC(C(=O)Oc2ccc(-c3ccc(OC(=O)C4CC(C)(C)NC(C)(C(C)C)C4)cc3OC(=O)C3CC(C)(C)NC(C)(C(C)C)C3)cc2)CC(C)(C)N1] |
| 289 | 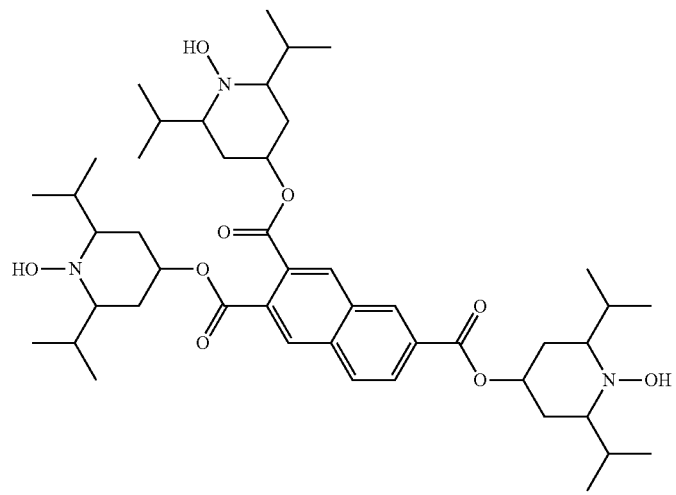 [SMILES: CC(C)C1CC(OC(=O)c2ccc3cc(C(=O)OC4CC(C(C)C)N(O)C(C(C)C)C4)c(C(=O)OC4CC(C(C)C)N(O)C(C(C)C)C4)cc3c2)CC(C(C)C)N1O] |
| 290 | 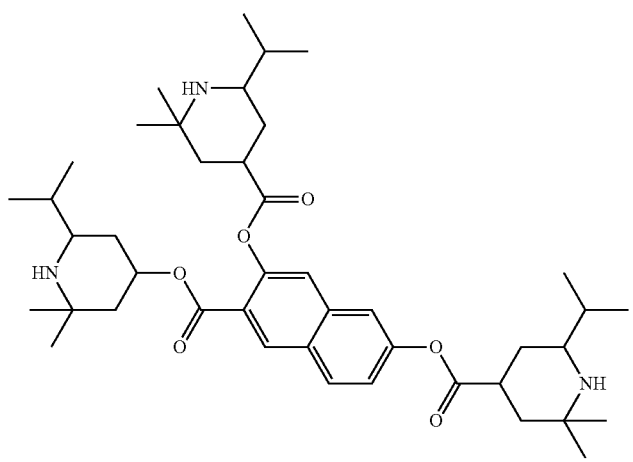 [SMILES: CC(C)C1CC(OC(=O)c2cc3ccc(OC(=O)C4CC(C(C)C)NC(C)(C)C4)cc3cc2OC(=O)C2CC(C(C)C)NC(C)(C)C2)CC(C)(C)N1] |

| No. |
|---|
| 291 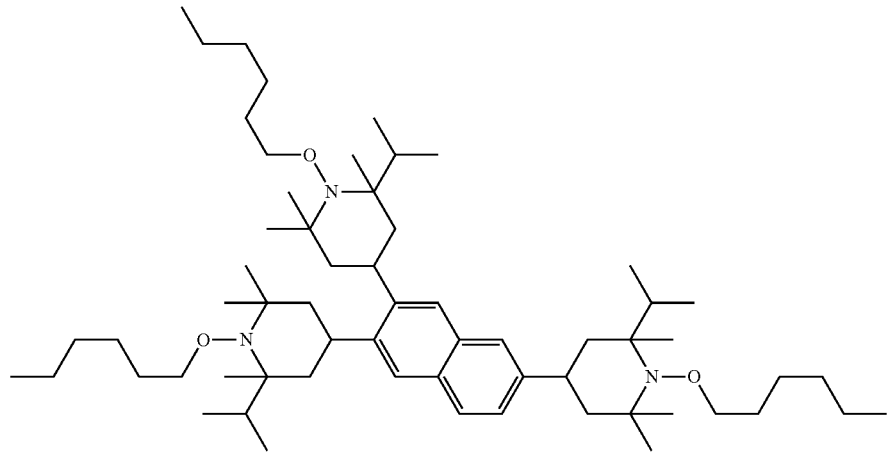 [SMILES: CCCCCCON1C(C)(C)CC(c2ccc3cc(C4CC(C)(C)N(OCCCCCC)C(C)(C(C)C)C4)c(C4CC(C)(C)N(OCCCCCC)C(C)(C(C)C)C4)cc3c2)CC1(C)C(C)C] |
| 292 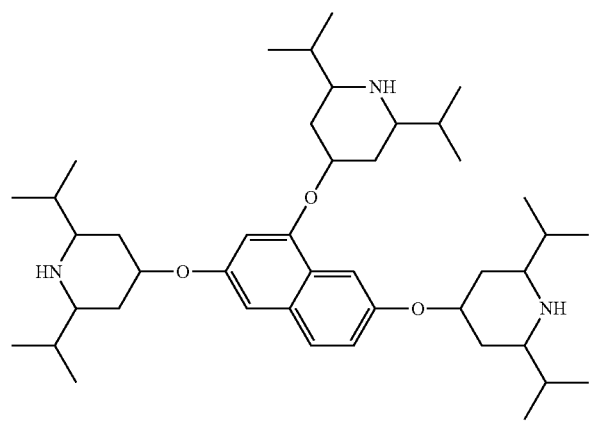 [SMILES: CC(C)C1CC(Oc2cc(OC3CC(C(C)C)NC(C(C)C)C3)c3cc(OC4CC(C(C)C)NC(C(C)C)C4)ccc3c2)CC(C(C)C)N1] |
| 293 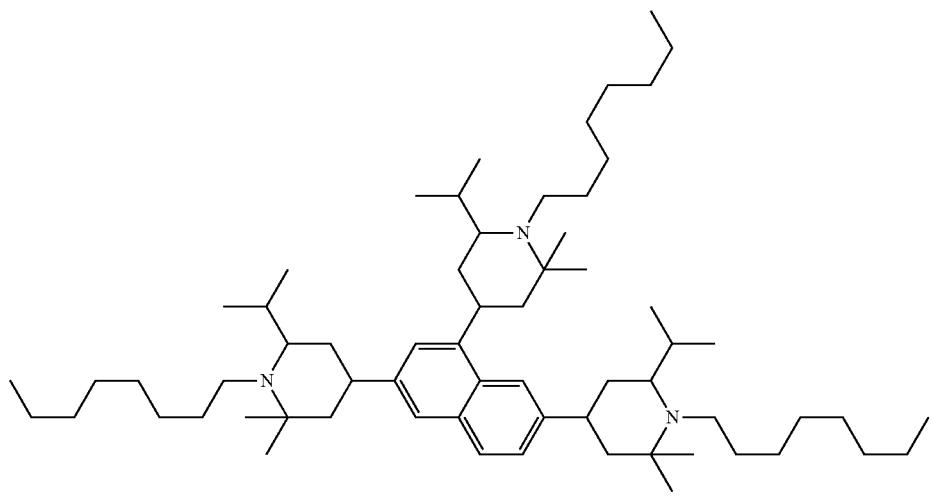 [SMILES: CCCCCCCCN1C(C(C)C)CC(c2cc(C3CC(C(C)C)N(CCCCCCCC)C(C)(C)C3)c3cc(C4CC(C(C)C)N(CCCCCCCC)C(C)(C)C4)ccc3c2)CC1(C)C] |

| No. | |
|---|---|
| 294 | 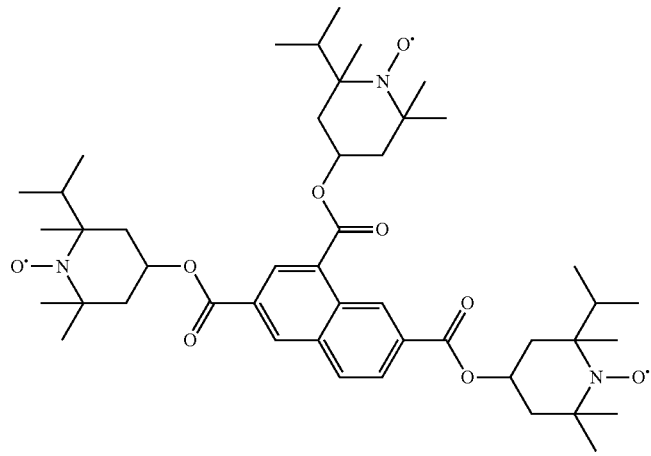 |
| 295 | 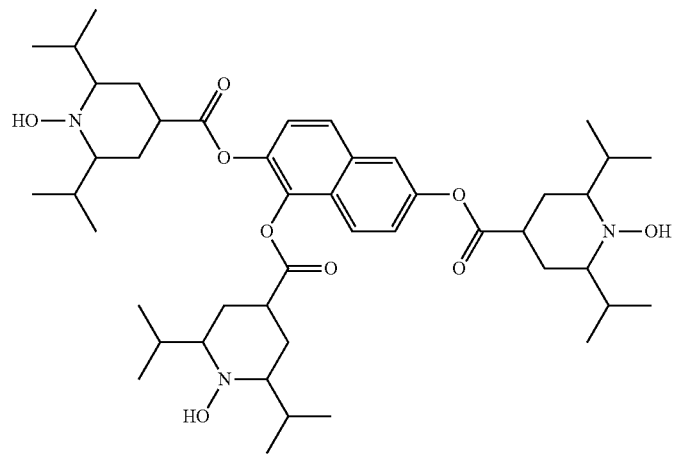 [SMILES: CC(C)C1CC(C(=O)Oc2ccc3c(OC(=O)C4CC(C(C)C)N(O)C(C(C)C)C4)c(OC(=O)C4CC(C(C)C)N(O)C(C(C)C)C4)ccc3c2)CC(C(C)C)N1O] |
| 296 | 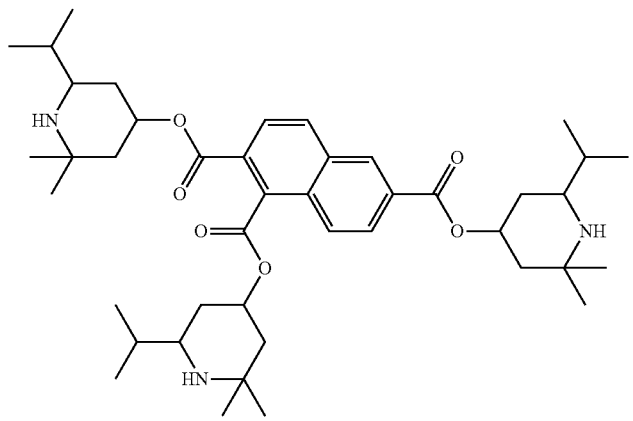 [SMILES: CC(C)C1CC(OC(=O)c2ccc3c(C(=O)OC4CC(C(C)C)NC(C)(C)C4)c(C(=O)OC4CC(C(C)C)NC(C)(C)C4)ccc3c2)CC(C)(C)N1] |

-continued
| No. | |
|---|---|
| 297 | 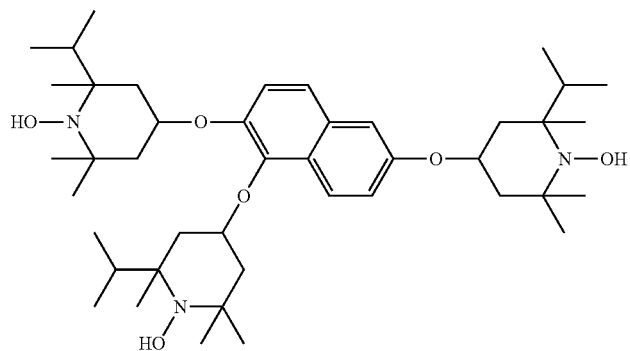 [SMILES: CC(C)C1(C)CC(Oc2ccc3c(OC4CC(C)(C)N(O)C(C)(C(C)C)C4)c(OC4CC(C)(C)N(O)C(C)(C(C)C)C4)ccc3c2)CC(C)(C)N1O] |
| 298 | 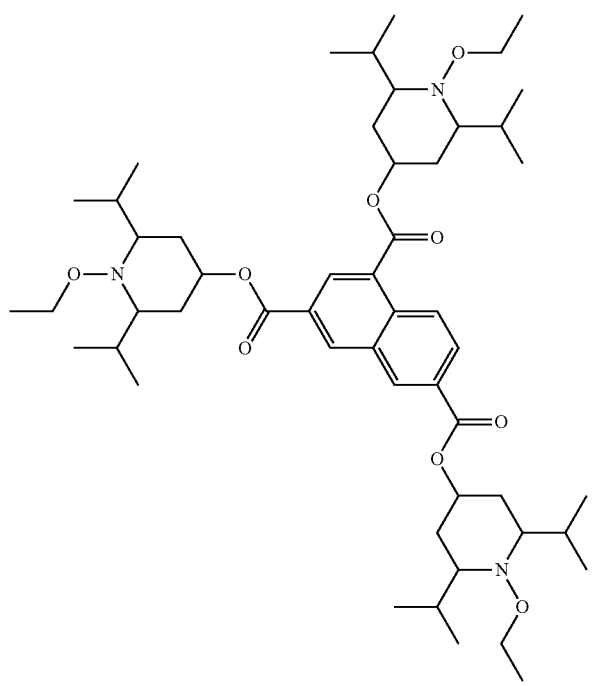 [SMILES: CCON1C(C(C)C)CC(OC(=O)c2ccc3c(C(=O)OC4CC(C(C)C)N(OCC)C(C(C)C)C4)cc(C(=O)OC4CC(C(C)C)N(OCC)C(C(C)C)C4)cc3c2)CC1C(C)C] |
| 299 | 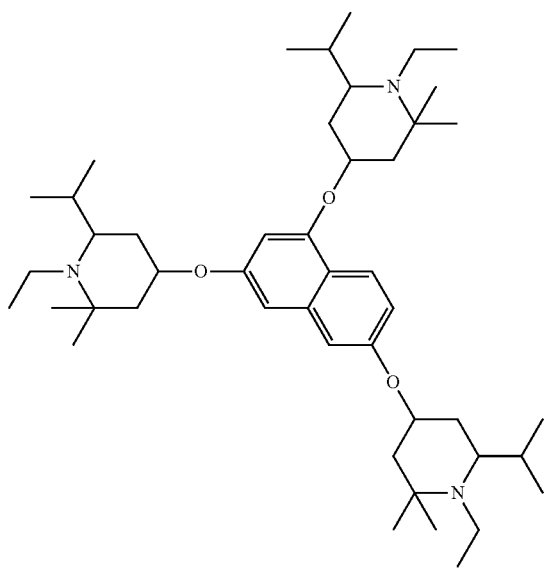 [SMILES: CCN1C(C(C)C)CC(Oc2ccc3c(OC4CC(C(C)C)N(CC)C(C)(C)C4)cc(OC4CC(C(C)C)N(CC)C(C)(C)C4)cc3c2)CC1(C)C] |

| No. |
|---|
| 300 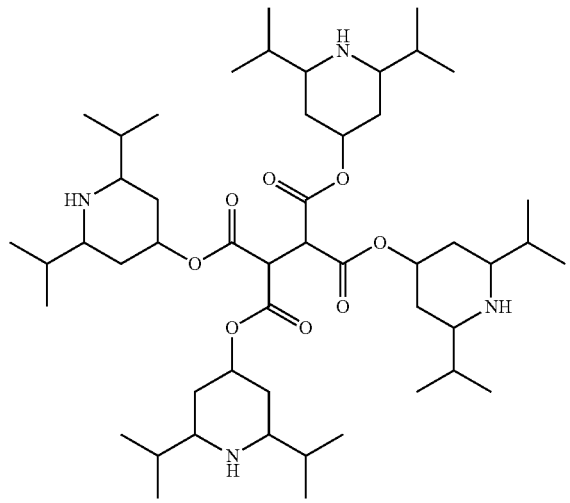 [SMILES: CC(C)C1CC(OC(=O)C(C(=O)OC2CC(C(C)C)NC(C(C)C)C2)C(C(=O)OC2CC(C(C)C)NC(C(C)C)C2)C(=O)OC2CC(C(C)C)NC(C(C)C)C2)CC(C(C)C)N1] |
| 301 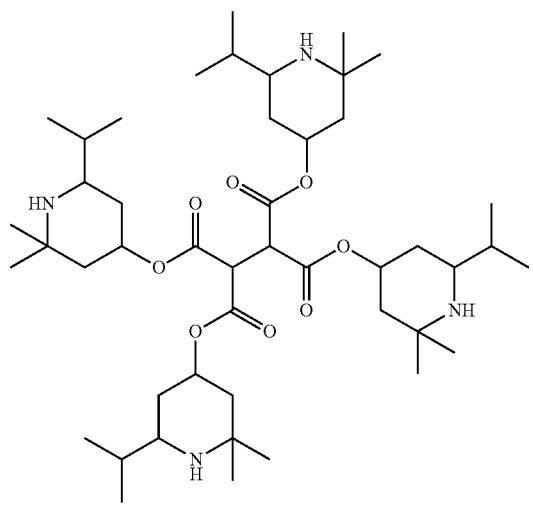 [SMILES: CC(C)C1CC(OC(=O)C(C(=O)OC2CC(C(C)C)NC(C)(C)C2)C(C(=O)OC2CC(C(C)C)NC(C)(C)C2)C(=O)OC2CC(C(C)C)NC(C)(C)C2)CC(C)(C)N1] |
| 302 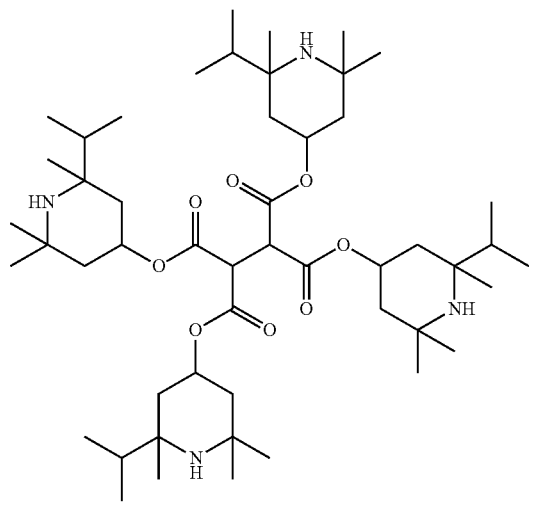 [SMILES: CC(C)C1(C)CC(OC(=O)C(C(=O)OC2CC(C)(C)NC(C)(C(C)C)C2)C(C(=O)OC2CC(C)(C)NC(C)(C(C)C)C2)C(=O)OC2CC(C)(C)NC(C)(C(C)C)C2)CC(C)(C)N1] |

-continued
| No. |
|---|
| 303 |
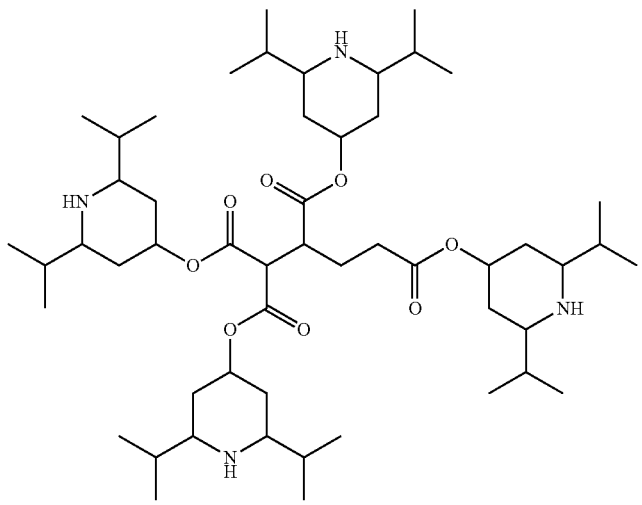 [SMILES: CC(C)C1CC(OC(=O)CCC(C(=O)OC2CC(C(C)C)NC(C(C)C)C2)C(C(=O)OC2CC(C(C)C)NC(C(C)C)C2)C(=O)OC2CC(C(C)C)NC(C(C)C)C2)CC(C(C)C)N1]
304
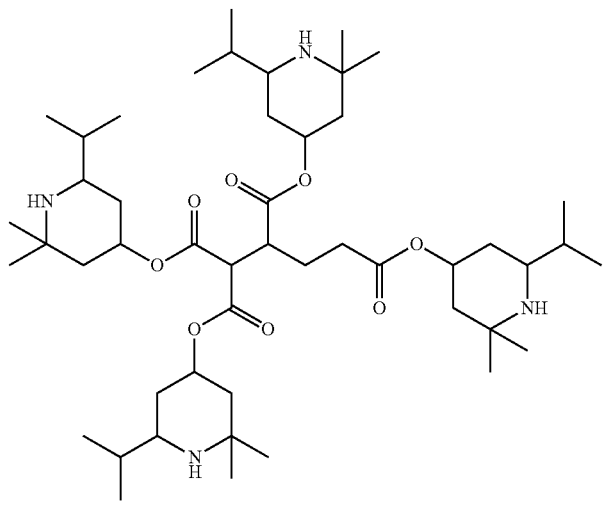 [SMILES: CC(C)C1CC(OC(=O)CCC(C(=O)OC2CC(C(C)C)NC(C)(C)C2)C(C(=O)OC2CC(C(C)C)NC(C)(C)C2)C(=O)OC2CC(C(C)C)NC(C)(C)C2)CC(C)(C)N1]
305
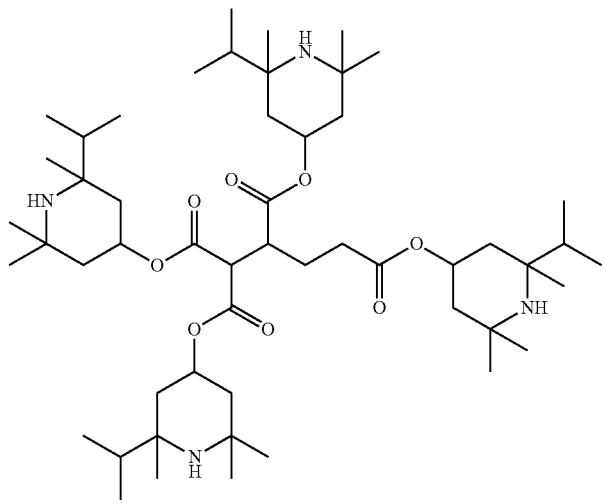 [SMILES: CC(C)C1(C)CC(OC(=O)CCC(C(=O)OC2CC(C)(C)NC(C)(C(C)C)C2)C(C(=O)OC2CC(C)(C)NC(C)(C(C)C)C2)C(=O)OC2CC(C)(C)NC(C)(C(C)C)C2)CC(C)(C)N1]

-continued
| No. | |
|---|---|
| 306 | 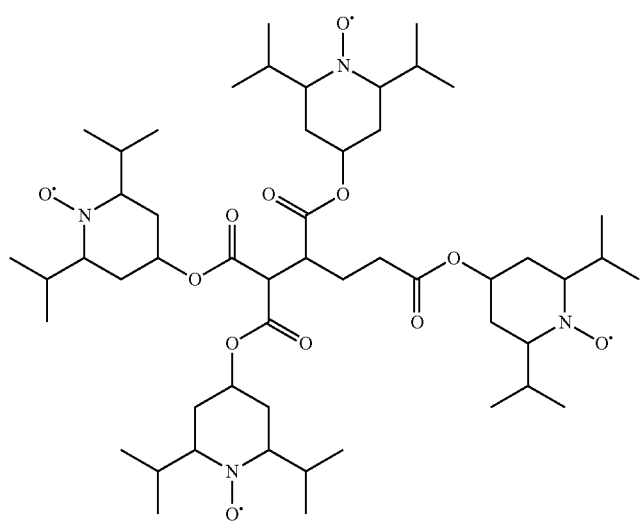 |
| 307 | 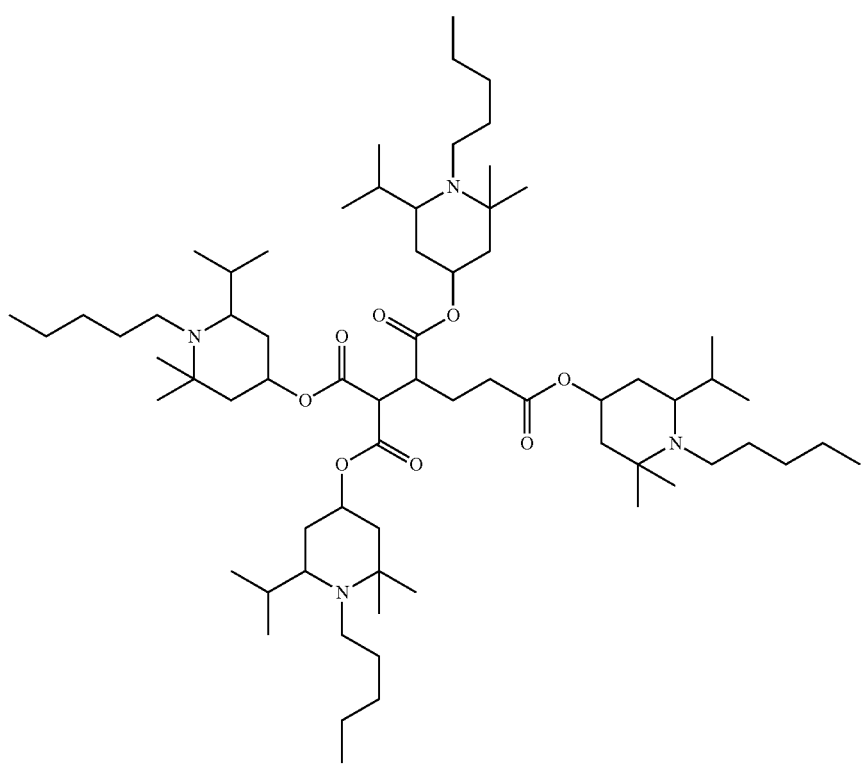 [SMILES: CCCCCN1C(C(C)C)CC(OC(=O)CCC(C(=O)OC2CC(C(C)C)N(CCCCC)C(C)(C)C2)C(C(=O)OC2CC(C(C)C)N(CCCCC)C(C)(C)C2)C(=O)OC2CC(C(C)C)N(CCCCC)C(C)(C)C2)CC1(C)C] |

| No. | |
|---|---|
| 308 | 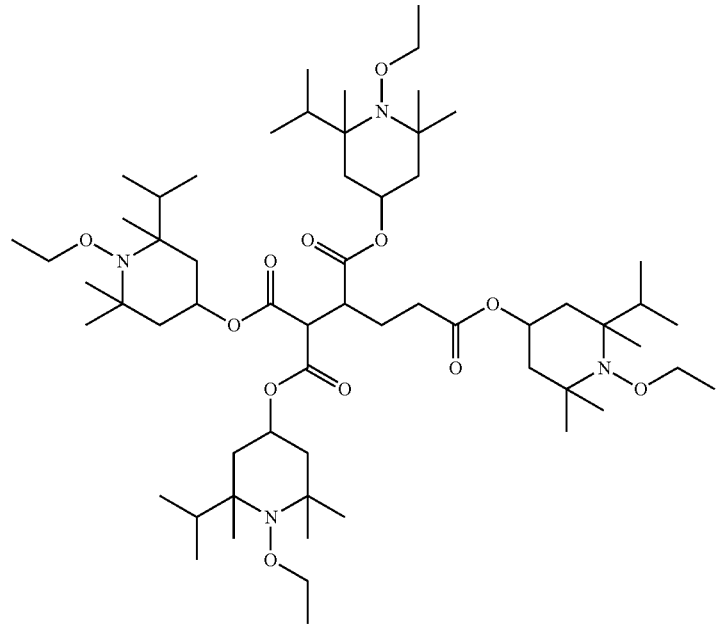 [SMILES: CCON1C(C)(C)CC(OC(=O)CCC(C(=O)OC2CC(C)(C)N(OCC)C(C)(C(C)C)C2)C(C(=O)OC2CC(C)(C)N(OCC)C(C)(C(C)C)C2)C(=O)OC2CC(C)(C)N(OCC)C(C)(C(C)C)C2)CC1(C)C(C)C] |
| 309 | 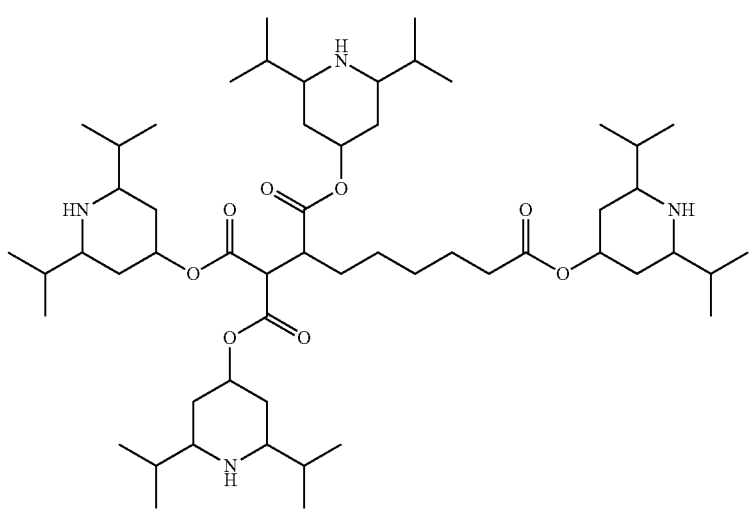 [SMILES: CC(C)C1CC(OC(=O)CCCCCC(C(=O)OC2CC(C(C)C)NC(C(C)C)C2)C(C(=O)OC2CC(C(C)C)NC(C(C)C)C2)C(=O)OC2CC(C(C)C)NC(C(C)C)C2)CC(C(C)C)N1] |

| No. |
|---|
| 310 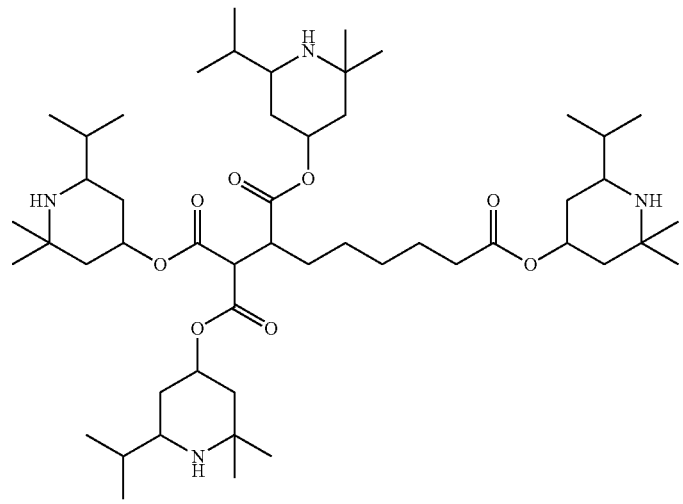 |
| 311 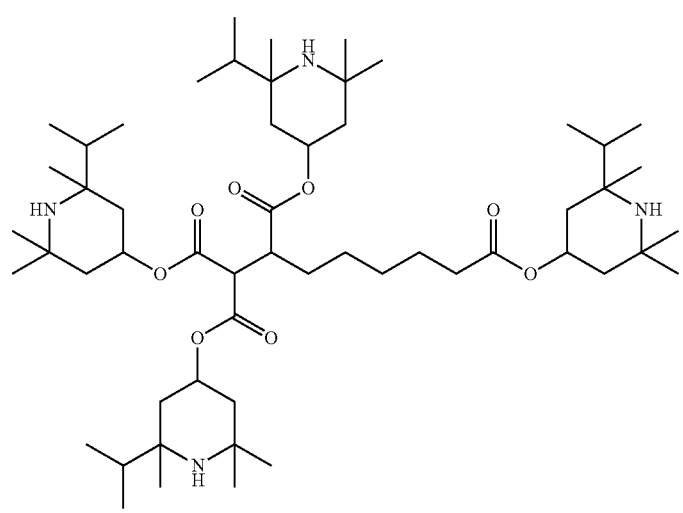 |
| 312 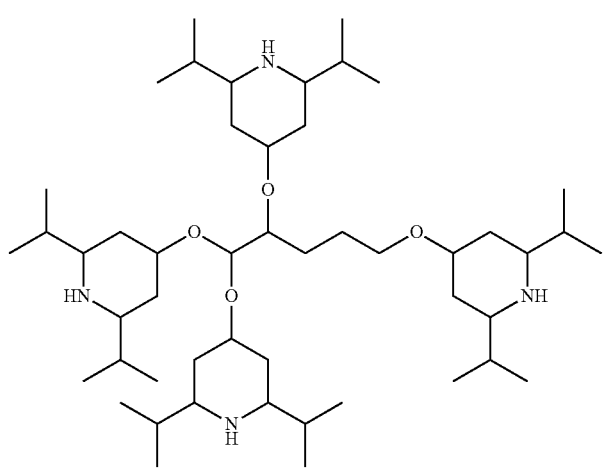 [SMILES: CC(C)C1CC(OCCCC(OC2CC(C(C)C)NC(C(C)C)C2)C(OC2CC(C(C)C)NC(C(C)C)C2)OC2CC(C(C)C)NC(C(C)C)C2)CC(C(C)C)N1] |

| No. |
|---|
| 313 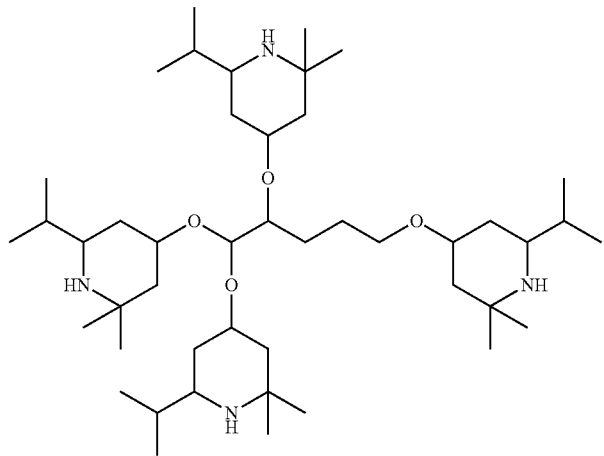 [SMILES: CC(C)C1CC(OCCCC(OC2CC(C(C)C)NC(C)(C)C2)C(OC2CC(C(C)C)NC(C)(C)C2)OC2CC(C(C)C)NC(C)(C)C2)CC(C)(C)N1] |
| 314 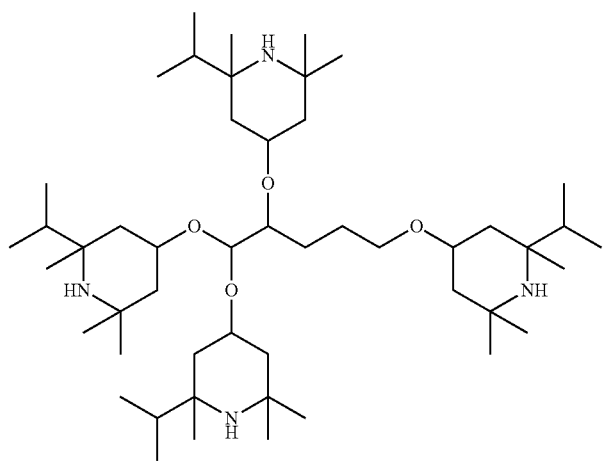 [SMILES: CC(C)C1(C)CC(OCCCC(OC2CC(C)(C)NC(C)(C(C)C)C2)C(OC2CC(C)(C)NC(C)(C(C)C)C2)OC2CC(C)(C)NC(C)(C(C)C)C2)CC(C)(C)N1] |
| 315 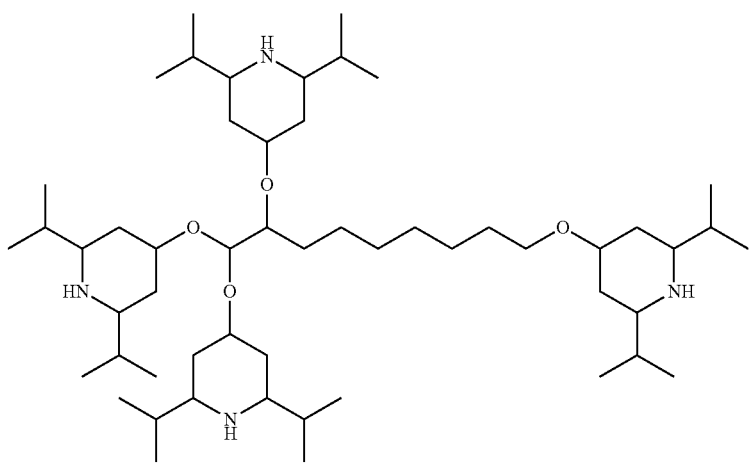 [SMILES: CC(C)C1CC(OCCCCCCCC(OC2CC(C(C)C)NC(C(C)C)C2)C(OC2CC(C(C)C)NC(C(C)C)C2)OC2CC(C(C)C)NC(C(C)C)C2)CC(C(C)C)N1] |

-continued
| No. |
|---|
| 316 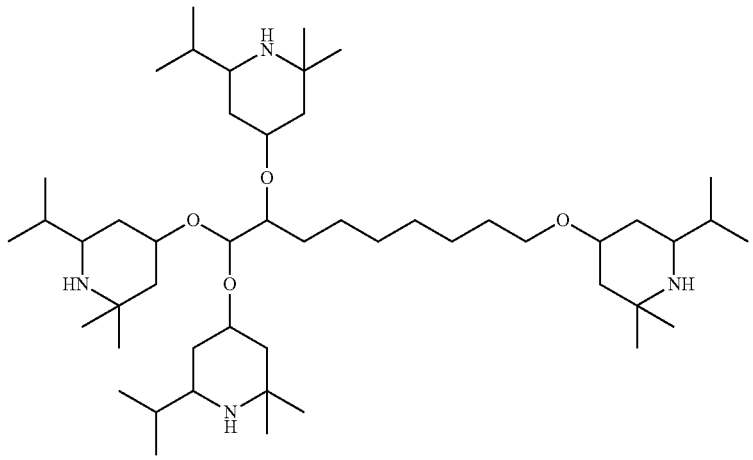 [SMILES: CC(C)C1CC(OCCCCCCCC(OC2CC(C(C)C)NC(C)(C)C2)C(OC2CC(C(C)C)NC(C)(C)C2)OC2CC(C(C)C)NC(C)(C)C2)CC(C)(C)N1] |
| 317 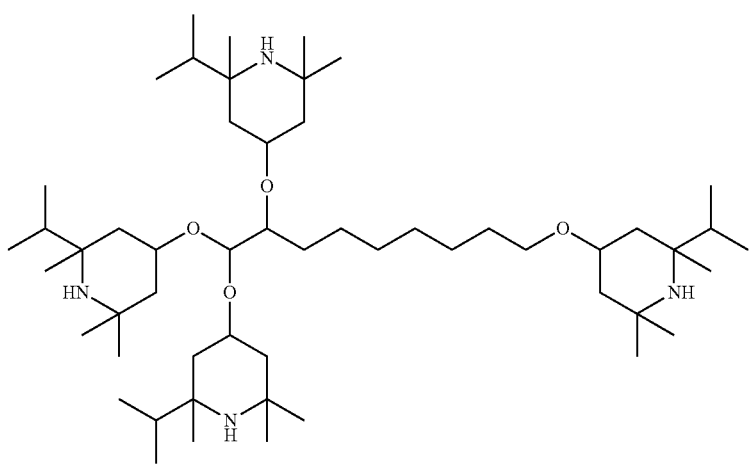 [SMILES: CC(C)C1(C)CC(OCCCCCCCC(OC2CC(C)(C)NC(C)(C(C)C)C2)C(OC2CC(C)(C)NC(C)(C(C)C)C2)OC2CC(C)(C)NC(C)(C(C)C)C2)CC(C)(C)N1] |
| 318 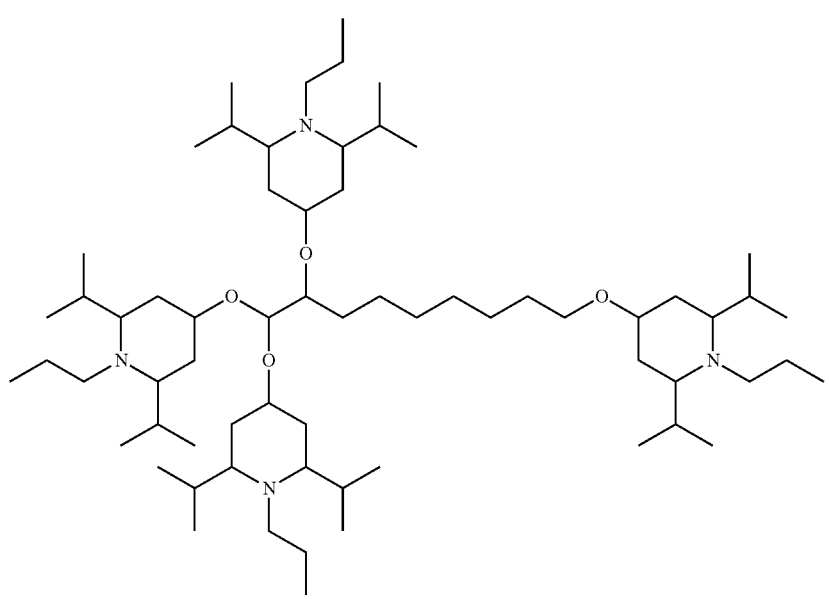 [SMILES: CCCN1C(C(C)C)CC(OCCCCCCCC(OC2CC(C(C)C)N(CCC)C(C(C)C)C2)C(OC2CC(C(C)C)N(CCC)C(C(C)C)C2)OC2CC(C(C)C)N(CCC)C(C(C)C)C2)CC1C(C)C] |

| No. |
|---|
| 319 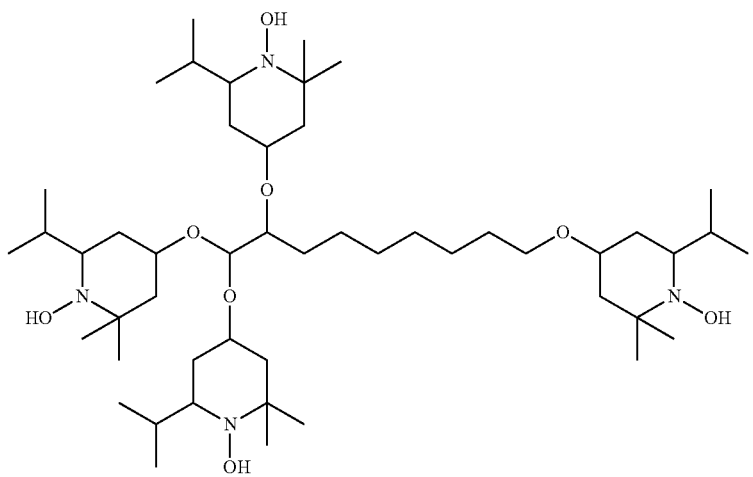 [SMILES: CC(C)C1CC(OCCCCCCCC(OC2CC(C(C)C)N(O)C(C)(C)C2)C(OC2CC(C(C)C)N(O)C(C)(C)C2)OC2CC(C(C)C)N(O)C(C)(C)C2)CC(C)(C)N1O] |
| 320 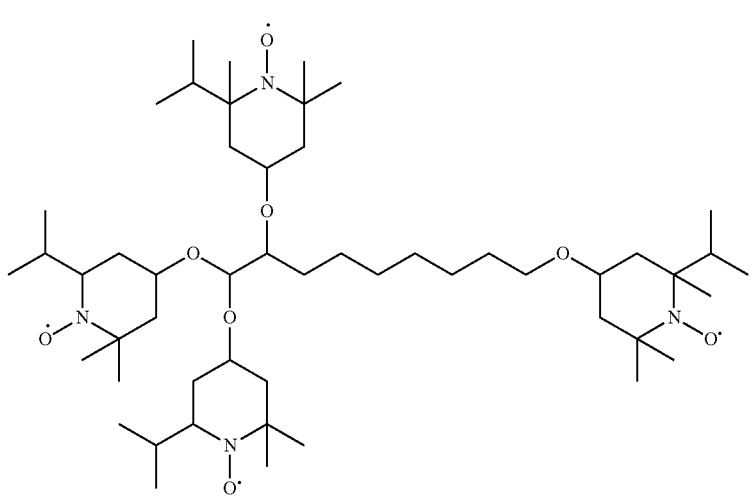 |
| 321 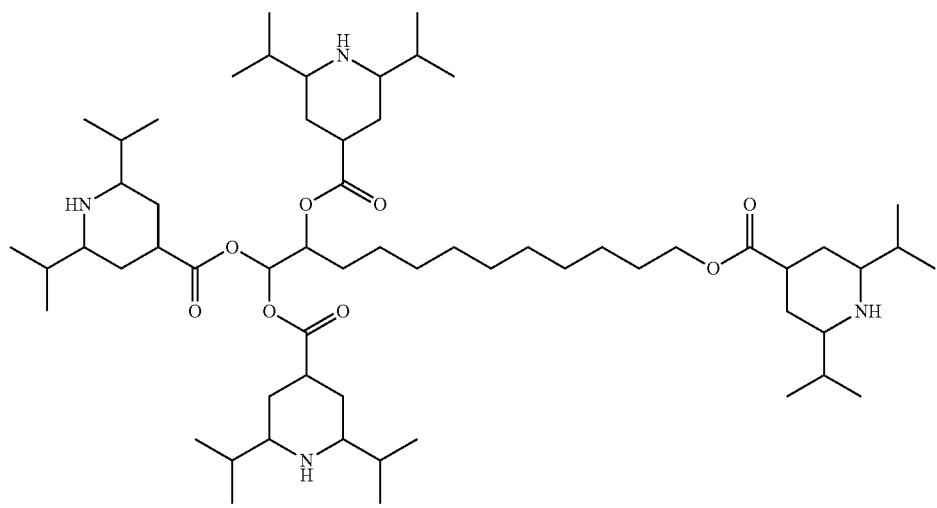 [SMILES: CC(C)C1CC(C(=O)OCCCCCCCCCCC(OC(=O)C2CC(C(C)C)NC(C(C)C)C2)C(OC(=O)C2CC(C(C)C)NC(C(C)C)C2)OC(=O)C2CC(C(C)C)NC(C(C)C)C2)CC(C(C)C)N1] |

| No. |
|---|
| 322 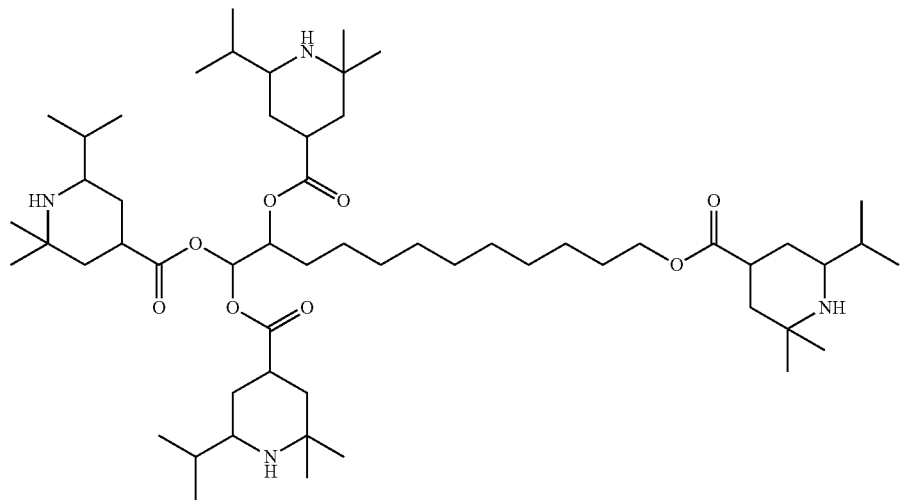 [SMILES: CC(C)C1CC(C(=O)OCCCCCCCCCCC(OC(=O)C2CC(C(C)C)NC(C)(C)C2)C(OC(=O)C2CC(C(C)C)NC(C)(C)C2)OC(=O)C2CC(C(C)C)NC(C)(C)C2)CC(C)(C)N1] |
| 323 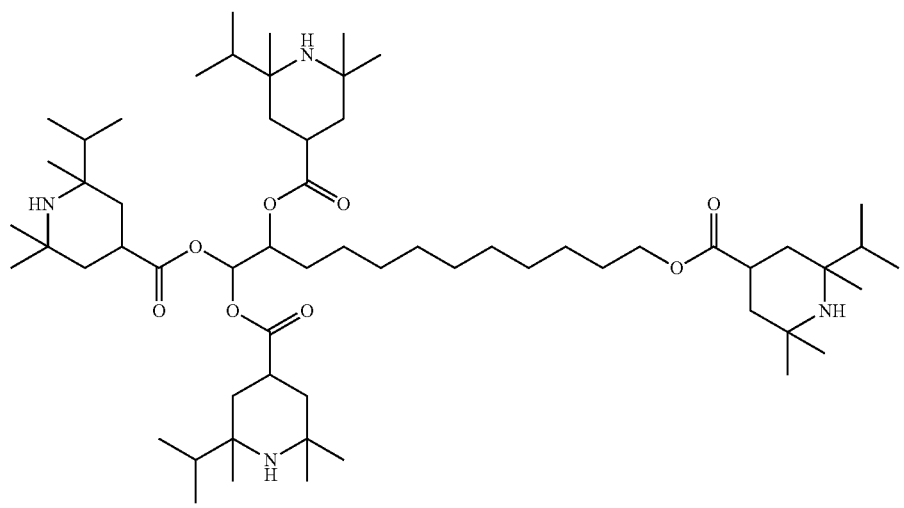 [SMILES: CC(C)C1(C)CC(C(=O)OCCCCCCCCCCC(OC(=O)C2CC(C)(C)NC(C)(C(C)C)C2)C(OC(=O)C2CC(C)(C)NC(C)(C(C)C)C2)OC(=O)C2CC(C)(C)NC(C)(C(C)C)C2)CC(C)(C)N1] |
| 324 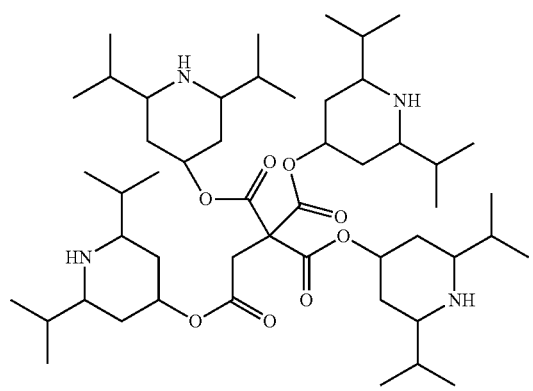 [SMILES: CC(C)C1CC(OC(=O)CC(C(=O)OC2CC(C(C)C)NC(C(C)C)C2)(C(=O)OC2CC(C(C)C)NC(C(C)C)C2)C(=O)OC2CC(C(C)C)NC(C(C)C)C2)CC(C(C)C)N1] |

| No. | |
|---|---|
| 325 | 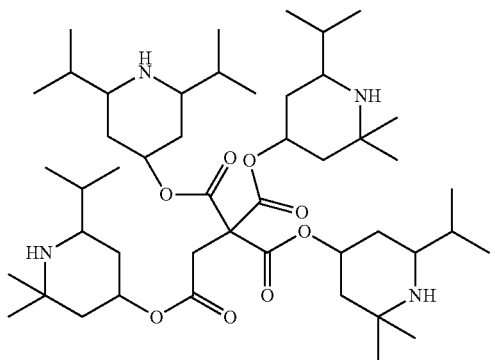 [SMILES: CC(C)C1CC(OC(=O)C(CC(=O)OC2CC(C(C)C)NC(C)(C)C2)(C(=O)OC2CC(C(C)C)NC(C)(C)C2)C(=O)OC2CC(C(C)C)NC(C)(C)C2)CC(C(C)C)N1] |
| 326 | 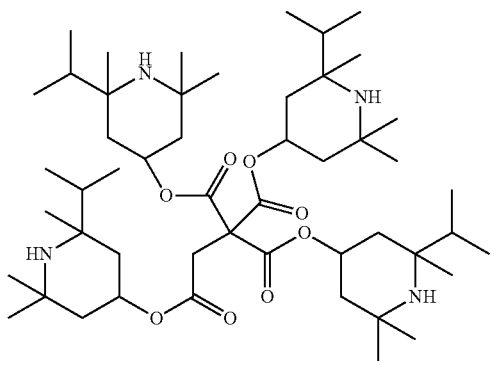 [SMILES: CC(C)C1(C)CC(OC(=O)CC(C(=O)OC2CC(C)(C)NC(C)(C(C)C)C2)(C(=O)OC2CC(C)(C)NC(C)(C(C)C)C2)C(=O)OC2CC(C)(C)NC(C)(C(C)C)C2)CC(C)(C)N1] |
| 327 | 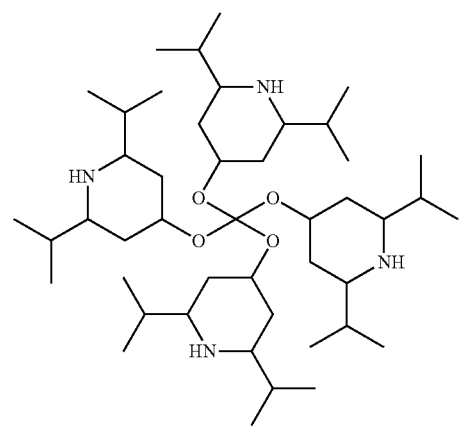 [SMILES: CC(C)C1CC(OC(OC2CC(C(C)C)NC(C(C)C)C2)(OC2CC(C(C)C)NC(C(C)C)C2)OC2CC(C(C)C)NC(C(C)C)C2)CC(C(C)C)N1] |
| 328 | 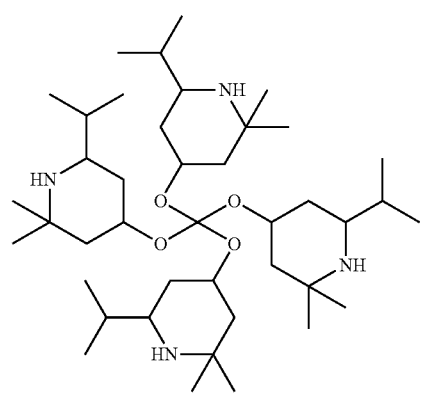 [SMILES: CC(C)C1CC(OC(OC2CC(C(C)C)NC(C)(C)C2)(OC2CC(C(C)C)NC(C)(C)C2)OC2CC(C(C)C)NC(C)(C)C2)CC(C)(C)N1] |

| No. |
|---|
| 329 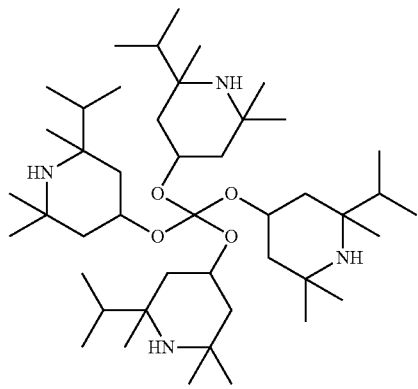 [SMILES: CC(C)C1(C)CC(OC(OC2CC(C)(C)NC(C)(C(C)C)C2)(OC2CC(C)(C)NC(C)(C(C)C)C2)OC2CC(C)(C)NC(C)(C(C)C)C2)CC(C)(C)N1] |
| 330 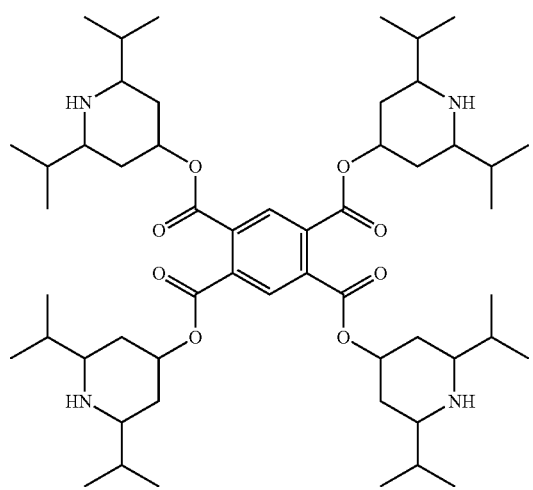 [SMILES: CC(C)C1CC(OC(=O)c2cc(C(=O)OC3CC(C(C)C)NC(C(C)C)C3)c(C(=O)OC3CC(C(C)C)NC(C(C)C)C3)cc2C(=O)OC2CC(C(C)C)NC(C(C)C)C2)CC(C(C)C)N1] |
| 331 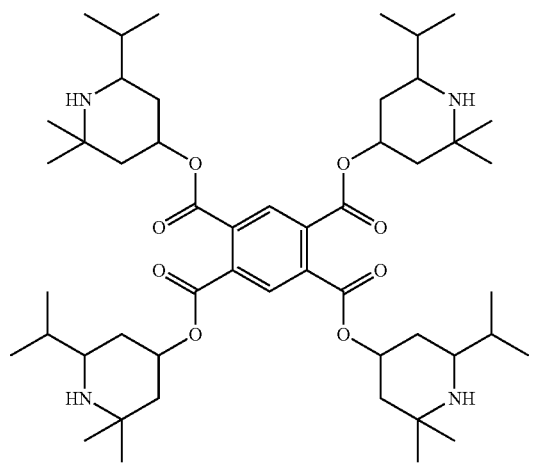 [SMILES: CC(C)C1CC(OC(=O)c2cc(C(=O)OC3CC(C(C)C)NC(C)(C)C3)c(C(=O)OC3CC(C(C)C)NC(C)(C)C3)cc2C(=O)OC2CC(C(C)C)NC(C)(C)C2)CC(C)(C)N1] |

| No. | |
|---|---|
| 332 | 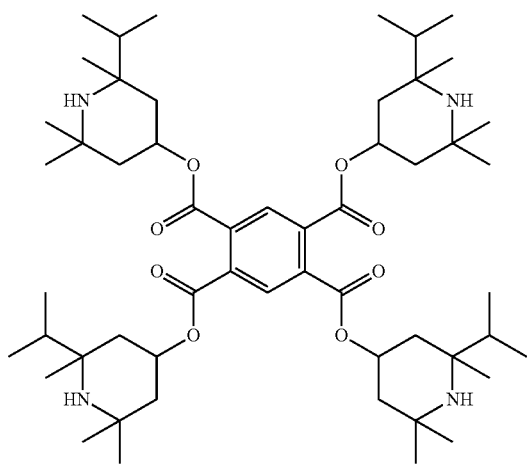 [SMILES: CC(C)C1(C)CC(OC(=O)c2cc(C(=O)OC3CC(C)(C)NC(C)(C(C)C)C3)c(C(=O)OC3CC(C)(C)NC(C)(C(C)C)C3)cc2C(=O)OC2CC(C)(C)NC(C)(C(C)C)C2)CC(C)(C)N1] |
| 333 | 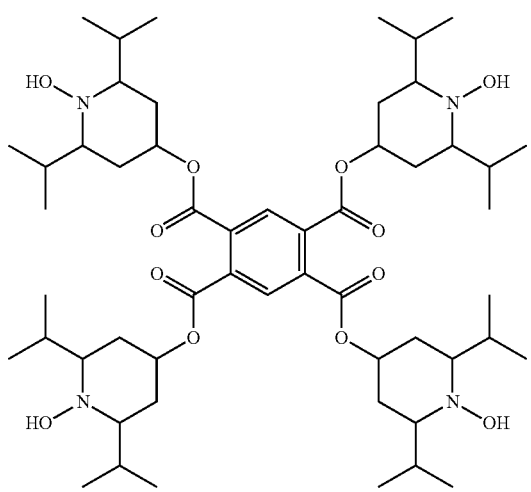 [SMILES: CC(C)C1CC(OC(=O)c2cc(C(=O)OC3CC(C(C)C)N(O)C(C(C)C)C3)c(C(=O)OC3CC(C(C)C)N(O)C(C(C)C)C3)cc2C(=O)OC2CC(C(C)C)N(O)C(C(C)C)C2)CC(C(C)C)N1O] |
| 334 | 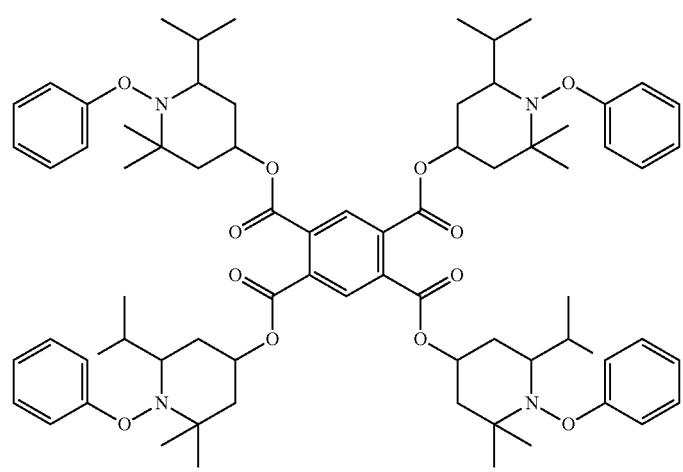 [SMILES: CC(C)C1CC(OC(=O)c2cc(C(=O)OC3CC(C(C)C)N(Oc4ccccc4)C(C)(C)C3)c(C(=O)OC3CC(C(C)C)N(Oc4ccccc4)C(C)(C)C3)cc2C(=O)OC2CC(C(C)C)N(Oc3ccccc3)C(C)(C)C2)CC(C)(C)N1Oc1ccccc1] |

-continued
| No. |
|---|
| 335 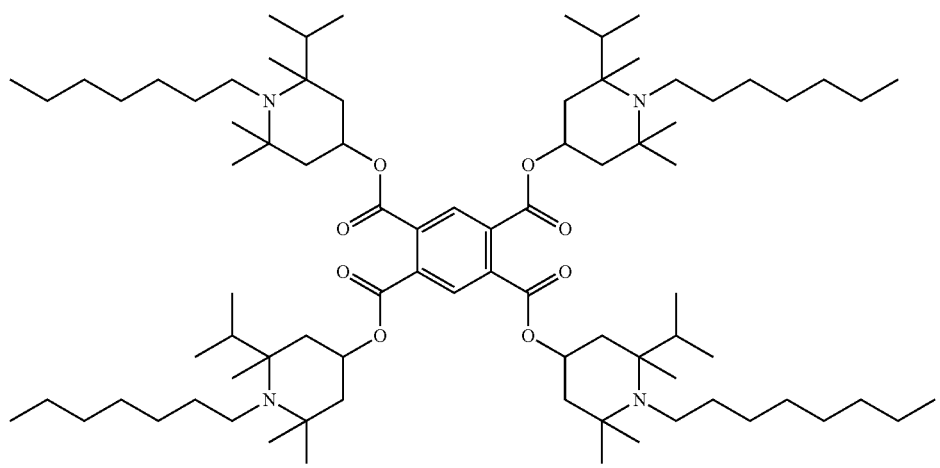 [SMILES: CCCCCCCCN1C(C)(C)CC(OC(=O)c2cc(C(=O)OC3CC(C)(C)N(CCCCCCC)C(C)(C(C)C)C3)c(C(=O)OC3CC(C)(C)N(CCCCCCC)C(C)(C(C)C)C3)cc2C(=O)OC2CC(C)(C)N(CCCCCCC)C(C)(C(C)C)C2)CC1(C)C(C)C] |
| 336 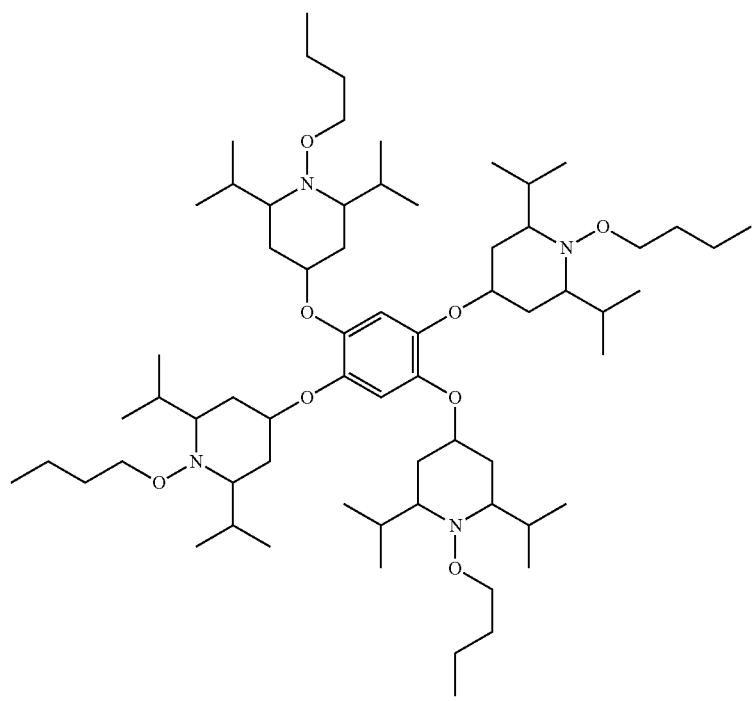 [SMILES: CCCCON1C(C(C)C)CC(Oc2cc(OC3CC(C(C)C)N(OCCCC)C(C(C)C)C3)c(OC3CC(C(C)C)N(OCCCC)C(C(C)C)C3)cc2OC2CC(C(C)C)N(OCCCC)C(C(C)C)C2)CC1C(C)C] |
| 337 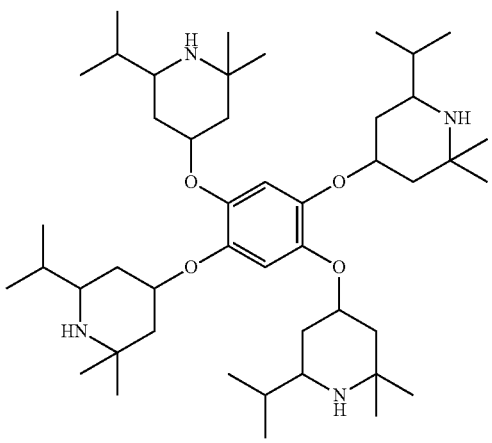 [SMILES: CC(C)C1CC(Oc2cc(OC3CC(C(C)C)NC(C)(C)C3)c(OC3CC(C(C)C)NC(C)(C)C3)cc2OC2CC(C(C)C)NC(C)(C)C2)CC(C)(C)N1] |

| No. |
|---|
| 338 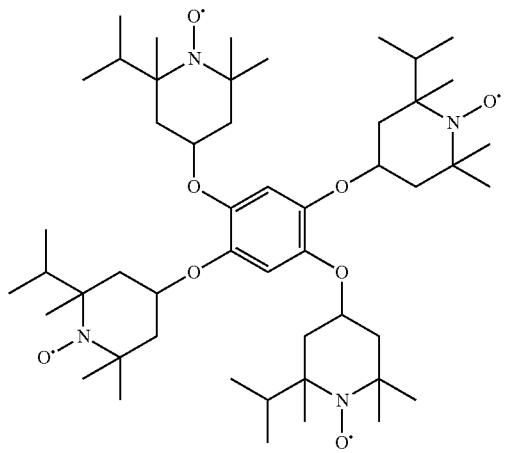 |
| 339 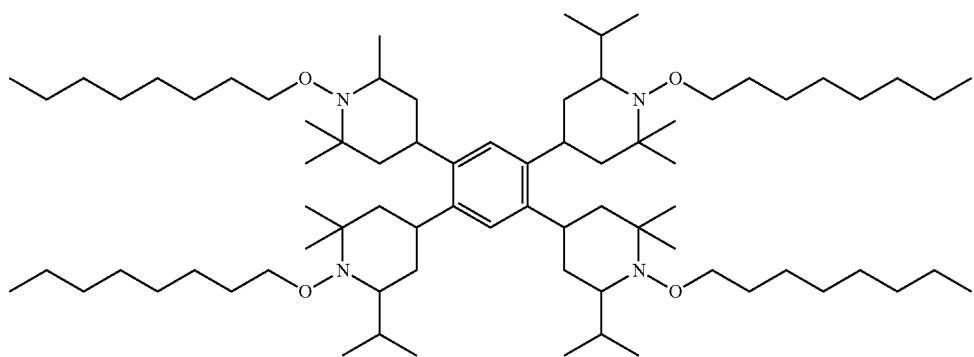 [SMILES: CCCCCCCCON1C(C)CC(c2cc(C3CC(C(C)C)N(OCCCCCCCC)C(C)(C)C3)c(C3CC(C(C)C)N(OCCCCCCCC)C(C)(C)C3)cc2C2CC(C(C)C)N(OCCCCCCCC)C(C)(C)C2)CC1(C)C] |
| 340 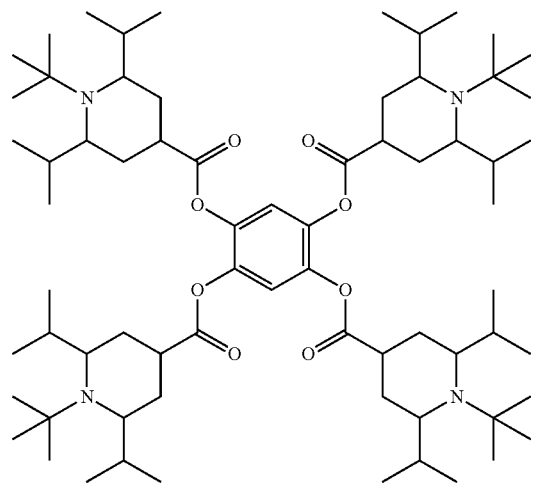 [SMILES: CC(C)C1CC(C(=O)Oc2cc(OC(=O)C3CC(C(C)C)N(C(C)(C)C)C(C(C)C)C3)c(OC(=O)C3CC(C(C)C)N(C(C)(C)C)C(C(C)C)C3)cc2OC(=O)C2CC(C(C)C)N(C(C)(C)C)C(C(C)C)C2)CC(C(C)C)N1C(C)(C)C] |

| No. | |
|---|---|
| 341 | 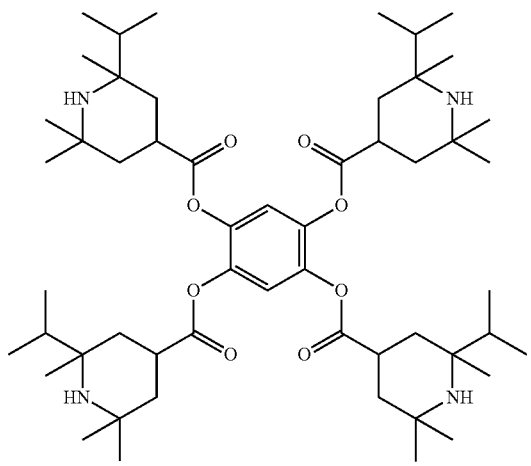 [SMILES: CC(C)C1(C)CC(C(=O)Oc2cc(OC(=O)C3CC(C)(C)NC(C)(C(C)C)C3)c(OC(=O)C3CC(C)(C)NC(C)(C(C)C)C3)cc2OC(=O)C2CC(C)(C)NC(C)(C(C)C)C2)CC(C)(C)N1] |
| 342 | 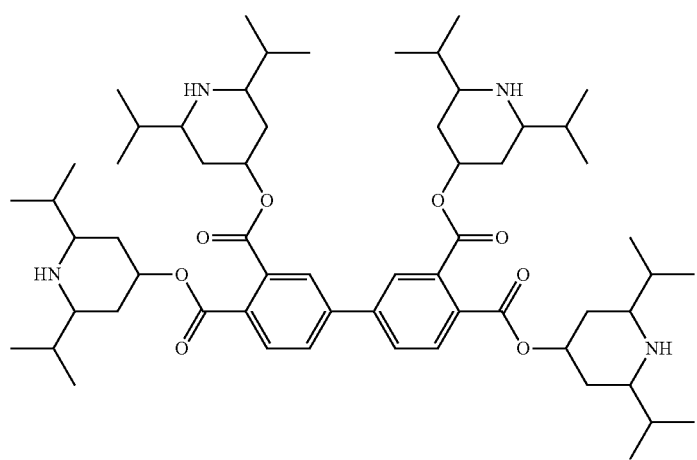 [SMILES: CC(C)C1CC(OC(=O)c2ccc(-c3ccc(C(=O)OC4CC(C(C)C)NC(C(C)C)C4)c(C(=O)OC4CC(C(C)C)NC(C(C)C)C4)c3)cc2C(=O)OC2CC(C(C)C)NC(C(C)C)C2)CC(C(C)C)N1] |
| 343 | 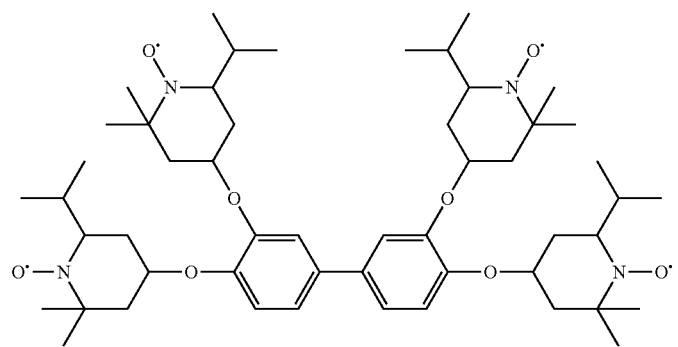 |

| No. |
|---|
| 344 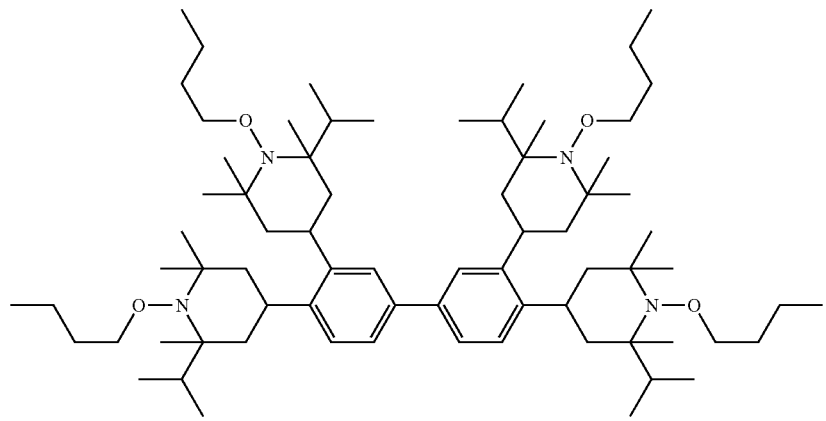 [SMILES: CCCCON1C(C)(C)CC(c2ccc(-c3ccc(C4CC(C)(C)N(OCCCC)C(C)(C(C)C)C4)c(C4CC(C)(C)N(OCCCC)C(C)(C(C)C)C4)c3)cc2C2CC(C)(C)N(OCCCC)C(C)(C(C)C)C2)CC1(C)C(C)C] |
| 345 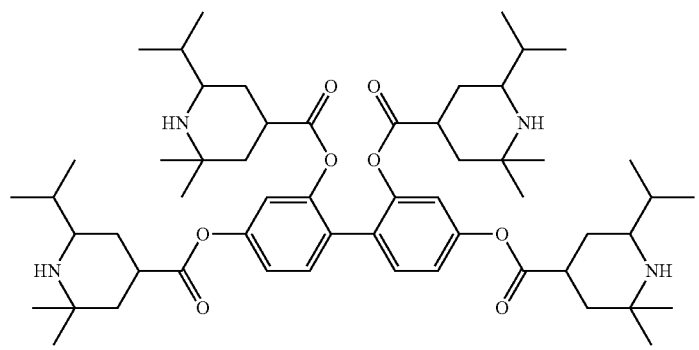 [SMILES: CC(C)C1CC(C(=O)Oc2ccc(-c3ccc(OC(=O)C4CC(C(C)C)NC(C)(C)C4)cc3OC(=O)C3CC(C(C)C)NC(C)(C)C3)c(OC(=O)C3CC(C(C)C)NC(C)(C)C3)c2)CC(C)(C)N1] |
| 346 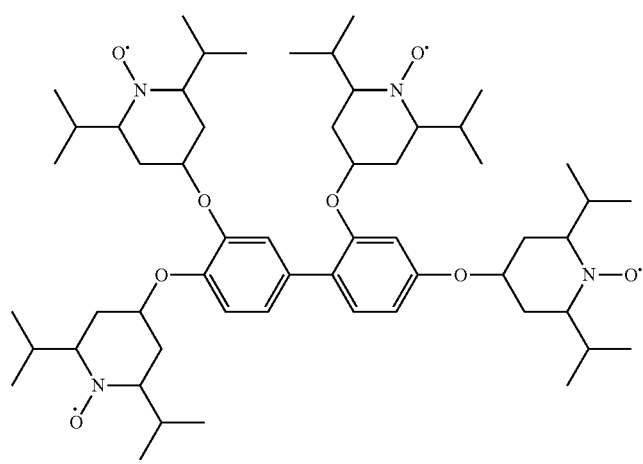 |

| No. | |
|---|---|
| 347 | 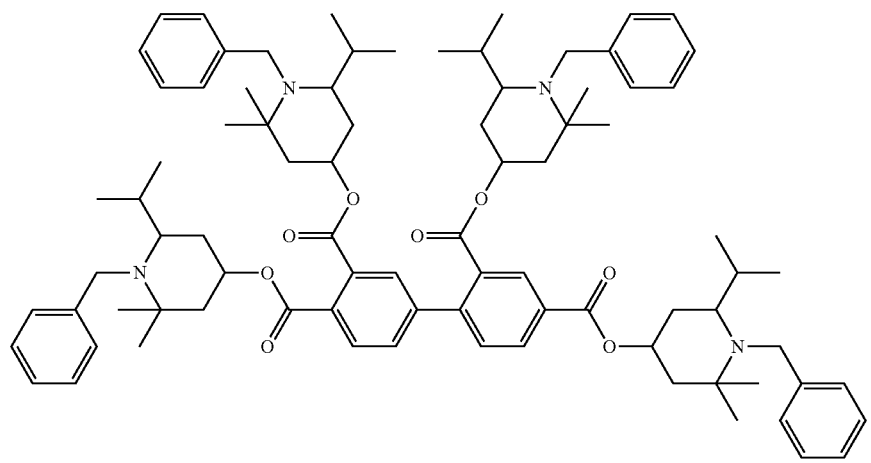 [SMILES: CC(C)C1CC(OC(=O)c2ccc(-c3ccc(C(=O)OC4CC(C(C)C)N(Cc5ccccc5)C(C)(C)C4)c(C(=O)OC4CC(C(C)C)N(Cc5ccccc5)C(C)(C)C4)c3)c(C(=O)OC3CC(C(C)C)N(Cc4ccccc4)C(C)(C)C3)c2)CC(C)(C)N1Cc1ccccc1] |
| 348 | 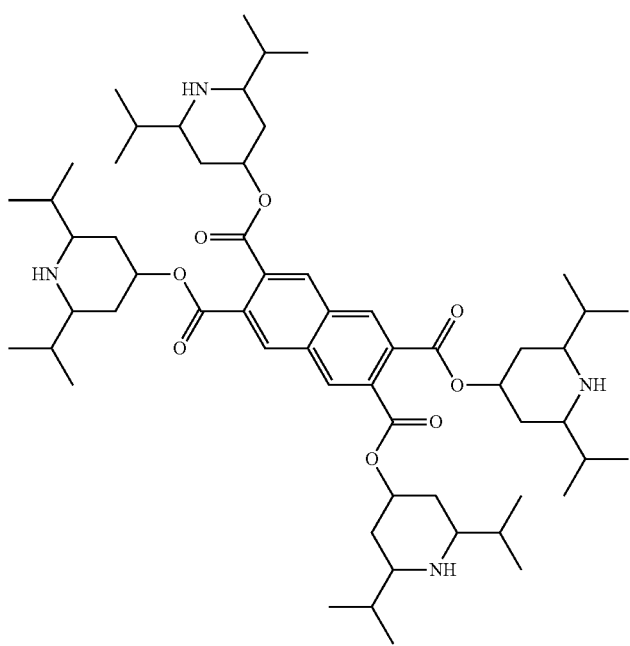 [SMILES: CC(C)C1CC(OC(=O)c2cc3cc(C(=O)OC4CC(C(C)C)NC(C(C)C)C4)c(C(=O)OC4CC(C(C)C)NC(C(C)C)C4)cc3cc2C(=O)OC2CC(C(C)C)NC(C(C)C)C2)CC(C(C)C)N1] |

| No. |
|---|
| 349 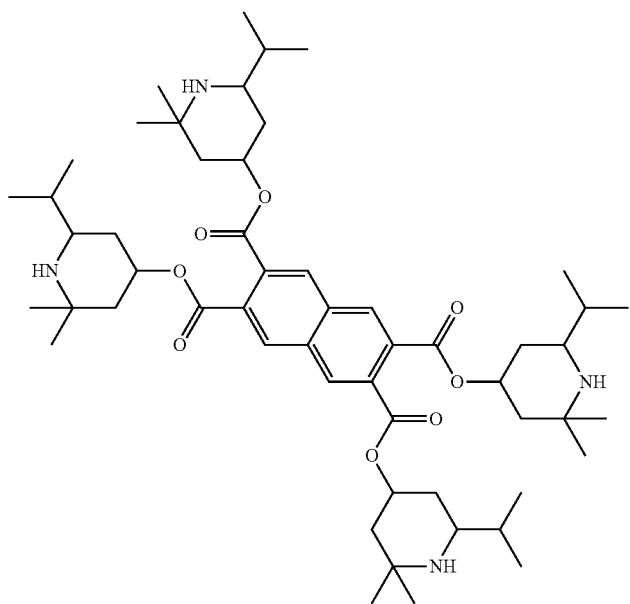 [SMILES: CC(C)C1CC(OC(=O)c2cc3cc(C(=O)OC4CC(C(C)C)NC(C)(C)C4)c(C(=O)OC4CC(C(C)C)NC(C)(C)C4)cc3cc2C(=O)OC2CC(C(C)C)NC(C)(C)C2)CC(C)(C)N1] |
| 350 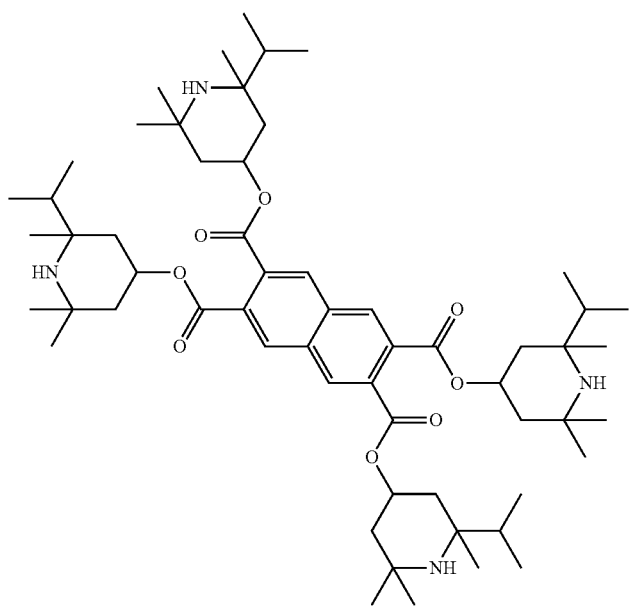 [SMILES: CC(C)C1(C)CC(OC(=O)c2cc3cc(C(=O)OC4CC(C)(C)NC(C)(C(C)C)C4)c(C(=O)OC4CC(C)(C)NC(C)(C(C)C)C4)cc3cc2C(=O)OC2CC(C)(C)NC(C)(C(C)C)C2)CC(C)(C)N1] |

| No. | |
|---|---|
| 351 | 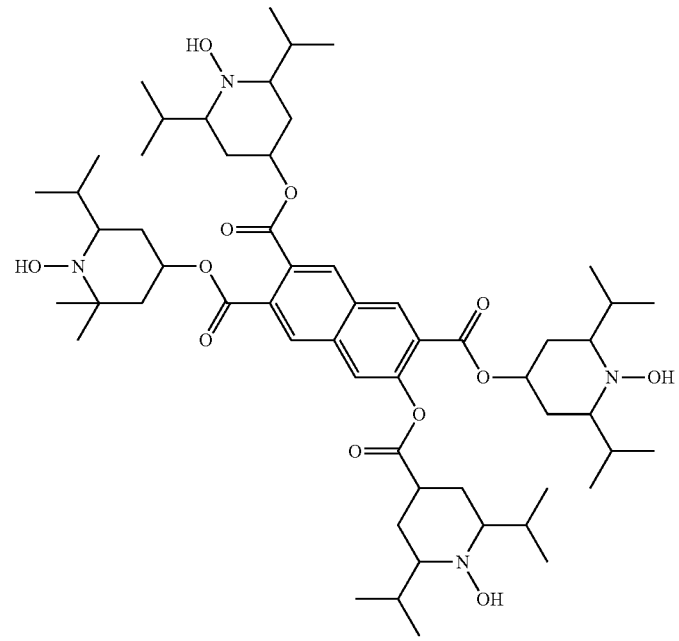 [SMILES: CC(C)C1CC(OC(=O)c2cc3cc(C(=O)OC4CC(C(C)C)N(O)C(C(C)C)C4)c(C(=O)OC4CC(C(C)C)N(O)C(C)(C)C4)cc3cc2OC(=O)C2CC(C(C)C)N(O)C(C(C)C)C2)CC(C(C)C)N1O] |
| 352 | 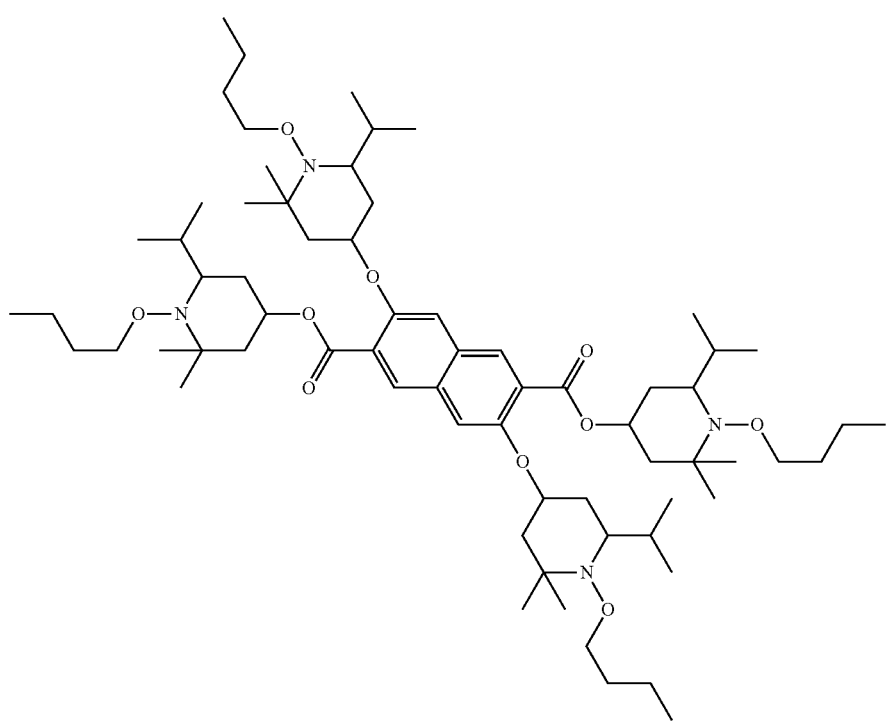 [SMILES: CCCCON1C(C(C)C)CC(OC(=O)c2cc3cc(OC4CC(C(C)C)N(OCCCC)C(C)(C)C4)c(C(=O)OC4CC(C(C)C)N(OCCCC)C(C)(C)C4)cc3cc2OC2CC(C(C)C)N(OCCCC)C(C)(C)C2)CC1(C)C] |

-continued
| No. | |
|---|---|
| 353 | 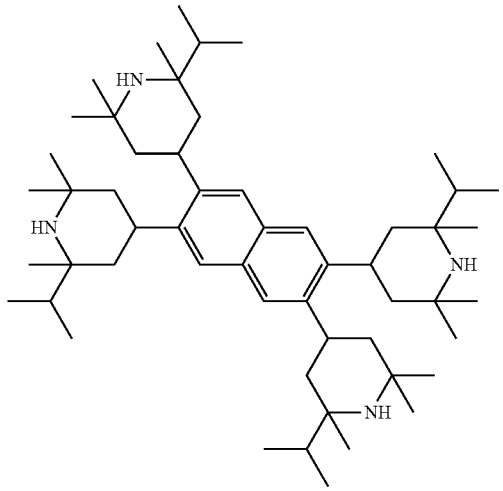 [SMILES: CC(C)C1(C)CC(c2cc3cc(C4CC(C)(C)NC(C)(C(C)C)C4)c(C4CC(C)(C)NC(C)(C(C)C)C4)cc3cc2C2CC(C)(C)NC(C)(C(C)C)C2)CC(C)(C)N1] |
| 354 | 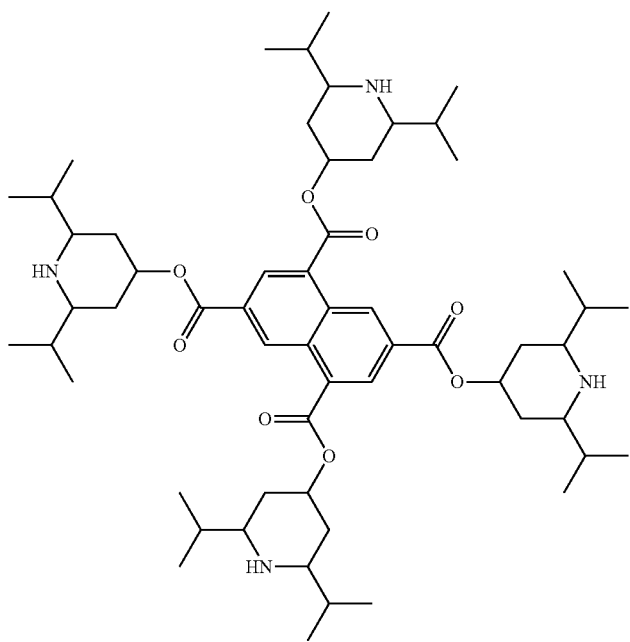 [SMILES: CC(C)C1CC(OC(=O)c2cc(C(=O)OC3CC(C(C)C)NC(C(C)C)C3)c3cc(C(=O)OC4CC(C(C)C)NC(C(C)C)C4)cc(C(=O)OC4CC(C(C)C)NC(C(C)C)C4)c3c2)CC(C(C)C)N1] |

| No. | |
|---|---|
| 355 | 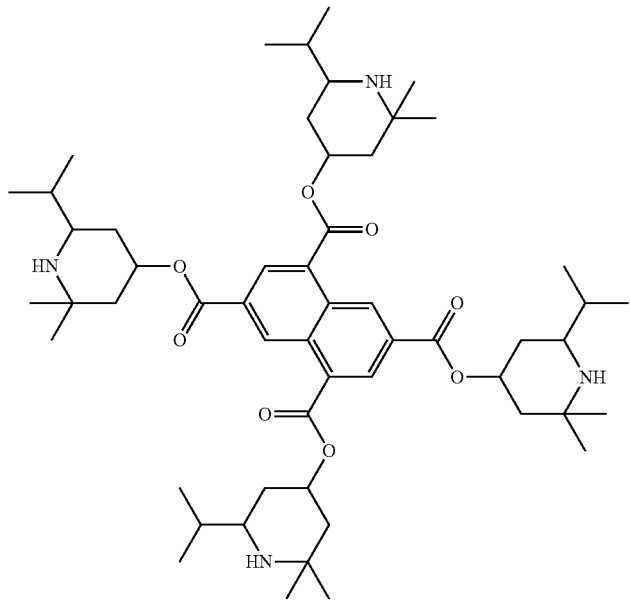 [SMILES: CC(C)C1CC(OC(=O)c2cc(C(=O)OC3CC(C(C)C)NC(C)(C)C3)c3cc(C(=O)OC4CC(C(C)C)NC(C)(C)C4)cc(C(=O)OC4CC(C(C)C)NC(C)(C)C4)c3c2)CC(C)(C)N1] |
| 356 | 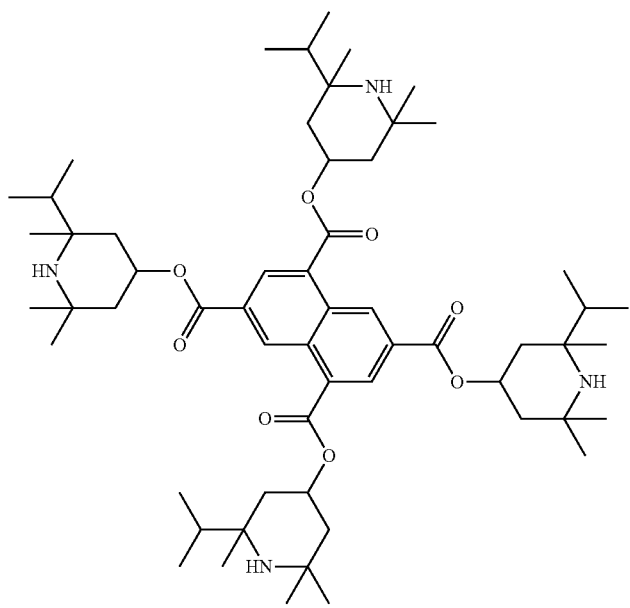 [SMILES: CC(C)C1(C)CC(OC(=O)c2cc(C(=O)OC3CC(C)(C)NC(C)(C(C)C)C3)c3cc(C(=O)OC4CC(C)(C)NC(C)(C(C)C)C4)cc(C(=O)OC4CC(C)(C)NC(C)(C(C)C)C4)c3c2)CC(C)(C)N1] |

| No. |
|---|
| 357 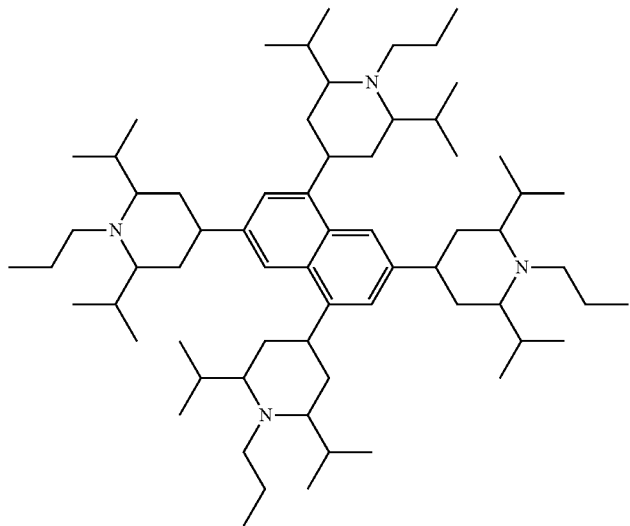 [SMILES: CCCN1C(C(C)C)CC(c2cc(C3CC(C(C)C)N(CCC)C(C(C)C)C3)c3cc(C4CC(C(C)C)N(CCC)C(C(C)C)C4)cc(C4CC(C(C)C)N(CCC)C(C(C)C)C4)c3c2)CC1C(C)C] |
| 358 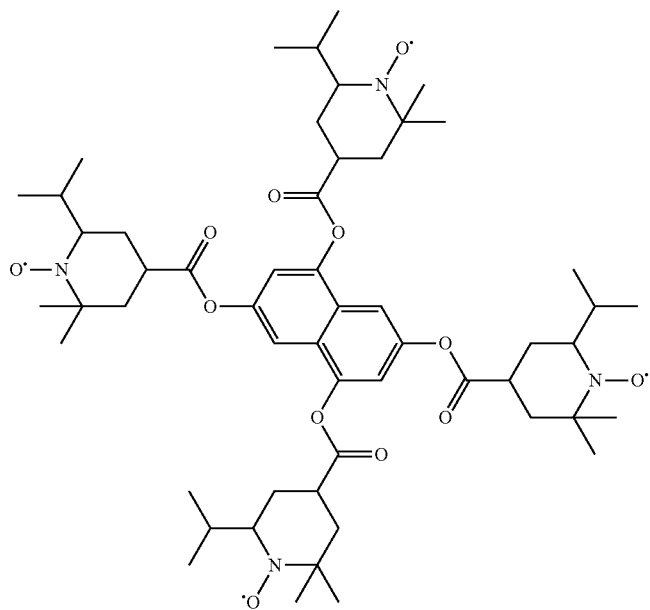 |

| No. |
|---|
| 359 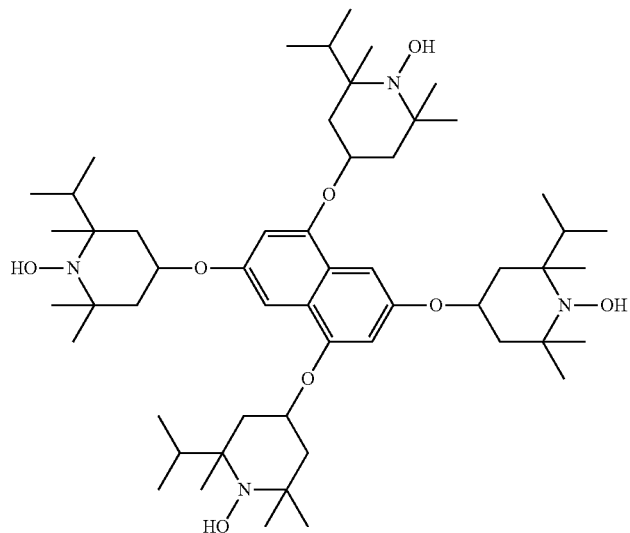 [SMILES: CC(C)C1(C)CC(Oc2cc(OC3CC(C)(C)N(O)C(C)(C(C)C)C3)c3cc(OC4CC(C)(C)N(O)C(C)(C(C)C)C4)cc(OC4CC(C)(C)N(O)C(C)(C(C)C)C4)c3c2)CC(C)(C)N1O] |
| 360 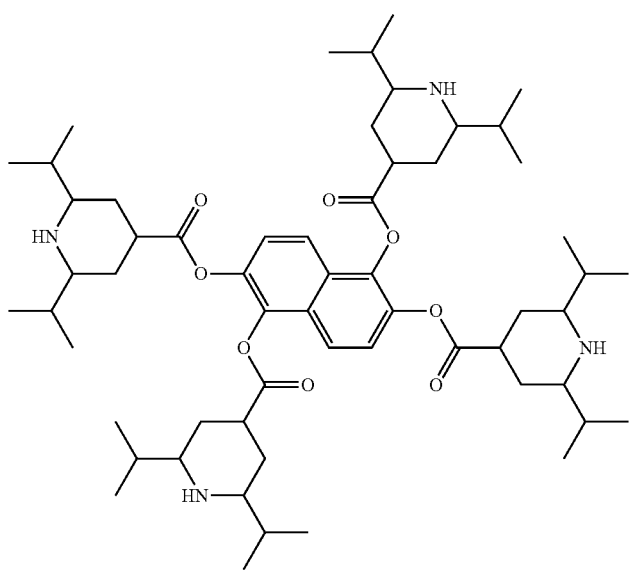 [SMILES: CC(C)C1CC(C(=O)Oc2ccc3c(OC(=O)C4CC(C(C)C)NC(C(C)C)C4)c(OC(=O)C4CC(C(C)C)NC(C(C)C)C4)ccc3c2OC(=O)C2CC(C(C)C)NC(C(C)C)C2)CC(C(C)C)N1] |
| 361 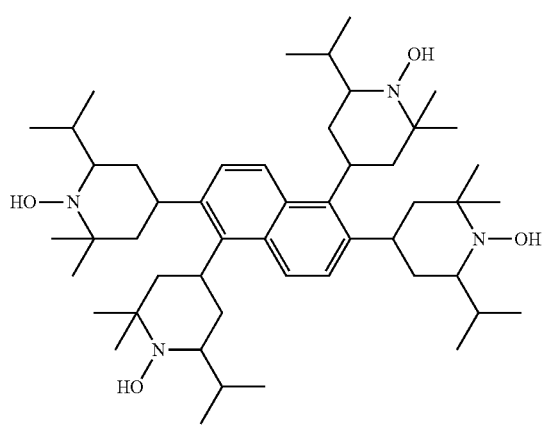 [SMILES: CC(C)C1CC(c2ccc3c(C4CC(C(C)C)N(O)C(C)(C)C4)c(C4CC(C(C)C)N(O)C(C)(C)C4)ccc3c2C2CC(C(C)C)N(O)C(C)(C)C2)CC(C)(C)N1O] |

-continued
| No. |
|---|
| 362 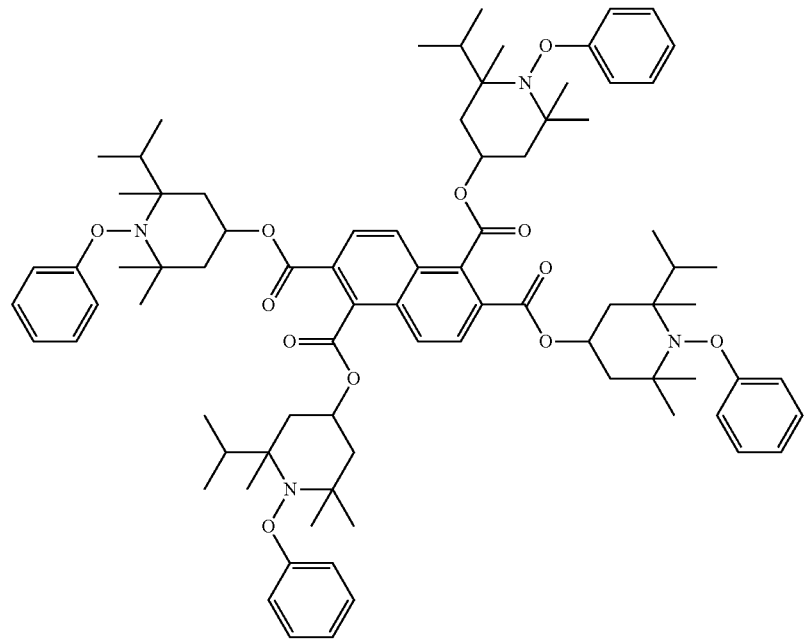 [SMILES: CC(C)C1(C)CC(OC(=O)c2ccc3c(C(=O)OC4CC(C)(C)N(Oc5ccccc5)C(C)(C(C)C)C4)c(C(=O)OC4CC(C)(C)N(Oc5ccccc5)C(C)(C(C)C)C4)ccc3c2C(=O)OC2CC(C)(C)N(Oc3ccccc3)C(C)(C(C)C)C2)CC(C)(C)N1Oc1ccccc1] |
| 363 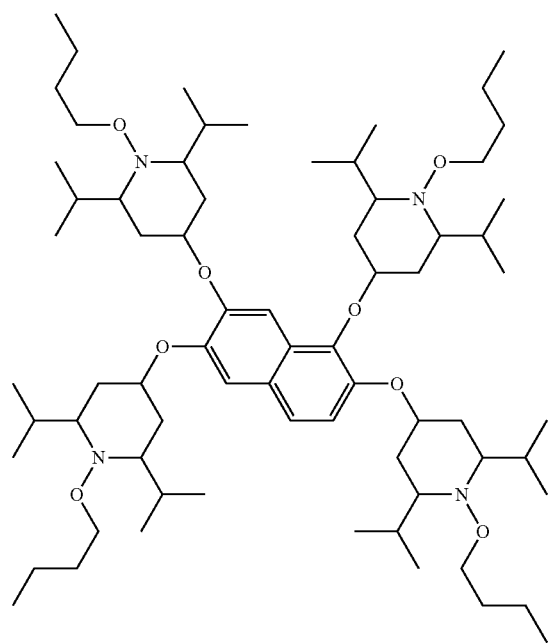 [SMILES: CCCCON1C(C(C)C)CC(Oc2cc3ccc(OC4CC(C(C)C)N(OCCCC)C(C(C)C)C4)c(OC4CC(C(C)C)N(OCCCC)C(C(C)C)C4)c3cc2OC2CC(C(C)C)N(OCCCC)C(C(C)C)C2)CC1C(C)C] |

| No. | |
|---|---|
| 364 | 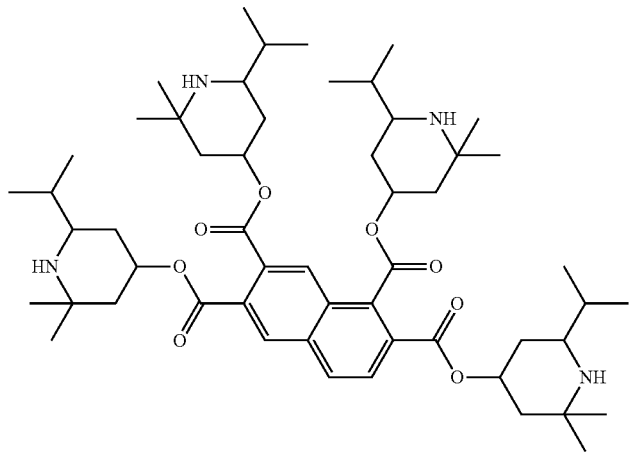 [SMILES: CC(C)C1CC(OC(=O)c2cc3ccc(C(=O)OC4CC(C(C)C)NC(C)(C)C4)c(C(=O)OC4CC(C(C)C)NC(C)(C)C4)c3cc2C(=O)OC2CC(C(C)C)NC(C)(C)C2)CC(C)(C)N1] |
| 365 | 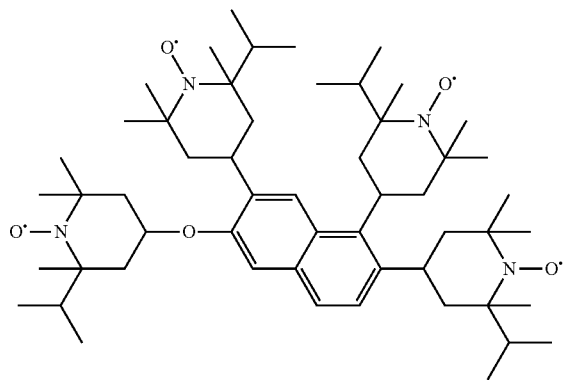 |
| 366 | 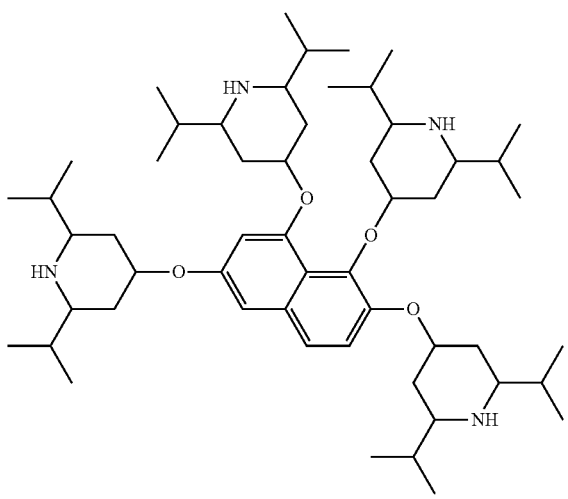 [SMILES: CC(C)C1CC(Oc2cc(OC3CC(C(C)C)NC(C(C)C)C3)c3c(OC4CC(C(C)C)NC(C(C)C)C4)c(OC4CC(C(C)C)NC(C(C)C)C4)ccc3c2)CC(C(C)C)N1] |

| No. |
|---|
| 367 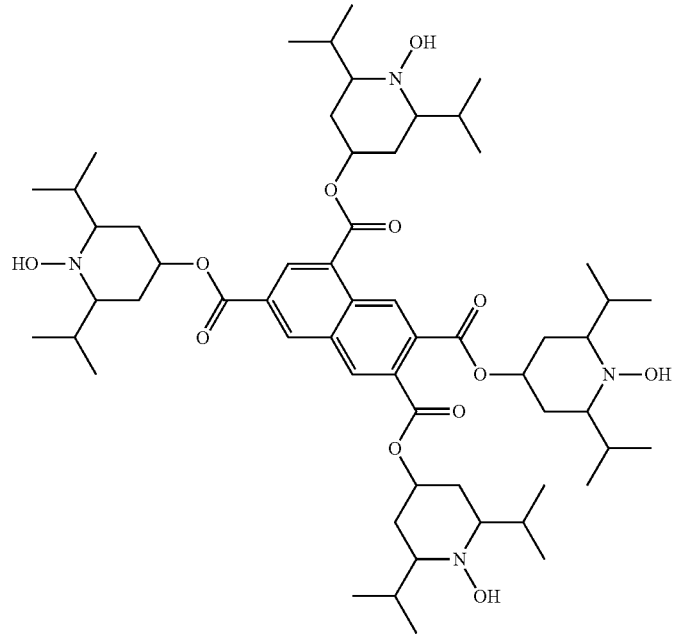 [SMILES: CC(C)C1CC(OC(=O)c2cc(C(=O)OC3CC(C(C)C)N(O)C(C(C)C)C3)c3cc(C(=O)OC4CC(C(C)C)N(O)C(C(C)C)C4)c(C(=O)OC4CC(C(C)C)N(O)C(C(C)C)C4)cc3c2)CC(C(C)C)N1O] |
| 368 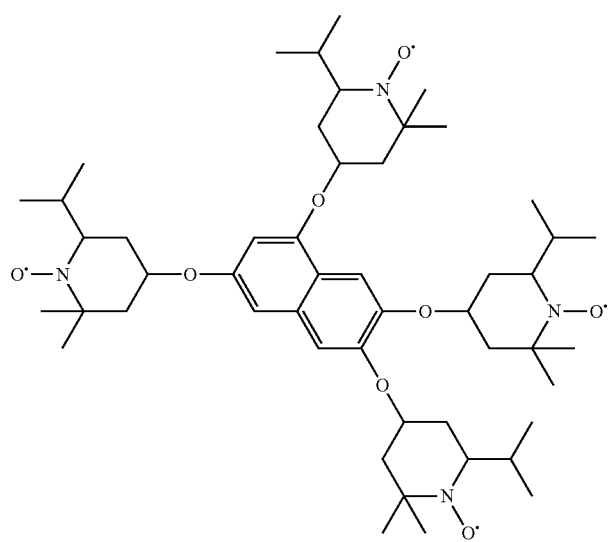 |

| No. |
|---|
| 369 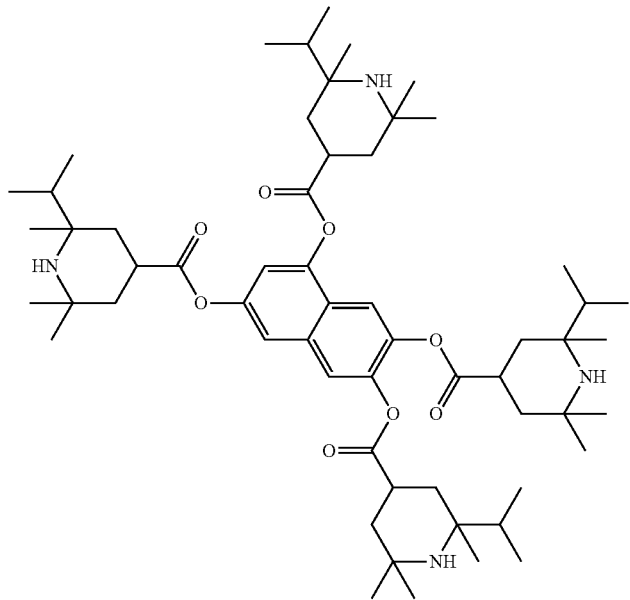 [SMILES: CC(C)C1(C)CC(C(=O)Oc2cc(OC(=O)C3CC(C)(C)NC(C)(C(C)C)C3)c3cc(OC(=O)C4CC(C)(C)NC(C)(C(C)C)C4)c(OC(=O)C4CC(C)(C)NC(C)(C(C)C)C4)cc3c2)CC(C)(C)N1] |
| 370 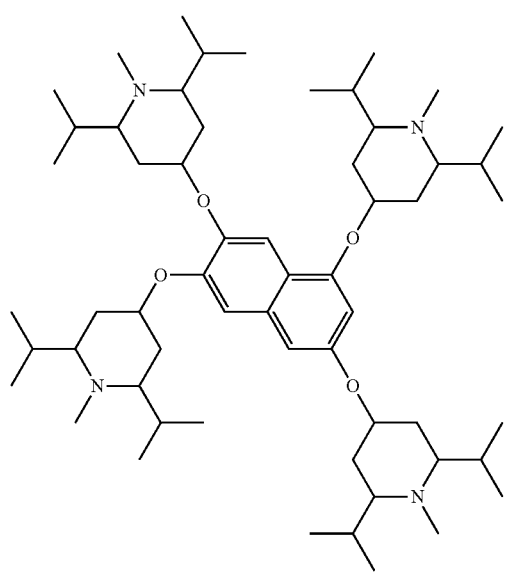 [SMILES: CC(C)C1CC(Oc2cc(OC3CC(C(C)C)N(C)C(C(C)C)C3)c3cc(OC4CC(C(C)C)N(C)C(C(C)C)C4)c(OC4CC(C(C)C)N(C)C(C(C)C)C4)cc3c2)CC(C(C)C)N1C] |

| No. | |
|---|---|
| 371 | 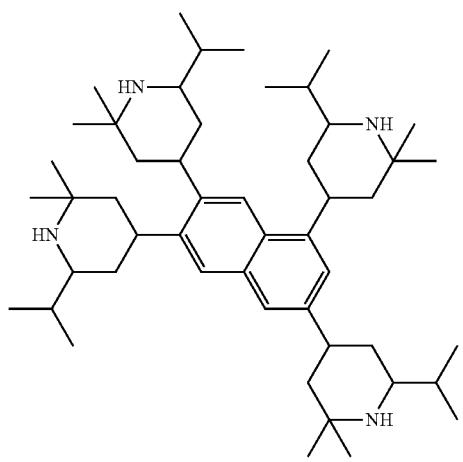 [SMILES: CC(C)C1CC(c2cc(C3CC(C(C)C)NC(C)(C)C3)c3cc(C4CC(C(C)C)NC(C)(C)C4)c(C4CC(C(C)C)NC(C)(C)C4)cc3c2)CC(C)(C)N1] |
| 372 | 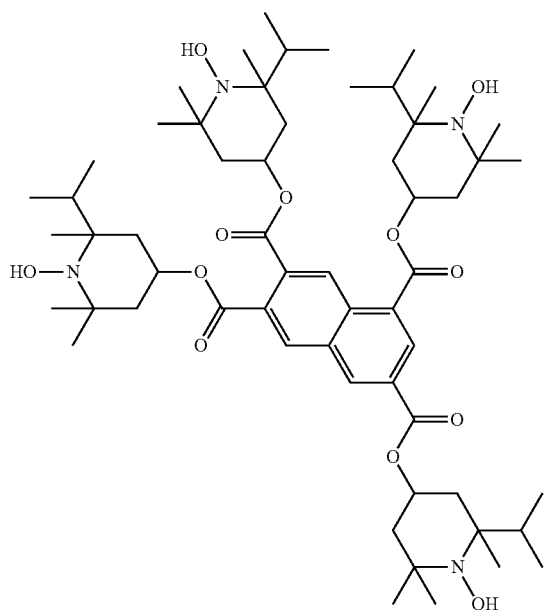 [SMILES: CC(C)C1(C)CC(OC(=O)c2cc(C(=O)OC3CC(C)(C)N(O)C(C)(C(C)C)C3)c3cc(C(=O)OC4CC(C)(C)N(O)C(C)(C(C)C)C4)c(C(=O)OC4CC(C)(C)N(O)C(C)(C(C)C)C4)cc3c2)CC(C)(C)N1O] |
| 373 | 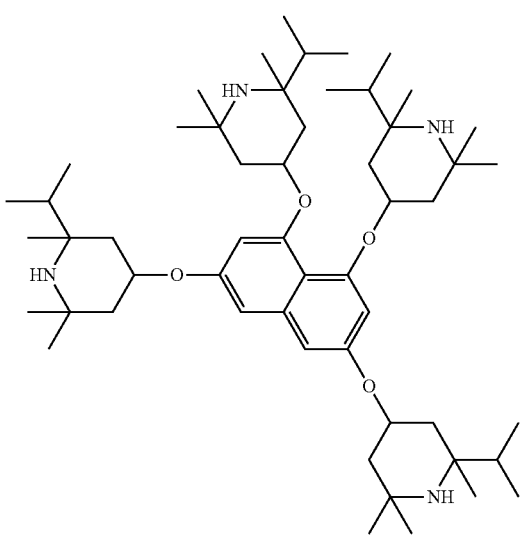 [SMILES: CC(C)C1(C)CC(Oc2cc(OC3CC(C)(C)NC(C)(C(C)C)C3)c3c(OC4CC(C)(C)NC(C)(C(C)C)C4)cc(OC4CC(C)(C)NC(C)(C(C)C)C4)cc3c2)CC(C)(C)N1] |

| No. |
|---|
| 374 |
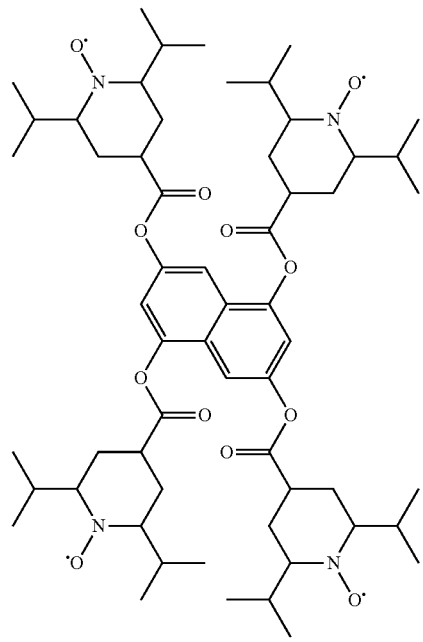
| 375 |
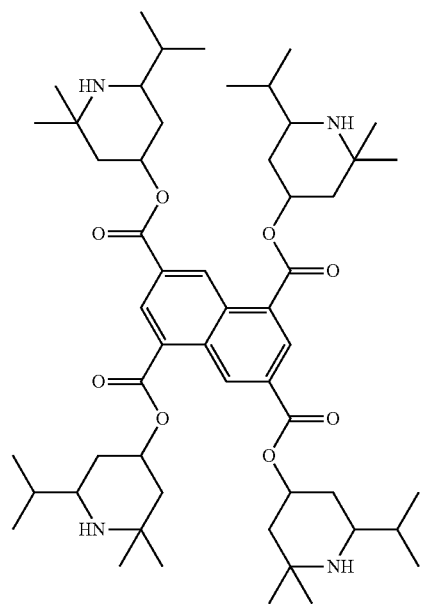 [SMILES: CC(C)C1CC(OC(=O)c2cc(C(=O)OC3CC(C(C)C)NC(C)(C)C3)c3cc(C(=O)OC4CC(C(C)C)NC(C)(C)C4)cc(C(=O)OC4CC(C(C)C)NC(C)(C)C4)c3c2)CC(C)(C)N1]

| No. | |
|---|---|
| 376 | 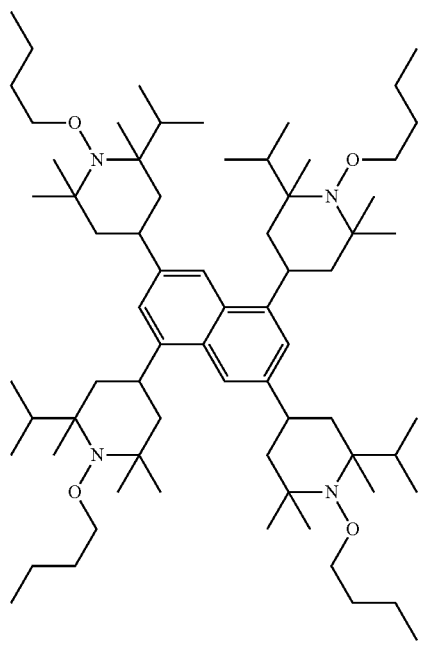 [SMILES: CCCCON1C(C)(C)CC(c2cc(C3CC(C)(C)N(OCCCC)C(C)(C(C)C)C3)c3cc(C4CC(C)(C)N(OCCCC)C(C)(C(C)C)C4)cc(C4CC(C)(C)N(OCCCC)C(C)(C(C)C)C4)c3c2)CC1(C)C(C)C] |

2. Example of Liquid Crystal Composition

Compounds in Examples (including Use Examples) were expressed using symbols according to definitions described in Table 2 below. In Table 2, a configuration of 1,4-cyclohexylene is trans. A parenthesized number next to a symbolized compound in Examples corresponds to the number of the compound. A symbol (-) means any other liquid crystal compound. A content (percentage) of a liquid crystal compound is expressed in terms of weight percent (% by weight) based on the weight of a liquid crystal composition. Values of characteristics of the liquid crystal composition were summarized in a last part. The characteristics were measured according to the methods described above, and measured values were directly described (without extrapolation).

TABLE 2

| Method for Description of Compounds using Symbols $R-(A_1)-Z_1- \ldots -Z_n-(A_n)-R'$ | |
|---|---|
| 1) Left-terminal Group R— | Symbol |
| $C_nH_{2n+1}-$ | n— |
| $C_nH_{2n+1}O-$ | nO— |
| $C_mH_{2m+1}OC_nH_{2n}-$ | mOn- |
| $CH_2=CH-$ | V— |
| $C_nH_{2n+1}-CH=CH-$ | nV— |
| $CH_2=CH-C_nH_{2n}-$ | Vn- |
| $C_mH_{2m+1}-CH=CH-C_nH_{2n}-$ | mVn- |
| $CF_2=CH-$ | VFF— |
| $CF_2=CH-C_nH_{2n}-$ | VFFn- |
| 2) Right-terminal Group —R' | Symbol |
| $-C_nH_{2n+1}$ | -n |
| $-OC_nH_{2n+1}$ | —On |
| $-COOCH_3$ | —EMe |
| $-CH=CH_2$ | —V |

TABLE 2-continued

| Method for Description of Compounds using Symbols $R-(A_1)-Z_1- \ldots -Z_n-(A_n)-R'$ | |
|---|---|
| $-CH=CH-C_nH_{2n+1}$ | —Vn |
| $-C_nH_{2n}-CH=CH_2$ | -nV |
| $-C_mH_{2m}-CH=CH-C_nH_{2n+1}$ | -mVn |
| $-CH=CF_2$ | —VFF |
| —F | —F |
| —Cl | —CL |
| $-OCF_3$ | —OCF3 |
| $-OCF_2H$ | —OCF2H |
| $-CF_3$ | —CF3 |
| $-OCH=CH-CF_3$ | —OVCF3 |
| $-C\equiv N$ | —C |
| 3) Bonding Group —$Z_n$— | Symbol |
| $-C_nH_{2n}-$ | n |
| —COO— | E |
| —CH=CH— | V |
| —CH$_2$O— | 1O |
| —OCH$_2$— | O1 |
| —CF$_2$O— | X |
| —C≡C— | T |
| 4) Ring Structure —$A_n$— | Symbol |
| cyclohexylene | H |
| phenylene | B |

TABLE 2-continued

Method for Description of Compounds using Symbols
R—(A$_1$)—Z$_1$—.....—Z$_n$—(A$_n$)—R'

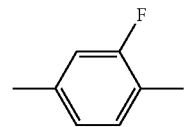 B(F)

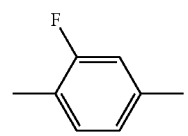 B(2F)

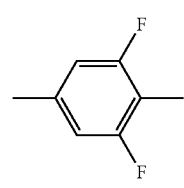 B(F,F)

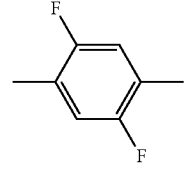 B(2F,5F)

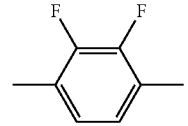 B(2F,3F)

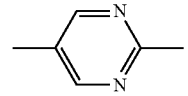 Py

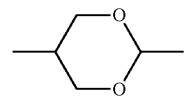 G

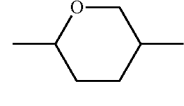 Dh

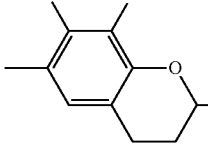 Cro

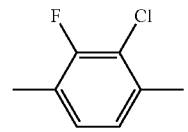 B(2F,3CL)

5) Examples of Description

Example 1  3-HH-V

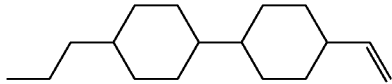 [SMILES: C=CC1CCC(C2CCC(CCC)CC2)CC1]

TABLE 2-continued

Method for Description of Compounds using Symbols
R—(A$_1$)—Z$_1$—.....—Z$_n$—(A$_n$)—R'

Example 2  3-BB(F,F)XB(F,F)-F

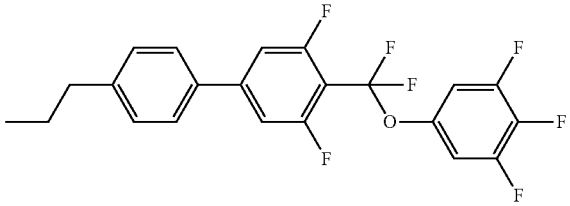 [SMILES: CCCc1ccc(-c2cc(F)c(C(F)(F)Oc3cc(F)c(F)c(F)c3)c(F)c2)cc1]

Example 3  3-HH-4

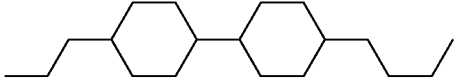

Example 4  3-HBB(2F,3F)-O2

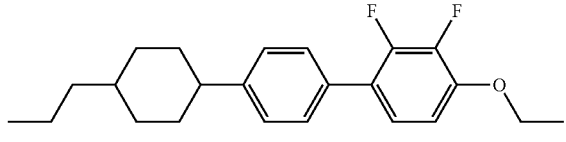 [SMILES: CCCC1CCC(c2ccc(-c3ccc(OCC)c(F)c3F)cc2)CC1]

Example 4

Comparative Experiment

Base liquid crystal M described below was prepared.

| | | |
|---|---|---|
| 3-HH-V | (2-1) | 29% |
| 1-BB-3 | (2-8) | 10% |
| 3-BB(2F,3F)-O2 | (9-3) | 13% |
| 2-HH1OB(2F,3F)-O2 | (10-5) | 20% |
| 3-HH1OB(2F,3F)-O2 | (10-5) | 14% |
| 3-HHB-1 | (3-1) | 8% |
| 2-BBB(2F)-5 | (3-8) | 6% |

Characteristics of base liquid crystal M were as described below: NI=74.5° C.; Δn=0.106; Δ∈=−3.0.

Test of Solubility at Low Temperature

Compound (No. 37) of the invention was added to base liquid crystal M at a ratio of 1,000 ppm to obtain composition (X-1). In a 10-mL vial, 0.5 mL of composition (X-1) and a glass capillary were put, and the vial was capped under a nitrogen flow. A cap portion was sealed with a Parafilm, and then the vial was stored in a freezer at −20° C. Next, compound (No. 38) of the invention was added to base liquid crystal M at a ratio of 1,000 ppm to prepare composition (X-2). The resulting composition was sealed into a vial in a similar procedure, and the vial was stored in the freezer at −20° C. When the two compositions were observed after 30 days, neither appearance of a smectic phase nor deposition of crystals was confirmed, and a nematic phase was maintained.

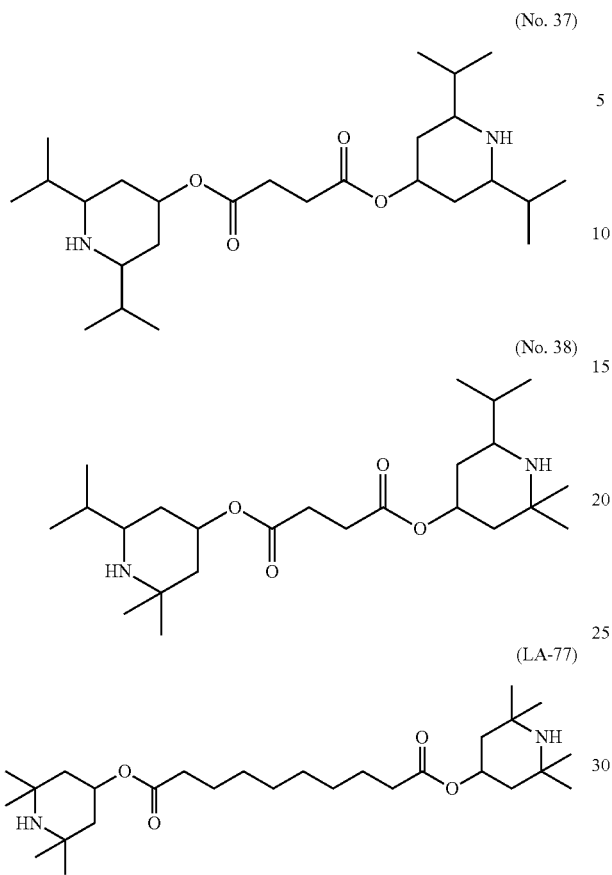

(No. 37)

(No. 38)

(LA-77)

As a comparative compound, LA-77 made by ADEKA Corporation was selected. LA-77 is a commercially available hindered amine light stabilizer. LA-77 was added to base liquid crystal M at a ratio of 1,000 ppm to prepare composition (X-3). When composition (X-3) was stored in the freezer at −20° C. in a manner similar to the procedure, appearance of the smectic phase was confirmed after one day.

The results described above show that the liquid crystal compositions to which compounds (No. 37) and (No. 38) of the invention were added maintained the nematic phase even under a low temperature. The compound of the invention has a high solubility in the liquid crystal composition, and therefore can be concluded to be significantly useful.

Use Example 1

| 3-HB-O2      | (2-5)  | 10% |
| 5-HB-CL      | (5-2)  | 13% |
| 3-HBB(F,F)-F | (6-24) | 10% |
| 3-PyB(F)-F   | (5-15) | 10% |
| 5-PyB(F)-F   | (5-15) | 10% |
| 3-PyBB-F     | (6-80) | 10% |
| 4-PyBB-F     | (6-80) | 10% |
| 5-PyBB-F     | (6-80) | 7%  |
| 5-HBB(F)B-2  | (4-5)  | 10% |
| 5-HBB(F)B-3  | (4-5)  | 10% |

To the composition described above, compound (No. 37) was added at a ratio of 0.1%.

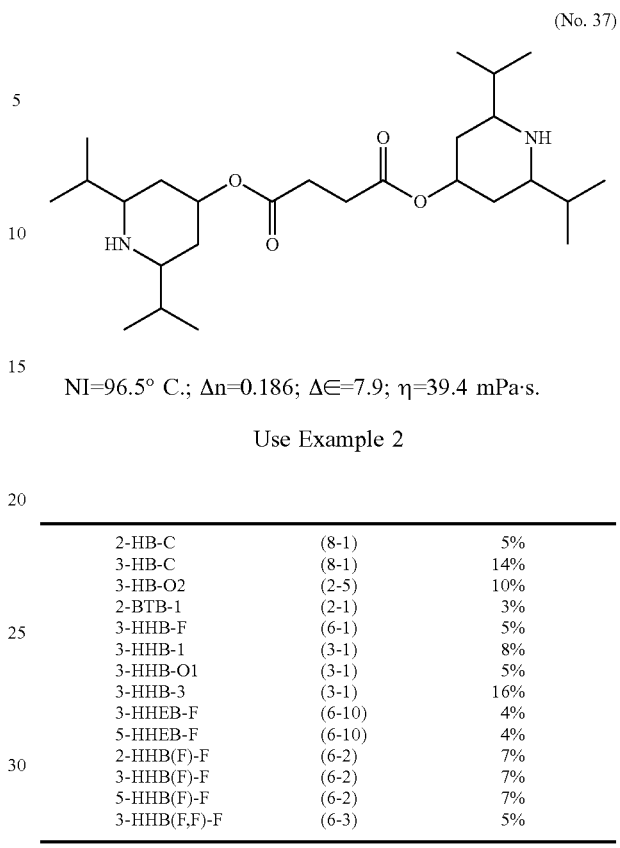

(No. 37)

NI=96.5° C.; Δn=0.186; Δ∈=7.9; η=39.4 mPa·s.

Use Example 2

| 2-HB-C       | (8-1)  | 5%  |
| 3-HB-C       | (8-1)  | 14% |
| 3-HB-O2      | (2-5)  | 10% |
| 2-BTB-1      | (2-1)  | 3%  |
| 3-HHB-F      | (6-1)  | 5%  |
| 3-HHB-1      | (3-1)  | 8%  |
| 3-HHB-O1     | (3-1)  | 5%  |
| 3-HHB-3      | (3-1)  | 16% |
| 3-HHEB-F     | (6-10) | 4%  |
| 5-HHEB-F     | (6-10) | 4%  |
| 2-HHB(F)-F   | (6-2)  | 7%  |
| 3-HHB(F)-F   | (6-2)  | 7%  |
| 5-HHB(F)-F   | (6-2)  | 7%  |
| 3-HHB(F,F)-F | (6-3)  | 5%  |

To the composition described above, compound (No. 38) was added at a ratio of 0.05%.

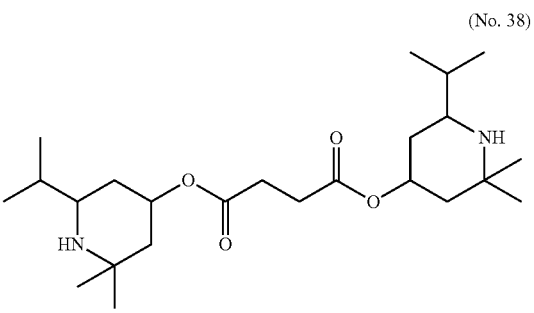 [SMILES: CC(C)C1CC(OC(=O)CCC(=O)OC2CC(C(C)C)NC(C)(C)C2)CC(C)(C)N1]

(No. 38)

NI=104.5° C.; Δn=0.102; Δ∈=4.9; η=19.3 mPa·s.

Use Example 3

| 3-HHB(F,F)-F   | (6-3)  | 9%  |
| 3-H2HB(F,F)-F  | (6-15) | 8%  |
| 4-H2HB(F,F)-F  | (6-15) | 8%  |
| 5-H2HB(F,F)-F  | (6-15) | 10% |
| 3-HBB(F,F)-F   | (6-24) | 21% |
| 5-HBB(F,F)-F   | (6-24) | 20% |
| 3-H2BB(F,F)-F  | (6-27) | 10% |
| 5-HHBB(F,F)-F  | (7-6)  | 3%  |
| 5-HHEBB-F      | (7-17) | 2%  |
| 3-HH2BB(F,F)-F | (7-15) | 3%  |
| 1O1-HBBH-4     | (4-1)  | 3%  |
| 1O1-HBBH-5     | (4-1)  | 3%  |

To the composition described above, compound (No. 167) was added at a ratio of 0.1%.

(No. 167)

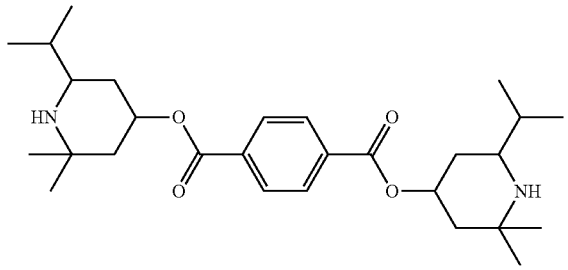

NT=94.8° C.; Δn=0.114; Δ∈=9.0; η=34.3 mPa·s.

Use Example 4

| | | |
|---|---|---|
| 5-HB-CL | (5-2) | 11% |
| 3-HH-4 | (2-1) | 8% |
| 3-HHB-1 | (3-1) | 5% |
| 3-HHB(F,F)-F | (6-3) | 8% |
| 3-HBB(F,F)-F | (6-24) | 17% |
| 5-HBB(F,F)-F | (6-24) | 15% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |
| 3-HB-O2 | (2-5) | 3% |

To the composition described above, compound (No. 64) was added at a ratio of 0.12%.

(No. 64)

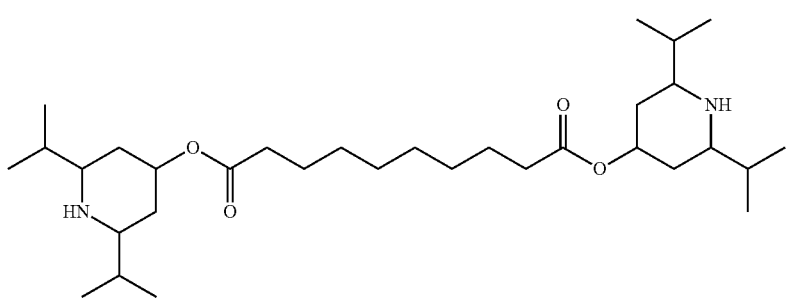

NI=79.4° C.; Δn=0.102; Δ∈=8.4; η=21.0 mPa·s.

Use Example 5

| | | |
|---|---|---|
| 5-HB-CL | (5-2) | 3% |
| 7-HB(F)-F | (5-3) | 7% |
| 3-HH-4 | (2-1) | 10% |
| 3-HH-EMe | (2-2) | 20% |
| 3-HHEB-F | (6-10) | 8% |
| 5-HHEB-F | (6-10) | 8% |
| 3-HHEB(F,F)-F | (6-12) | 10% |
| 4-HHEB(F,F)-F | (6-12) | 6% |
| 4-HGB(F,F)-F | (6-103) | 6% |

-continued

| | | |
|---|---|---|
| 5-HGB(F,F)-F | (6-103) | 6% |
| 2-H2GB(F,F)-F | (6-106) | 4% |
| 3-H2GB(F,F)-F | (6-106) | 6% |
| 5-GHB(F,F)-F | (6-109) | 6% |

To the composition described above, compound (No. 65) was added at a ratio of 0.1%.

(No. 65)

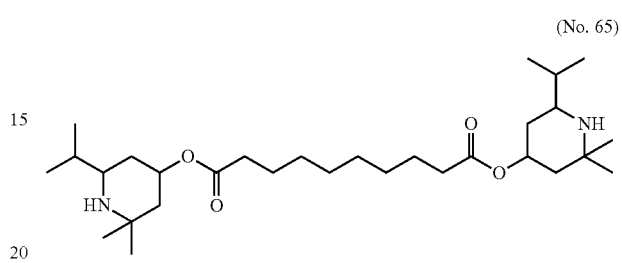

NI=79.5° C.; Δn=0.064; Δ∈=5.8; η=20.0 mPa·s.

Use Example 6

| | | |
|---|---|---|
| 3-HB-O1 | (2-5) | 15% |
| 3-HH-4 | (2-1) | 5% |
| 3-HH-V | (2-1) | 4% |
| 3-HB(2F,3F)-O2 | (9-1) | 11% |
| 5-HB(2F,3F)-O2 | (9-1) | 11% |
| 2-HHB(2F,3F)-1 | (10-1) | 10% |
| 3-HHB(2F,3F)-1 | (10-1) | 12% |
| 3-HHB(2F,3F)-O2 | (10-1) | 13% |
| 5-HHB(2F,3F)-O2 | (10-1) | 13% |
| 3-HHB-1 | (3-1) | 6% |

To the composition described above, compound (No. 184) was added at a ratio of 0.12%.

(No. 184)

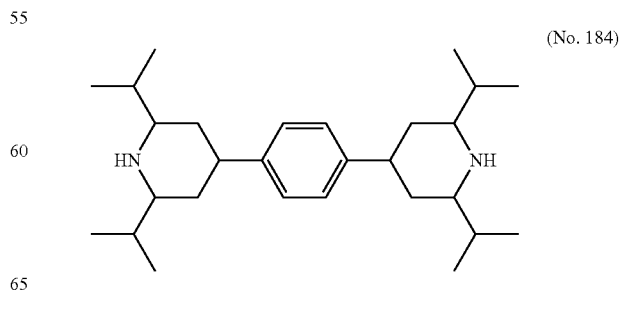

NI=86.8° C.; Δn=0.088; Δ∈=−3.2; η=33.9 mPa·s.

Use Example 7

| | | |
|---|---|---|
| 3-HH-4 | (2-1) | 8% |
| 3-HH-V | (2-1) | 8% |
| 3-H2B(2F,3F)-O2 | (9-4) | 18% |
| 5-H2B(2F,3F)-O2 | (9-4) | 18% |
| 2-HHB(2F,3CL)-O2 | (10-12) | 2% |
| 3-HHB(2F,3CL)-O2 | (10-12) | 3% |
| 4-HHB(2F,3CL)-O2 | (10-12) | 2% |
| 5-HHB(2F,3CL)-O2 | (10-12) | 2% |
| 3-HBB(2F,3F)-O2 | (10-7) | 9% |
| 5-HBB(2F,3F)-O2 | (10-7) | 9% |
| V-HHB-1 | (3-1) | 6% |
| 3-HHB-3 | (3-1) | 6% |
| 3-HHEBH-3 | (4-6) | 3% |
| 3-HHEBH-4 | (4-6) | 3% |
| 3-HHEBH-5 | (4-6) | 3% |

To the composition described above, compound (No. 185) was added at a ratio of 0.1%.

(No. 185)

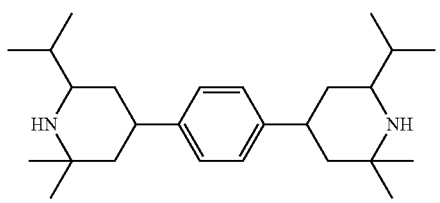

NI=93.2° C.; Δn=0.096; Δ∈=−3.6; η=25.8 mPa·s.

Use Example 8

| | | |
|---|---|---|
| 2-HH-5 | (2-1) | 3% |
| 3-HH-4 | (2-1) | 14% |
| 3-HH-5 | (2-1) | 4% |
| 3-HB-O2 | (2-5) | 12% |
| 3-H2B(2F,3F)-O2 | (9-4) | 15% |
| 5-H2B(2F,3F)-O2 | (9-4) | 15% |
| 3-HHB(2F,3CL)-O2 | (10-12) | 5% |
| 2-HBB(2F,3F)-O2 | (10-7) | 3% |
| 3-HBB(2F,3F)-O2 | (10-7) | 8% |
| 5-HBB(2F,3F)-O2 | (10-7) | 8% |
| 3-HHB-1 | (3-1) | 5% |
| 3-HHB-3 | (3-1) | 3% |
| 3-HHB-O1 | (3-1) | 5% |

To the composition described above, compound (No. 330) was added at a ratio of 0.1%.

(No. 330)

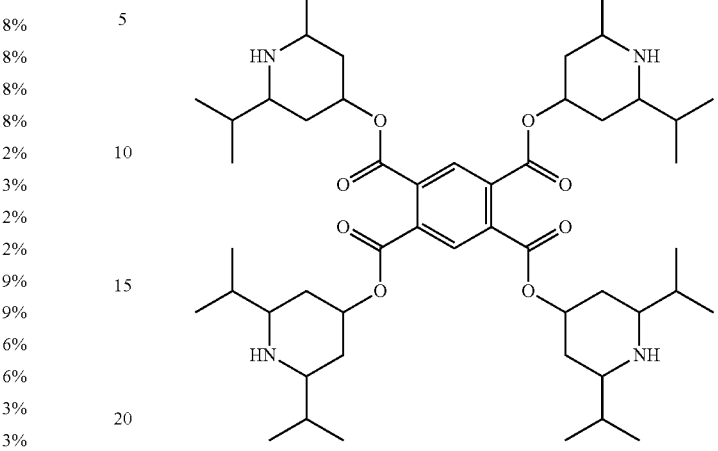

NI=77.3° C.; Δn=0.092; Δ∈=−3.9; η=18.9 mPa·s.

Use Example 9

| | | |
|---|---|---|
| 2-HH-3 | (2-1) | 11% |
| 3-HH-4 | (2-1) | 9% |
| 1-BB-3 | (2-8) | 9% |
| 3-HH-V | (2-1) | 10% |
| 3-HB-O2 | (2-5) | 2% |
| 3-BB(2F,3F)-O2 | (9-3) | 9% |
| 5-BB(2F,3F)-O2 | (9-3) | 6% |
| 2-HH1OB(2F,3F)-O2 | (10-5) | 13% |
| 3-HH1OB(2F,3F)-O2 | (10-5) | 21% |
| 3-HHB-1 | (3-1) | 5% |
| 3-HHB-O1 | (3-1) | 3% |
| 2-BBB(2F)-5 | (3-8) | 2% |

To the composition described above, compound (No. 37) was added at a ratio of 0.05%.

(No. 37)

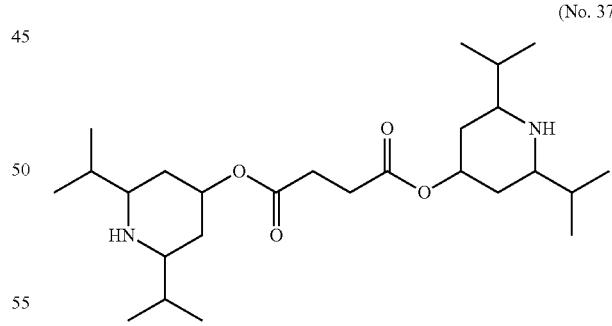

NI=75.4° C.; Δn=0.099; Δ∈=−3.1; η=14.4 mPa·s.

Use Example 10

| | | |
|---|---|---|
| 2-HH-3 | (2-1) | 16% |
| 7-HB-1 | (2-5) | 10% |
| 5-HB-O2 | (2-5) | 8% |
| 3-HB(2F,3F)-O2 | (9-1) | 17% |

-continued

| | | |
|---|---|---|
| 5-HB(2F,3F)-O2 | (9-1) | 16% |
| 3-HHB(2F,3CL)-O2 | (10-12) | 3% |
| 4-HHB(2F,3CL)-O2 | (10-12) | 3% |
| 5-HHB(2F,3CL)-O2 | (10-12) | 2% |
| 3-HH1OCro-5 | (13-6) | 5% |
| 3-HHB-1 | (3-1) | 5% |
| 5-HBB(F)B-2 | (4-5) | 8% |
| 5-HBB(F)B-3 | (4-5) | 7% |

To the composition described above, compound (No. 38) was added at a ratio of 0.1%.

(No. 38)

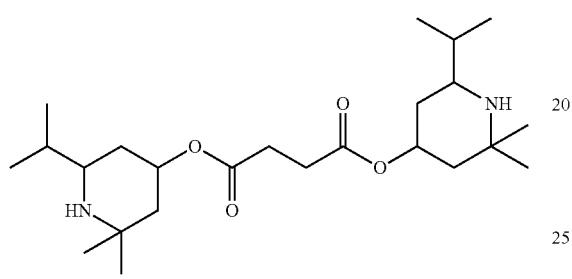

NI=71.7° C.; Δn=0.097; Δ∈=−2.5; η=20.9 mPa·s.

Use Example 11

| | | |
|---|---|---|
| 2-HH-3 | (2-1) | 8% |
| 3-HH-4 | (2-1) | 10% |
| 1-BB-3 | (2-8) | 10% |
| 3-HH-V | (2-1) | 15% |
| 3-BB(2F,3F)-O2 | (9-3) | 13% |
| 2-HH1OB(2F,3F)-O2 | (10-5) | 16% |
| 3-HH1OB(2F,3F)-O2 | (10-5) | 14% |
| 3-HHB-1 | (3-1) | 8% |
| 2-BBB(2F)-5 | (3-8) | 6% |

To the composition described above, compound (No. 167) was added at a ratio of 0.12%.

(No. 167)

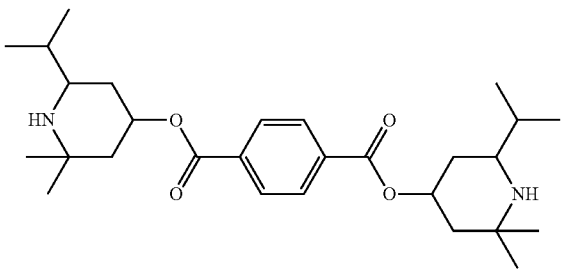

NI=72.7° C.; Δn=0.102; Δ∈=−2.7; η=13.7 mPa·s.

Use Example 12

| | | |
|---|---|---|
| 1V2-BEB(F,F)-C | (8-15) | 6% |
| 3-HB-C | (8-1) | 18% |
| 2-BTB-1 | (2-10) | 10% |
| 5-HH-VFF | (2-1) | 30% |
| 3-HHB-1 | (3-1) | 4% |
| VFF-HHB-1 | (3-1) | 10% |
| VFF2-HHB-1 | (3-1) | 11% |
| 3-H2BTB-2 | (3-17) | 5% |
| 3-H2BTB-3 | (3-17) | 3% |
| 3-H2BTB-4 | (3-17) | 3% |

To the composition described above, compound (No. 64) was added at a ratio of 0.1%.

(No. 64)

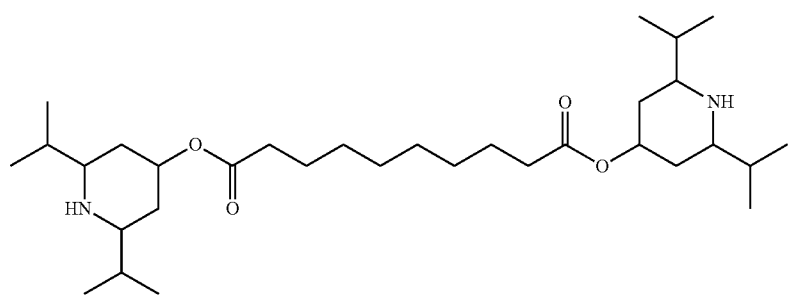

NI=80.7° C.; Δn=0.128; Δ∈=6.5; η=11.6 mPa·s.

Use Example 13

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 36% |
| 3-HH-V1 | (2-1) | 7% |
| 3-HHEH-5 | (3-13) | 3% |
| 3-HHB-1 | (3-1) | 6% |
| V-HHB-1 | (3-1) | 5% |
| V2-BB(F)B-1 | (3-6) | 5% |
| 1V2-BB-F | (5-1) | 3% |
| 3-BB(F,F)XB(F,F)-F | (6-97) | 11% |
| 3-HHBB(F,F)-F | (7-6) | 6% |

To the composition described above, compound (No. 65) was added at a ratio of 0.1%.

(No. 65)

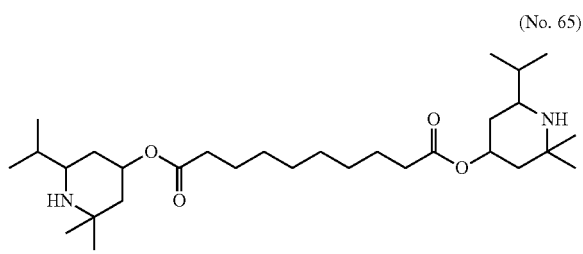 [SMILES: CC(C)C1CC(OC(=O)CCCCCCCCC(=O)OC2CC(C(C)C)NC(C)(C)C2)CC(C)(C)N1]

NI=88.4° C.; Δn=0.110; Δ∈=6.8; η=15.7 mPa·s.

Use Example 14

| 3-GB(F)B(F,F)XB(F,F)-F | (7-57)  | 5%  |
|------------------------|---------|-----|
| 3-BB(F)B(F,F)XB(F,F)-F | (7-47)  | 3%  |
| 4-BB(F)B(F,F)XB(F,F)-F | (7-47)  | 7%  |
| 5-BB(F)B(F,F)XB(F,F)-F | (7-47)  | 3%  |
| 3-HH-V                 | (2-1)   | 41% |
| 3-HH-V1                | (2-1)   | 10% |
| 3-HHEH-5               | (3-13)  | 3%  |
| V-HHB-1                | (3-1)   | 6%  |
| V2-BB(F)B-1            | (3-6)   | 5%  |
| 1V2-BB-F               | (5-1)   | 3%  |
| 3-BB(F,F)XB(F,F)-F     | (6-97)  | 6%  |
| 3-GB(F,F)XB(F,F)-F     | (6-113) | 5%  |
| 3-HHBB(F,F)-F          | (7-6)   | 3%  |

To the composition described above, compound (No. 184) was added at a ratio of 0.1%.

(No. 184)

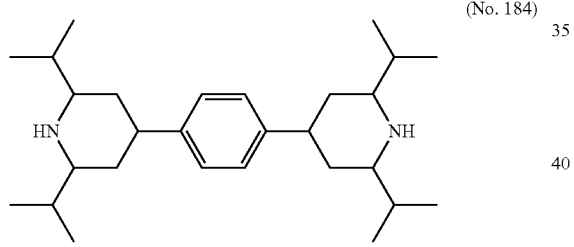

NI=78.8° C.; Δn=0.101; Δ∈=7.3; η=11.6 mPa·s.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

Compound (1) has an effect for preventing photolysis of a liquid crystal composition, and has a high solubility in the liquid crystal composition. A liquid crystal composition containing compound (1) satisfies at least one of characteristics such as a high maximum temperature, a low minimum temperature, a small viscosity, a suitable optical anisotropy, a large dielectric anisotropy, a suitable elastic constant and a large specific resistance. The composition is stable to light. A liquid crystal display device including the composition has characteristics such as a short response time, a large voltage holding ratio, a large contrast ratio and a long service life, and thus can be used for a liquid crystal projector, a liquid crystal television and so forth.

What is claimed is:
1. A compound represented by any of formulas (1-1) to (1-4):

(1-1)

(1-2)

(1-3)

(1-4)

wherein, in formulas (1-1) to (1-4),
M is aliphatic hydrocarbon group having 1 to 20 carbons or aromatic hydrocarbon group having 1 to 20 carbons, and in the groups, at least one —CH$_2$— may be replaced by —O— or —S—, one or two —CH=CH— may be replaced by —CH=N—, and at least one of hydrogen may be replaced by fluorine or chlorine;
Z is a single bond, —O—, —COO—, or —OCO—;
Q is a monovalent group represented by formula (Q-1), (Q-2) or (Q-3), in which R$^a$ is hydrogen, —O., —OH, or —R$^1$;

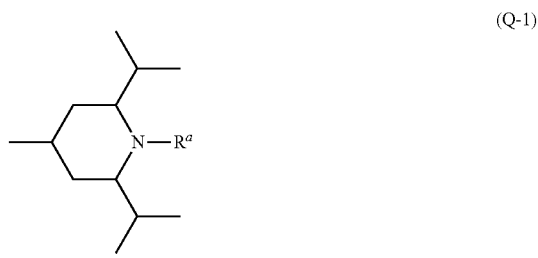

(Q-1)

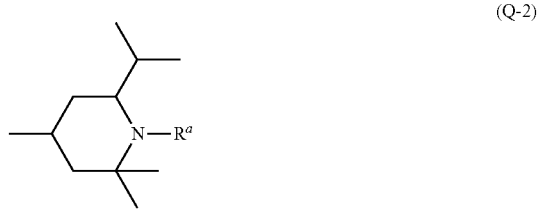

(Q-2)

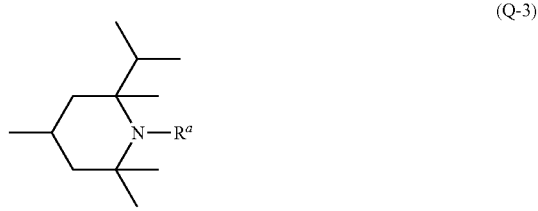

(Q-3)

R$^b$ is hydrogen, fluorine or —R$^2$;
R$^1$ and R$^2$ are independently an alkyl having 1 to 20 carbons, arylalkyl having 1 to 20 carbons, or aryl having 1 to 20 carbons, and in the alkyl, at least one —CH$_2$— may be replaced by —O—, —CO—, —COO—, or —OCO—, and —CH$_3$ located at a terminal may be replaced by —NHR$^3$ or —NR$^4$R$^5$, in which R$^3$, R$^4$, and R$^5$ are independently alkyl having 1 to 10 carbons.

2. The compound according to claim 1, represented by any of formulas (1-1a) to (1-4a):

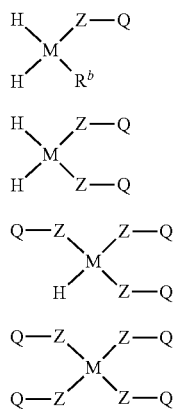

wherein, in formulas (1-1a) to (1-4a),

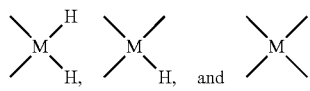

are a divalent group, a trivalent group or a tetravalent group derived by eliminating hydrogen from a) alkane having 1 to 15 carbons, b) alkane having 1 to 15 carbons in which at least one —CH$_2$— is replaced by —O—, c) cyclohexane, d) bicyclohexane, e) decahydronaphthalene, f) tetrahydropyran, g) dioxane, h) benzene, i) benzene in which at least one of hydrogen is replaced by fluorine, j) biphenyl, k) naphthalene, l) pyridine, or m) pyrimidine;

Z is a single bond, —O—, —COO—, or —OCO—;

Q is a monovalent group represented by formula (Q-1), (Q-2) or (Q-3), in which R$^a$ is hydrogen, —O., —OH, or —R$^1$;

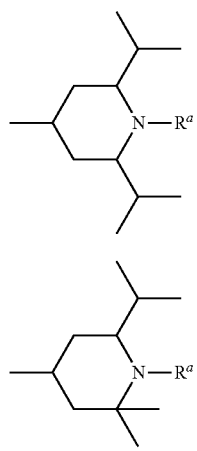

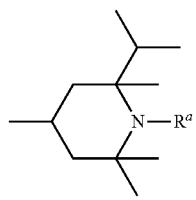

R$^b$ is hydrogen, fluorine or —R$^2$; and

R$^1$ and R$^2$ are independently an alkyl having 1 to 20 carbons, arylalkyl having 1 to 20 carbons, or aryl having 1 to 20 carbons, and in the alkyl, at least one —CH$_2$— may be replaced by —O—, and —CH$_3$ located at a terminal may be replaced by —NHR$^3$ or —NR$^4$R$^5$, in which R$^3$, R$^4$, and R$^5$ are independently alkyl having 1 to 10 carbons.

3. The compound according to claim 2, wherein, in formulas (1-1a) to (1-4a) described in claim 2,

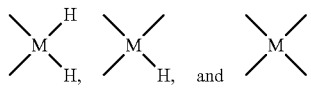

are each any of a divalent group represented by formulas (M-1) to (M-7), a trivalent group represented by formulas (M-8) to (M-23) and a tetravalent group represented by formulas (M-24) to (M-42), in which c is an integer from 0 to 16:

-continued
(M-8) 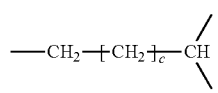
(M-9) 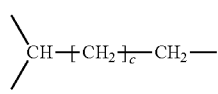
(M-10) 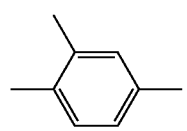
(M-11) 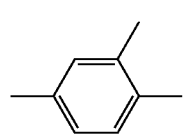
(M-12) 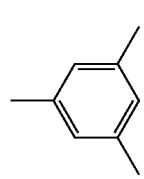
(M-13) 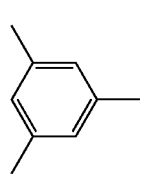
(M-14) 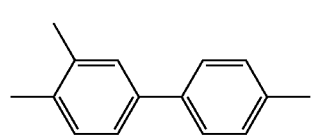
(M-15) 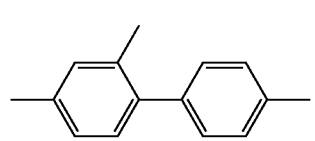
(M-16) 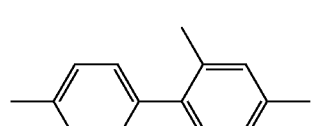
(M-17) 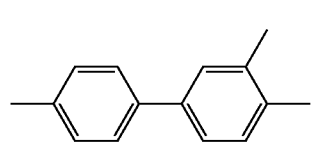
(M-18) 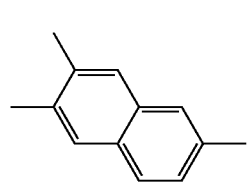
-continued
(M-19) 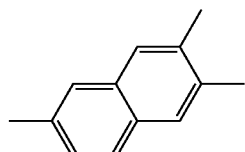
(M-20) 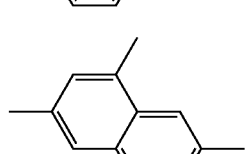
(M-21) 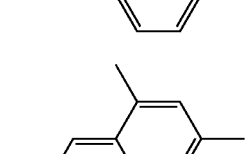
(M-22) 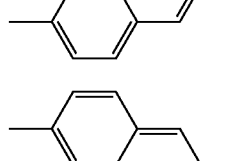
(M-23) 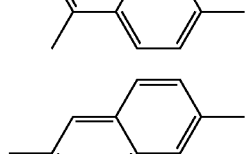
(M24) 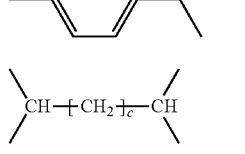
(M-25) 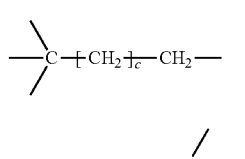
(M-26) 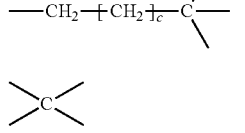
(M-27) 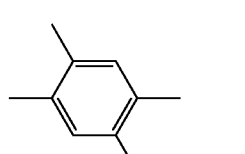
(M-28) 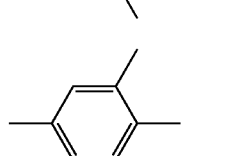
(M-29) 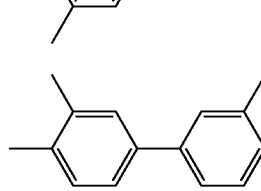
(M-30)

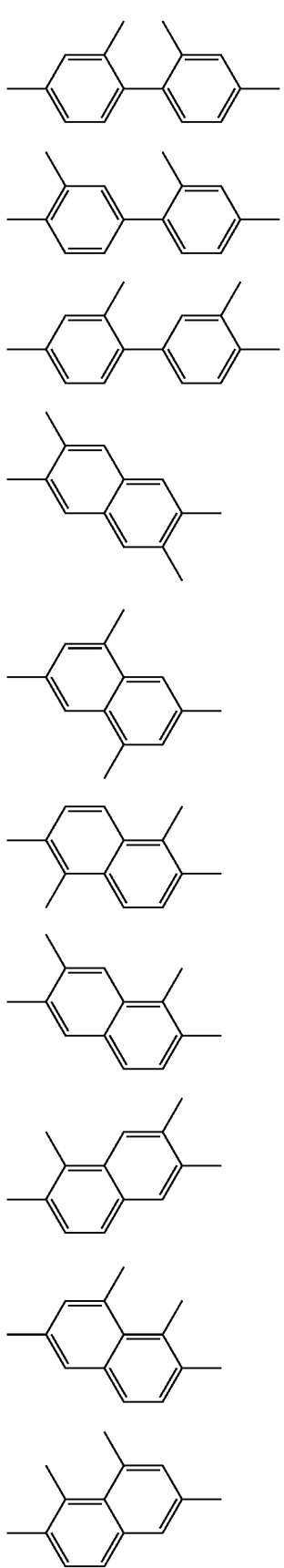
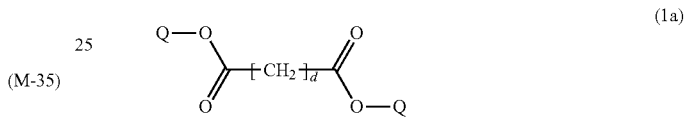
4. The compound according to claim 1, represented by any of formulas (1a) to (1s):
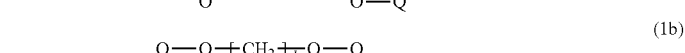
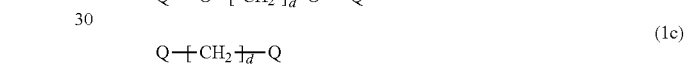
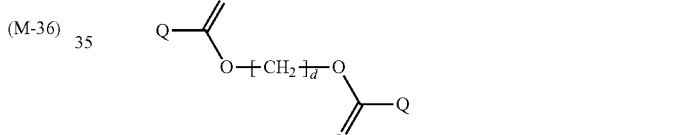
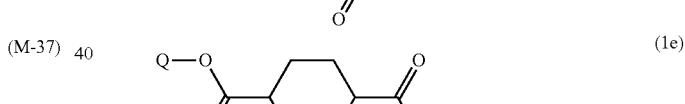
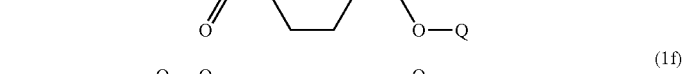
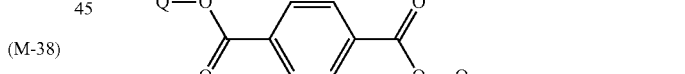
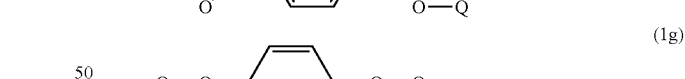
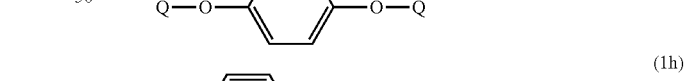

(1k) 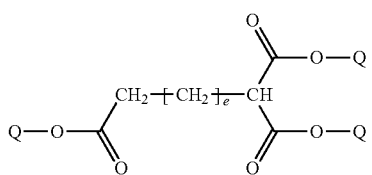

(1l) 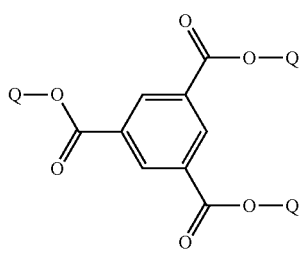

(1m) 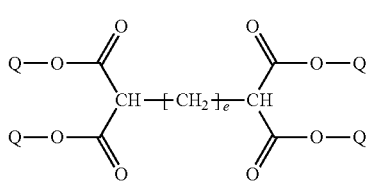

(1n) 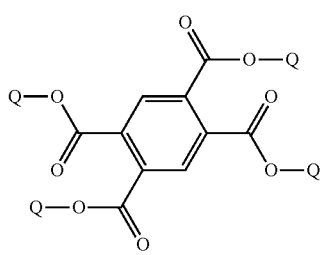

(1o) 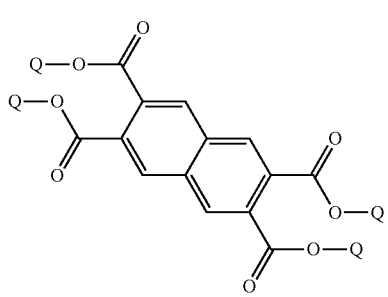

(1p) 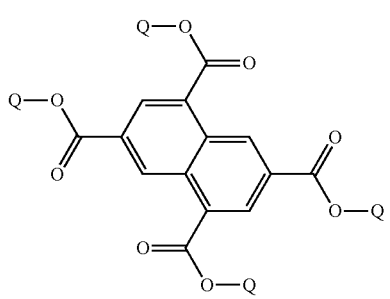

(1q) 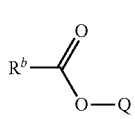

(1r) 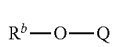

(1s) 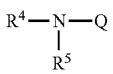

wherein, in the formula described above, d is an integer from 1 to 14;

e is an integer from 0 to 13;

Q is a monovalent group represented by formula (Q-1), (Q-2) or (Q-3), in which $R^a$ is hydrogen, —O., —OH, or —$R^1$;

(Q-1) 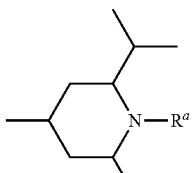

(Q-2) 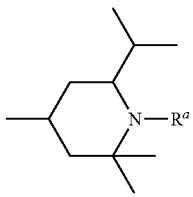

(Q-3) 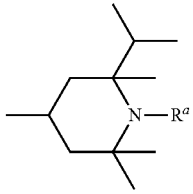

$R^b$ is hydrogen or —$R^2$;

$R^1$ and $R^2$ are independently alkyl having 1 to 20 carbons, arylalkyl having 1 to 20 carbons or aryl having 1 to 20 carbons, and in the alkyl, at least one —CH$_2$— may be replaced by —O—; and $R^4$ and $R^5$ are independently alkyl having 1 to 10 carbons.

5. The compound according to claim 4, wherein, in formulas (1a) to (1s) described in claim 4, $R^a$ in formulas (Q-1) to (Q-3) is hydrogen, —O., —OH, alkyl having 1 to 10 carbons, or alkoxy having 1 to 10 carbons.

6. The compound according to claim 1, represented by any of formulas (1a-1), (1f), (1h) and (1n):

(1a-1) 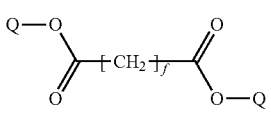

(1f) 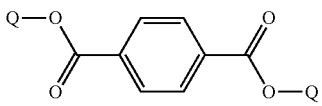

-continued
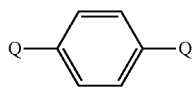
(1h)
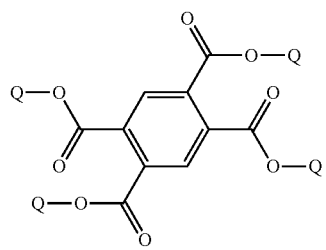
(1n)
wherein, in formulas (1a-1), (1f-1), (1h), and (1n),
f is an integer from 1 to 12; and
Q is a monovalent group represented by any of formulas (Q-1), (Q-2) or (Q-3), in which $R^a$ is hydrogen or alkyl having 1 to 15 carbons:
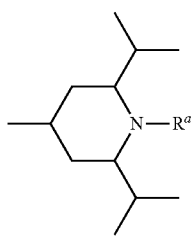
(Q-1)
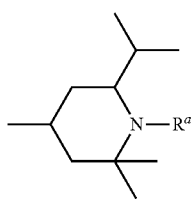
(Q-2)
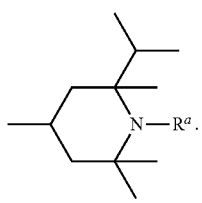
(Q-3)
7. The compound according to claim 1, represented by any of formulas (1a-1-1) to (1a-1-6), formulas (1f-1-1) to (1f-1-6), and formulas (1n-1-1) to (1n-1-3):
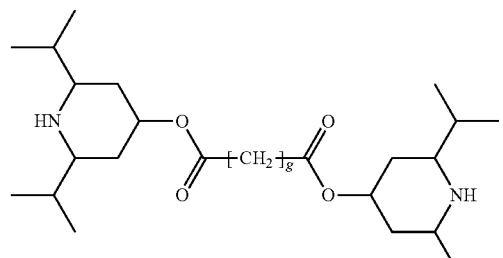
(1a-1-1)
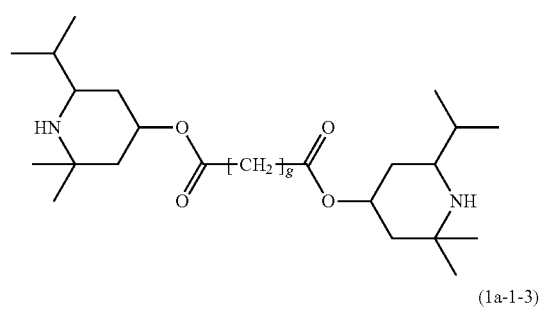
(1a-1-2)
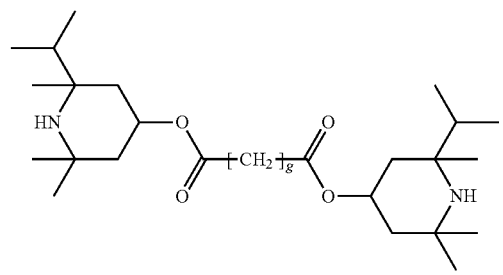
(1a-1-3)
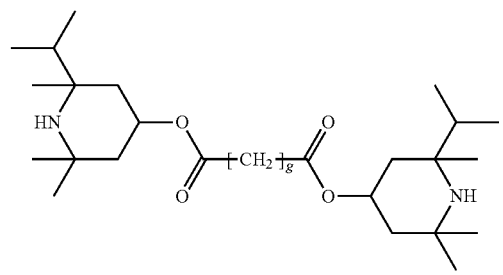
(1a-1-4)
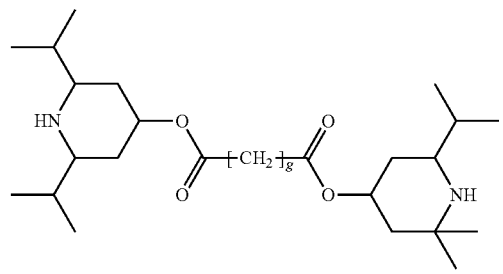
(1a-1-5)
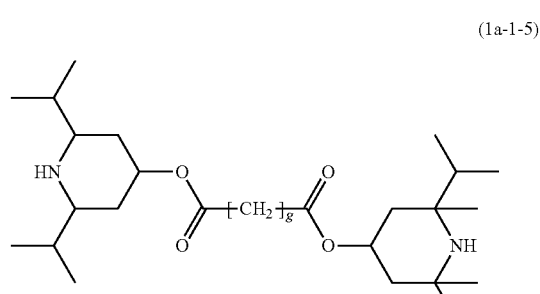

(1a-1-6)
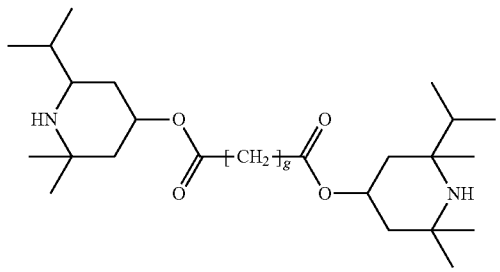
(1f-1-1)
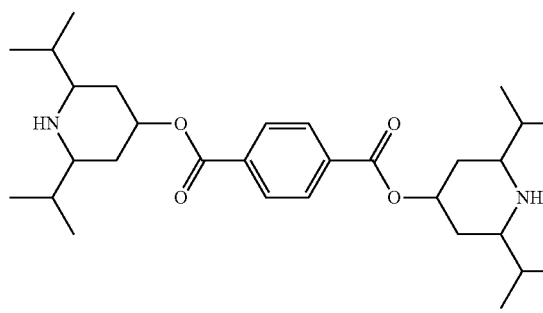
(1f-1-2)
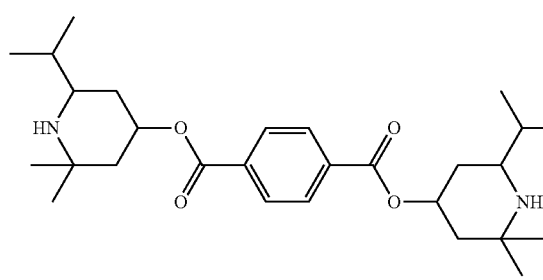
(1f-1-3)
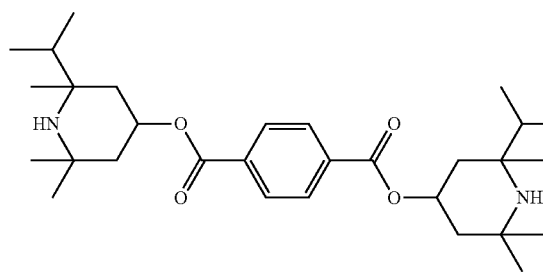
(1f-1-4)
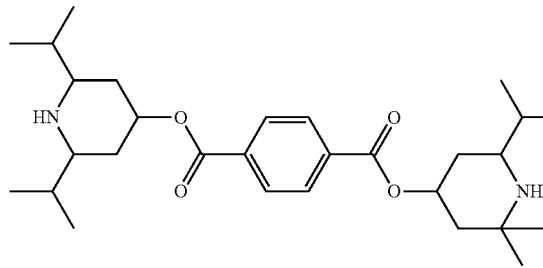
(1f-1-5)
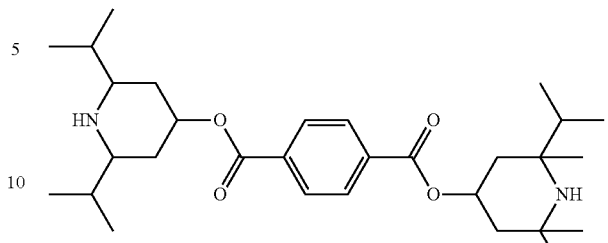
(1f-1-6)
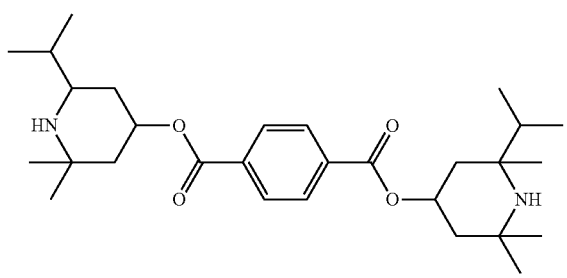
(1n-1-1)
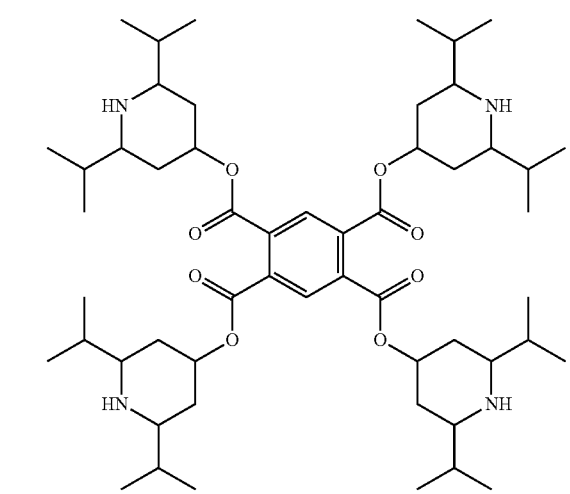
(1n-1-2)
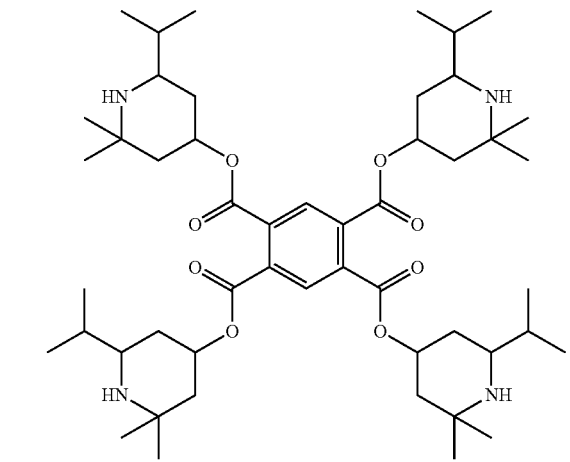

(1n-1-3)

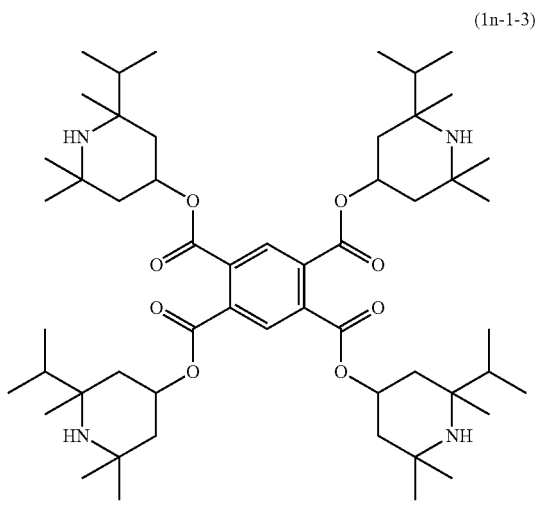 [SMILES: CC(C)C1(C)CC(OC(=O)c2cc(C(=O)OC3CC(C)(C)NC(C)(C(C)C)C3)c(C(=O)OC3CC(C)(C)NC(C)(C(C)C)C3)cc2C(=O)OC2CC(C)(C)NC(C)(C(C)C)C2)CC(C)(C)N1]

(5)
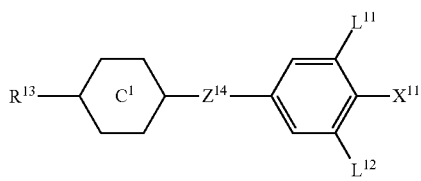

(6)
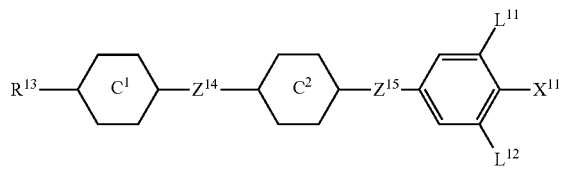

(7)
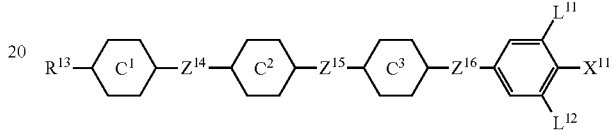

wherein, in formulas (1a-1-1) to (1a-1-6), g is an integer from 1 to 10.

8. A liquid crystal composition, containing at least one compound according to claim 1.

9. The liquid crystal composition according to claim 8, further containing at least one compound selected from the group of compounds represented by formulas (2) to (4):

(2)
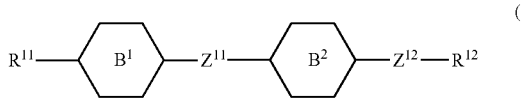

(3)
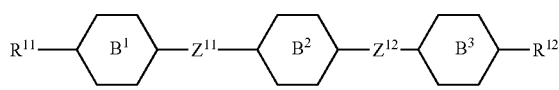

(4)
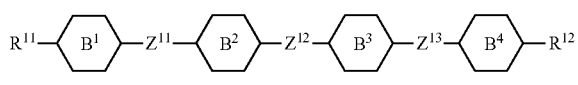

wherein, in formulas (2) to (4),
$R^{11}$ and $R^{12}$ are independently alkyl having 1 to 10 carbons or alkenyl having 2 to 10 carbons, and in the alkyl or the alkenyl, at least one —$CH_2$— may be replaced by —O—, and at least one hydrogen may be replaced by fluorine;
ring $B^1$, $B^2$, $B^3$ and $B^4$ are independently 1,4-cyclohexylene, 1,4-phenylene, 2-fluoro-1,4-phenylene, 2,5-difluoro-1,4-phenylene or pyrimidine-2,5-diyl; and
$Z^{11}$, $Z^{12}$ and $Z^{13}$ are independently a single bond, —$CH_2CH_2$—, —CH=CH—, —C≡C—, or —COO—.

10. The liquid crystal composition according to claim 8, further containing at least one compound selected from the group of compounds represented by formulas (5) to (7):

wherein, in formulas (5) to (7),
$R^{13}$ is alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
$X^{11}$ is fluorine, chlorine, —$OCF_3$, —$OCHF_2$, —$CF_3$, —$CHF_2$, —$CH_2F$, —$OCF_2CHF_2$, or —$OCF_2CHFCF_3$;
ring $C^1$, $C^2$, and $C^3$ are independently 1,4-cyclohexylene, 1,4-phenylene in which at least one of hydrogen may be replaced by fluorine, tetrahydropyran-2,5-diyl, 1,3-dioxane-2,5-diyl, or pyrimidine-2,5-diyl;
$Z^{14}$, $Z^{15}$, and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and
$L^{11}$ and $L^{12}$ are independently hydrogen or fluorine.

11. The liquid crystal composition according to claim 8, further containing at least one compound selected from the group of compounds represented by formula (8):

(8)
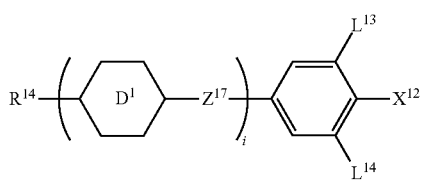

wherein, in formula (8),
$R^{14}$ is alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
$X^{12}$ is —C≡N or —C≡C—C≡N;
ring $D^1$ is 1,4-cyclohexylene, 1,4-phenylene in which at least one of hydrogen may be replaced by fluorine, tetrahydropyran-2,5-diyl, 1,3-dioxane-2,5-diyl, or pyrimidine-2,5-diyl;
$Z^{17}$ is a single bond, —$CH_2CH_2$—, —C≡C—, —COO—, —$CF_2O$—, —$OCF_2$—, or —$CH_2O$—;
$L^{13}$ and $L^{14}$ are independently hydrogen or fluorine; and
i is 1, 2, 3, or 4.

12. The liquid crystal composition according to claim 8, further containing at least one compound selected from the group of compounds represented by formulas (9) to (15):

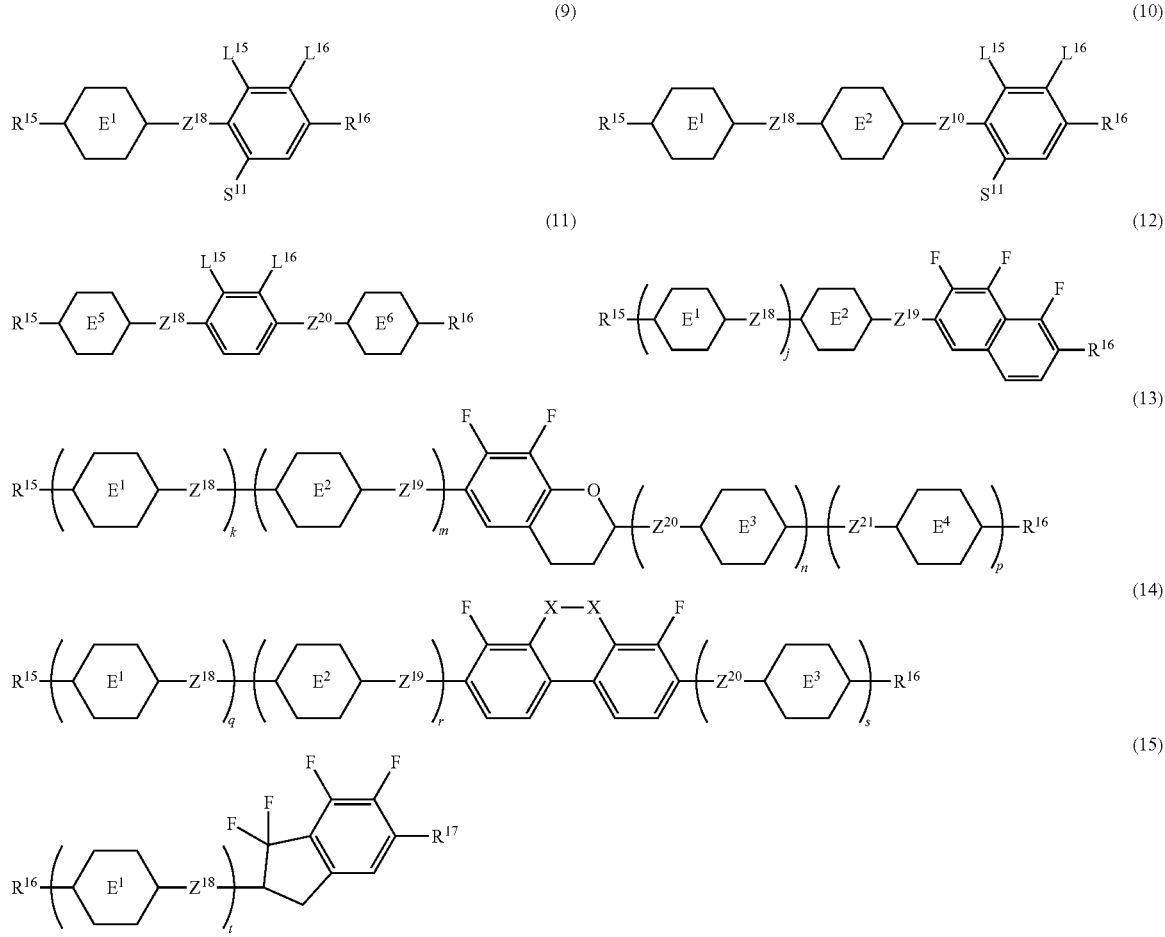

wherein, in formulas (9) to (15), $R^{15}$ and $R^{16}$ are independently alkyl having 1 to 10 carbons or alkenyl having 2 to 10 carbons, and in the alkyl and the alkenyl, at least one —CH$_2$— may be replaced by —O—, and at least one hydrogen may be replaced by fluorine;

$R^{17}$ is hydrogen, fluorine, alkyl having 1 to 10 carbons or alkenyl having 2 to 10 carbons, and in the alkyl and the alkenyl, at least one —CH$_2$— may be replaced by —O—, and at least one ef hydrogen may be replaced by fluorine;

rings $E^1$, $E^2$, $E^3$ and $E^4$ are independently 1,4-cyclohexylene, 1,4-cyclohexenylene, 1,4-phenylene in which at least one of hydrogen may be replaced by fluorine, tetrahydropyran-2,5-diyl, or decahydronaphthalene-2,6-diyl;

rings $E^5$ and $E^6$ independently 1,4-cyclohexylene, 1,4-cyclohexenylene, 1,4-phenylene, tetrahydropyran-2,5-diyl, or decahydronaphthalene-2,6-diyl;

$Z^{18}$, $Z^{19}$, $Z^{20}$, and $Z^{21}$ are independently a single bond, —CH$_2$CH$_2$—, —COO—, —CH$_2$O—, —OCF$_2$—, or —OCF$_2$CH$_2$CH$_2$—;

$L^{15}$ and $L^{16}$ are independently fluorine or chlorine;

$S^{11}$ is hydrogen or methyl;

X is —CHF— or —CF$_2$—; and j, k, m, n, p, q, r, and s are independently 0 or 1, a sum of k, m, n, and p is 1 or 2, a sum of q, r, and s is 0, 1, 2, or 3, and t is 1, 2, or 3.

13. The liquid crystal composition according to claim 8, further containing at least one of a polymerizable compound, a polymerization initiator, a polymerization inhibitor, an optically active compound, an antioxidant, an ultraviolet light absorber, a light stabilizer, a heat stabilizer, and an antifoaming agent.

14. A liquid crystal display device, including at least one liquid crystal composition according to claim 8.

* * * * *

UNITED STATES PATENT AND TRADEMARK OFFICE
CERTIFICATE OF CORRECTION

PATENT NO. : 9,631,142 B2
APPLICATION NO. : 14/859615
DATED : April 25, 2017
INVENTOR(S) : Y. Gotoh et al.

Page 1 of 1

It is certified that error appears in the above-identified patent and that said Letters Patent is hereby corrected as shown below:

On the Title Page

Item [57], Line 13, change "(Q-2)" to -- (Q-2), --.

In the Claims

Column 296, Claim 1, Line 12, change "(Q-2)" to -- (Q-2), --.
Column 297, Claim 2, Line 4, change "group" to -- group, --.
Column 297, Claim 2, Line 15, change "(Q-2)" to -- (Q-2), --.
Column 298, Claim 2, Line 17, change "fluorine" to -- fluorine, --.
Column 298, Claim 3, Line 5, change "(M-23)" to -- (M-23), --.
Column 304, Claim 4, Line 12, change "(Q-2)" to -- (Q-2), --.
Column 304, Claim 4, Line 16, change "carbons" to -- carbons, --.
Column 305, Claim 6, Line 6, change "(Q-2)" to -- (Q-2), --.
Column 309, Claim 9, Line 10, change "$B^3$" to -- $B^3$, --.
Column 309, Claim 9, Line 12, change "phenylene" to -- phenylene, --.
Column 309, Claim 9, Line 13, change "$Z^{12}$" to -- $Z^{12}$, --.
Column 310, Claim 10, Line 17, change "or" to -- , or --.
Column 311, Claim 12, Line 13, change "one ef" to -- one --.
Column 311, Claim 12, Line 15, change "$E^3$" to -- $E^3$, --.
Column 312, Claim 12, sequence 10, change "$Z^{10}$" to -- $Z^{19}$ --.

Signed and Sealed this
Twenty-fourth Day of July, 2018

Andrei Iancu
*Director of the United States Patent and Trademark Office*